(12) United States Patent
Que et al.

(10) Patent No.: US 12,195,737 B2
(45) Date of Patent: *Jan. 14, 2025

(54) SIMULTANEOUS GENE EDITING AND HAPLOID INDUCTION

(71) Applicant: SYNGENTA PARTICIPATIONS AG, Basel (CH)

(72) Inventors: Qiudeng Que, Research Triangle Park, NC (US); Timothy Kelliher, Research Triangle Park, NC (US)

(73) Assignee: SYNGENTA CROP PROTECTION AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/060,362

(22) Filed: Nov. 30, 2022

(65) Prior Publication Data

US 2023/0227836 A1 Jul. 20, 2023

Related U.S. Application Data

(63) Continuation of application No. 16/678,286, filed on Nov. 8, 2019, now abandoned, which is a continuation of application No. 16/245,923, filed on Jan. 11, 2019, now Pat. No. 10,519,456, which is a continuation of application No. 15/901,464, filed on Feb. 21, 2018, now Pat. No. 10,285,348, which is a continuation of application No. PCT/US2017/064512, filed on Dec. 4, 2017.

(60) Provisional application No. 62/429,260, filed on Dec. 2, 2016.

(51) Int. Cl.
  C12N 15/82 (2006.01)
  C12N 15/10 (2006.01)
  C12N 15/113 (2010.01)
  C12N 15/65 (2006.01)

(52) U.S. Cl.
  CPC ....... *C12N 15/8213* (2013.01); *C12N 15/102* (2013.01); *C12N 15/113* (2013.01); *C12N 15/65* (2013.01); *C12N 15/8218* (2013.01); C12N 2310/20 (2017.05)

(58) Field of Classification Search
  None
  See application file for complete search history.

(56) References Cited

U.S. PATENT DOCUMENTS

| 7,135,615 | B2 | 11/2006 | Kato |
| 8,269,061 | B2 | 9/2012 | Williams |
| 9,677,082 | B2 | 6/2017 | Chintamanani et al. |
| 10,285,348 | B2* | 5/2019 | Kelliher .................. C12N 15/11 |
| 10,448,588 | B2* | 10/2019 | Chintamanani .... C12N 15/8218 |
| 10,487,336 | B2 | 11/2019 | Michelmore |
| 10,519,456 | B2 | 12/2019 | Que et al. |
| 11,193,131 | B2 | 12/2021 | Campbell et al. |
| 2003/0005479 | A1 | 1/2003 | Kato |
| 2008/0216198 | A1 | 9/2008 | Zhao et al. |
| 2009/0297495 | A1 | 12/2009 | Kerovuo et al. |
| 2013/0198893 | A1 | 8/2013 | Zhao et al. |
| 2015/0067922 | A1 | 3/2015 | Yang et al. |
| 2015/0307889 | A1 | 10/2015 | Petolino et al. |
| 2017/0240912 | A1 | 8/2017 | Chintamanani et al. |
| 2018/0245090 | A1 | 8/2018 | Campbell et al. |
| 2019/0136250 | A1 | 5/2019 | Que et al. |

FOREIGN PATENT DOCUMENTS

| BR | 112017013406 A2 | 2/2018 |
| BR | 112017028460 A2 | 9/2018 |
| CN | 102487816 A | 6/2012 |
| CN | 104737757 A | 7/2015 |
| EP | 2574234 A1 | 4/2013 |
| EP | 1602717 B1 | 12/2014 |
| EP | 3037540 A1 | 6/2016 |
| RU | 2349642 C2 | 3/2009 |
| RU | 2551313 C2 | 5/2015 |
| RU | 2560599 C2 | 8/2015 |
| WO | 0185969 A2 | 11/2001 |
| WO | 2009089928 A1 | 7/2009 |
| WO | 2011044132 | 4/2011 |
| WO | 2011072246 A2 | 6/2011 |

(Continued)

OTHER PUBLICATIONS

Ryu et al., "Characterization of a cDNA Encoding *Arabidopsis* Secretory Phospholipase A2-α, an Enzyme That Generates Bioactive Lysophospholipids and Free Fatty Acids", Biochimica et Biophysica Acta (BBA)—Molecular and Cell Biology of Lipids, vol. 1736, No. 2, Sep. 15, 2005, pp. 144-151.

Bakos et al., "Regeneration of Haploid Plants After Distant Pollination of Wheat via Zygote Rescue", Acta Biologica Cracoviensia, vol. 47, No. 1, 2005, pp. 167-171.

Begheyn et al., "Haploid and Doubled Haploid Techniques in Perennial Ryegrass (*Lolium perenne* L.) to Advance Research and Breeding", Agronomy, vol. 6, No. 4, Nov. 28, 2016, pp. 1-18.

(Continued)

*Primary Examiner* — Weihua Fan

(74) *Attorney, Agent, or Firm* — Kilpatrick Townsend & Stockton LLP

(57) ABSTRACT

The presently disclosed subject matter relates to using a haploid inducing line (whether existing or created) and transforming the haploid line so that it encodes cellular machinery capable of editing genes. The transformed haploid inducing line is used as a parent in a cross between two plants. During pollination, the parental gametes fuse to form an embryo; and the gene editing machinery is also delivered to the embryo at this time. During embryonic development, one set of parental chromosomes are lost, and the gene editing machinery operates on the remaining set of chromosomes. Thus, at least one haploid progeny with edited genes is produced from the cross.

13 Claims, 24 Drawing Sheets

Specification includes a Sequence Listing.

(56) References Cited

FOREIGN PATENT DOCUMENTS

| WO | 2014110274 A2 | 7/2014 |
|---|---|---|
| WO | 2015171894 | 11/2015 |
| WO | 2016075255 A1 | 5/2016 |
| WO | 2016106121 A1 | 6/2016 |
| WO | 2016149352 A1 | 9/2016 |
| WO | 2016177887 A1 | 11/2016 |
| WO | 2017004375 A1 | 1/2017 |
| WO | 2017087682 A1 | 5/2017 |
| WO | 2018015956 A1 | 1/2018 |
| WO | 2018015957 A1 | 1/2018 |
| WO | 2018052919 A1 | 3/2018 |
| WO | 2021252619 A1 | 12/2021 |

OTHER PUBLICATIONS

Brazauskas et al., "Improved Approaches in Wheat x Maize Crossing for Wheat Doubled Haploid Production", Biologija, vol. 51, No. 4, Oct. 1, 2005, pp. 15-18.
Chen et al., "A Comparison of Hordeum Bulbosum-Mediated Haploid Production Efficiency in Barley Using in Vitro Floret and Tiller Culture", Theoretical and Applied Genetics, vol. 77, No. 5, May 1989, pp. 701-704.
Chen et al., "Wide Hybridization of Hordeum Vulgare x *Zea mays*", Genome, vol. 34, No. 4, Aug. 1991, pp. 603-605.
Comai, "Genome Elimination: Translating Basic Research in to a Future Tool for Plant Breeding", PLOS Biology, vol. 12, No. 6, Jun. 2014, pp. 1-4.
Devaux, "The Hordeum Bulbosum (L.) Method", Doubled Haploid Production in Crop Plants, 2003, pp. 15-19.
Gilles et al., "Loss of Pollen-Specific Phospolipase Not Like Dad Triggers Gynogenesis in Maize", The Embo Journal, vol. 36, No. 6, Feb. 9, 2017, pp. 707-717.
Gu et al., "Study on the In Vitro Culture of Cut Plants in Wheat Haploid Embryo Induction by a Wheat X Maize Cross", Frontiers of Agriculture in China, vol. 2, No. 4, Dec. 2008, pp. 391-395.
Gurushidze et al., "True-Breeding Targeted Gene Knock-Out in Barley Using Designer TALE-Nuclease in Haploid Cells", PLoS ONE, vol. 9, No. 3, Mar. 2014, pp. 1-9.
Haberer et al., "Structure and Architecture of the Maize Genome", Plant Physiology, vol. 139, No. 4, Dec. 9, 2005, pp. 1612-1624.
Hahn et al., "An Efficient Visual Screen for CRISPR/Cas9 Activity in *Arabidopsis thaliana*", Frontiers in Plant Science, vol. 8, Article 39, Jan. 24, 2017, pp. 1-13.
Huang et al., "Cloning of an Arabidopsis Patatin-Like Gene, Sturdy, by Activation T-DNA Tagging", Plant Physiology, vol. 125, No. 2, Feb. 2001, pp. 573-584.
Inagaki, "Doubled Haploid Production in Wheat Through Wide Hybridization", In Doubled Haploid Production in Crop Plants: A Manual, 2003, pp. 53-58.
Kasha et al., "High Frequency Haploid Production in Barley (*Hordeum vulgare* L.)", Nature, vol. 225, No. 5235, Feb. 28, 1970, pp. 874-876.
Kelliher et al., "MATRILINEAL, A Sperm-Specific Phospholipase, Triggers Maize Haploid Induction", Nature, vol. 542, Feb. 2, 2017, pp. 105-122.
Kelliher et al., "One-Step Genome Editing of Elite Crop Germplasm During Haploid Induction", Nature Biotechnology, vol. 37, No. 3, Mar. 1, 2019, pp. 287-292.
Knox et al., "Dicamba and Growth Condition Effects on Doubled Haploid Production in Durum Wheat Crossed with Maize", Plant Breeding, vol. 119, No. 4, Aug. 2000, pp. 289-298.
Laurie et al., "Chromosome Behavior in Wheat X Maize, Wheat X Sorghum and Barley X Maize Crosses", In Kew Chromosome Conference Proceedings III, 1988, pp. 167-177.
Laurie et al., "The Production of Haploid Wheat Plants from Wheat X Maize Crosses", Theoretical and Applied Genetics, vol. 76, Sep. 1988, pp. 393-397.
Li et al., "Multiplex and Homologous Recombination-mediated Plant Genome Editing via Guide RNA/Cas9", Nature Biotechnology, vol. 31, No. 8, Aug. 2013, pp. 1-8.

Liang et al., "Targeted Mutagenesis in *Zea mays* Using TALENs and the CRISPR/Cas System", Journal of Genetics and Genomics, vol. 41, No. 2, Feb. 20, 2014, pp. 63-68.
Liu et al., "A 4bp Insertion at ZmPLA1 Encoding a Putative Phospholipase a Generates Haploid Induction in Maize", Molecular Plant, vol. 10, No. 3, Jan. 31, 2017, 7 pages.
Makarova et al., "Evolution and Classification of the CRISPR-Cas Systems", Nature Reviews Microbiology, vol. 9, No. 6, Jun. 2011, pp. 467-477.
Mao et al., "Development of Germ-Line-Specific CRISPR-Cas9 Systems to Improve the Production of Heritable Gene Modifications in *Arabidopsis*", Plant Biotechnology Journal, vol. 14, No. 2, Feb. 2016, pp. 519-532.
Muiruri et al., "Expressed Centromere Specific Histone 3 (CENH3) Variants in Cultivated Triploid and Wild Diploid Bananas (*Musa* spp.)", Frontiers in Plant Science, vol. 8, Article 1034, Jun. 29, 2017, pp. 1-12.
Nair et al., "Dissection of a Major QTL qhir1 Conferring Maternal Haploid Induction Ability in Maize", Theoretical and Applied Genetics, vol. 130, No. 7639, Feb. 4, 2017, pp. 1113-1122.
Application No. PCT/US2017/064512, International Search Report and Written Opinion, Mailed On Mar. 7, 2018, 7 pages.
Prigge et al., "Production of Haploids and Doubled Haploids in Maize", Methods in Molecular Biology, vol. 877, Jan. 1, 2012, pp. 161-172.
Puchta, "Using CRISPR/Cas in Three Dimensions: Towards Synthetic Plant Genomes, Transcriptomes and Epigenomes", The Plant Journal, vol. 87, No. 1, Jul. 2016, pp. 5-15.
Ravi et al., "Haploid Plants Produced by Centromere-Mediated Genome Elimination", Nature, vol. 464, No. 7288, Mar. 25, 2010, pp. 615-618.
Riera-Lizarazu et al., "Cytological and Molecular Characterization of Oat X Maize Partial Hybrids", Theoretical and Applied Genetics, vol. 93, No. 1, Jul. 1996, pp. 123-135.
Rietz et al., "Roles of Arabidopsis Patatin-Related Phospholipases A in Root Development Are Related to Auxin Responses and Phosphate Deficiency", Molecular Plant, vol. 3, No. 3, May 2010, pp. 524-538.
Rines, "Oat Haploids from Wide Hybridization", Doubled Haploid Production in Crop Plants, 2003, pp. 155-159.
Scherer et al., "Patatin-Related Phospholipase A: Nomenclature, Subfamilies and Functions in Plants", Trends in Plant Science, vol. 15, No. 12, Dec. 2010, pp. 693-700.
Shen et al., "Haploid Strategies for Functional Validation of Plant Genes", Trends in Biotechnology, vol. 33, No. 10, Oct. 1, 2015, pp. 611-620.
Shukla et al., "Precise Genome Modification in the Crop Species *Zea mays* Using Zinc-Finger Nucleases", Nature, vol. 459, No. 7245, May 21, 2009, pp. 437-441.
Singh et al., "Rice Phospholipase A Superfamily: Organization, Phylogenetic and Expression Analysis During Abiotic Stresses and Development", PLoS ONE, vol. 7, No. 2, Feb. 2012, pp. 1-15.
Voytas, "Plant Genome Engineering with Sequence-Specific Nucleases", Annual Review of Plant Biology, vol. 64, May 2013, pp. 327-350.
Wan et al., "Efficient Production of Doubled Haploid Plants Through Colchicine Treatment of Anther-Derived Maize Callus", Theoretical and Applied Genetics, vol. 77, No. 6, Jun. 1989, pp. 889-892.
Wedzony et al., "Production of Doubled Haploids in Triticale (xTriticosecale Wittm.) by Means of Crosses With Maize (*Zea mays* L.) Using Picloram and Dicamba", Plant Breeding, vol. 117, No. 3, Jul. 1998, pp. 211-215.
Wedzony, "Protocol for Doubled Haploid Production in Hexaploidy Triticale (x Triticosecale Wittm.) by Crosses with Maize", Doubled Haploid Production in Crop Plants, 2003, pp. 135-140.
Xing et al., "A Crispr/Cas9 Toolkit for Multiplex Genome Editing in Plants", BMC Plant Biology, Biomed Central, vol. 14, No. 1, Nov. 29, 2014, pp. 1-12.
Zhang et al., "The CRISPR/Cas9 System Produces Specific and Homozygous Targeted Gene Editing in Rice in One Generation", Plant Biotechnology Journal, vol. 12, No. 6, Aug. 2014, pp. 797-807.

(56) References Cited

OTHER PUBLICATIONS

U.S. Appl. No. 17/327,016, "Final Office Action", Jan. 17, 2024, 14 pages.
U.S. Appl. No. 17/327,016, "Response to Final Office Action", Apr. 9, 2024, 6 pages.

* cited by examiner

FIG. 24

SIMULTANEOUS GENE EDITING AND HAPLOID INDUCTION

This application claims the benefit under 35 U.S.C. § 120 of U.S. patent application Ser. No. 16/678,286, filed Nov. 8, 2019, which claims benefit under 35 U.S.C. § 120 of U.S. patent application Ser. No. 16/245,923, filed Jan. 11, 2019, now U.S. Pat. No. 10,519,456, which claims the benefit under 35 U.S.C. § 120 of U.S. application Ser. No. 15/901,464, filed Feb. 21, 2018, now U.S. Pat. No. 10,285,348, which claims the benefit under 35 U.S.C. § 365(c) of International Application No. PCT/US2017/064512, filed Dec. 4, 2017 and designating the U.S., which claims priority under 35 U.S.C. § 119 to U.S. Provisional Application 62/429,260, filed Dec. 2, 2016, all of which are incorporated herein by reference in their entirety.

FIELD OF THE INVENTION

This invention is related to the field of plant biotechnology, specifically agriculture biotechnology and gene editing, as well as plant breeding. The presently disclosed subject matter relates to using a haploid inducing line (whether existing or created) and transforming the haploid inducing line so that it contains DNA coding for cellular machinery capable of editing genes.

SEQUENCE LISTING

This application is accompanied by a sequence listing entitled 086879-1359385_ST26.xml, created Nov. 30, 2022, which is approximately 492,637 bytes in size. This sequence listing is incorporated herein by reference in its entirety. This sequence listing is submitted herewith via EFS-Web, and is in compliance with 37 C.F.R. § 1.824(a)(2)-(6) and (b).

BACKGROUND

Targeted mutagenesis (also known as "gene editing") is a very important technology to crop breeding. There are numerous methods to edit specific gene targets now, including CRISPR, TALEN, meganucleases, and zinc fingers. One method to introduce editing machinery into plants is to use *Agrobacterium* or biolistic transformation of plant tissue. In transformation, DNA coding for the editing machinery (e.g., CAS9 and guide RNA) is introduced into plant callus, seed or embryonic tissue. Stably-transformed plants ("events") are then recovered, optionally with the help of a selectable marker. But because tissue culture is genotype-dependent, this route will not work for all crops, or even all varieties of the crops for which it does work. These are known as transformation-recalcitrant crops or varieties. These crops or varieties may be valued for their performance but it is a challenge for biotechnology that they cannot be transformed and thus cannot be directly edited via transformation. For recalcitrant varieties, one of two alternative approaches could be used to introduce desirable mutations. First, one could introduce the edits via trait introgression. This route is expensive, laborious, and time-consuming. It also means impurity of the final product because of genetic linkage—that is, there will be a linked block surrounding the introgressed edits, containing genes and alleles from the transformable donor line. This linkage can be an issue if any of those genes or alleles impact the performance of the transformation-recalcitrant line (may also be referred to as an "elite line"). Secondly, one could introduce the editing machinery transiently to the growing plant without tissue culture, such as floral dipping for *Arabidopsis* transformation. The challenge is ensuring edits end up in cells that contribute to the germ-line, so they are passed on to progeny seed. There are few established or routine methods to do this in crops.

Here we show a new method to transiently introduce editing machinery during haploid induction. Haploid induction ("HI") is a class of plant phenomena characterized by loss of one parent's set of chromosomes (the chromosomes from the haploid inducer parent) from the embryo at some time during or after fertilization, often during early embryo development. Haploid induction is also known as gynogenesis if the inducer line is used as the male in the cross, or androgenesis if the inducer line is used as the female in the cross. Haploid induction has been observed in numerous plant species, such as sorghum, barley, wheat, maize, *Arabidopsis*, and many other species.

Commonly, during haploid induction, both parent lines used in the induction cross are both diploids, so their gametes (egg cells and sperm cells) are haploids. Haploid induction is frequently a medium to low penetrance trait of the inducer line, so the resulting progeny, depending on the species or situation, may be either diploid (if no genome loss takes place) or haploids (if genome loss does indeed take place). If the parent line that is crossed to the haploid inducer is not diploid, but rather a tetraploid, hexaploid, or other plant of higher ploidy, the term haploid induction is something of a misnomer, because the "haploid" progeny produced will have a gametic chromosome number, and thus would not really be haploids, but rather diploids (if the parent is tetraploid) or triploids (if the parent is hexaploid) and so on. Therefore, as used herein, "haploids" possess half the number of chromosomes of either parent; thus haploids of diploid organisms (e.g., maize) exhibit monoploidy; haploids of tetraploid organisms (e.g., ryegrasses) exhibit diploidy; haploids of hexaploid organisms (e.g., wheat) exhibit triploidy.

Haploid induction can occur during self-pollination or intercrossing of two lines within the same species, or it can occur during wide crosses, where it can be viewed as a hybridization barrier, preventing the formation of interspecific hybrids. In maize, the most commonly employed method of inducing haploids is through the use of an intraspecific haploid inducer male line, which is primarily triggered by rearrangements of, mutations in, and/or recombinations, insertion, or deletions within a region of chromosome 1, specifically the MATRILINEAL (MATL) gene, also known as NOT LIKE DAD1 (NLD1) and PHOSPHOLIPASE A1 (PLA1) (with the notable exception of the ig type haploid induction, which is a result of a mutation in the INDETERMINATE GAMETOPHYTE1 gene on chromosome 3). In wheat, the most common method of inducting haploids is by wide cross to maize pollen—regardless of parent genotype or lineage, this works with almost any wheat crossed by almost any maize pollen.

HI maize lines contain a quantitative trait locus ("QTL") on Chromosome 1 responsible for at least 66% of the variation in haploid induction. The QTL causes haploid induction at different rates when it is introgressed into various backgrounds. All maize haploid inducer lines used in the seed industry are derivatives of the founding HI line, known as Stock6, and all have the haploid inducer chromosome 1 QTL mutation.

In maize, haploid seed or embryos are specifically produced by making crosses between a haploid inducer male (i.e., "haploid inducer pollen") and virtually any ear that one chooses—the ear could be of any inbred, hybrid, or other germplasm. Haploids are produced when the haploid inducer pollen DNA is not fully transmitted and/or maintained through the first cell divisions of the embryos. The resulting phenotype is not fully penetrant, with some ovules containing haploid embryos, and others containing diploid embryos, aneuploid embryos, chimeric embryos, or aborted embryos. The haploid kernels have embryos that contain only the maternal DNA plus normal triploid endosperm. After haploid induction, haploid embryos or seed are typically segregated from diploid and aneuploid siblings using a phenotypic or genetic marker screen and grown or cultured into haploid plants. These plants are then converted either naturally or via chemical manipulation (e.g., using an anti-microtubule agent such as colchicine) into doubled haploid ("DH") plants which then produce inbred seed.

Plant breeding is facilitated by the use of doubled haploid (DH) plants. The production of DH plants enables plant breeders to obtain inbred lines without multigenerational inbreeding, thus decreasing the time required to produce homozygous plants. DH plants provide an invaluable tool to plant breeders, particularly for generating inbred lines, QTL mapping, cytoplasmic conversions, trait introgression, and F2 screening for high throughput trait improvement. A great deal of time is spared as homozygous lines are essentially generated in one generation, negating the need for multi-generational single-seed decent (conventional inbreeding). In particular, because DH plants are entirely homozygous, they are very amenable to quantitative genetics studies. The production of haploid seed is critical for the doubled haploid breeding process. Haploid seed are produced on maternal germplasm when fertilized with pollen from a gynogenetic inducer, such as Stock 6 and Stock 6-derivative lines.

Here, we describe a novel method in which the in vivo haploid induction process can be co-opted to transiently introduce editing machinery into any germplasm by including it in the haploid inducer parent, either stably integrated as a transgene, or transiently expressed. Simultaneous editing plus haploid induction can be done in almost any crop via wide cross or de novo haploid induction for instance via CENH3 mutation (i.e., CENH3-modified haploid inducer; see, e.g., WO 2017/004375, incorporated herein by reference in its entirety) or via lipid spray (see P.C.T. Patent Application No. PCT/US2016/62548, incorporated herein by reference in its entirety). We show examples of HI in maize, both field corn and sweet corn, using a haploid inducer male as the editing donor line. Further, we show examples of HI in *Arabidopsis* using CENH3-modified haploid inducer lines.

We also show examples of HI in wheat using maize pollen as the editing donor line in a wide cross. In wheat, rice, barley, brassica, and other crops, the route to haploid induction would be to use a pollen donor that induces haploids via wide cross. For example, one could use corn pollen on wheat, millet pollen on wheat, barley pollen on other barley species, or any other wide crossing method. In those cases of gynogenetic haploid induction it would be preferable for the male line to contain the editing machinery, because it is the male (pollen-derived) DNA that is eliminated in the haploid induction process. In cases of androgenic haploid induction, for instance in the ig1 system in maize or via altered CENH3 in any crop (which can work via either the male or the female), the editing machinery would be optimally present in the female parent, because the female chromosomes are eliminated in the haploid induction process.

In simultaneous editing plus haploid induction, the goal is to rapidly and cost-effectively edit crops and elite lines ("editing destination lines") without tissue culture. The line that receives the edits could be elite germplasm, and the editing machinery itself would be eliminated during the haploid induction process. At the same time, edited doubled haploid lines are produced.

SUMMARY

Tissue culture recalcitrance is a major challenge to rapid elite line editing across crops. Using haploid inducing lines to deliver the targeted mutagenesis machinery to elite lines and simultaneously induce haploids represents the surmounting of this major obstacle. Next-generation breeding programs may come to depend on this process.

The editing machinery is delivered via the inducer line. The editing machinery is most often DNA-binding proteins combined in some cases with RNA and in some cases also with DNA. The DNA, RNA, and proteins that make up the editing machinery are encoded by and are present in the inducer line because they have been stably inserted in the inducer, for example, via bombardment or *Agrobacterium* mediated transformation. In other examples, the editing machinery is transiently introduced (through exogenous application) or transiently expressed in the gametophyte prior to fertilization. After fertilization, edits are made by the editing machinery in the non-inducer target genes prior to or during elimination of the inducer chromosomes. The result is a haploid embryo or plant or seed that contains the chromosome set only from the non-inducer parent, where that chromosome set contains DNA sequences that have been edited. These edited haploids can be identified, grown, and their chromosomes doubled, preferably by colchicine or other mitotic inhibitor. This line can then be directly used in downstream breeding programs.

In one embodiment, the invention provides a method of editing a plant's genomic DNA. This is done by taking a first plant—which is a haploid inducing plant and which also has encoded into its DNA the machinery necessary for accomplishing the editing (for example, a Cas9 enzyme and a guide RNA)—and using that first plant's pollen to pollinate a second plant. The second plant is the plant to be edited. From that pollination event, progeny (e.g., embryos or seeds) are produced; at least one of which will be a haploid seed. This haploid seed will only contain the chromosomes of the second plant; the first plant's chromosomes have vanished (having been eliminated, lost or degraded), but before doing so, the first plant's chromosomes permitted the gene-editing machinery to be expressed. Alternately, and without wishing to be bound by theory, the first plant delivers the already-expressed editing machinery upon pollination via the pollen tube. Or, in the case that the haploid inducer line is the female in the cross, the haploid inducing plant's egg cell contains the editing machinery that is present and perhaps already being expressed, upon fertilization with the "wild type" or non-haploid inducing pollen grain. Through any of these routes, the haploid progeny obtained by the cross will also have had its genome edited.

In one aspect, the editing machinery is any DNA modification enzyme, but is preferably a site-directed nuclease. The site-directed nuclease is preferably CRISPR-based, but could also be a meganuclease, a transcription-activator like effector nuclease (TALEN), or a zinc finger nuclease. The nuclease used in this invention could be Cas9, Cfp1, dCas9-FokI, chimeric FEN1-FokI. In one aspect, the DNA modification enzyme is a site-directed base editing enzyme such as Cas9-cytidine deaminase or Cas9-adenine deaminase, wherein the Cas9 can have one or both of its nuclease activity inactivated, i.e. chimeric Cas9 nickase (nCas9) or deactivated Cas9 (dCas9) fused to cytidine deaminase or adenine deaminase. The optional guide RNA targets the genome at the specific site intended to be edited. In one aspect, the optional guide RNA comprises an 18-21 nucleotide sequence with homology to any of SEQ ID NOs: 2, 4, 8, 21, 23, 25, 29, 32, and 33.

Once the edited haploid progeny is obtained, it may optionally have its chromosomes doubled by a chromosome doubling agent (for example colchicine, pronamide, dithipyr, trifluralin, or another known anti-microtubule agent).

In one embodiment, the first plant is a monocot or a dicot. Aspects of the first plant include maize, wheat, rice, barley, oats, triticale, sorghum, pearl millet, teosinte, bamboo, sugar cane, asparagus, onion, and garlic. In one embodiment, the second plant is a monocot or a dicot. Aspects of the second plant include maize, wheat, rice, barley, oats, triticale, sorghum, pearl millet, teosinte, bamboo, sugar cane, asparagus, onion, and garlic. In one embodiment, the first plant is a monocot or a dicot of a different species than the second plant. For example, in one aspect, the first plant is maize and the second plant is wheat. In another aspect, the first plant is wheat and the second plant is maize. In another embodiment, the first plant is a maize plant selected and/or derived from the lines Stock 6, RWK, RWS, UH400, AX5707RS, NP2222-matl, or any of the several other known HI lines. In yet another embodiment, the first plant comprises a mutation in a CENH3 gene, an ig1 gene, or another mutation conferring paternal-haploid inducing systems. In another embodiment, the first plant is a rice plant with the MATL gene modified or knocked out which makes it a haploid inducer line.

In another embodiment, the first plant is not necessarily a haploid inducer, yet the first plant comprises the genes necessary for encoding the gene editing machinery. In this embodiment, haploid induction is produced by administering a compound during, immediately before, or immediately following pollination. In one aspect, the composition comprises a lipid or a phospholipase inhibitor. In another aspect, the composition comprises methyl alpha-linolenoyl fluorophosphonate (MALFP), linoleic acid ethyl ester (LLAEE), linoleic acid (LLA), corn oil, distearoyl-phosphatidyl choline (DSPC), methyl arachidonyl fluorophosphonate (MAFP), Palmityl trifluoromethylketone (PACOCF3), Arachidonyl trifluoromethylketone (AACOCF3), Manoalide, Linolenic acid ethyl ester (LNAEE), Linolenic acid ethyl ester (LNAEE), Oleic acid methyl ester (OAME), Oleic acid ethyl ester (OAEE), Palmitic acid ethyl ester (PAEE), Palmitoleic acid ethyl ester (PLAEE), Linseed oil, corn oil, alpha-Linolenic acid (aLNA), gamma-Linolenic acid (gLNA), Oleic acid, Arachidonic acid, Stearic Acid, 9(Z)-11(E)-conjugated Linoleic acid, or 2-oleoyl-1-palmitoyl-sn-glycero-3-phospho-ethanolamine.

BRIEF DESCRIPTION OF THE SEQUENCES IN THE SEQUENCE LISTING

SEQ ID NO: 1 is a nucleotide sequence for vector 23396.
SEQ ID NO: 2 is the nucleotide sequence encoding the gRNA sequence for editing VLHP1 in maize.
SEQ ID NO: 3 is a nucleotide sequence for vector 23399.
SEQ ID NO: 4 is the gRNA sequence for editing GW2-2 in maize.
SEQ ID NO: 5 is the nucleotide sequence for vector 22808, comprising a TALEN construct.
SEQ ID NO: 6 is the target sequence for the TALEN of 22808.
SEQ ID NO: 7 is the nucleotide sequence for vector 23123 comprising a Cas9 construct.
SEQ ID NO: 8 is the gRNA for editing MATL in maize.
SEQ ID NO: 9 is nucleotide sequence for the relevant portion of MATL in NP2222.
SEQ ID NO: 10 is nucleotide sequence for the relevant portion of MATL in Stock6.
SEQ ID NO: 11 is nucleotide sequence for the relevant portion of MATL in USR01350333-3 Allele 1.
SEQ ID NO: 12 is nucleotide sequence for the relevant portion of MATL in USR01350333-3 Allele 2.
SEQ ID NO: 13 is nucleotide sequence for the relevant portion of MATL in USR01350344-2 Allele 1.
SEQ ID NO: 14 is nucleotide sequence for the relevant portion of MATL in USR01350344-2 Allele 2.
SEQ ID NO: 15 is nucleotide sequence for the relevant portion of MATL in USR01350343-1 Allele 1.
SEQ ID NO: 16 is nucleotide sequence for the relevant portion of MATL in USR01350328-1 Allele 1.
SEQ ID NO: 17 is nucleotide sequence for the relevant portion of MATL in USR01350337-2 Allele 1.
SEQ ID NO: 18 is nucleotide sequence for the relevant portion of MATL in USR01350337-2 Allele 2.
SEQ ID NO: 19 is the nucleotide sequence of cDNA wildtype MATL.
SEQ ID NO: 20 is the nucleotide sequence for vector 23397.
SEQ ID NO: 21 is the gRNA sequence for editing VLHP2 in maize.
SEQ ID NO: 22 is the nucleotide sequence for vector 23398.
SEQ ID NO: 23 is the gRNA sequence for editing GW2-1 in maize.
SEQ ID NO: 24 is the nucleotide sequence for vector 23763.
SEQ ID NO: 25 is the gRNA sequence for VLHP1 in wheat.
SEQ ID NO: 26 is the wheat VLHP target sequence for TaVLHP2.
SEQ ID NO: 27 is the wheat VLHP target sequence for TaVLHP3.
SEQ ID NO: 28 is the target sequence in ZmVLHP2-03 for editing.
SEQ ID NO: 29 is the edited sequence in ZmVLHP2-03.
SEQ ID NO: 30 is the repair donor template sequence for creating E149L mutation in ZmPYL-D.
SEQ ID NO: 31 is the nucleotide sequence for vector 23136.
SEQ ID NO: 32 is the gRNA of vector 23136.
SEQ ID NO: 33 is the nucleotide sequence of rice PLA gene Os03g27610.
SEQ ID NO: 34 is the nucleotide sequence for vector 24038.
SEQ ID NO: 35 is the nucleotide sequence for vector 24039.
SEQ ID NO: 36 is the nucleotide sequence for vector 24079.
SEQ ID NO: 37 is the nucleotide sequence for vector 24091.
SEQ ID NO: 38 is the nucleotide sequence for vector 24094.
SEQ ID NOs: 39 through 97 are primers and probes used in the identified PCR Taqman assays.
SEQ ID NO: 98 is the nucleotide sequence for vector 24075.

SEQ ID NO: 99 is a portion of the edited GW2-02 target site in haploid sweet corn line JSER82A063, shown in FIG. 13.

SEQ ID NO: 100 is the reverse complement of SEQ ID NO: 99 shown in FIG. 13.

SEQ ID NO: 101 is a portion of the edited TaVLHP1-4B target site in haploid wheat line JSWER30A22, shown in FIG. 16.

SEQ ID NO: 102 is the nucleotide sequence of the gRNA used in editing the *Arabidopsis* GL1 gene.

SEQ ID NO: 103 is the relevant portion of the wildtype *Arabidopsis* GL1 gene.

SEQ ID NO: 104 is the relevant portion of the edited GL1 gene (by single nucleotide deletion) in individual 135.

SEQ ID NO: 105 is the relevant portion of the edited GL1 gene (by single nucleotide insertion) in individual 135.

SEQ ID NO: 106 is the relevant portion of the unedited GL1 gene in individual 1033-A3 (product of cross between USR01424135 and Ler-425).

SEQ ID NO: 107 is the relevant portion of the edited GL1 gene (by single nucleotide insertion) in individual 1033-C3 (product of cross between USR01424135 and Ler-427).

SEQ ID NO: 108 is the relevant portion of the edited GL1 gene (by single nucleotide insertion) in individual 1033-E4 (product of cross between USR01424135 and Ler-437).

SEQ ID NO: 109 is the relevant portion of the edited GL1 gene (by deletion of three nucleotides) in individual 1041-H12.

SEQ ID NO: 110 is the relevant portion of the edited GL1 gene (by single nucleotide insertion) in individual 1042-E5 (product of cross between USR01424136 and Ler-25).

SEQ ID NO: 111 is the relevant portion of the edited GL1 gene (by single nucleotide deletion) in individual 1042-G12 (product of cross between USR01424136 and Ler-83).

SEQ ID NO: 112 is the relevant portion of the edited GL1 gene (by deletion of two nucleotides) in individual 1042-G10 (product of cross between USR01424136 and Ler-67).

SEQ ID NO: 113 is the relevant portion of the edited GL1 gene (by deletion of two nucleotides) in individual 1045-E3 (product of cross between USR01424136 and Ler-261).

SEQ ID NO: 114 is the relevant portion of the edited GL1 gene (by single nucleotide insertion) in individual 1045-D3 (product of cross between USR01424136 and Ler-260).

SEQ ID NO: 115 is the relevant portion of the edited GL1 gene (by single nucleotide insertion) in individual 1046-D11 (product of cross between USR01431609 and Ler-111).

SEQ ID NO: 116 is the relevant portion of the edited GL1 gene (by single nucleotide insertion) in individual 1046-G12 (product of cross between USR01431609 and Ler-122).

SEQ ID NO: 117 is the relevant portion of the edited GL1 gene (by deletion of sixteen nucleotides and insertion of eight nucleotides) in individual 1045-F2 (product of cross between USR01424136 and Ler-254).

BRIEF DESCRIPTION OF THE FIGURES

FIG. 24 shows the GL1 target site sequence mutations in the parent #USR01424135 and all of the sequenced edited haploids from outcrosses by Landsberg erecta pollen. It is clear that the precise edit made is different in the different haploids. From top to bottom, the sequences shown are represented by SEQ ID NOs: 102-117, respectively.

DEFINITIONS

Figure 1:
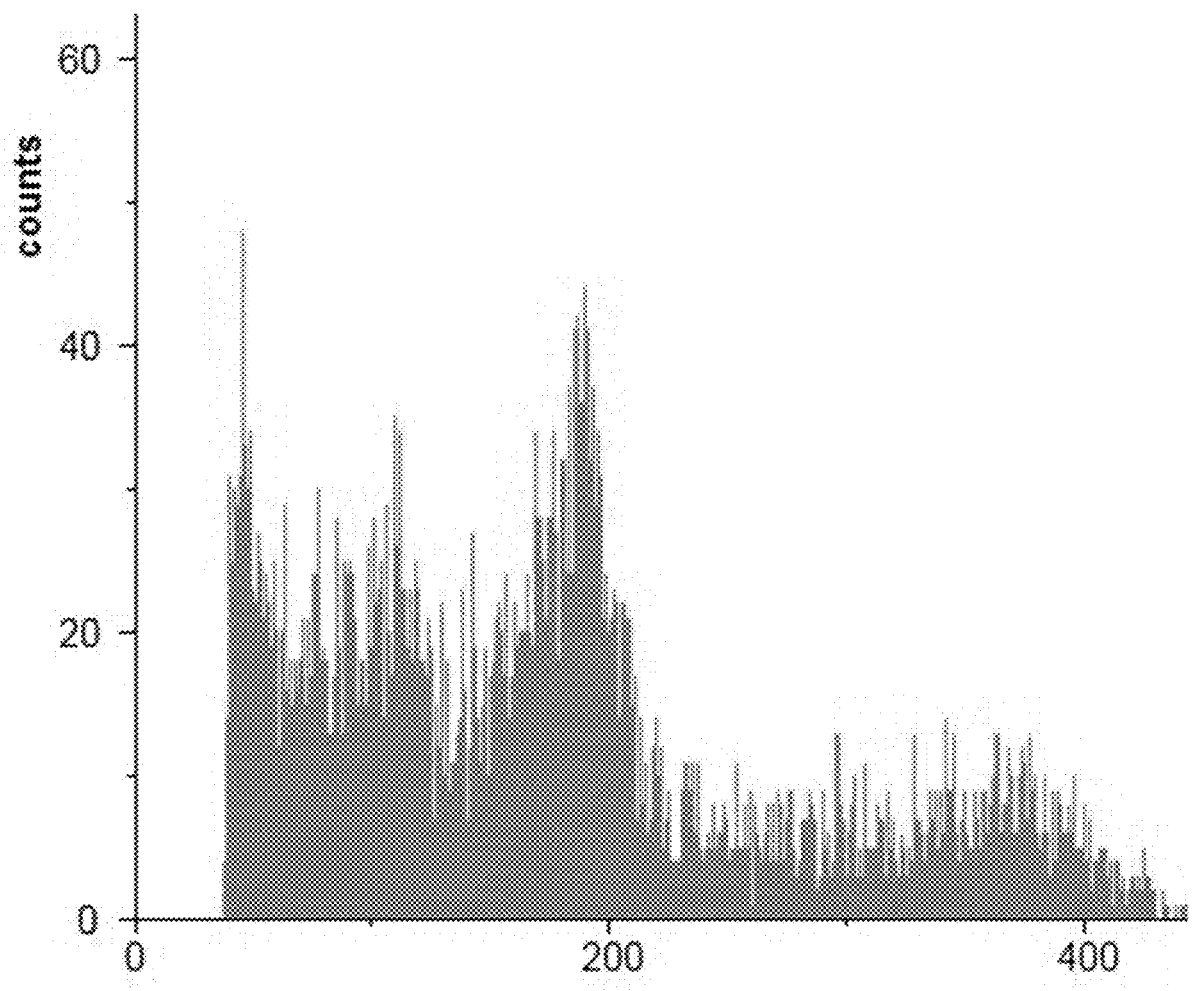
FIG. 1 shows the ploidy analysis (flow cytometry) data for USR01350334-3: DIPLOID (major peak at 200, secondary peak at 400).
Figure 2:
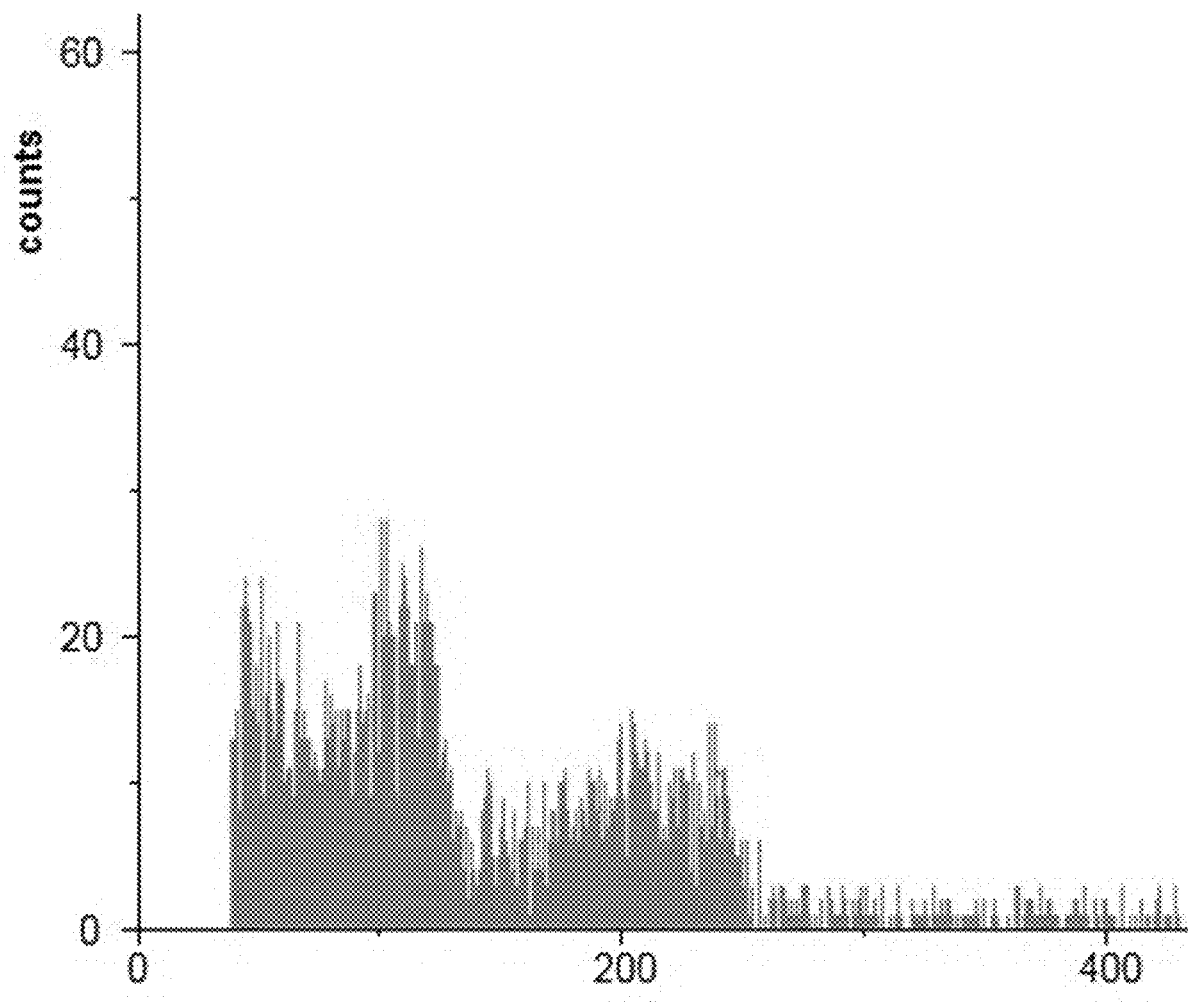
FIG. 2 shows the ploidy analysis (flow cytometry) data for USR01350333-3: HAPLOID (major peak at 100, secondary peak at 200).
Figure 3:
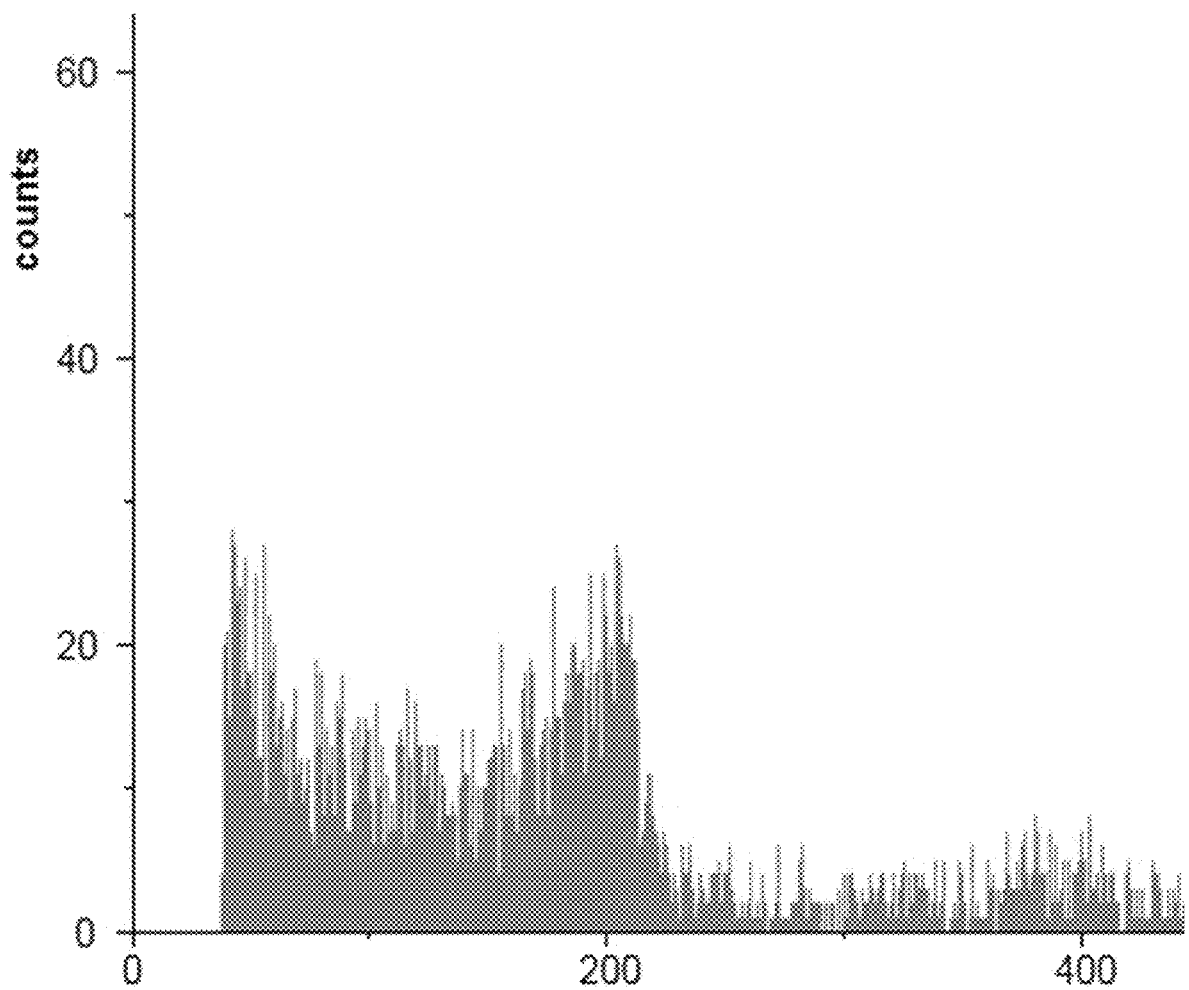
FIG. 3 shows the ploidy analysis (flow cytometry) data for USR01350333-10: DIPLOID (major peak at 200, secondary peak at 400).
Figure 4:
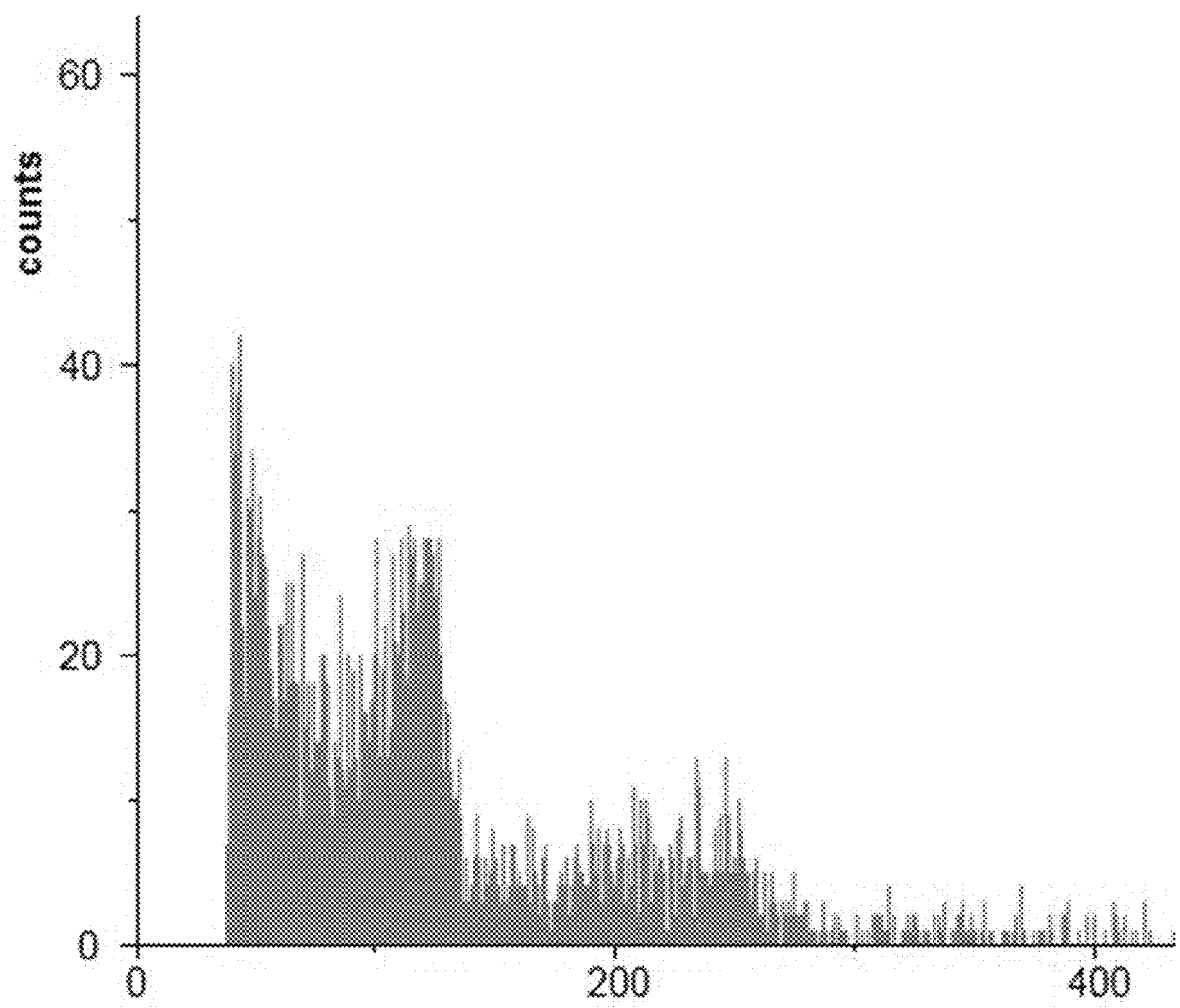
FIG. 4 shows the ploidy analysis (flow cytometry) data for USR01350344-2: HAPLOID (major peak at 100, secondary peak at 200).
Figure 5:
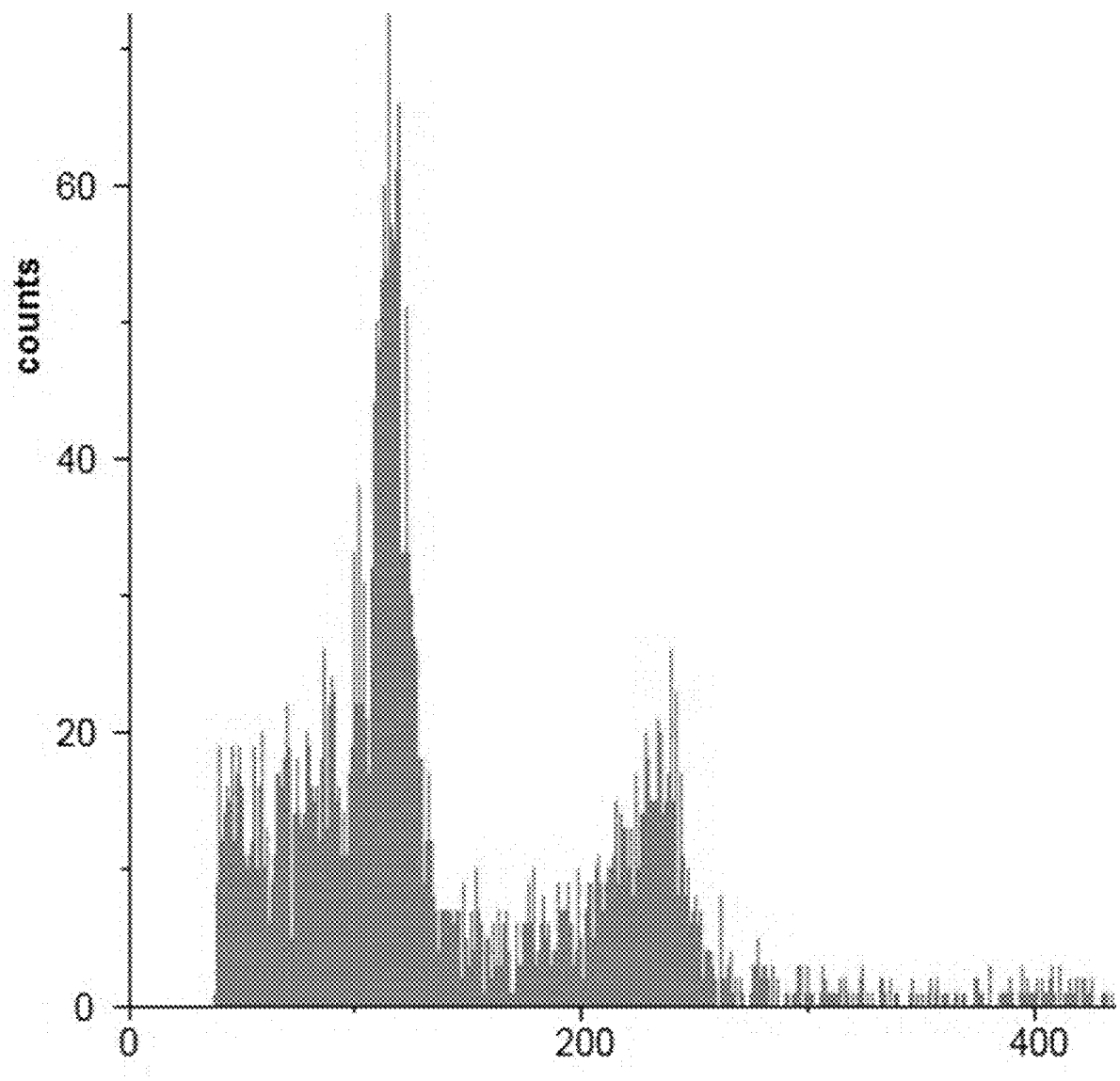
FIG. 5 shows the ploidy analysis (flow cytometry) data for USR01350343-1: HAPLOID (major peak at 100, secondary peak at 200).
Figure 6:
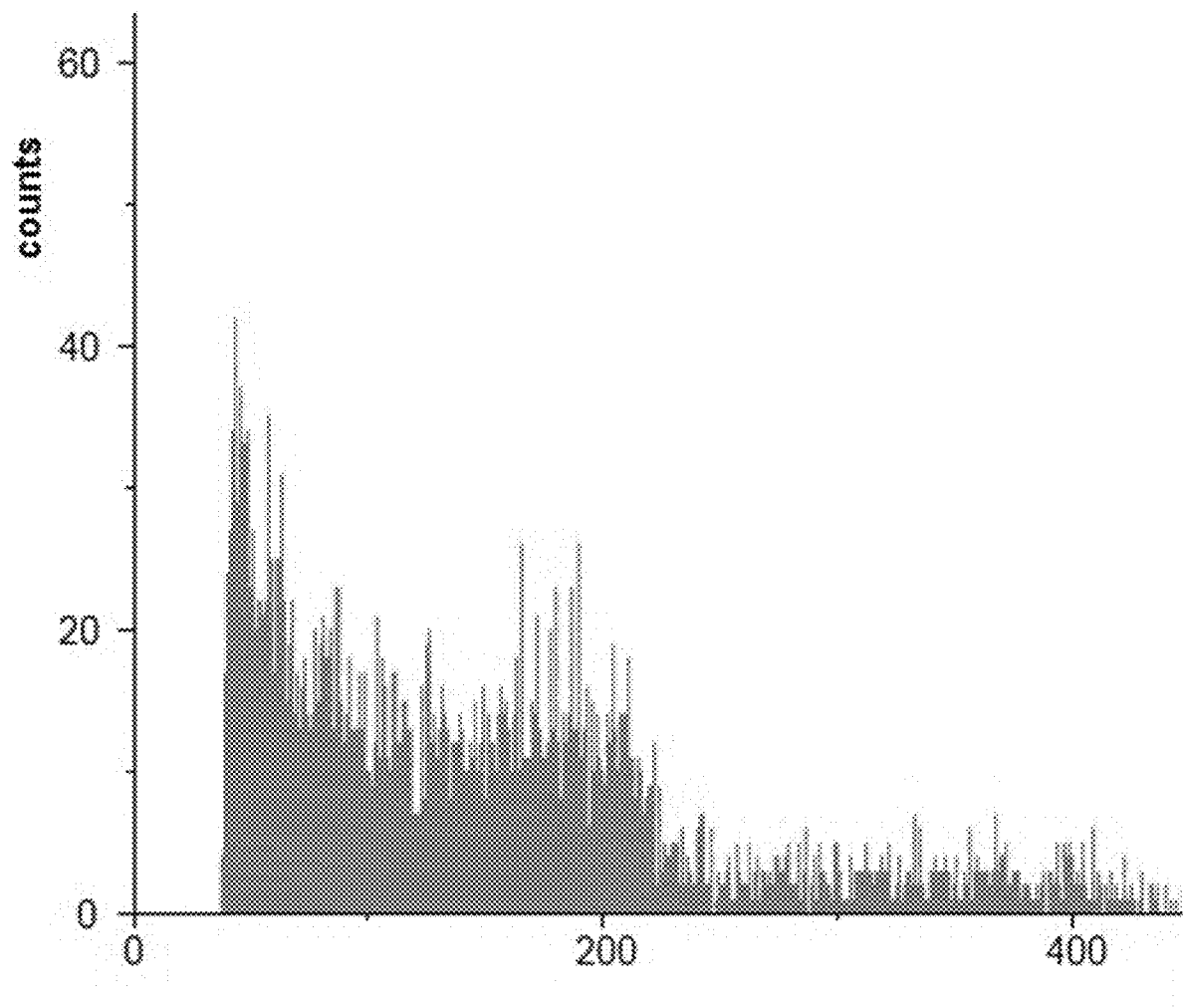
FIG. 6 shows the ploidy analysis (flow cytometry) data for USR01350341-1: DIPLOID (major peak at 200, secondary peak at 400).
Figure 7:
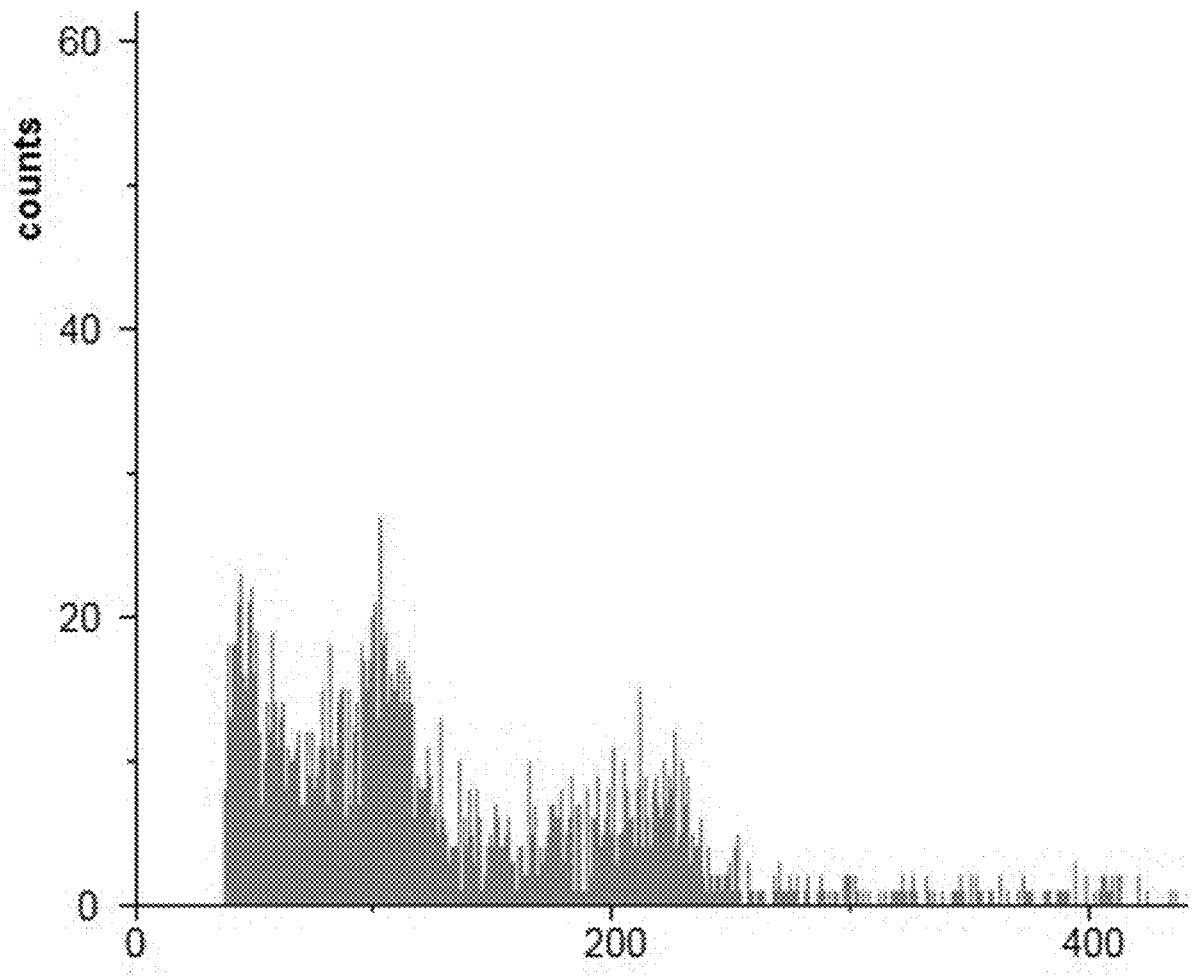
FIG. 7 shows the ploidy analysis (flow cytometry) data for USR01350328-1: HAPLOID (major peak at 100, secondary peak at 200).
Figure 8:
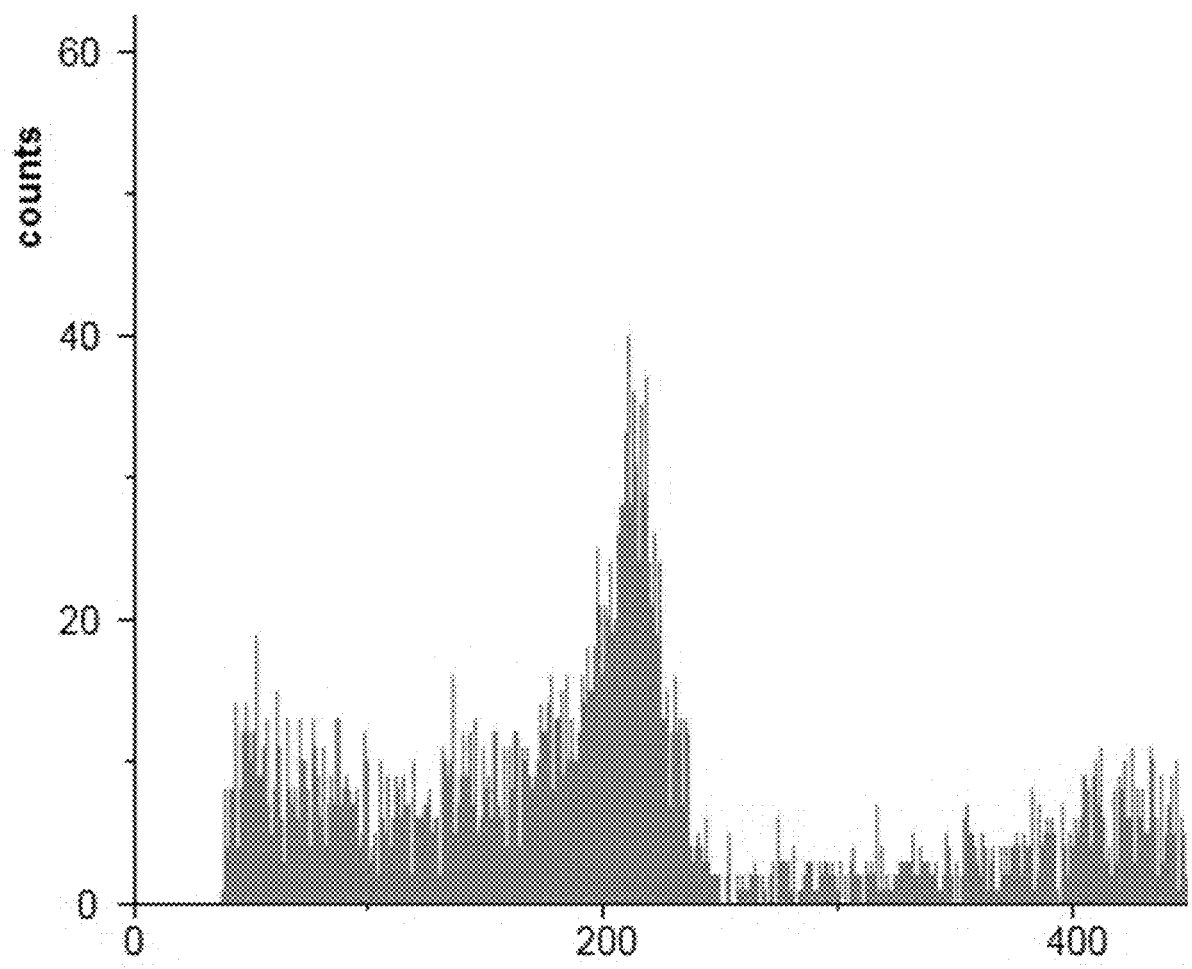
FIG. 8 shows the ploidy analysis (flow cytometry) data for USR01350321-3: DIPLOID (major peak at 200, secondary peak at 400).

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about," as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, the phrase "associated with HI" refers to a trait, locus, gene, allele, marker, phenotype, etc., or the expression thereof, the presence or absence of which can influence an extent and/or degree at which a plant or its progeny exhibits HI. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with HI" refers to a marker whose presence or absence can be used to predict whether and/or to what extent a plant will display haploid induction.

The term "comprising," which is synonymous with "including," "containing," and "characterized by," is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising," "consisting essentially of," and "consisting of," where one of these three terms is used herein, the presently disclosed and claimed subject matter can include in some embodiments the use of either of the other two terms. For example, if a subject matter relates in some embodiments to nucleic acids that encode polypeptides comprising amino acid sequences that are at least 95% identical to a SEQ ID NO: 9 or 19. It is understood that the disclosed subject matter thus also encompasses nucleic acids that encode polypeptides that in some embodiments consist essentially of amino acid sequences that are at least 95% identical to that SEQ ID NO: 9 or 19 as well as nucleic acids that encode polypeptides that in some embodiments consist of amino acid sequences that are at least 95% identical to that SEQ ID NO: 9 or 19. Similarly, it is also understood that in some embodiments the methods for the disclosed subject matter comprise the steps that are disclosed herein, in some embodiments the methods for the presently disclosed subject matter consist essentially of the steps that are disclosed, and in some embodiments the methods for the presently disclosed subject matter consist of the steps that are disclosed herein.

As used herein, the term "de novo haploid induction" refers to the triggering of haploid induction by the introduction of a spontaneous haploid inducing agent. Such introduction can be achieved by topical spray, hand-pollination, mutagenesis, or transgenic methods. The terms "de novo haploid induction," "de novo HI," and "haploid induction de novo" are used interchangeably throughout this specification.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form.

As used herein, a plant referred to as "haploid" has a reduced number of chromosomes (n) in the haploid plant, and its chromosome set is equal to that of the gamete. In a haploid organism, only half of the normal number of chromosomes are present. Thus haploids of diploid organisms (e.g., maize) exhibit monoploidy; haploids of tetraploid organisms (e.g., ryegrasses) exhibit diploidy; haploids of hexaploid organisms (e.g., wheat) exhibit triploidy; etc. As used herein, a plant referred to as "doubled haploid" is developed by doubling the haploid set of chromosomes. A plant or seed that is obtained from a doubled haploid plant that is selfed to any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes; that is, a plant will be considered doubled haploid if it contains viable gametes, even if it is chimeric in vegetative tissues.

As used herein, the term "human-induced mutation" refers to any mutation that occurs as a result of either direct or indirect human action. This term includes, but is not limited to, mutations obtained by any method of targeted mutagenesis.

As used herein, "introduced" means delivered, expressed, applied, transported, transferred, permeated, or other like term to indicate the delivery, whether of nucleic acid or protein or combination thereof, of a desired object to an object. For example, nucleic acids encoding a site directed nuclease and optionally at least one guide RNA may be introduced into a haploid embryo upon haploid induction. Likewise, extant editing machinery (comprising a site directed nuclease protein and optionally at least one guide RNA) may be introduced to a haploid embryo upon application of appropriate cell-penetrating peptides.

As used herein, the terms "marker probe" and "probe" refer to a nucleotide sequence or nucleic acid molecule that can be used to detect the presence or absence of a sequence within a larger sequence, e.g., a nucleic acid probe that is complementary to all of or a portion of the marker or marker locus, through nucleic acid hybridization. Marker probes comprising about 8, 10, 15, 20, 30, 40, 50, 60, 70, 80, 90, 100 or more contiguous nucleotides can be used for nucleic acid hybridization.

As used herein, the term "molecular marker" can be used to refer to a genetic marker, as defined above, or an encoded product thereof (e.g., a protein) used as a point of reference when identifying the presence/absence of a HI-associated locus. A molecular marker can be derived from genomic nucleotide sequences or from expressed nucleotide sequences (e.g., from an RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution (e.g., according to Watson-Crick base pairing rules). This term also refers to the genetic markers that indicate a trait by the absence of the nucleotide sequences complementary to or flanking the marker sequences, such as nucleotide sequences used as probes and/or primers capable of amplifying the marker sequence.

As used herein, the terms "nucleotide sequence," "polynucleotide," "nucleic acid sequence," "nucleic acid molecule," and "nucleic acid fragment" refer to a polymer of RNA or DNA that is single- or double-stranded, optionally containing synthetic, non-natural, and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. In some embodiments, the percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, California, United States of America. See also Smith & Waterman, 1981; Needleman & Wunsch, 1970; Pearson & Lipman, 1988; Ausubel et al., 1988; and Sambrook & Russell, 2001.

One example of an algorithm that is suitable for determining percent sequence identity and sequence similarity is the BLAST algorithm, which is described in Altschul et al., 1990. In some embodiments, a percentage of sequence identity refers to sequence identity over the full length of one of the gDNA, cDNA, or the predicted protein sequences in the largest ORF of SEQ ID No: 1 being compared. In some embodiments, a calculation to determine a percentage of nucleic acid sequence identity does not include in the calculation any nucleotide positions in which either of the compared nucleic acids includes an "N" (i.e., where any nucleotide could be present at that position).

The term "open reading frame" (ORF) refers to a nucleic acid sequence that encodes a polypeptide. In some embodiments, an ORF comprises a translation initiation codon (i.e., start codon), a translation termination (i.e., stop codon), and the nucleic acid sequence there between that encodes the amino acids present in the polypeptide. The terms "initiation codon" and "termination codon" refer to a unit of three adjacent nucleotides (i.e., a codon) in a coding sequence that specifies initiation and chain termination, respectively, of protein synthesis (mRNA translation).

Patatin-like phospholipase A2α may also be known as PLA, pPLA, pPLAIIA pPLAIIα, PLA2alpha, or PLA2, or other similar variation. Patatin-like phospholipase AIIα is also referred to as MATRILINEAL (MATL). These terms are used interchangeably throughout. A MATRILINEAL gene comprising a four basepair frameshift mutation is referred to as matrilineal (matl).

As used herein, the terms "phenotype," "phenotypic trait" or "trait" refer to one or more traits of a plant or plant cell. The phenotype can be observable to the naked eye, or by any other means of evaluation known in the art, e.g., microscopy, biochemical analysis, or an electromechanical assay. In some cases, a phenotype is directly controlled by a single gene or genetic locus (i.e., corresponds to a "single gene trait"). In the case of haploid induction use of color markers, such as R Navajo, and other markers including transgenes visualized by the presences or absences of color within the seed evidence if the seed is an induced haploid seed. The use of R Navajo as a color marker and the use of transgenes is well known in the art as means to detect induction of haploid seed on the female plant. In other cases, a phenotype is the result of interactions among several genes, which in some embodiments also results from an interaction of the plant and/or plant cell with its environment.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "primer" refers to an oligonucleotide which is capable of annealing to a nucleic acid target (in some embodiments, annealing specifically to a nucleic acid target) allowing a DNA polymerase and/or reverse transcriptase to attach thereto, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, one or more pluralities of primers are employed to amplify plant nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from vegetative or sexual reproduction from one or more parent plants. In gynogenesis-mediated haploid induction, the haploid embryo on the female parent comprises female chromosomes to the exclusion of male chromosomes—thus it is not a progeny of the male haploid-inducing line. The haploid corn seed typically still has normal triploid endosperm that contains the male genome. The edited haploid progeny and subsequent edited doubled haploid plants and subsequent seed is not the only desired progeny. There is also the seed from the haploid inducer line itself, often carrying the Cas9 transgene, and subsequent plant and seed progeny of the haploid inducing plant. Both the haploid seed and the haploid inducer (self-pollination-derived) seed can be progeny. A progeny plant can be obtained by cloning or selfing a single parent plant, or by crossing two or more parental plants. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are specimens produced from selfings, intercrosses, backcrosses, and/or other crosses of $F_1$s, $F_2$s, and the like. An $F_1$ can thus be (and in some embodiments is) a hybrid resulting from a cross between two true breeding parents (i.e., parents that are true-breeding are each homozygous for a trait of interest or an allele thereof), while an $F_2$ can be (and in some embodiments is) a progeny resulting from self-pollination of the $F_1$ hybrids.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer in some embodiments to a meiotic crossover.

As used herein, the term "reference sequence" refers to a defined nucleotide sequence used as a basis for nucleotide sequence comparison. In some embodiments, any of SEQ ID NOs: 2, 4, 8, 21, 23, 25, 29, 32, and 33 can serve as a reference sequence for comparing to other sequences obtained from plants.

As used herein, the term "regenerate," and grammatical variants thereof, refers to the production of a plant from tissue culture.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Sambrook & Russell, 2001. Generally, stringent conditions are selected to be about 5-10° C. lower than the thermal melting point ($T_m$) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "trait" refers to a phenotype of interest, a gene that contributes to a phenotype of interest, as well as a nucleic acid sequence associated with a gene that contributes to a phenotype of interest. For example, a "HI trait" refers to a haploid induction phenotype as well as a gene (e.g., matl in maize or Os03g27610 in rice) that contributes to a haploid induction and a nucleic acid sequence (e.g., a HI-associated gene product) that is associated with the presence or absence of the haploid induction phenotype.

As used herein, the term "transgene" refers to a nucleic acid molecule introduced into an organism or one or more of its ancestors by some form of artificial transfer technique. The artificial transfer technique thus creates a "transgenic organism" or a "transgenic cell." It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

As used herein, the term "targeted mutagenesis" or "mutagenesis strategy" refers to any method of mutagenesis that results in the intentional mutagenesis of a chosen gene. Targeted mutagenesis includes the methods CRISPR, TILLING, TALEN, and other methods not yet discovered but which may be used to achieve the same outcome.

As used herein, haploid induction rate ("HIR") means the number of surviving haploid kernels over the total number of kernels after an ear is pollinated with haploid inducer pollen.

Particular problems plague that haploid induction: increased embryo abortion rates and increased fertilization failure rates (reduced seed set rates). For these reasons, there exists a need to successfully determine the cause of HI, and to use that knowledge to determine methods of stably or increasingly creating haploid plants while simultaneously reducing fertilization failure and embryo abortions.

It is specifically contemplated that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the promoter via mutation. It is further contemplated that one could mutagenize these sequences in order to enhance their expression of transgenes in a particular species. The means for mutagenizing a DNA segment encoding a promoter sequence of the current invention are well-known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory sequence. In particular, site-specific mutagenesis is a technique useful in the preparation of promoter mutants, through specific mutagenesis of the underlying DNA. RNA-guided endonucleases ("RGEN," e.g., CRISPR/Cas9) may also be used. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

Where a clone comprising a promoter has been isolated in accordance with the instant invention, one may wish to delimit the essential promoter regions within the clone. One efficient, targeted means for preparing mutagenized promoters relies upon the identification of putative regulatory elements within the promoter sequence. This can be initiated by comparison with promoter sequences known to be expressed in similar tissue specific or developmentally unique patterns. Sequences which are shared among promoters with similar expression patterns are likely candidates for the binding of transcription factors and are thus likely elements which confer expression patterns. Confirmation of these putative regulatory elements can be achieved by deletion analysis of each putative regulatory sequence followed by functional analysis of each deletion construct by assay of a reporter gene which is functionally attached to each construct. As such, once a starting promoter sequence is provided, any of a number of different deletion mutants of the starting promoter could be readily prepared.

The invention disclosed herein provides polynucleotide molecules comprising regulatory element fragments that may be used in constructing novel chimeric regulatory elements. Novel combinations comprising fragments of these polynucleotide molecules and at least one other regulatory element or fragment can be constructed and tested in plants and are considered to be within the scope of this invention. Thus the design, construction, and use of chimeric regulatory elements is one embodiment of this invention. Promoters of the present invention include homologues of cis elements known to affect gene regulation that show homology with the promoter sequences of the present invention.

Functional equivalent fragments of one of the transcription regulating nucleic acids described herein comprise at least 50, 100, 150, 200, 250, 300, 350, 400, 450, 500, 550, 600, 650, 700, 750, 800, 850, 900, 950, or 1000 base pairs of a transcription regulating nucleic acid. Equivalent fragments of transcription regulating nucleic acids, which are obtained by deleting the region encoding the 5'-untranslated region of the mRNA, would then only provide the (untranscribed) promoter region. The 5'-untranslated region can be easily determined by methods known in the art (such as 5'-RACE analysis). Accordingly, some of the transcription regulating nucleic acids, described herein, are equivalent fragments of other sequences.

As indicated above, deletion mutants of the promoter of the invention also could be randomly prepared and then assayed. Following this strategy, a series of constructs are prepared, each containing a different portion of the promoter (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

An expression cassette as described herein may comprise further regulatory elements. The term in this context is to be understood in the broad meaning comprising all sequences which may influence construction or function of the expression cassette. Regulatory elements may, for example, modify transcription and/or translation in prokaryotic or eukaryotic organisms. The expression cassette described herein may be downstream (in 3' direction) of the nucleic acid sequence to be expressed and optionally contain additional regulatory elements, such as transcriptional or translational enhancers. Each additional regulatory element may be operably liked to the nucleic acid sequence to be expressed (or the transcription regulating nucleotide sequence). Additional regulatory elements may comprise additional promoters, minimal promoters, promoter elements, or transposon elements which may modify or enhance the expression regulating properties. The expression cassette may also contain one or more introns, one or more exons and one or more terminators.

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters which are useful for plant transgene expression include those that are inducible, viral, synthetic, constitutive (Odell Nature 313: 810-812 (1985)), temporally regulated, spatially regulated, tissue specific, and spatial temporally regulated. Using the regulatory elements described herein, numerous agronomic genes can be expressed in transformed plants. More particularly, plants can be genetically engineered to express various phenotypes of agronomic interest.

DETAILED DESCRIPTION

One embodiment of the invention provides a method of editing plant genomic DNA, comprising: (i) obtaining a first plant, wherein the first plant is a haploid inducer line of the plant, and wherein said first plant is capable of expressing a DNA modification enzyme and optionally a guide nucleic acid; (ii) obtaining a second plant, wherein the second plant comprises the plant genomic DNA which is to be edited; (iii) pollinating the second plant with pollen from the first plant; and (iv) selecting at least one haploid progeny produced by the pollination of step (c) wherein the haploid progeny comprises the genome of the second plant but not the first plant, and the genome of the haploid progeny has been modified by the DNA modification enzyme and optional guide nucleic acid delivered by the first plant.

In one aspect of the method, the DNA modification enzyme is a site-directed nuclease selected from the group consisting of meganucleases (MNs), zinc-finger nucleases (ZFNs), transcription-activator like effector nucleases (TALENs), Cas9 nuclease, Cfp1 nuclease, dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease and dCpf1 non-FokI nuclease; and further wherein the guide nucleic acid is a guide RNA.

In another aspect of the method, the edited haploid progeny is treated with a chromosome doubling agent, thereby creating an edited doubled haploid progeny. For example, the chromosome doubling agent is colchicine, pronamide, dithipyr, trifluralin, or another known anti-microtubule agent.

In another aspect of the method, the first plant is a monocot or a dicot. For example, the first plant is a monocot selected from the group consisting of maize, wheat, rice, barley, oats, triticale, sorghum, pearl millet, teosinte, bamboo, sugar cane, asparagus, onion, and garlic. In another aspect, the second plant is a monocot or a dicot. For example the second plant is a monocot selected from the group consisting of maize, wheat, rice, barley, oats, triticale, sorghum, pearl millet, teosinte, bamboo, sugar cane, asparagus, onion, and garlic.

In another aspect of the method, the optional guide RNA is an 18-21 nucleotide sequence and is homologous to a sequence selected from the group consisting of SEQ ID NOs: 2, 4, 8, 21, 23, 25, 29, 32, and 33. In another aspect, the first plant expresses a marker gene. For example, the marker gene is selected from the group consisting of GUS, PMI, PAT, GFP, RFP, CFP, B1, C1, R-nj, anthocyanin pigments, and any other marker gene.

In another aspect of the method, the first plant is a maize plant selected and/or derived from the lines Stock 6, RWK, RWS, UH400, AX5707RS, NP2222-matl, or any of the several other known HI lines.

In one embodiment, the first plant and the second plant are different species. In one aspect, first plant is a wheat plant and the second plant is a maize plant. In another aspect, the first plant is a maize plant and the second plant is a wheat plant.

One object of the invention is a gene-edited plant produced by the method provided.

In another embodiment, the invention provides a method of editing plant genomic DNA, comprising: (i) obtaining a first plant, wherein said first plant is capable of expressing a DNA modification enzyme and optionally a guide nucleic acid; (ii) obtaining a second plant, wherein the second plant comprises the plant genomic DNA which is to be edited; (iii) pollinating the second plant with pollen from the first plant; (iv) applying a composition comprising a lipid or a phospholipase inhibitor immediately preceding, during, or following the pollination of step (iii); and (v) selecting at least one haploid progeny produced by the pollination of step (iii) wherein the haploid progeny comprises the genome of the second plant but not the first plant, and the genome of the haploid progeny has been modified by the DNA modification enzyme and optional guide nucleic acid delivered by the first plant. In one aspect, the composition comprises methyl alpha-linolenoyl fluorophosphonate (MALFP), linoleic acid ethyl ester (LLAEE), linoleic acid (LLA), corn oil, distearoyl-phosphatidyl choline (DSPC), methyl arachidonyl fluorophosphonate (MAFP), Palmityl trifluoromethylketone (PACOCF3), Arachidonyl trifluoromethylketone (AA-COCF3), Manoalide, Linolenic acid ethyl ester (LNAEE), Linolenic acid ethyl ester (LNAEE), Oleic acid methyl ester (OAME), Oleic acid ethyl ester (OAEE), Palmitic acid ethyl ester (PAEE), Palmitoleic acid ethyl ester (PLAEE), Linseed oil, corn oil, alpha-Linolenic acid (aLNA), gamma-Linolenic acid (gLNA), Oleic acid, Arachidonic acid, Stearic Acid, 9(Z)-11(E)-conjugated Linoleic acid, or 2-oleoyl-1-palmitoyl-sn-glycero-3-phospho-ethanolamine.

In another embodiment, the invention provides a method of editing plant genomic DNA, comprising: (i) obtaining a first plant, wherein said first plant is capable of expressing a DNA modification enzyme and optionally a guide nucleic acid; (ii) obtaining a second plant, wherein the second plant comprises the plant genomic DNA which is to be edited; (iii) crossing the first plant with the second plant; and (iv) selecting at least one haploid progeny produced by the crossing of step (iii) wherein the haploid progeny comprises the genome of the second plant but not the first plant, and the genome of the haploid progeny has been modified by the DNA modification enzyme and optional guide nucleic acid delivered by the first plant. In one aspect, the first plant acts as the female parent in the cross of step (iii). In another aspect, the first plant comprises a mutation in a CENH3 gene, an ig1 gene, or another mutation conferring paternal-haploid inducing systems.

EXAMPLES

I. Producing New Haploid Inducer Lines Comprising the Editing Machinery.

We transformed a transformable line of maize called NP2222 with a TALEN construct, and separately transformed this line with a Cas9 and guide RNA construct. The TALEN construct (pBSC22808 (SEQ ID NO: 5), with TALENs targeting cleavage within target sequence, 5'-TCCAGGGTCAACGTGGAGACAGG-GAGGTACGAACCGGTGACTGGCGAAGGAAG CA-3', SEQ ID NO: 6; TALEN recognition sequence underlined) and the Cas9 construct (pBSC23123 (SEQ ID NO: 7) with guide RNA sequence of xZmPLAIIA, 5'-GGGT-CAACGTGGAGACAGGG-3', SEQ ID NO: 8) were designed to target mutations into the fourth exon of maize gene called MATRILINEAL (MATL; GRAMENE ID: GRMZM2G471240). This gene, when mutated at the target site by the TALEN or by the Cas9 and guide RNA, is knocked out, resulting in a loss of function of the protein product. We previously established that lines that are homozygous for loss of function mutations in MATL are haploid inducer lines, meaning that when they are used as pollen donors in crosses, they induce the formation of haploids on the resulting ears (see P.C.T. Patent Application No. PCT/US2016/62548, filed Nov. 17, 2016, incorporated herein by reference in its entirety).

We produced several events and self-pollinated them to make T1 seed. We grew up T1 individuals from event MZET152408A042A. We recovered five T1 progeny that retained two copies of the Cas9 and guide RNA editing machinery stably transformed, and were also homozygous mutant for the MATL gene. See Table 1.

TABLE 1

New HI lines comprising the genome editing machinery.

| New HI Line Individual ID | wt MATL Presence | Cas9 Presence | Mutation in MATL |
| --- | --- | --- | --- |
| USR01283349 | − | + | 13 bp deletion, homozygous |
| USR01283378 | − | + | 13 bp deletion, homozygous |
| USR01283388 | − | + | 8 bp deletion, homozygous |
| USR01283391 | − | + | 8 bp deletion, homozygous |
| USR01283398 | − | + | 13 bp deletion, homozygous |

The MATL mutations are detected using a TaqMan assay, which amplifies the wildtype copy of MATL (referred to herein as MATL or wt-MATL; these terms are used interchangeably throughout). When both copies of MATL are mutated, this assays reads negative (i.e., "−"). The Cas9 and guide RNA editing machinery were stably inserted via Construct 23123 (SEQ ID NO: 7). We sequenced the mutations in MATL via PCR and subcloning. Four colonies of each PCR product was sequenced, and all of the colonies for a given individual had the same sequence, indicating these plants are all homozygous mutant for the MATL allele (also referred to herein as matl when referencing the 4 basepair insertion in MATRILINEAL found in Stock6 and other Stock6-derived lines, or µMATL when referencing any other human-induced mutation in MATRILINEAL;). There were two plants that had 8 bp deletions, and three plants that had 13 bp deletions.

II. Using the New HI Lines as Male Parents and Progeny Analysis.

We crossed the above new HI plants as male pollen donors to a female tester line, which contained a recessive color marker but were wild type for the MATL gene. The male haploid inducer line is homozygous wild type for the same color marker. This female line was thus a non-haploid inducer and were homozygous wild-type for the MATL gene but homozygous mutant for the color marker. We recovered seeds from the crosses, and germinated seedlings therefrom.

Progeny seedlings were subjected to several assays. Progeny seedlings were scored as diploids if they do not exhibit the color marker (because the recessive marker is complemented by the male inducer DNA). Progeny seedlings were scored as putative haploids if they do exhibit the color marker because the recessive marker is not complemented. Of the 2656 seeds planted, we used the color assay and identified 90 seedlings as putative haploids.

We further analyzed the 90 putative haploids for presence of the wildtype MATL gene using a Taqman marker assay. Of these, 82 were positive for MATL, meaning they were not edited by the editing machinery provided by the male parent. The remaining 8 putative haploid seedlings were negative for wildtype MATL using the Taqman marker, indicating that they may have been edited by the editing machinery provided by the male parent.

We performed ploidy analysis via Flow Cytometry on these 8 putative, edited haploid seedlings using leaf tissue in a ploidy analyzer. See FIGS. 1-8. We found that four of them were true haploids, while the others were actually diploids. As we discuss below, we ran PCR and sequenced the mutations in the MATL gene in these four true haploids as well as for plant USR01350337-2 which, according to the MATL Taqman assay, was not edited by the genome editing machinery.

The finding that there were four diploids among the 90 putative haploids was not unexpected—the seedling assay is not perfect and there are occasional false positives. We tested the 90 haploids for the presence of the Cas9 construct (Construct 23123), and found it was missing in 86 out of 90, including the four true haploids above. In contrast, the four edited diploids that we found during the ploidy analysis all had the Cas9 construct present, confirming their status as hybrid diploids that were falsely identified by the haploid seedling assay as being haploids.

We then used the leaf tissue to isolate genomic DNA and ran a PCR reaction to sequence the MATL gene in those four true haploid, putative edited individuals, specifically focusing on the sequence flanking the guide RNA target mutagenesis site. This was to determine the nature of the edits that may or may not have occurred there. We sub-cloned the PCR fragment using commercially-available TOPO Blunt IV kit, and sequenced at least four colonies each (forward and reverse sequencing). See Table 2, below, for comparisons of the edited alleles and the reference wt-MATL allele.

TABLE 2

Comparing the Edited Alleles against wt-MATL.

| Individual ID | Allele Type | Sequence (corresponds to 1126-1166 of SEQ ID NO: 19) | SEQ ID NO: |
|---|---|---|---|
| NP2222 | wt-MATL | AGGGTCAACGTGGAGACAGGGAGGTACGAACCGGTGACTGG | 9 |
| Stock6 | matl | AGGGTCAACGTGGAGACAGGCGAGGAGGTACGAACCGGTGACTGG | 10 |
| USR01350333-3 Allele 1 | edited | AGGGTCAACGTGGAGACAAGGGAGGTACGAACCGGTGACTGG | 11 |
| USR01350333-3 Allele 2 | PCR contamination | AGGGTCAACGTGGA::::::::::::GAACCGGTGACTGG | 12 |
| USR01350344-2 Allele 1 | edited | AGGGTCAACGTGGAGAC:GGGAGGTACGAACCGGTGACTGG | 13 |
| USR01350344-2 Allele 2 | PCR contamination | AGGGTCAACGTGGA::::::::::::GAACCGGTGACTGG | 14 |
| USR01350343-1 Allele 1 | edited | AGGGTCAACGTGGAGACAAGGGAGGTACGAACCGGTGACTGG | 15 |
| USR01350328-1 Allele 1 | edited | AGGGTCAACGTGGAGAC:GGGAGGTACGAACCGGTGACTGG | 16 |
| USR01350337-2 Allele 1 | not edited | AGGGTCAACGTGGAGACAGGGAGGTACGAACCGGTGACTGG | 17 |
| USR01350337-2 Allele 2 | PCR contamination | AGGGTCAACGTGGA::::::::::::GAACCGGTGACTGG | 18 |

Individual USR01350333-3 produced an edited MATL allele with an insertion of alanine at basepair 1143 of the cDNA sequence (underlined in Table 2). This would be sufficient to cause a frameshift in the coding sequence, which would produce a premature STOP codon. What we previously thought was Edited Allele #2 of USR01350333-3 (a 13 basepair deletion of GACAAGGGAGGTAC) was actually the result of PCR contamination. After resequencing, we confirmed that this plant only has one edited allele, and it was found in 6 out of 6 colonies.

This alleles is novel in that it is not in either the male or the female parent plant of this individual. The male parent ID for this individual was USR01283391, and that plant was found to be homozygous for an 8 bp deletion.

Individual USR01350344-2 provides a deletion of A (a deletion of basepair 1143 of the wild type cDNA sequence). This mutation would be sufficient to cause a frame-shift in the coding sequence, and produce a premature STOP codon. After resequencing and discovering the PCR contamination, we confirmed this was found in 6 out of 6 colonies. Previously identified as Edited Allele #2 of USR01350344-2, this was identified as PCR contamination.

Individual USR01350343-1 provides an insertion of A at basepair 1143 of the cDNA sequence. This would be sufficient to cause a frame-shift in the coding sequence, and produce a premature STOP codon. This was found in 4 out of 4 colonies.

Individual USR01350328-1 provides a deletion of A (a deletion of basepair 1143 from the wild type cDNA sequence). This mutation would be sufficient to cause a frame-shift in the coding sequence, and produce a premature STOP codon. It was found in 4 out of 4 colonies.

Individual USR01350337-2 had no change: its sequence was 100% identical to that of wt-MATL.

In summary, we found that 4 out of 86 confirmed haploids had mutations in the MATL gene. We have confirmed that these plants are haploids and do not contain any Cas9 DNA. It is clear that the Cas9 transgene has been eliminated along with the rest of the male-derived DNA during embryogenesis, and that edits have occurred to the female (egg cell-derived) genome in the process of embryogenesis.

We know that the edits are novel and occurred in the female genome in the process of embryogenesis because the haploid inducer line typically makes maternal haploids and we have confirmed that these are indeed haploids. One might try to argue that there is a chance that these are actually paternal haploids, and that the edits we are seeing are actually edits that were already present in the paternal DNA. However, we can prove that this is not the case. First, the mutations do not match those of the paternal parent. This can clearly be seen in Table 3 and 4 (shown below). The edited haploid plant USR01350343-1 was homozygous for an insertion of a single nucleotide (an "A"), but the male parent plant had a deletion of 13 nucleotides. Similarly, plant USR01350328-1 was homozygous for a deletion of an A, but the male parent had a deletion of 13 nucleotides. These examples, taken together, prove that during the haploid induction process, it is possible to have editing of the maternal genome occur, resulting in the formation of edited maternal haploids. According to these and based on the assay detecting MATL presence and the confirmation via ploidy analysis, and using the Cas9 transgene on the male side under control of the maize ubiquitin promoter, the rate of editing during the haploid induction process is about 4/86, or 4.65%.

Furthermore, the rate of editing during haploid induction may be very different when using different haploid inducer lines or using wide crosses. It appears that both haploid induction in maize using MATL mutant lines and wide crosses in barley, wheat, or other crops all work via similar mechanisms: fertilization is followed by genome elimination. It also appears that the time period between fertilization and genome elimination is long enough for the editing machinery to edit the target gene in the genome of the line to which the inducer line has been hybridized (the target germplasm). It is noted that the choice of promoter driving expression of the stably transformed editing proteins system may have a large impact on the rate of editing in haploids. We used a constitutive sugarcane promoter (prSoUbi4) but other promoters driving high or specific expression in the embryo sac, the egg cell, in the pollen, or in sperm cells might be more effective, particularly in the case of wide crosses, in which the male DNA is eliminated in a much more robust and rapid fashion than in intraspecific haploid inducer systems like the maize haploid inducer system or CENH3 type haploid inducer systems. In other words, during a wide cross, for instance when crossing maize pollen on to wheat ears, which is done in order to induce wheat maternal haploids, it might work best to have the editing machinery in the maize pollen driven by a promoter that has strong pollen or sperm cell expression, perhaps in addition to zygote expression, so that abundant editing machinery (RNA and protein) is delivered and present in the zygote cell and during the subsequent two, four, or eight cell embryo stage, even if the male DNA is eliminated or lost very quickly.

TABLE 3

Haploid Progeny Produced

| Individual Progeny ID code | wt MATL Presence | Ploidy Analysis | Cas9 Presence | Allele 1 |
| --- | --- | --- | --- | --- |
| USR01350333-3 | − | Haploid | − | insertion of A |
| USR01350344-2 | − | Haploid | − | deletion of A |
| USR01350343-1 | − | Haploid | − | insertion of an A |
| USR01350328-1 | − | Haploid | − | deletion of A |
| USR01350337-2 | + | Haploid | − | no mutation |
| USR01350334-3 | − | Diploid | + | |
| USR01350333-10 | − | Diploid | + | |
| USR01350341-1 | − | Diploid | + | |
| USR01350321-3 | − | Diploid | + | |

TABLE 4

Male Parent Information and Their Progeny

| Male Parent ID | wt MATL Presence | Sequencing (# colonies) | Cas9 Presence | Progeny ID |
| --- | --- | --- | --- | --- |
| USR01283391 | − | deletion of 8 nt (4) | + | USR01350333-3 and USR01350333-10 |
| USR01283349 | − | deletion of 13 nt (4) | + | USR01350344-2, USR01350328-1 and USR01350321-3 |
| USR01283378 | − | deletion of 13 nt (4) | + | USR01350343-1 and USR01350341-1 |

TABLE 4-continued

Male Parent Information and Their Progeny

| Male Parent ID | wt MATL Presence | Sequencing (# colonies) | Cas9 Presence | Progeny ID |
|---|---|---|---|---|
| USR01283398 | – | deletion of 13 nt (4) | + | USR01350337-2 |
| USR01283388 | – | deletion of 8 nt (4) | + | USR01350334-3 |

III. Simultaneous Haploid Induction and Editing in Elite Maize Inbred Lines.

A transformable haploid inducer line, NP2222-HI, RWK, RWS, or UH400 or Stock6 or any other haploid inducer line, all of which already have the mutant versions of MATL, is stably transformed with construct expressing genome modification system such as Cas9+guide RNA (Cong, L. et al. 2013. Multiplex genome engineering using CRISPR/Cas systems. *Science* 339, 819-823), dCas9-FokI+ guide RNA (Tsai, S. Q. et al. 2014, Dimeric CRISPR RNA-guided FokI nucleases for highly specific genome editing. *Nature Biotechnol.* 32, 569-576), TALEN (Li et al., 2012, High-efficiency TALEN-based gene editing produces disease-resistant rice. Nature Biotech. 30, 390-392), engineered meganuclease (Gao et al., 2010, Heritable targeted mutagenesis in maize using a designed endonuclease. *Plant Journal.* 61:176-187), zinc finger nuclease (Shukla et al. 2009. Precise genome modification in the crop species *Zea mays* using zinc-finger nucleases. Nature 459, 437-441), dCas9-cytidine deaminase (Komor et al. 2016, Programmable editing of a target base in genomic DNA without double-stranded DNA cleavage. Nature doi:10.1038/nature17946) or any other genome modification system. The transgenic haploid inducer line also expressing the editing machinery is then used as pollen donor to create mutations and haploids in target lines via outcrossing. Haploid embryos or seeds are then recovered, identified as haploids, and tested for the edits at the target site (whatever target site is chosen by virtue of the TALEN construct design or the Cas9 guide RNA design). Haploids containing the desired edits is chromosomally doubled using standard procedures using standard means such as colchicine, trifluralin or other chromosome doubling agent. Identification of the induced haploids can be simplified by using a color marker as is typically done in corn doubled haploid production—this color marker can display in the resulting embryos, seeds, seedlings, or adult plant. Presence of mutations at the target site can be checked by sequence analysis (DNA sequencing), by marker analysis, or by phenotype. Because there is only one copy of the DNA to mutate in haploid plants, recessive phenotypes should display so that could be another way to identify the haploids that were edited.

A. Mutagenesis of VLHP Targets in Elite Maize Inbred Line with Transgenic Editing Locus Generated Directly in a Haploid Inducer Line.

VLHP1 and VLHP2 are homeodomain-leucine zipper I-class homeobox genes and members of a class of proteins that is unique to plants. The HD domain is involved in DNA binding whereas the Zip domain is involved in protein homo- and hetero-dimerization. HD-Zip I proteins are generally involved in responses related to abiotic stress, abscisic acid (ABA), blue light, de-etiolation and embryogenesis (Elhiti and Stasolla, 2009. Structure and function of homodomain-leucine zipper (HD-Zip) proteins. *Plant Signal Behav.* 4: 86-88). VLHP1 and VLHP2 are in the same gene family as Grassy Tillers1 (GT1). GT1 promotes lateral bud dormancy and suppresses elongation of lateral ear branches in maize.

Figure 9:
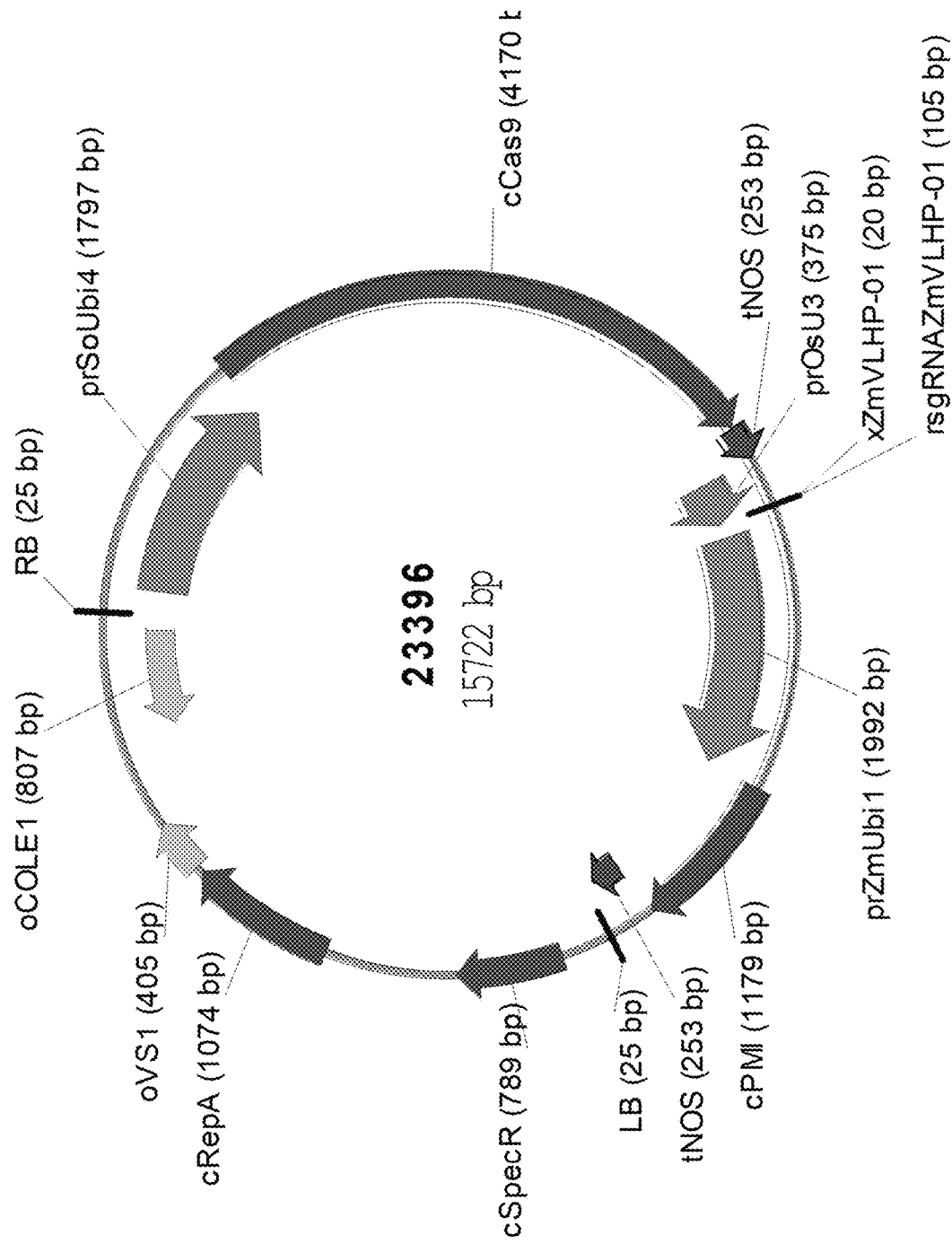
FIG. 9 is a schematic drawing of vector 23396 (SEQ ID NO: 1) used for *Agrobacterium*-mediated transformation of maize immature embryos to generate targeted mutations in ZmVLHP1 genes. xZmVLHP-01: guide RNA (gRNA) sequence (5'-GCAGGAGGCGTCGAGCAGCG-3', SEQ ID NO: 2); rsgRNAZmVLHP-01: single guide RNA (sgRNA) comprising of gRNA, tracRNA and PolIII termination sequences. cPMI: PMI selectable marker gene; cCas9: Cas9 nuclease gene; RB: T-DNA right border; LB: T-DNA left border; tNOS: Nopaline synthetase terminator. cSpec: Spectinomycin resistance gene.

In this example, vector 23396 (SEQ ID NO: 1; see also FIG. 9) for expressing Cas9 and single guide RNA (sgRNA) was made to target maize VLHP1 (GRMZM2G104204) and its homolog VLHP2 (GRMZM2G062244) genes. Vector 23396 expresses a sgRNA with 20-nucleotide targeting sequence xZmVLHP-01 (5'-GCAG-GAGGCGTCGAGCAGCG-3', SEQ ID NO: 2). xZmVLHP-01 targets both VLHP1 and VLHP2 genes at the second exon. Vector 23396 was introduced into a transformable haploid inducer line NP2222-HI using *Agrobacterium*-mediated transformation with mannose selection. NP2222-HI was derived from crossing of transformable maize inbred line NP2222 with Stock 6 derivative line RWKS to introgress the haploid induction (HI) locus. NP2222-HI has an average haploid induction rate of about 9.2%.

NP2222-HI transformants from vector 23396 were assayed for modification of genomic VLHP target sequences (5'-GCAGGAGGCGTCGAGCA/GCG-3'; SEQ ID NO: 2). The slash ("/") represents the Cas9 cleavage position. Target locus editing activity was determined using quantitative PCR Taqman method as described before (WO2016106121, incorporated herein by reference). Transgenic lines with high target site modification activities—i.e., both VLHP1 and VLHP2 genes were modified, and preferably containing single copy transgene—were selected for further studies and used for crossing or progeny production.

Pollen from T0 transformants of 23396 is used directly to pollinate ears of elite inbred line ID5829 or other maize lines including sweet corn lines to induce production of haploid embryos. Alternatively, T0 transformants of 23396 in NP2222-HI background are selfed to produce progeny lines carrying homozygous transgene and pollen from the progeny plants are used to pollinate other corn lines to induce haploid embryo formation. The induced haploid embryos are extracted from kernels and placed on embryo rescue media for direct germination or allowed to mature to form seeds. Tissues from the induced haploid embryos and the resulting plants are assayed to determine if editing has occurred in the VLHP target sequences. If the induced haploid embryos or plants contain desired mutations, chromosome doubling treatment is applied to produce doubled haploid lines from them. For example, using embryo rescue method, embryos are extracted from elite line ID5829 ears pollinated with transgenic haploid inducer line carrying 23396 editing locus at 18-22 days after pollination ("DAP," extraction between 10-25 DAP is theoretically possible). DNA is isolated from germinated haploid seedlings and used for assay. Colchicine treatment is applied to seedling for chromosome doubling. Alternatively, chromosome doubling agent can be applied to the isolated embryos during germination. DNA is extracted from germinated seedlings and used for determining that mutation has occurred at the xZmVLHP-01 target sequence.

Alternate methods are available. One could allow the seed to mature and select haploids later by another phenotype. One could let the seed dry down and at a later date germinate the seeds to determine haploids without a marker (e.g., using plant size rather than a gene conferring a color marker), at which point one would test for edits and apply chromosome doubling agents where appropriate. This method may have its advantages in that embryo screening and/or rescue is avoided.

B. Mutagenesis of GW2 Targets in Elite Maize Inbred Line with Transgenic Editing Locus Introduced Directly in a Haploid Inducer Line.

A mutation in DA2, an E3-ubiquitin ligase gene, in rice resulted in larger seeds (Song et al., 2007). Rice DA2 has 2 maize homologs, GW2-1 (GRMZM2G170088) and GW2-2 (GRMZM2G007288). The maize genes are 94% identical at the protein level and 90% identical at the DNA level. GRMZM2G170088 has a large 177 bp insert (59 aa) in comparison with GRMZM2G007288.

Figure 10:
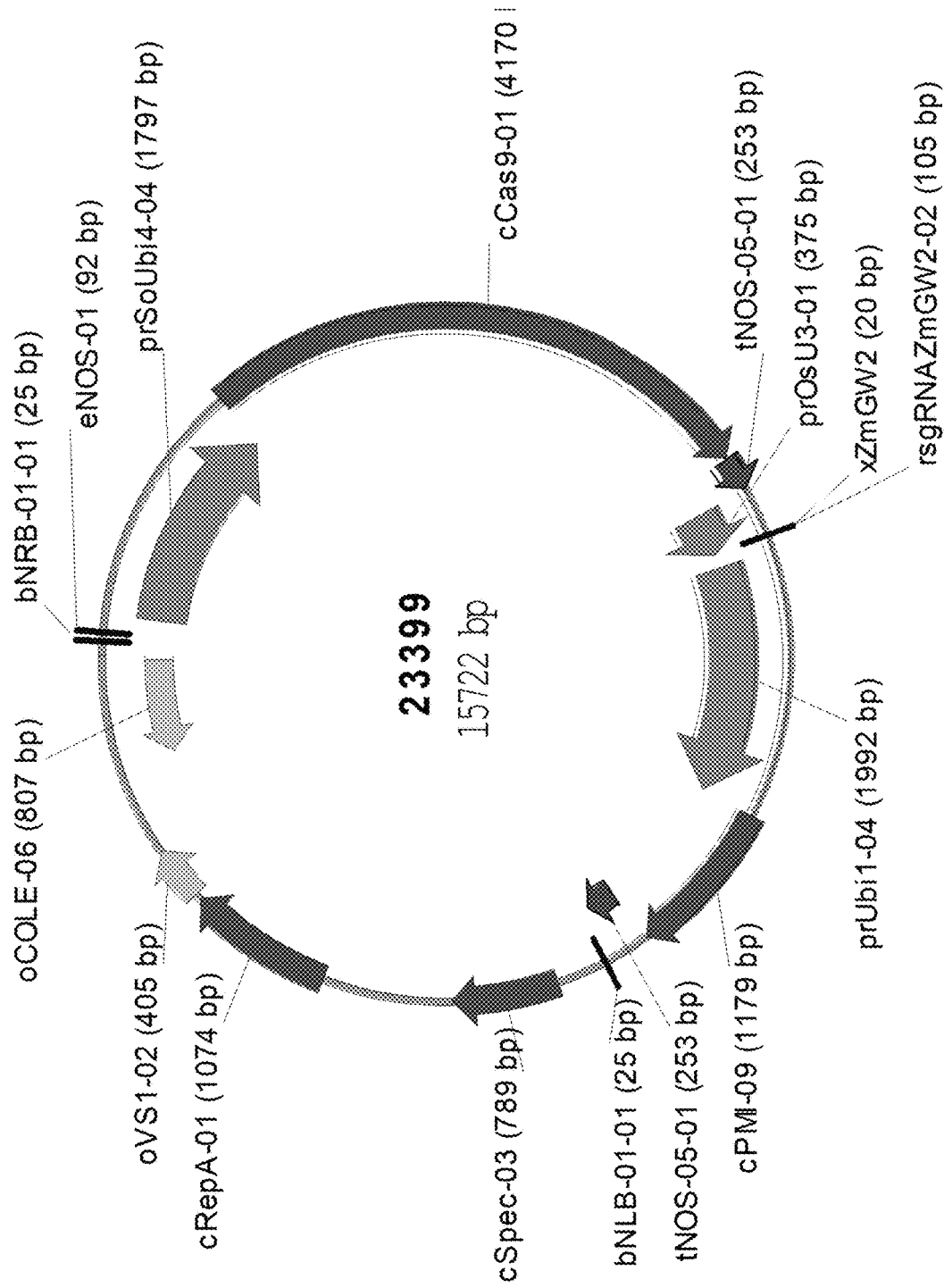
FIG. 10 is a schematic drawing of vector 23399 (SEQ ID NO: 3) used for *Agrobacterium*-mediated transformation of maize immature embryos to generate targeted mutations in ZmGW2 genes. xZmGW2-02: guide RNA (gRNA) sequence (5'-AAGCTCGCGCCCTGCTACCC-3', SEQ ID NO: 4); rsgRNAZmGW2-02: single guide RNA (sgRNA) comprising of gRNA, tracrRNA and PolIII termination sequences. cPMI-09: PMI selectable marker gene; cCas9-01: Cas9 nuclease gene; RB: T-DNA right border; LB: T-DNA left border; tNOS: Nopaline synthetase terminator. cSpec: Spectinomycin resistance gene.

In this example, vector 23399 (SEQ ID NO: 3, see also FIG. 10) was made for expression of Cas9 and sgRNA to target both maize GW2-1 (GRMZM2G170088) and its homolog GW2-2 (GRMZM2G007288) genes. Both GW2-1 and GW2-2 genes contain target sequence xZmGW2-02 (5'-AAGCTCGCGCCCTGCTACCC-3', SEQ ID NO: 4) in exon 1 and this sequence was used to design sgRNA expressed from vector 23399. Binary vector 23399 expresses single guide RNA (sgRNA) with 20-nucleotide targeting sequence xZmGW2-02 fused to single guide RNA scaffold comprising of both crRNA and tracrRNA. Vector 23399 was introduced into a transformable haploid inducer line NP2222-HI using *Agrobacterium*-mediated transformation with mannose selection. NP2222-HI was derived from crossing of transformable maize inbred line NP2222 with Stock 6 derivative line RWKS to introgress the haploid induction (HI) locus.

NP2222-HI transformants of vector 23399 were assayed for modification of genomic GW2-2 target sequences (5'-AAGCTCGCGCCCTGCTA/CCC-3', SEQ ID NO: 4; the slash ("/") indicates the Cas9 cleavage position). Target sequence editing activity was determined using quantitative PCR Taqman method as described before (WO2016106121). Transgenic lines with high target site modification activities—i.e. both GW2-1 and GW2-2 genes were modified, and preferably containing single copy transgene—were selected for further studies and used for crossing or progeny production.

Pollen from T0 transformants of 23399 is used directly to pollinate ears of elite inbred line ID5829 or other maize line including sweet corn lines to induce production of haploid embryos. Alternatively, T0 transformants of 23399 in NP2222-HI background are selfed to produce progeny lines carrying homozygous transgene and pollen from the progeny plants are used to pollinate other corn lines to induce haploid embryo formation. The induced haploid embryos are extracted from kernels and placed on embryo rescue media for direct germination or allowed to mature to form seeds. Tissues from the induced haploid embryos and the resulting plants are assayed to determine if editing has occurred in the maize GW2 target sequences. If the induced haploid embryos or plants contain desired mutations, chromosome doubling treatment is applied to produce doubled haploid lines from them. For example, using embryo rescue method, embryos are extracted from elite line ID5829 ears pollinated with transgenic haploid inducer line carrying 23396 editing locus at 18-22 days after pollination. DNA is isolated from germinated haploid seedlings and used for assay. Colchicine treatment is applied to seedling for chromosome doubling. Alternatively, chromosome doubling agent can be applied to the isolated embryos during germination. DNA is extracted from germinated seedlings and used for determining if mutation has occurred at the xZmGW2-02 target sequence. Alternately, one could allow the seed to mature and select haploids later by another phenotype. One could even let the seed dry down and at a later date germinate the seeds to determine haploids without a marker (e.g., using plant size rather than a gene conferring a color marker), at which point one would test for edits and apply chromosome doubling agents where appropriate. This method may have its advantages in that embryo screening and/or rescue is avoided.

IV. Simultaneous Haploid Induction and Editing in Corn, Rice, Sunflower, or any Other Crop Via Chemical-Based Haploid Induction Any line of corn, rice, wheat, tomato, sunflower, barley, or any other crop is transformable with the editing construct (Cas9 plus guide RNAs designed to mutate a particular target site) and then optionally make the editing construct either heterozygous or homozygous (via self-pollination of the transformed event), and then using lipid or oil applications during outcrossing (pollination onto target lines) in order to induce de novo haploids and simultaneously edit the target sites in the target genomes. These lipid applications have the ability to induce haploids when applied to pollen, silks, flowers, or tassels of any plant—regardless of male parent. In particular, the male parent is not required to have any mutations in the MATL gene (i.e., it can be homozygous wild type for the MATRILINEAL gene). These lipid applications induce haploids de novo, without any genetic requirement on behalf of either parent. See P.C.T. Patent Application No. PCT/US2016/62548, incorporated herein by reference in its entirety. The mechanism of de novo haploid induction via lipid spray apparently works the same way as it does in matl mutant (genetic haploid inducer) lines: via chromosome elimination post-fertilization. Haploid progeny are isolated and checked for the induced mutations (caused via the editing process) and then doubled to make edited, doubled haploid plants.

V. Mutagenesis of Target Sequences in Elite Field Corn and Sweet Corn Inbred Lines with Transgenic Editing Locus Introgressed into a Haploid Inducer Line.

Transgenic locus expressing genome editing machinery can also be generated in conventional transformable maize line without haploid inducing activity such as A188, Hi-II or NP2222 and then introgressed into haploid inducer line such as NP2222-HI, RWK, RWKS, RWS, or UH400 or Stock6 or any other haploid inducer line.

In this example, maize inbred line NP2222 is transformed with VLHP Cas9-sgRNA vectors (23396 and 23397) and GW2 Cas9-sgRNA vectors (23398 and 23399). Vectors 23396 and 23399 have been described in previous examples (Example IIIA and Example IIIB). Vector 23397 (SEQ ID NO: 20) is identical to 23396 except the gRNA-coding sequence xZmVLHP-01 (5'-GCAG-GAGGCGTCGAGCAGCG-3', SEQ ID NO: 2) is replaced with xZmVLHP-02 (5'-GCTGGAGCTGAGCTTCCGGG-3', SEQ ID NO: 21). Vector 23398 (SEQ ID NO: 23) is identical to 23399 except the gRNA-coding sequence xZmGW2-02 (5'-AAGCTCGCGCCCTGCTACCC-3', SEQ ID NO: 4) in 23399 is replaced by xZmGW2-01 (5'-GAGCGGTTCACGCGGCCGCA-3', SEQ ID NO: 23). These vectors were introduced into *Agrobacterium* strain LBA4404 (pVGW7). The resulting *Agrobacterium* strain containing vector 23396, 23397, 23398, or 23399 was used to transform immature embryos of transformable elite inbred line NP2222. Calli were induced from infected immature embryos and selected on mannose media to recover transgenic calli. Transgenic calli were placed on regeneration and rooting media to recover transgenic plants expressing the CRISPR-Cas9 editing machinery. Transgenic plants were assayed for transgene copy number and moved to greenhouse for seed production.

Single copy transformants of vector 23396 (MZET154902A004A, MZET154902B006A), 23397 (MZET154903B009A, MZET154903B012A), 23398 (MZET154904B005A, MZET154904B014A) and 23399 (MZET154905A002A, MZET154905A010A) were identified and backcrossed with non-transgenic NP2222. Ears of transgenic progeny plants containing T-DNA insert of each of the above vectors were pollinated with pollen of haploid inducer line RWKS to produce F1 progeny. F1 progeny containing transgenic locus and haploid induction locus were identified by genotyping assays and self-pollinated to produce F2 progeny seeds. F2 progeny seeds were planted and seedling plants assayed to identify plants homozygous for transgenic Cas9-sgRNA locus (assay #2540) and haploid induction locus (assay #2827) with qPCR Taqman assays.

Lines homozygous for the haploid induction locus and preferably homozygous transgenic 23396, 23397, 23398, and 23399 Cas9-sgRNA editing locus were used to pollinate ears from target elite field corn line ID5829 and sweet corn lines (SWC726 or SWC412F) for haploid induction. Induced haploid embryos were isolated from pollinated ID5829, SWC412F, SWC726 ears and geminated on embryo rescue media. Alternatively, pollinated ears were allowed to mature and kernels with haploid embryos were germinated. Leaf samples were collected and analyzed with Taqman assay to identify plants containing mutations in VLHP and GW2 genes but absence of genetic components from induction line such as transgenic Cas9-sgRNA or other non-transgenic marker gene sequences. Identified haploid plants with targeted GW2 or VLHP gene mutations were treated with colchicine for chromosome doubling to recover doubled haploid plants for seed production. Alternatively, extracted haploid embryos can be treated with chromosome doubling agent such as colchicine and the resulting plants are analyzed for ploidy level and presence of targeted mutations in GW2 or VLHP genes. Plants with targeted GW2 and VLHP gene mutations are grown to maturity for seed production and further progeny evaluation.

Figure 11:
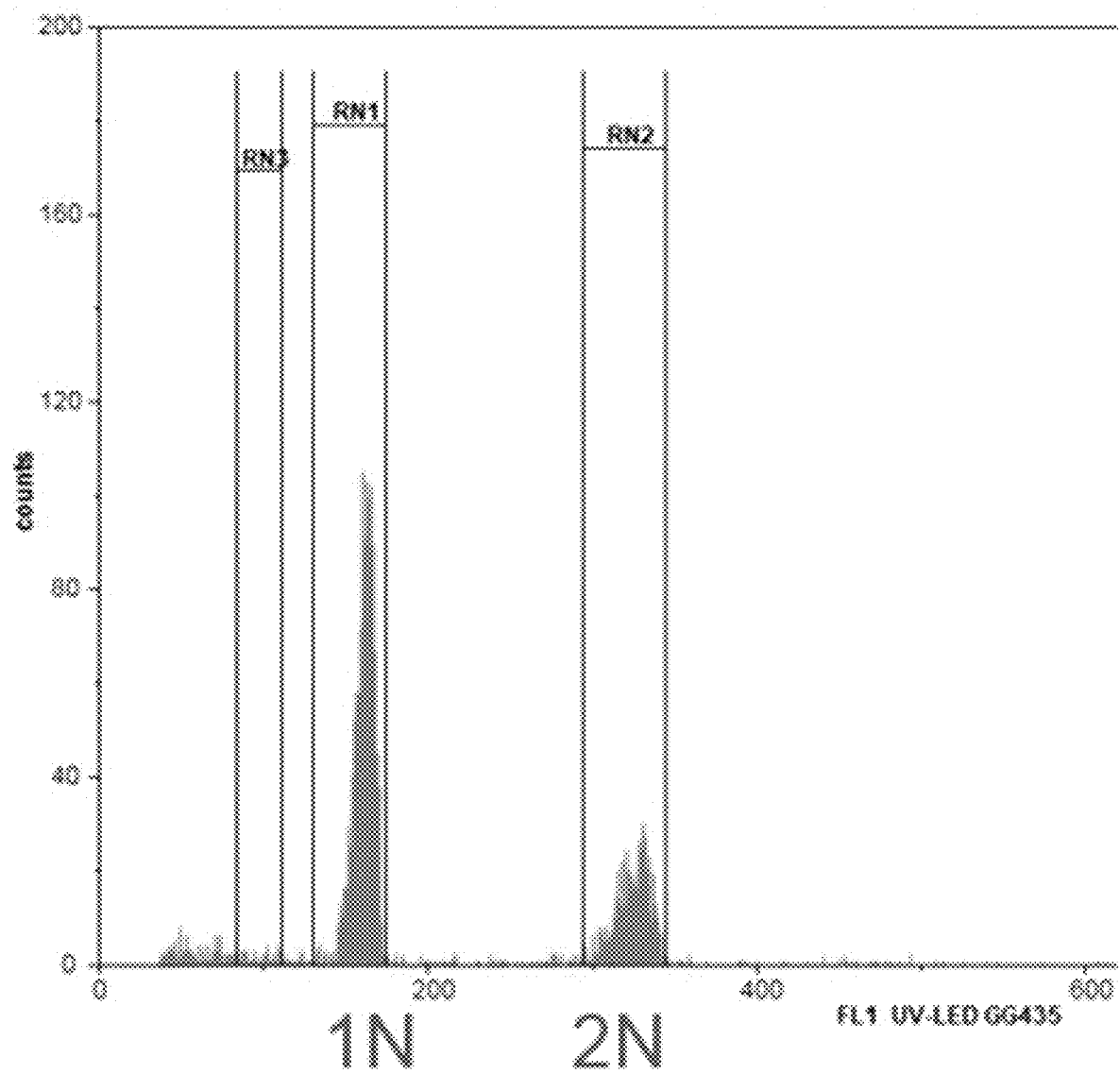
FIG. 11 shows ploidy assay of edited haploid sweet corn line JSER82A056 and FIG. 12 shows the same for edited haploid sweet corn line JSER82A063. These lines were obtained through crossing with RWKS haploid induction line carrying transgene locus of CRISPR-Cas9 expression vector 23399.
Figure 12:
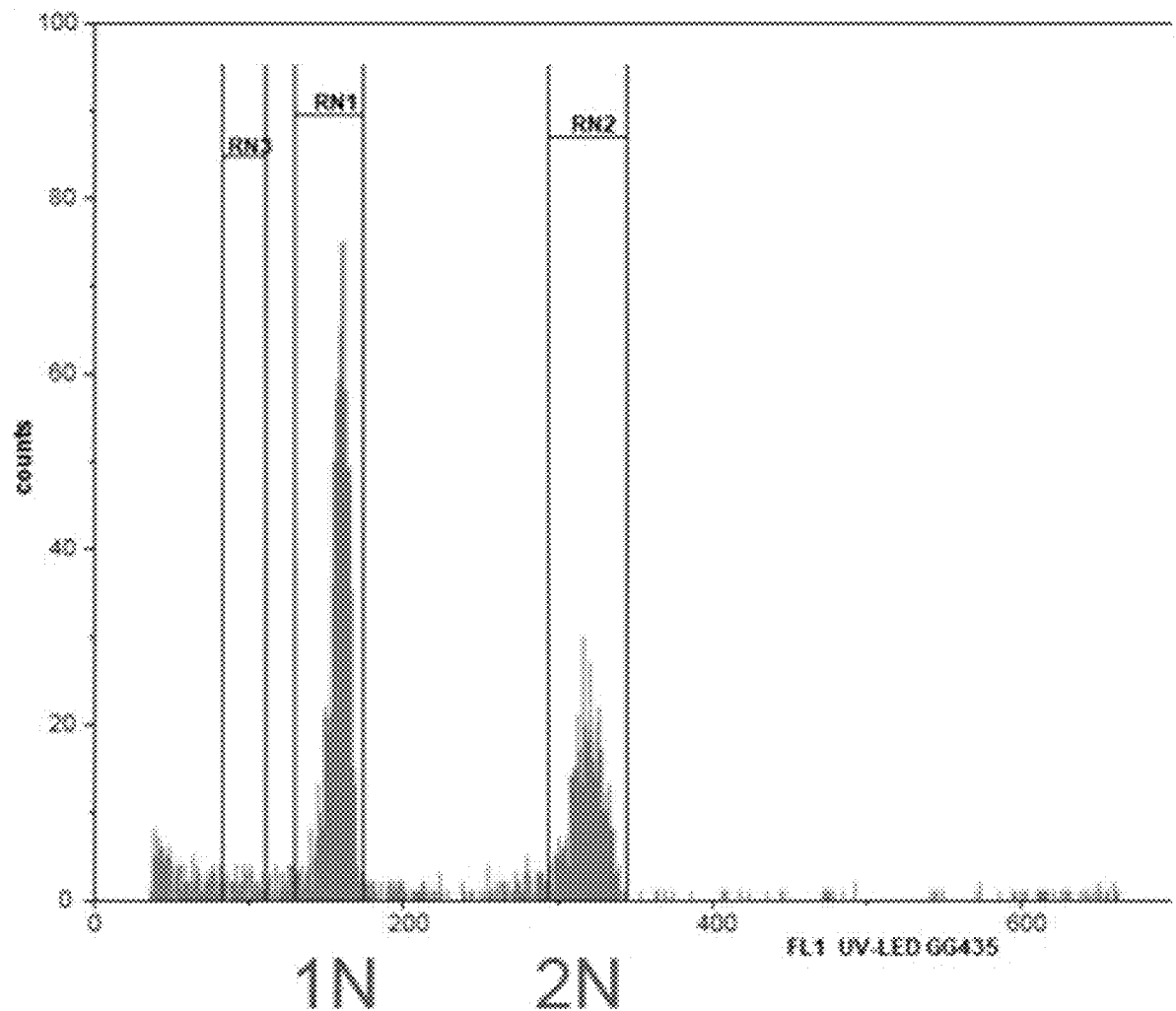

For example, edited haploid lines (JSER82A056 and JSER82A063) were identified from crosses between sweet corn line SWC412F ears pollinated with haploid inducer containing 23399 Cas9-sgRNA transgene. Line JSER82A056 has both GW2-01 and GW2-02 target genes mutated, whereas line JSER82A063 only has GW2-02 gene mutated (See Table 5). Neither of these lines contain Cas9 transgene (assay #2540 for Cas9 or #1750 for PMI selectable marker gene) or haploid inducer gene (assay #2827) as the male genome has been eliminated from the haploids. Ploidy level analysis confirmed that both lines are haploids (FIGS. 11 and 12). Note that wildtype ("WT") genes in the haploids have a copy number of "2" and mutant will be "0" since the copy call is relative to the endogenous ADH gene copy number. Therefore, haploid lines carrying WT unedited GW2-01 or GW2-02 genes will have a copy call of "2." WT haploid inducer locus will have copy call of "2" for assay #2826 and "0" for assay #2827 (haploid inducer variant). If a corn plant line is a diploid between sweet corn and transgenic inducer, it will be heterozygous for the haploid inducer gene and thus have copy call of "1" for both assay #2826 and assay #2827.

TABLE 5

Progeny zygosity analysis from crosses. Taqman analysis results showing the lines do not contain transgene or haploid inducer locus from pollen donor, but have edits in GW2-01 and/or GW2-02 targets.

| Plant ID | Construct ID | cCas9-01 Allele: Assay ID: 2540 Copy# level | cPMI-09 1750 Copy# level | CRISPR target in GW2-01 (23399) 3065 Copy# level | CRISPR target in GW2-02 (23399) 3095 Copy# level | pPLAIIa WT allele 2826 Copy# level | RWK (Haploid Inducer) allele of pPLAIIa 2827 Copy# level |
|---|---|---|---|---|---|---|---|
| 1-copy control |  | + | 1 | ND | ND | 1 | 1 |
| wild type control |  | 0 | 0 | 2 | 2 | 2 | 0 |
| JSER82A056 | 23399 | 0 | 0 | 0 | 0 | 2 | 0 |
| JSER82A063 | 23399 | 0 | 0 | 1 or 2 | 0 | 2 | 0 |
| JSER85A021 | 23399 | 0 | 0 | 0 | >2 | 2 | 0 |
| JSER85A022 | 23399 | 0 | 0 | 0 | >2 | 2 | 0 |
| JSER85A024 | 23399 | 0 | 0 | 0 | >2 | 2 | 0 |
| JSER85A027 | 23399 | 0 | 0 | 0 | >2 | 2 | 0 |
| JSER85A037 | 23399 | 0 | 0 | 0 | >2 | 2 | 0 |
| JSER85A039 | 23399 | 0 | 0 | 0 | >2 | 2 | 0 |
| JSER85A044 | 23399 | 0 | 0 | 0 | >2 | 2 | 0 |
| JSER85A055 | 23399 | 0 | 0 | 0 | >2 | 2 | 0 |

Figure 13:
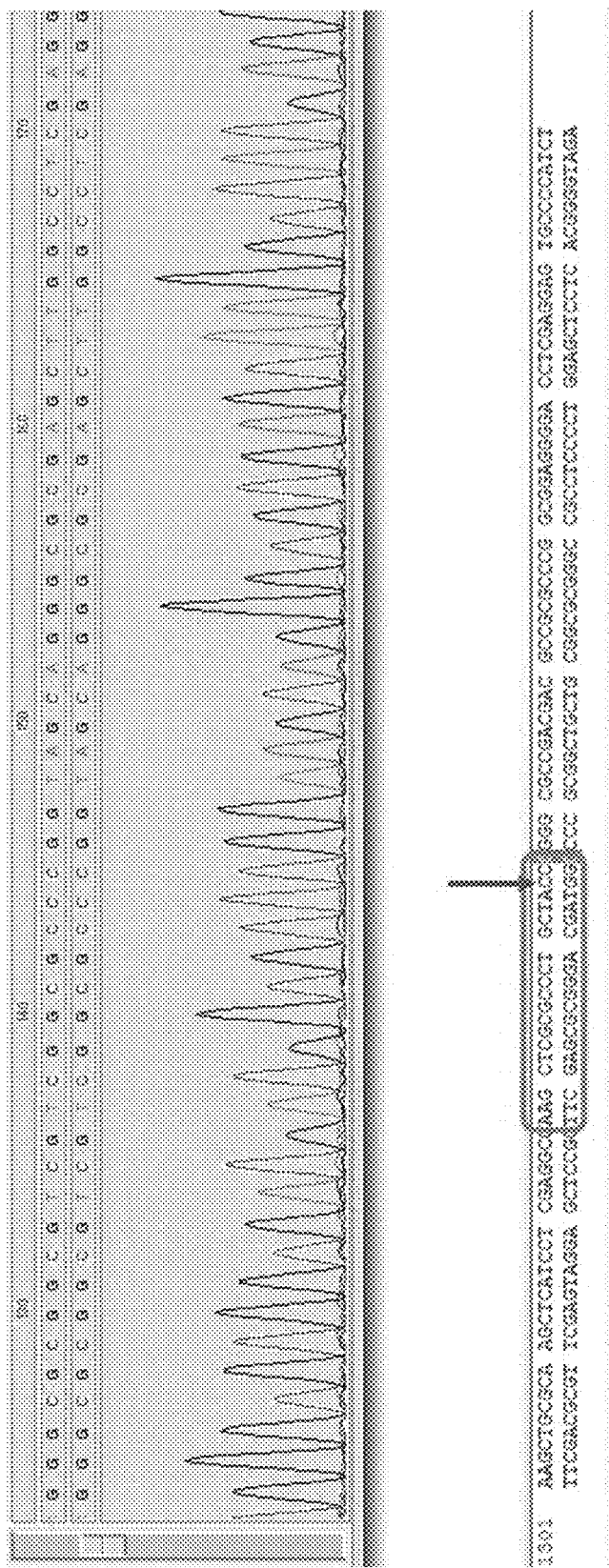
FIG. 13 shows sequencing confirmation of GW2-02 target site editing in haploid sweet corn line JSER82A063. A single base C next to the predicted Cas9 cleavage site was deleted. The sequence presented within the box is identical to SEQ ID NO: 4. The top-line sequence presented at the bottom of the figure is represented by SEQ ID NO: 99. The bottom-line sequence is represented by SEQ ID NO: 100 and is the reverse complement of SEQ ID NO: 99.

To further confirm target-specific editing in these haploid lines, GW2-02 target region was amplified from JSER82A063 by PCR and the PCR product was sequenced. A single base C was deleted in JSER82A063 in comparison with the WT sequence precisely at the Cas9 cleavage site (FIG. 13). These results clearly demonstrated that editing machinery brought into the egg cell from the male gametophyte can edit the female genome before the male genome is eliminated after double fertilization to form haploid embryo. Candidate edited haploid lines without transgene were treated with injection of 0.125% colchicine in 0.5% DMSO or seedling drenching in 0.06% colchicine solution (Eder and Chalyk, 2002, In vivo haploid induction in maize. Theor. Appl. Genetics 104:703-708). Treated lines were planted in soil and grown in greenhouse for progeny seed production.

VI. Simultaneous Haploid Induction and Editing in Wheat and Other Monocots Via Wide Cross.

Haploid induction is also achieved using interspecific or intergeneric wide crosses (Kasha and Kao, 1970, High frequency haploid production in barley (*Hordeum vulgare* L.). Nature 225:874-886). For example, wheat haploids can be obtained by pollination with various intergeneric crosses with maize (Suenaga and Nakajima 1989), pearl millet (Inagaki and Mujeeb-Kazi 1995), teosinte (Ushiyama et al. 1991), *H. bulbosum* (Barclay 1975), and sorghum (Ohkawa et al. 1992). Barley haploids are obtained by pollination with *Hordeum bulbosum* pollen. Tobacco haploids can be obtained by crossing with *N. africana* pollen. Many other examples exist in other crops.

Similar to examples above in introducing transgenic editing locus into Stock6 induction line, transgenic editing locus can be introduced into these lines used for wide crosses to induce haploid induction and targeted sequence mutation. Transgenic lines expressing editing machinery can be generated in any line of corn, wheat, barley, rye, pearl millet, rice, brassica, lettuce, tomato, or any other crop by direct transformation or outcrossing. Preferably the transgenic locus is made homozygous and then the line is used as pollen donor in a wide cross with other compatible recipient crops to induce haploids to produce desired edits. The process of post-fertilization genome elimination in wide crosses is basically the same as the process in the maize MATL mutant system, although in some cases the foreign pollen-derived DNA and editing machinery may be eliminated slightly earlier in embryo development, which is why this method is preferably practiced using a promoter that drives expression of the editing machinery in the pollen, sperm cells, and/or zygote cell, so that the editing RNA and protein is present and able to edit the target genome even though the male DNA is eliminated rather quickly after fertilization.

To demonstrate feasibility of simultaneous haploid induction and editing via wide crosses, maize transgenic lines expressing Cas9 and sgRNA targeting wheat VLHP gene sequences were generated. Vector 23763 (SEQ ID NO: 24) contains expression cassettes for Cas9 and sgRNA containing protospacer sequence xTaVLHP1 (5'-GACGAGCAGGCGCAGTTCC-3', SEQ ID NO: 25) for guiding Cas9-mediated cleavage of TaVLHP1 target sites in wheat. The wheat genome has three xTaVLHP1 targets in total (TaVLHP1-4A, TaVLHP1-4B and TaVLHP1-4D), with each one in its three sub-genomes. The guide sequence in 23397 (SEQ ID NO: 20), xZmVLHP (5'-GCTGGAGCT-GAGCTTCCGGG-3', SEQ ID NO: 21) will also direct cleavage of wheat VLHP target sequences, xTaVLHP2-1A (5'-GCTGGAGCTGAGCTTCCGGG-3', SEQ ID NO: 26) or xTaVLHP2-1B (5'-TCTGGAGCTGAGCTTCCGGG-3', SEQ ID NO: 27). There are three VLHP2A genes containing xTaVLHP2-1A and 3 VLHP2B genes containing xTaVLHP2-1B sequences in the Chinese Spring wheat genome. Vectors 23397 and 23763 were transformed into maize inbred line NP2222 using *Agrobacterium*-mediated transformation to generate transgenic lines expressing Cas9 and sgRNA. Transgenic maize lines were grown in greenhouse and selfed to produce T1 plants.

Pollen collected from transgenic maize T0 or progeny T1 plants carrying T-DNA of vector 23397 or 23763 were used to pollinate emasculated spring wheat line AC-Nanda. At one to two days before anthesis, wheat florets were emasculated and two days later are pollinated with fresh maize pollen carrying the editing machinery. For convenience, spikelets from a Syngenta elite cytoplasmic male sterile ("CMS") wheat line (16A300292) were also directly used as female donors to induce haploid embryo formation with transgenic maize pollen expressing 23397 or 23763 Cas9-sgRNA. Embryos were extracted from pollinated florets at 14-20 days after pollination for embryo rescue to recover haploid plantlets from the wheat×maize haploid induction system. Excised embryos were cultured on either full strength MS (Murashige and Skoog 1962) or ½ MS or B5 basal medium containing various modifications of organic supplements and grown in vitro for 3-5 weeks at 20-25° C. and 16-hour day length.

Figure 14:
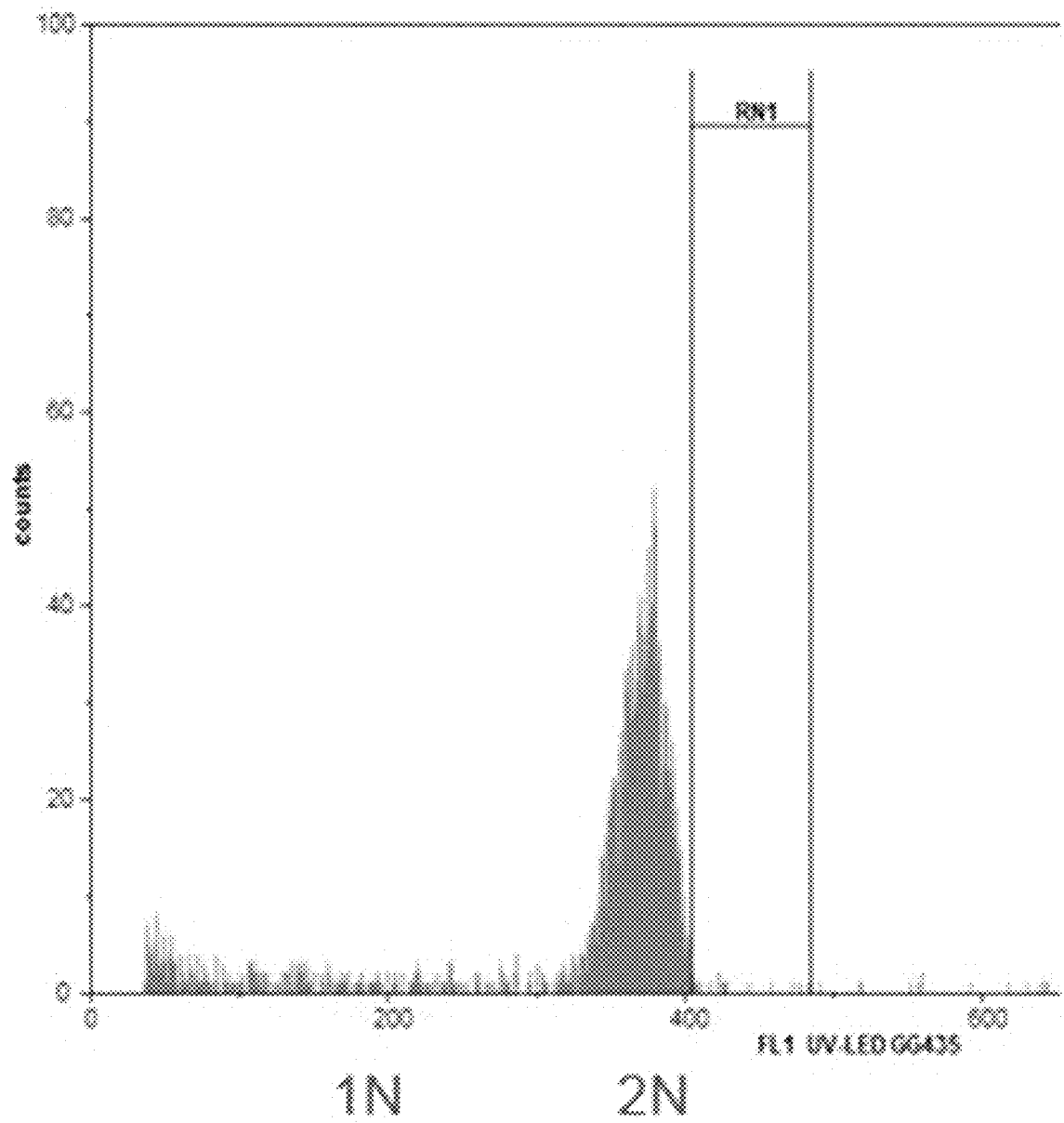
FIG. 14 shows ploidy analysis of wild type control.
Figure 15:
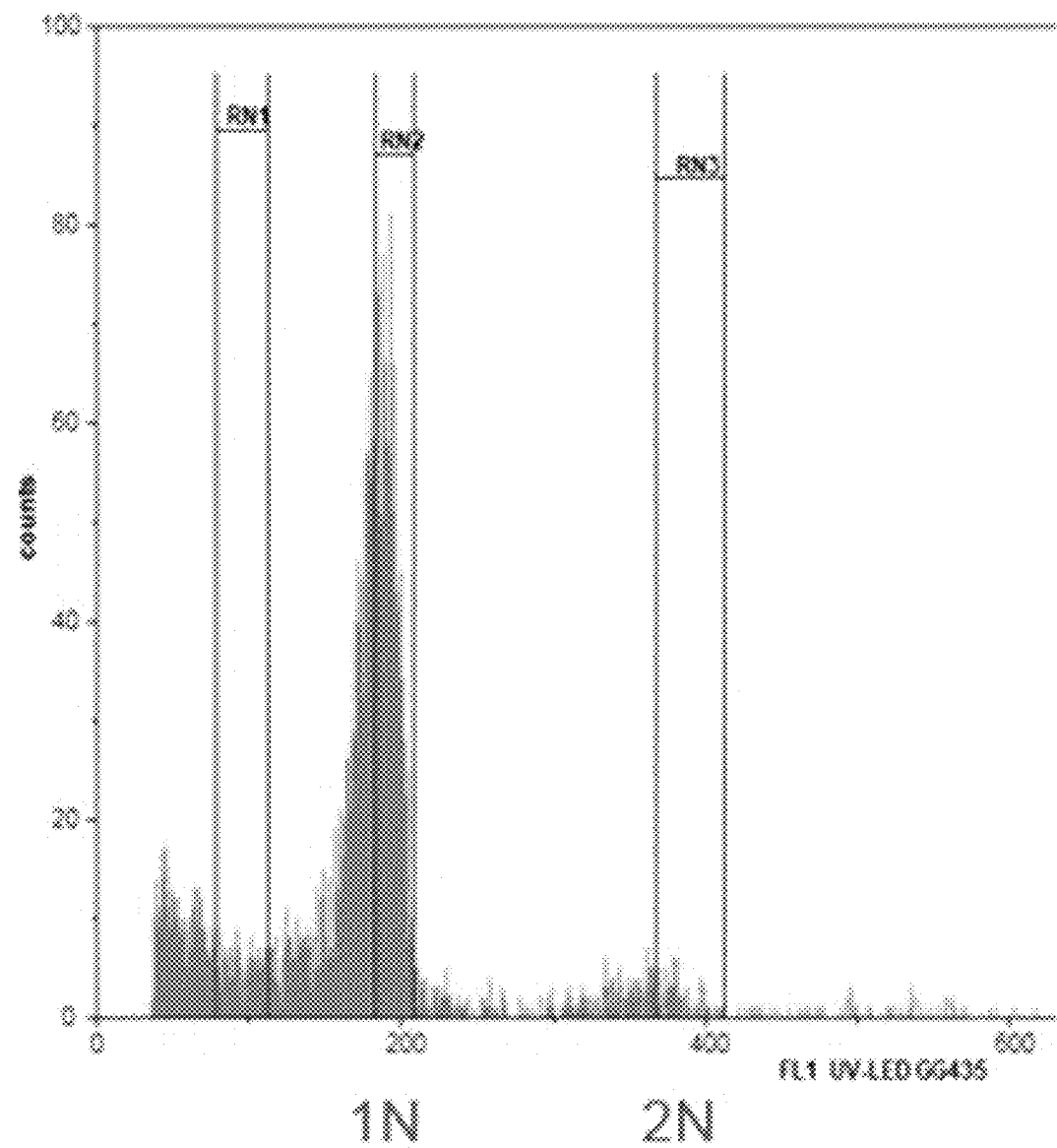
FIG. 15 shows ploidy analysis of edited haploid wheat line JSWER30A22.
Figure 16:
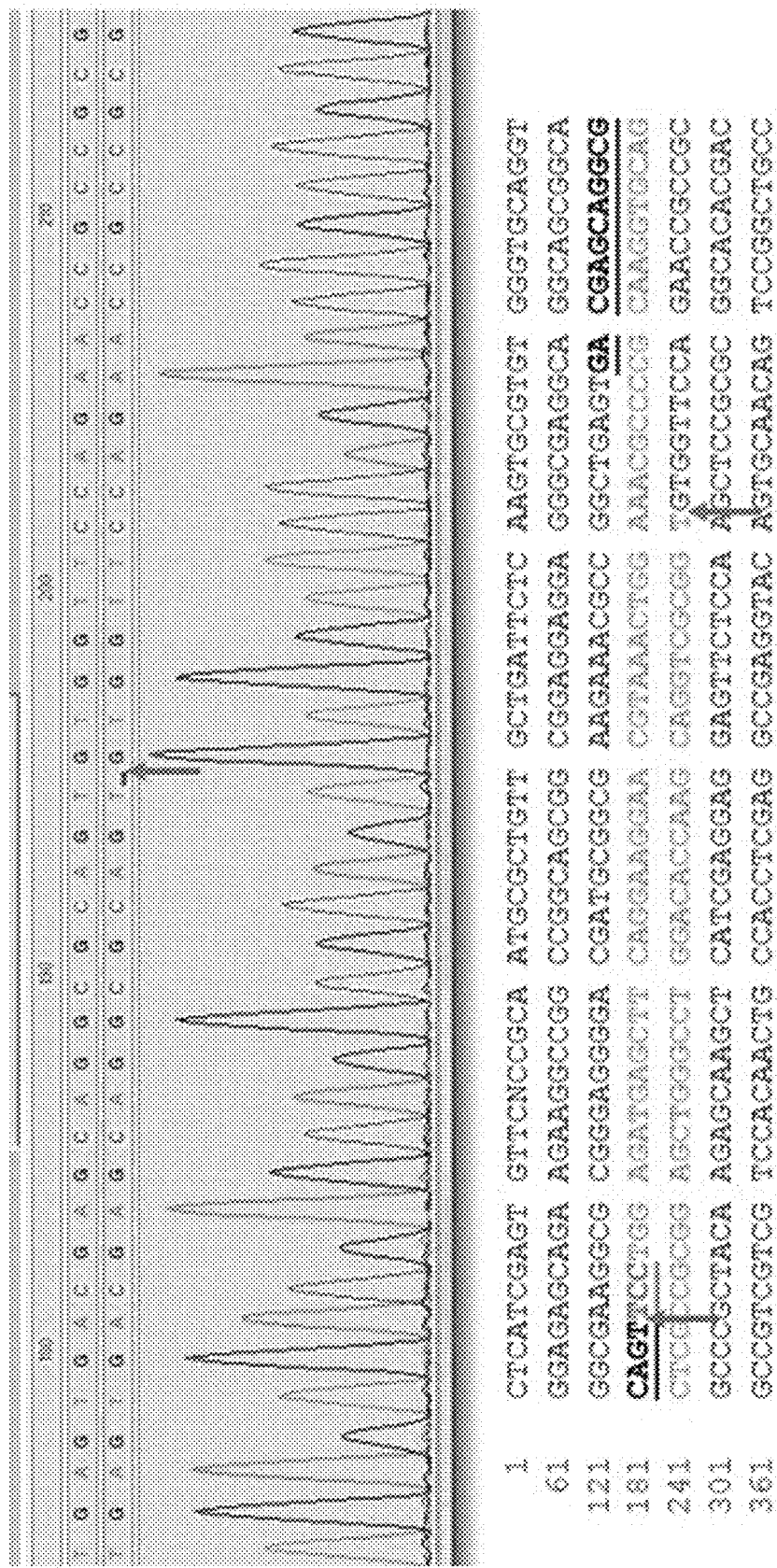
FIG. 16 shows sequencing confirmation of TaVLHP1-4B target site editing in haploid wheat line JSWER30A22. Lower panel showing 97 bp of TaVLHP1-4B sequence was deleted immediately downstream of the predicted Cas9 cleavage site. The 97 bp deleted sequences were marked by 2 arrows. The underlined sequence matches the gRNA sequence of SEQ ID NO: 25. The entire sequence is represented by SEQ ID NO: 101.

For example, pollen of T1 progeny from transgenic maize line MZET164902A044A containing vector 23763 was used to pollinate spikes of CMS line 16A300292 to induce wheat haploids. Haploid embryos were rescued and the resulting wheat haploid seedling were sampled for qPCR analysis to determine the copy number of VLHP target sequences (See Table 6). One of the haploid lines (JSWER30A22) was found to contain mutation in TaVLHP1-4B gene, but not in its orthologs TaVLHP1-4A and TaVLHP1-4D in the A and D sub-genomes. Ploidy level analysis confirmed that JSWER30A22 is a true haploid (See FIGS. 14 and 15). The mutation within the TaVLHP1-4B target region was further characterized by sequencing and was found to contain 97 bp deletion starting from the predicted Cas9 cleavage site (FIG. 16). We also identified another line JSW16A07 with "0" copy in TaVLHP1-4A gene (assay #3252), suggesting targeted editing in the target sequence. However, the deletion in this target gene is probably quite large in deleting the primer binding site(s) since we were not able to recover PCR product for sequencing. Haploid seedlings with an edited target site were transplanted to soil after 3-5 weeks in vitro culture. The transplanted seedlings were hardened for one week in a growth chamber under the same environmental regime. Colchicine was added after shoots had formed. However, the chromosome doubling treatment can be done earlier at embryo rescue in vitro culture stage or later after transplanting. When whole wheat seedlings are treated for doubling, roots of the haploid seedling are trimmed leaving a zone of 2-3 cm and then submerged in a 0.1% colchicine solution with 2% dimethyl sulfoxide (DMSO) and ca. 0.05% Tween-20 at 20° C. for 5 hours. After this treatment, the roots are washed to remove residual colchicine and potted in peat soil. Plant tissue samples can be removed from haploid seedlings for mutation detection to identify plants containing mutations in TaVLHP target gene sequences but with the maize chromosomes including sequences encoding the transgenic editing machinery completely eliminated. Since JSWER30A22 is from a CMS line, the plant is pollinated with a restorer to produce progeny seeds.

TABLE 6

Taqman analysis for wheat progeny from wide crosses. Line JSW30A22 is edited.

| Plant ID | Allele: Assay ID: Construct ID | TAV_4A 3252 Copy# level | TAV_4B 3253 Copy# level | TAV_4D 3254 Copy# level | PMI 1750 Copy# level | CAS9 2540 Copy# level |
|---|---|---|---|---|---|---|
| WT, AC-Nanda | N/A | >2 | 2 | >2 | 0 | 0 |
| WT, AC-Nanda | N/A | 2 | 2 | 2 | 0 | 0 |
| WT, CMS | N/A | 2 | 2 | 2 | 0 | 0 |
| WT, CMS | N/A | 2 | 2 | 2 | 0 | 0 |
| JSW29A01 | 23763 | 2 | 2 | 2 | 0 | 0 |
| JSW29A02 | 23763 | 2 | 2 | 2 | 0 | 0 |
| JSW29A03 | 23763 | 2 | 2 | 2 | 0 | 0 |
| JSW29A04 | 23763 | 2 | 2 | 2 | 0 | 0 |
| JSW29A05 | 23763 | 1 or 2 | 2 | 2 | 0 | 0 |
| JSW29A06 | 23763 | 2 | 2 | 2 | 0 | 0 |
| JSW29A07 | 23763 | 2 | 2 | 2 | 0 | 0 |
| JSW29A08 | 23763 | 2 | 2 | 2 | 0 | 0 |
| JSW29A09 | 23763 | 2 | 2 | 2 | 0 | 0 |
| JSW29A10 | 23763 | 2 | 2 | 2 | 0 | 0 |
| JSW29A11 | 23763 | 2 | 2 | 2 | 0 | 0 |
| JSW29A12 | 23763 | 2 | 2 | 2 | 0 | 0 |
| JSW29A13 | 23763 | 2 | 2 | 2 | 0 | 0 |
| JSW29A14 | 23763 | 2 | 2 | 2 | 0 | 0 |
| JSW29A15 | 23763 | 2 | 2 | 2 | 0 | 0 |
| JSW29A16 | 23763 | 2 | 2 | 2 | 0 | 0 |
| JSW30A01 | 23763 | 2 | 2 | 2 | 0 | 0 |
| JSW30A02 | 23763 | 2 | 1 or 2 | 2 | 0 | 0 |
| JSW30A03 | 23763 | 2 | 2 | 2 | 0 | 0 |
| JSW30A04 | 23763 | 2 | 2 | 2 | 0 | 0 |
| JSW30A05 | 23763 | 2 | 2 | 2 | 0 | 0 |
| JSW30A06 | 23763 | 2 | 2 | 2 | 0 | 0 |
| JSW30A07 | 23763 | 2 | 2 | 2 | 0 | 0 |
| JSW30A08 | 23763 | 2 | 2 | 2 | 0 | 0 |
| JSW30A09 | 23763 | 2 | 2 | 2 | 0 | 0 |
| JSW30A10 | 23763 | 2 | 2 | 2 | 0 | 0 |
| JSW30A11 | 23763 | 2 | 2 | 2 | 0 | 0 |
| JSW30A12 | 23763 | 2 | 2 | 2 | 0 | 0 |
| JSW30A13 | 23763 | 2 | 2 | 2 | 0 | 0 |
| JSW30A14 | 23763 | 2 | 2 | 2 | 0 | 0 |
| JSW30A15 | 23763 | 2 | 2 | 2 | 0 | 0 |
| JSW30A16 | 23763 | 2 | 2 | 2 | 0 | 0 |
| JSW30A17 | 23763 | 2 | 2 | 2 | 0 | 0 |
| JSW30A18 | 23763 | 2 | 2 | 2 | 0 | 0 |
| JSW30A19 | 23763 | >2 | 2 | 2 | 0 | 0 |
| JSW30A20 | 23763 | 2 | 2 | 2 | 0 | 0 |
| JSW30A21 | 23763 | 2 | 2 | 2 | 0 | 0 |
| JSW30A22 | 23763 | 2 | 0 | 2 | 0 | 0 |
| JSW30A23 | 23763 | 2 | 2 | 1 or 2 | 0 | 0 |
| JSW30A24 | 23763 | 2 | 2 | 2 | 0 | 0 |
| JSW30A25 | 23763 | 2 | 2 | 2 | 0 | 0 |
| JSW30A26 | 23763 | 2 | 2 | 2 | 0 | 0 |
| JSW30A27 | 23763 | 2 | 2 | 2 | 0 | 0 |
| JSW30A28 | 23763 | 2 | 2 | 2 | 0 | 0 |
| JSW30A29 | 23763 | 2 | 2 | 2 | 0 | 0 |
| JSW30A30 | 23763 | 2 | 1 or 2 | 1 or 2 | 0 | 0 |
| JSW30A31 | 23763 | 2 | 2 | 2 | 0 | 0 |

To further demonstrate feasibility of simultaneous haploid induction and editing via wide crosses, maize transgenic lines expressing Cas9 from five promoters that have high and/or specific expression in pollen, along with sgRNA targeting wheat VLHP gene sequences, were generated. These five vectors were 24038 (SEQ ID NO: 34), 24039 (SEQ ID NO: 35), 24079 (SEQ ID NO: 36), 24091 (SEQ ID NO: 37), and 24094 (SEQ ID NO: 38). All five of these vectors utilized the same sgRNA containing protospacer sequence xTaVLHP2 (5'-GCTGGAGCT-GAGCTTCCGGG-3', SEQ ID NO: 21) for guiding Cas9-mediated cleavage of TaVLHP2 target sites in wheat. The wheat genome has three xTaVLHP2 targets in total (TaVLHP2-2A, TaVLHP2-2B and TaVLHP2-2D), with each one in its three sub-genomes. The guide sequence in these five constructs also directs cleavage of wheat VLHP target sequences, xTaVLHP2 (5'-GCTGGAGCT-GAGCTTCCGGG-3', SEQ ID NO: 26) or xTaVLHP3 (5'-TCTGGAGCTGAGCTTCCGGG-3', SEQ ID NO: 27). There are three TaVLHP2 genes containing xTaVLHP2 and 3 TaVLHP3 genes containing xTaVLHP2-1B sequences in the Chinese Spring wheat genome.

Vector 24038 (SEQ ID NO: 34) contains expression cassettes for Cas9 under control of a pollen-preferred high expression promoter prZmGRMZM5G876285 and terminator tZmGRMZM5G876285 from the maize prf3 (profilin homolog3) gene, which has an extremely high native expression at the RNA and protein level in pollen and which has evidence of high sperm cell expression.

Vector 24039 (SEQ ID NO: 35) contains expression cassettes for Cas9 under control of a pollen-preferred high expression promoter prZmGRMZM2G020852 and terminator tZmGRMZM2G020852 from the maize EXPB2 (BETA EXPANSIN2) gene, which has an extremely high native expression at the RNA and protein level in pollen and which has evidence of sperm cell expression.

Vector 24079 (SEQ ID NO: 36) contains expression cassettes for Cas9 under control of a pollen-preferred high expression promoter prZmGRMZM2G146551 and terminator tZmGRMZM2G146551 from the maize EXPB1 (BETA EXPANSIN1) gene, which has an extremely high native expression at the RNA and protein level in pollen and which has evidence of sperm cell expression.

Vector 24091 (SEQ ID NO: 37) contains expression cassettes for Cas9 under control of a pollen-preferred promoter prZmGRMZM2G471240 and terminator tZmGMRMZM2G471240 from the maize MATL (MATRILINEAL) gene, which shows evidence of pollen and possibly sperm cell expression at the RNA and protein level.

Vector 24094 (SEQ ID NO: 38) contains expression cassettes for Cas9 under control of a pollen-preferred promoter prZmGRMZM2G471240 and terminator tZmGMRMZM2G471240 from the maize MATL (MATRILINEAL) gene, which shows evidence of pollen and possibly sperm cell expression at the RNA and protein level. This construct additionally has an N-terminal fusion of AmCyan fluorescent protein on the Cas9 molecule for imaging and visualization of the Cas9 localization in pollen.

These five vectors (24038, 24039, 24079, 24091, and 24094) were transformed into maize inbred line NP2222 using *Agrobacterium*-mediated transformation to generate transgenic lines expressing Cas9 and sgRNA.

Figure 17:
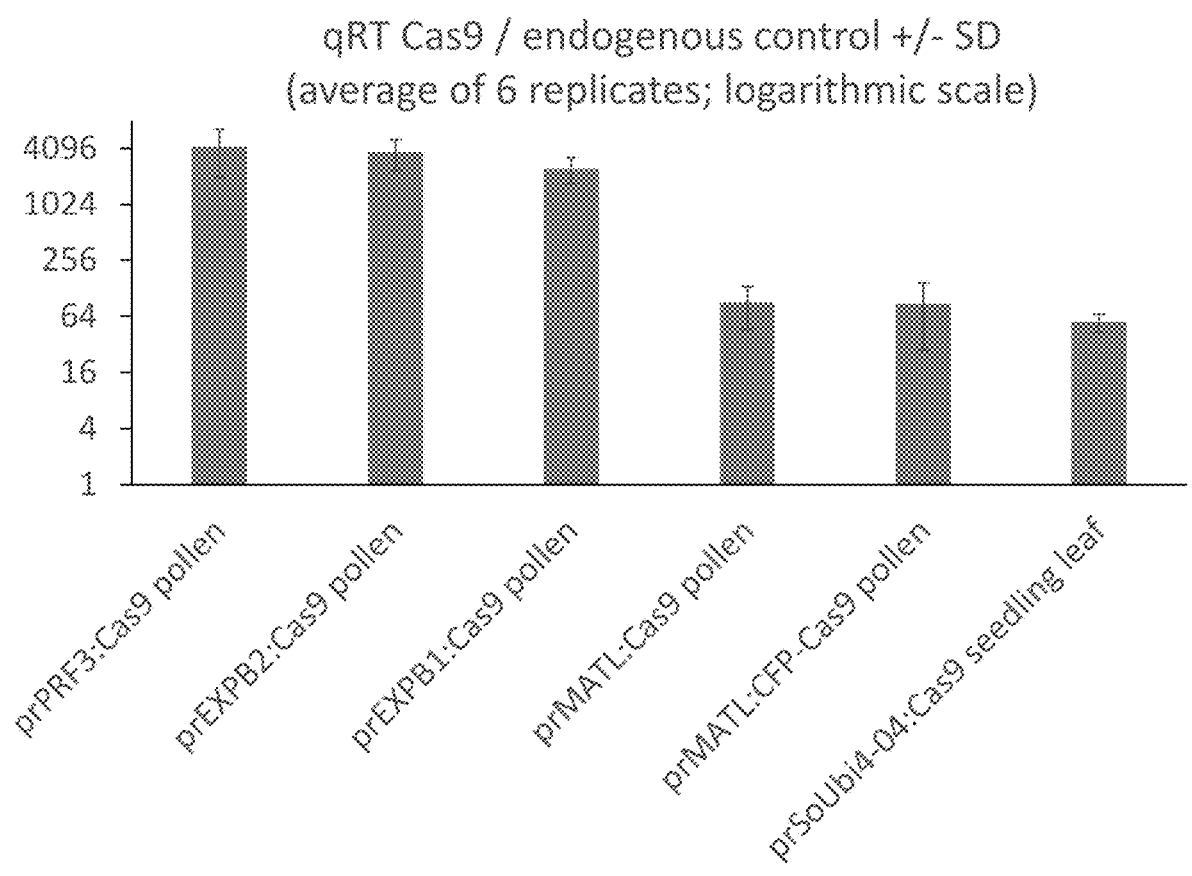
FIG. 17 shows pollen expression as measured by pollen collected from transgenic maize T0 plants carrying T-DNA of vector 24038, 24039, 24079, 24091, and 24094, which were used to pollinate emasculated spring wheat line AC-Nanda. The expression was high in the pollen, averaging about 100 fold higher in plants carrying T-DNA vectors 24038, 24039, and 24079 compared to the sugar cane ubiquitin promoter used in many of the corn and wheat examples. The expression was also higher in pollen from plants containing vectors 24038, 24039, and 24079 when compared to the pollen carrying the MATRILINEAL promoter constructs (24094 and 24091).
Figure 18:
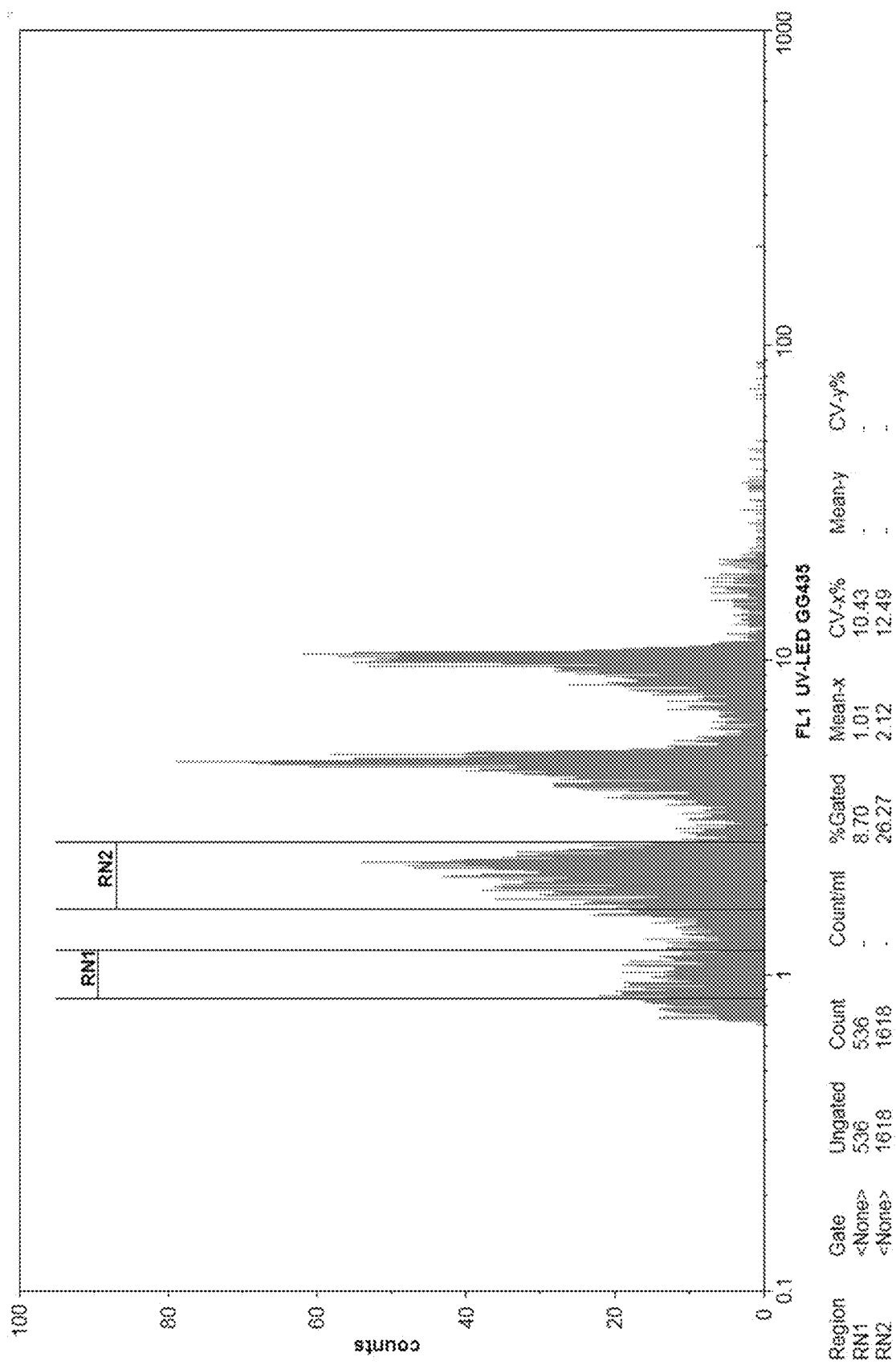
FIG. 18 shows the ploidy analysis histogram of a diploid control (parent USR01424135). The first peak is located at the "2" position on the logarithmic X-axis. Because this is leaf tissue from *Arabidopsis*, we see multiple peaks indicating the normal level of endoreduplication.
Figure 19:
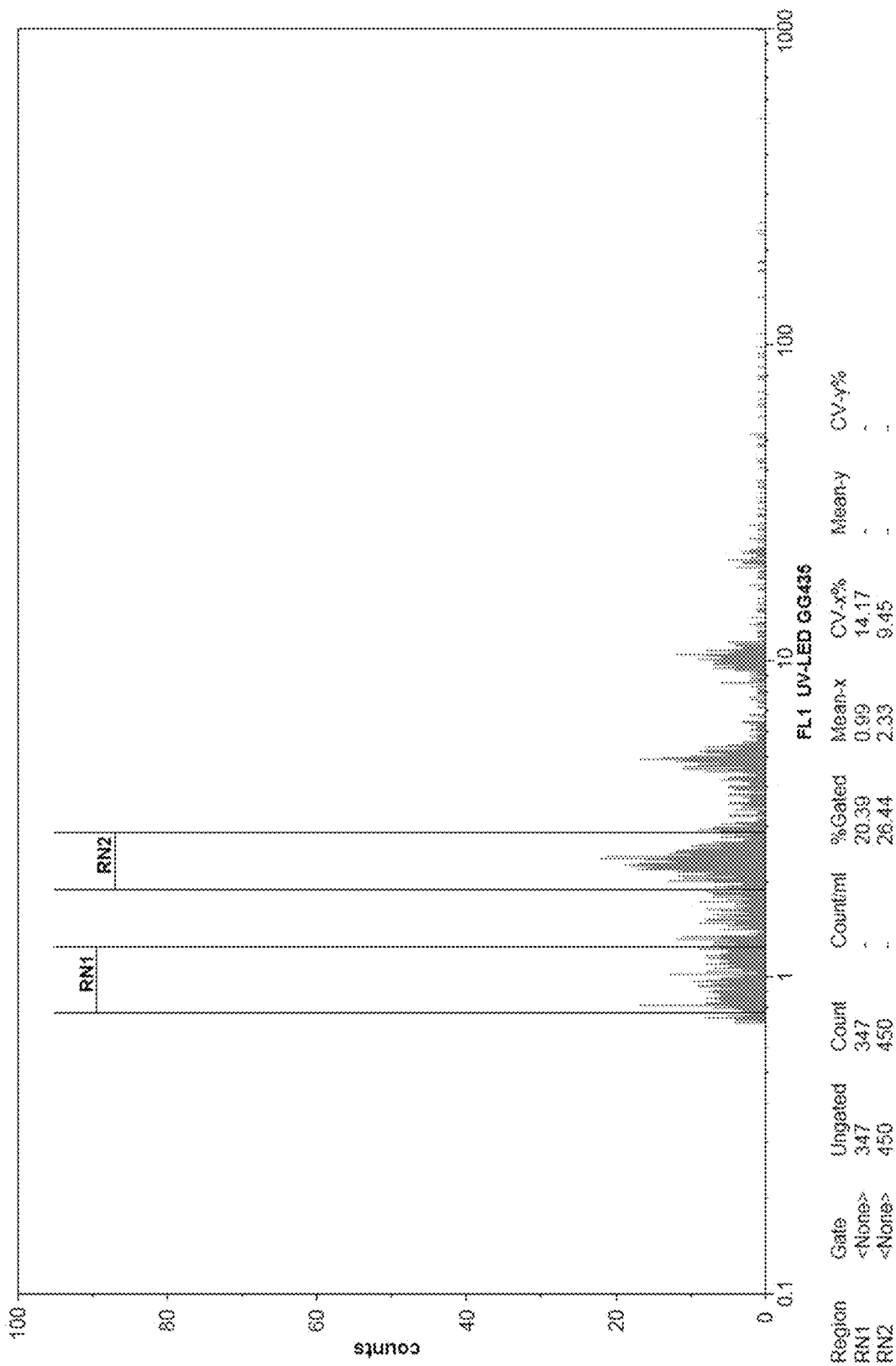
FIG. 19 shows the ploidy analysis histogram of a diploid control (parent USR01431603). The first peak is located at the "2" position on the logarithmic X-axis. Because this is leaf tissue from *Arabidopsis*, we see multiple peaks indicating the normal level of endoreduplication.
Figure 20:
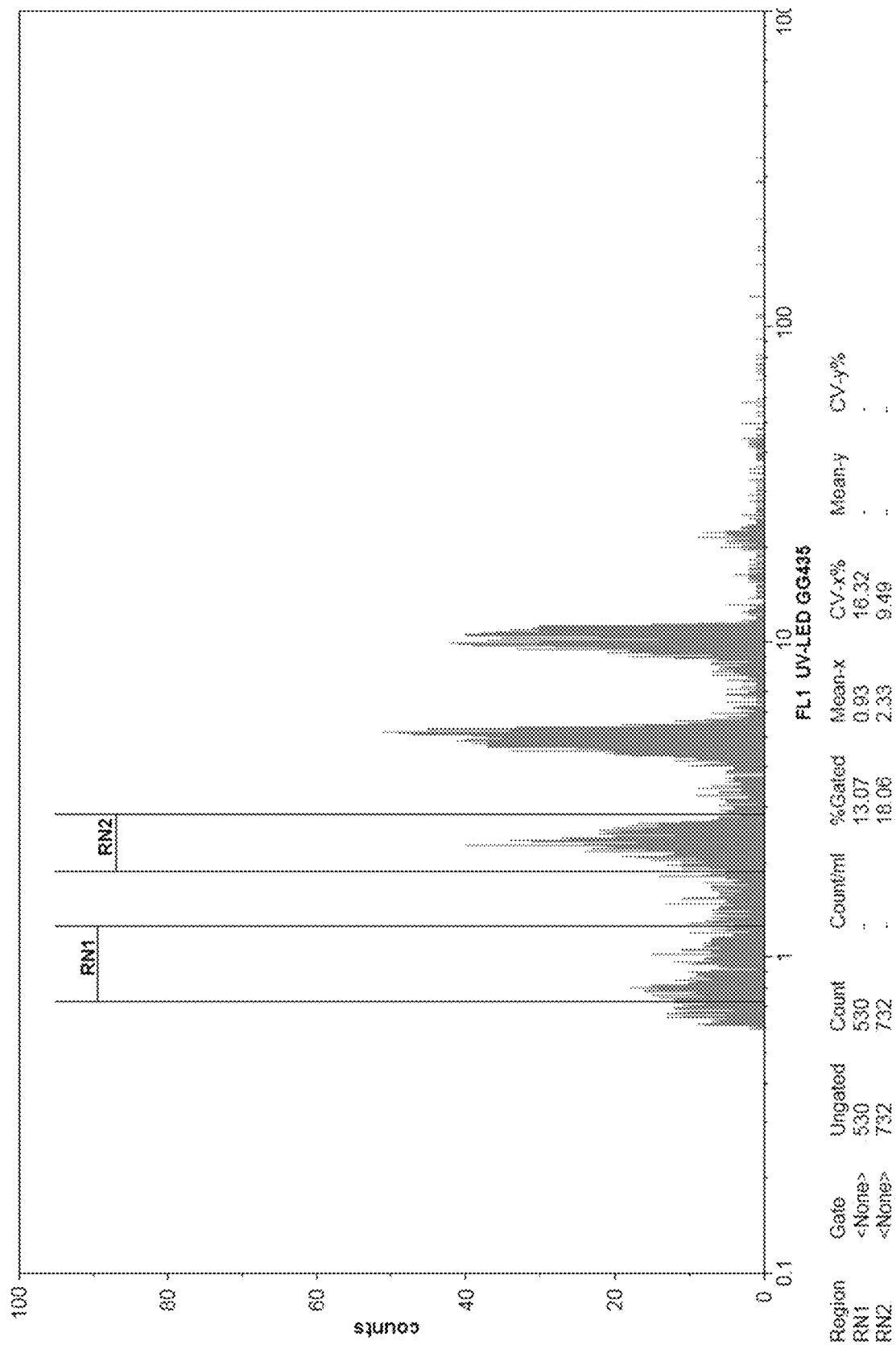
FIG. 20 shows the ploidy analysis histogram of a diploid control (parent USR01431609). The first peak is located at the "2" position on the logarithmic X-axis. Because this is leaf tissue from *Arabidopsis*, we see multiple peaks indicating the normal level of endoreduplication.
Figure 21:
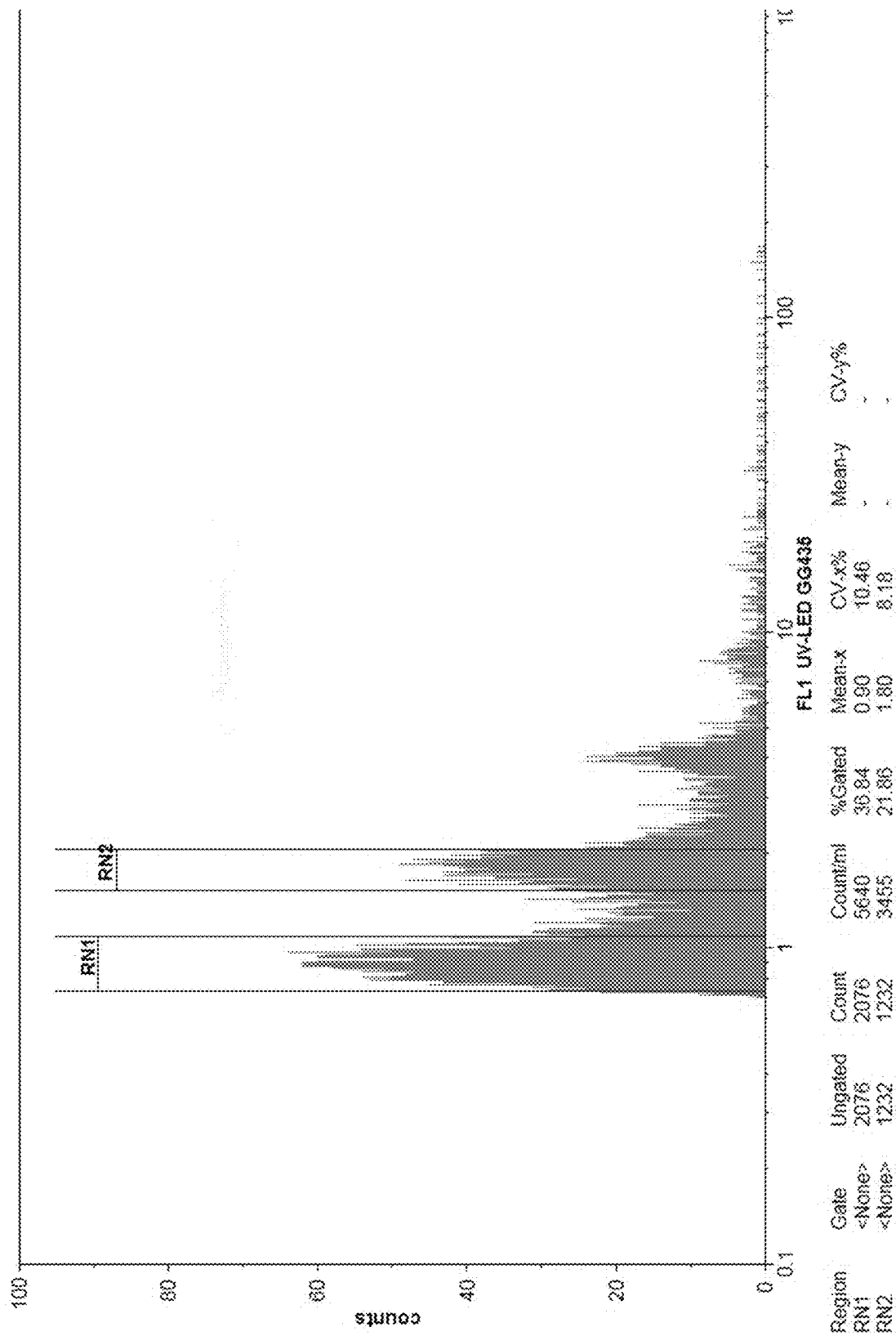
FIG. 21 shows the ploidy analysis histogram of an edited haploid from plate 1033, well C3 (USR01424135 X Ler-427). The first peak is located at the "1" position on the logarithmic X-axis, indicating it is a haploid. Because this is leaf tissue from *Arabidopsis*, we see multiple peaks indicating the normal level of endoreduplication.
Figure 22:
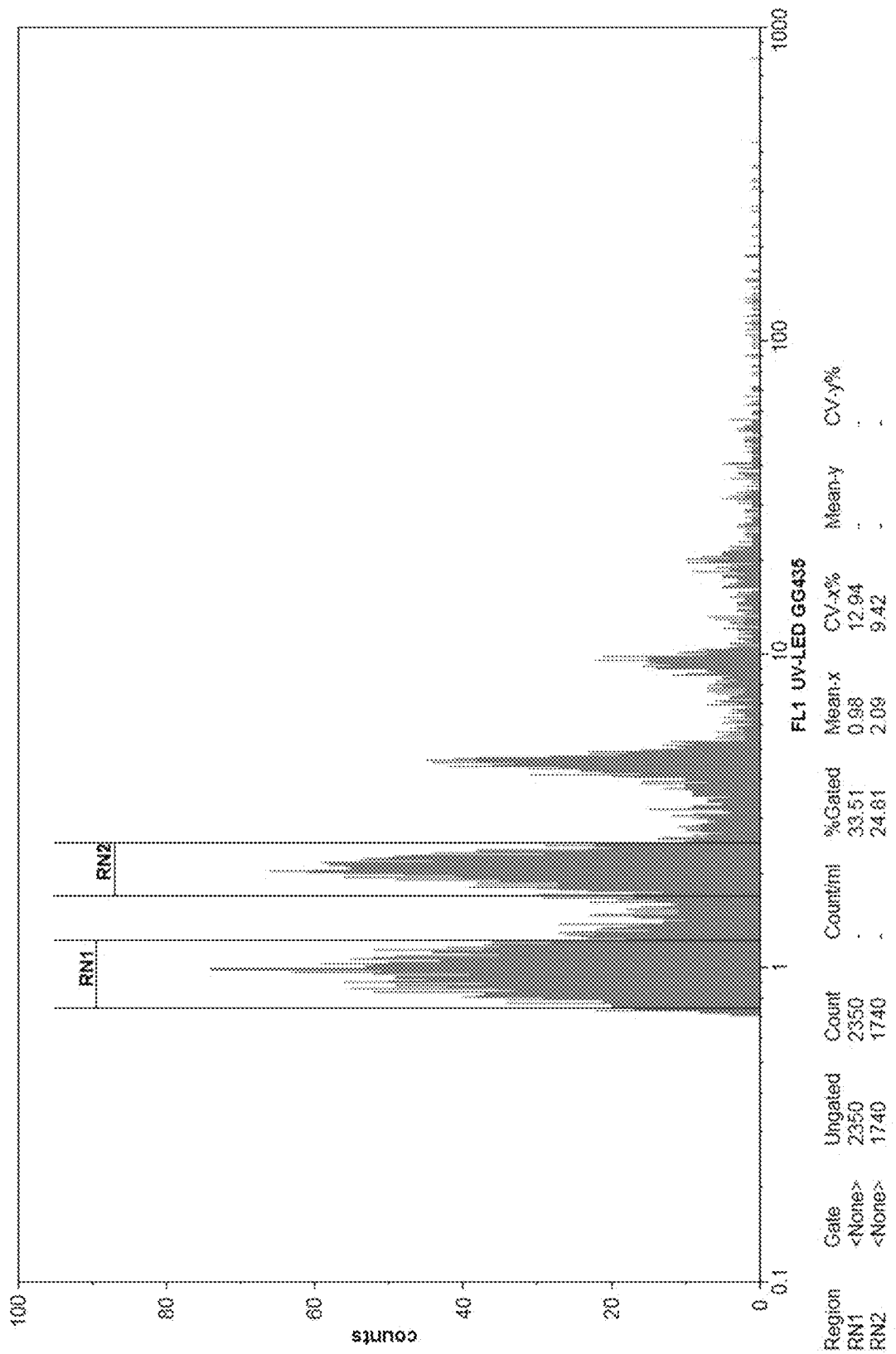
FIG. 22 shows the ploidy analysis histogram of an edited haploid from plate 1033, well E4 (USR01424135 X Ler-437). The first peak is located at the "1" position on the logarithmic X-axis, indicating it is a haploid. Because this is leaf tissue from *Arabidopsis*, we see multiple peaks indicating the normal level of endoreduplication.
Figure 23:
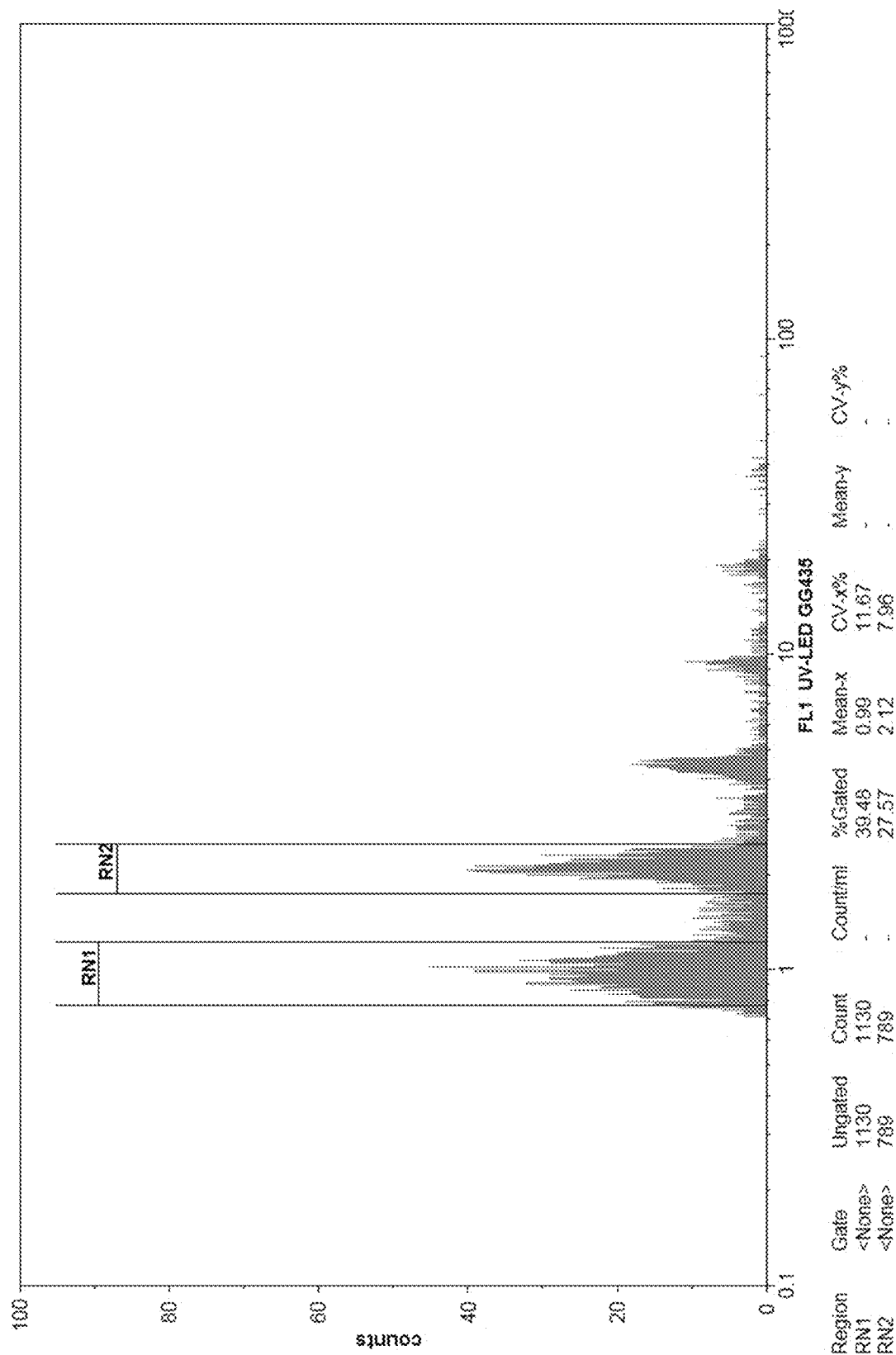
FIG. 23 shows the ploidy analysis histogram of an edited haploid from plate 1046, well H12 (USR01431609 X Ler-123). The first peak is located at the "1" position on the logarithmic X-axis, indicating it is a haploid. Because this is leaf tissue from *Arabidopsis*, we see multiple peaks indicating the normal level of endoreduplication.

Transgenic maize lines were grown in greenhouse and single and two-copy transgenic plants were outcrossed onto spring wheat and a CMS wheat line. Pollen collected from transgenic maize T0 plants carrying T-DNAs of one of the vectors 24038, 24039, 24079, 24091, and 24094 were used to pollinate emasculated spring wheat line AC-Nanda. Pollen was also used for a qRT experiment, in which the expression of the Cas9 was measured at the RNA level and compared to Cas9 expression in leaf samples when the Cas9 was driven by a sugar cane ubiquitin promoter used in many of the corn and wheat examples given above. As you can see in FIG. 17, the expression was high in the pollen, averaging about 100 fold higher in plants carrying the T-DNA vectors 24038, 24039, and 24079 compared to the Ubiquitin promoter. The expression was also higher in pollen from plants containing vectors 24038, 24039, and 24079 when compared to the pollen carrying the MATRILINEAL promoter constructs (24094 and 24091), which is known to have lower native gene expression. All five of these promoters have expression patterns that are restricted to pollen. As an indication that the promoters were working properly, we observed no T0 expression of Cas9 in callus seedling leaves, and there was no editing of the VLHP target sites in the T0 maize leaves (without wishing to be bound by theory, editing may happen at the maize target sites, in all likelihood, at the mature pollen stage, when the Cas9 is expressed for the first time).

At one to two days before anthesis, wheat florets were emasculated from the CMS line and the AC Nanda line. Two days later the florets were pollinated with fresh maize pollen carrying the editing machinery, Cas9-sgRNA, from either construct 24038, 24039, 24091, or 24094 (T0 plants transformed with construct 24079 were delayed, and not crossed to wheat in this manner). Wheat embryos were extracted from pollinated florets at 14-20 days after pollination for embryo rescue to recover haploid plantlets from the wheat× maize haploid induction system. Excised embryos were cultured on either full strength MS (Murashige and Skoog 1962) or ½ MS or B5 basal medium containing various modifications of organic supplements and grown in vitro for 1-5 weeks at 20-25° C. and 16-hour day length. For example, pollen of T0 progeny from transgenic maize line MZKE172601A100A containing vector 24039 was used to pollinate spikes of CMS line 16A300292 to induce wheat haploids. Haploid embryos were rescued and the resulting wheat haploid seedlings were sampled for qPCR analysis to determine the copy number of VLHP target sequences (Table 7). In this analysis, we tested for the Cas9 transgene using assay #2540. All wheat embryos rescued and tested lacked this transgene and gave scores of "0" for Cas9, because they do not have any corn DNA in the developing embryo and therefore do not have the transgene. The corn DNA is totally eliminated, kicked out or fails to be fully delivered in the first place during the haploid induction process, taking place during and/or after fertilization). In addition to Cas9, we test for assays #3332 and #3333, which give non-specific amplification of both VLHP2-2A and -2D alleles. These assays typically read as "2" or ">2" in haploid wheat, and the majority of the haploids we produced using the transgenic maize pollen scored 2 or >2 for these assays. We used these assays to look for putative edited haploids, by looking for scores of 0 or 1. A call of "1" might indicate that one of the two alleles, either VLHP2-2A, or -2D, was edited. Finally, we tested for assay 3255 in AC Nanda haploids, which detects VLHP2-2B specifically. The CMS line does not amplify this assay, even when it is wild-type, so we did not use it for the CMS haploids. The unedited haploids give a score of a "2," while putative edited haploids are found because they have a score of "0." A score of "1" might indicate a faulty reading or a chimeric, partially-edited sample.

As an example, one of the AC Nanda haploid plants 440-A5 was found to contain mutation in TaVLHP2-2B gene, but not in its orthologs TaVLHP2-2A and TaVLHP2-2D in the A and D sub-genomes (Table 7). The Taqman data also showed that it lacked the Cas9 transgene. The mutation within the TaVLHP2-2B target region was further characterized by sequencing, but although we were able to amplify the A and D alleles, we could no longer amplify the B allele, suggesting that there is a larger edit present, likely a large deletion, that results in the PCR product no longer amplifying.

As another example, one of the CMS haploid plants 450-D11 was found to contain mutation in either the TaVLHP2-2D or -2A homologues, according to the score of "1" for both assays 3332 and 3333. (Table 7). The taqman data showed that it lacked the Cas9 transgene. The TaVLHP2-2A, 2B and 2D target regions were further characterized by sequencing, but although we were able to amplify the A and B alleles, we could no longer amplify the D allele, suggesting that there is a larger edit present that led to PCR failure.

Considering the 2295 wheat haploids produced from crosses to maize pollen carrying one of the following five preferred-pollen expression constructs (24038, 24039, 24091, and 24094), we found 15 haploids that gave Taqman assay data that indicated possible editing at either the VLHP-2A, VLHP-2D, or VLHP-2B target sites. After sequencing, seven of those haploids were found to have wild-type sequences at the target sites, and were called false positives due to Taqman error. These errors are thought to be either due to the fact that assays #3332 and #3333 gave non-specific amplification of both VLHP-2A and -2D alleles, leading to some missed calls, or due to low DNA quantity.

Of the remaining 8 putative edited haploids, six were AC Nanda (440-B3, 440-D3, 440-A5, 447-G8, 456-G9, 459-A2) where the editing transgene was from construct 24038. Four of those (440-B3, 440-D3, 440-A5, and 456-G9) contained edits in VLHP2-2B. These were found because they had a Taqman score of "0" for assay 3255. These plants lacked Cas9 (score of "0") but had wild-type "2" scores for VLHP2-2A or VLHP2-2D (assays #3332 and #3333) indicating they were not edited that those sites. These six plants were confirmed to be haploids by ploidy analysis. We attempted to sequence the edited alleles, but while the PCR and sequencing reactions worked well for 2A and 2D, we were not able to obtain a PCR product for 2B. We repeated the PCR several times using a range of reaction conditions but could not amplify the 2B homeologs from these haploid plants. This may indicate that the editing caused a large change in the 2B gene in these plants that may end up deleting the primer annealing site. We expect that many of the CMS plants also have edits at the VLHP2-2B target site, but we did not have an assay to detect the VLHP2-2B allele from the CMS line.

Considering AC Nanda alone, we calculate an overall editing rate at that allele of 0.7% for all constructs, but a particularly high editing rate of 1.4% for construct 24038.

In addition to these four edited haploids with scores of "0" for 3255, several other plants gave scores of "0 or 1" or "1" for 3255, which indicates possible chimerism (partial editing in certain cell lineages of the embryo or plantlet), but we did not follow up on those plants. For AC Nanda homolog VLHP2-2A, plant 447-G8 contained an edit which we were also not able to sequence because the PCR reaction failed, even though 2B and 2D did amplify and contained wild-type sequence. We repeated the PCR several times using a range of reaction conditions but could not amplify the 2A homolog. Similarly, for VLHP2-2D, plant 459-A2 contained an edit which we were not able to sequence because the PCR reaction failed. We repeated the PCR several times using a range of reaction conditions but could not amplify the 2D homolog. We also found putative edits in 447-H12 and 440-G6, but upon sequencing we found that these were false positives.

For the CMS haploids, plant 450-D11 gave scores of "1" for both assay #3332 and 3333 (Table 7). Upon sequencing, we found that the 2A homolog had wild-type sequence, but we could not PCR-amplify the 2D homolog, suggesting that a large edit had occurred. We repeated the PCR several times using a range of reaction conditions but could not amplify the 2D homolog. For plant 452-B11, the Taqman score was "0" for #3332 (VLHP2-2A), and we could not amplify that allele for sequencing, even though the 2D and 2B PCR products and sequences were normal. We repeated the PCR several times using a range of reaction conditions but could not amplify the 2A homolog. We also found five plants that had putative edits according to the Taqman data for assays 3332 and 3333, but PCR-sequencing showed these to be false positives; the sequence was wild-type (unedited).

In total, we found two edited CMS haploids and six edited AC Nanda haploids. There may be many more edited haploids that we were not able to detect because we did not have assays for the 2B gene for the CMS plants, nor for the VLHP3 gene target sites of the guide RNA in these five constructs.

The sequencing data from these edited haploids are consistent with the concept of a large deletion, inversion or rearrangement around the guide RNA target site, and extending far enough away to possibly include removal of one of the primer binding sites. This type of large change is not uncommon during editing by Cas9, especially in tissues where DNA repair via non-homologous end-joining is slower or inhibited—which may be the case in the just-fertilized zygote or early haploid wheat embryo.

TABLE 7

Sequencing data from edited wheat haploids.

| Plant ID | Construct ID | copy # | TAV_2A 3332 Raw Copy # | TAV_2A 3332 Copy # level | TAV_2D 3333 Raw Copy # | TAV_2D 3333 Copy # level | TAV_2B 3255 Raw Copy # | TAV_2B 3255 Copy # level | PMI 1750 Raw Copy # | PMI 1750 Copy # level | Cas9 2540 Raw Copy # | Cas9 2540 Copy # level | Sequencing result |
|---|---|---|---|---|---|---|---|---|---|---|---|---|---|
| CMS | | | | | | | | | | | | | |
| 427-A2 | WT | N/A | 2.44 | >2 | 2.38 | 2 | Not tested | | 0.00 | 0 | 0.00 | 0 | not sequenced |
| 427-B2 | WT | N/A | 1.99 | 2 | 1.99 | 2 | Not tested | | 0.00 | 0 | 0.00 | 0 | not sequenced |
| 427-C2 | WT | N/A | 2.02 | 2 | 2.07 | 2 | Not tested | | 0.00 | 0 | 0.00 | 0 | not sequenced |
| 427-D2 | WT | N/A | 2.31 | 2 | 2.16 | 2 | Not tested | | 0.00 | 0 | 0.00 | 0 | not sequenced |
| 427-A10 | 24091 | 2 | 2.07 | 2 | 1.66 | 2 | Not tested | | 0.00 | 0 | 0.00 | 0 | not sequenced |
| 427-B10 | 24091 | 2 | 1.95 | 2 | 1.84 | 2 | Not tested | | 0.00 | 0 | 0.00 | 0 | not sequenced |
| 427-C10 | 24091 | 2 | 1.93 | 2 | 2.28 | 2 | Not tested | | 0.00 | 0 | 0.00 | 0 | not sequenced |
| 427-D10 | 24091 | 2 | 2.59 | >2 | 2.48 | >2 | Not tested | | 0.00 | 0 | 0.00 | 0 | not sequenced |
| 427-E10 | 24091 | 2 | 1.90 | 2 | 1.78 | 2 | Not tested | | 0.00 | 0 | 0.00 | 0 | not sequenced |
| 427-F10 | 24091 | 2 | 2.03 | 2 | 1.96 | 2 | Not tested | | 0.00 | 0 | 0.00 | 0 | not sequenced |
| 427-G10 | 24091 | 2 | 2.08 | 2 | 2.25 | 2 | Not tested | | 0.00 | 0 | 0.00 | 0 | not sequenced |
| 427-H10 | 24091 | 2 | 0.58 | 1 | 0.81 | 1 | Not tested | | 0.00 | 0 | 0.00 | 0 | A and D were both WT |
| 427-A11 | 24091 | 2 | 1.57 | 1 or 2 | 1.93 | 2 | Not tested | | 0.00 | 0 | 0.00 | 0 | not sequenced |
| 427-B11 | 24091 | 2 | 1.41 | 1 or 2 | 1.63 | 2 | Not tested | | 0.00 | 0 | 0.00 | 0 | not sequenced |

TABLE 7-continued

Sequencing data from edited wheat haploids.

| Plant ID | Construct ID | copy # | TAV_2A 3332 Raw Copy # | TAV_2A 3332 Copy # level | TAV_2D 3333 Raw Copy # | TAV_2D 3333 Copy # level | TAV_2B 3255 Raw Copy # | TAV_2B 3255 Copy # level | PMI 1750 Raw Copy # | PMI 1750 Copy # level | Cas9 2540 Raw Copy # | Cas9 2540 Copy # level | Sequencing result |
|---|---|---|---|---|---|---|---|---|---|---|---|---|---|
| 427-C11 | 24091 | 2 | 1.06 | 1 | 1.21 | 1 | Not tested | | 0.01 | 0 | 0.01 | 0 | not sequenced |
| 427-D11 | 24091 | 2 | 1.98 | 2 | 2.03 | 2 | Not tested | | 0.00 | 0 | 0.00 | 0 | not sequenced |
| 427-E11 | 24091 | 2 | 1.94 | 2 | 1.94 | 2 | Not tested | | 0.00 | 0 | 0.00 | 0 | not sequenced |
| 427-F11 | 24091 | 2 | 1.84 | 2 | 1.84 | 2 | Not tested | | 0.00 | 0 | 0.00 | 0 | not sequenced |
| 427-G11 | 24091 | 2 | 1.54 | 1 or 2 | 1.76 | 2 | Not tested | | 0.00 | 0 | 0.00 | 0 | not sequenced |
| 427-H11 | 24091 | 2 | 1.75 | 2 | 1.76 | 2 | Not tested | | 0.00 | 0 | 0.00 | 0 | not sequenced |
| 427-A12 | 24091 | 2 | 1.99 | 2 | 2.15 | 2 | Not tested | | 0.00 | 0 | 0.00 | 0 | not sequenced |
| 427-B12 | 24091 | 2 | 0.72 | 1 | 1.26 | 1 | Not tested | | 0.00 | 0 | 0.00 | 0 | A and D were both WT |
| 427-C12 | 24091 | 2 | 1.69 | 2 | 1.50 | 1 or 2 | Not tested | | 0.00 | 0 | 0.01 | 0 | not sequenced |
| 427-D12 | 24091 | 1 | 2.34 | 2 | 2.03 | 2 | Not tested | | 0.00 | 0 | 0.00 | 0 | not sequenced |
| 427-E12 | 24091 | 1 | 1.98 | 2 | 2.04 | 2 | Not tested | | 0.00 | 0 | 0.00 | 0 | not sequenced |
| 427-F12 | 24091 | 1 | 1.89 | 2 | 1.97 | 2 | Not tested | | 0.00 | 0 | 0.00 | 0 | not sequenced |
| 427-G12 | 24091 | 1 | 1.56 | 1 or 2 | 1.77 | 2 | Not tested | | 0.00 | 0 | 0.00 | 0 | not sequenced |
| 427-H12 | 24091 | 1 | 1.57 | 1 or 2 | 2.36 | 2 | Not tested | | 0.00 | 0 | 0.00 | 0 | not sequenced |
| 428-A3 | 24091 | 1 | 2.12 | 2 | 1.75 | 2 | Not tested | | 0.00 | 0 | 0.00 | 0 | not sequenced |
| 428-B3 | 24091 | 1 | 2.69 | >2 | 1.89 | 2 | Not tested | | 0.00 | 0 | 0.00 | 0 | not sequenced |
| 428-C3 | 24091 | 1 | 2.09 | 2 | 2.44 | >2 | Not tested | | 0.00 | 0 | 0.00 | 0 | not sequenced |
| 428-D3 | 24091 | 1 | 2.05 | 2 | 2.39 | 2 | Not tested | | 0.00 | 0 | 0.00 | 0 | not sequenced |
| 428-E3 | 24091 | 1 | 2.48 | >2 | 2.87 | >2 | Not tested | | 0.00 | 0 | 0.00 | 0 | not sequenced |
| 428-F3 | 24091 | 1 | 2.33 | 2 | 2.76 | >2 | Not tested | | 0.00 | 0 | 0.00 | 0 | not sequenced |
| 428-G3 | 24091 | 1 | 2.84 | >2 | 0.22 | 0 | Not tested | | 0.00 | 0 | 0.00 | 0 | A and D were both WT |
| 428-H3 | 24091 | 1 | 2.83 | >2 | 2.60 | >2 | Not tested | | 0.00 | 0 | 0.00 | 0 | not sequenced |
| 450-A11 | 24094 | 1 | 1.97 | 2 | 2.24 | 2 | Not tested | | 0.00 | 0 | 0.00 | 0 | not sequenced |
| 450-B11 | 24094 | 1 | 2.13 | 2 | 2.04 | 2 | Not tested | | 0.00 | 0 | 0.00 | 0 | not sequenced |
| 450-C11 | 24094 | 1 | 2.15 | 2 | 2.18 | 2 | Not tested | | 0.00 | 0 | 0.00 | 0 | not sequenced |
| 450-D11 | 24094 | 1 | 1.04 | 1 | 0.99 | 1 | Not tested | | 0.00 | 0 | 0.00 | 0 | A & B were WT; D failed |
| 450-E11 | 24094 | 1 | 2.35 | 2 | 2.01 | 2 | Not tested | | 0.00 | 0 | 0.00 | 0 | not sequenced |
| 450-F11 | 24094 | 1 | 2.02 | 2 | 1.90 | 2 | Not tested | | 0.00 | 0 | 0.00 | 0 | not sequenced |
| 450-G11 | 24039 | 1 | 1.76 | 2 | 1.72 | 2 | Not tested | | 0.00 | 0 | 0.00 | 0 | not sequenced |
| 450-H11 | 24039 | 1 | 2.07 | 2 | 2.04 | 2 | Not tested | | 0.00 | 0 | 0.00 | 0 | not sequenced |
| 452-H4 | 24038 | 2 | 2.62 | >2 | 0.01 | 0 | Not tested | | 0.00 | 0 | 0.00 | 0 | A and D were both WT |
| 452-A11 | 24038 | 2 | 2.24 | 2 | 2.28 | 2 | Not tested | | 0.00 | 0 | 0.00 | 0 | not sequenced |
| 452-B11 | 24038 | 2 | 0.00 | 0 | 2.22 | 2 | Not tested | | 0.00 | 0 | 0.00 | 0 | B & D were WT; A failed |
| 452-C11 | 24038 | 2 | 2.55 | >2 | 2.22 | 2 | Not tested | | 0.00 | 0 | 0.00 | 0 | not sequenced |
| 452-D11 | 24038 | 2 | 0.82 | 1 | 1.26 | 1 | Not tested | | 0.00 | 0 | 0.00 | 0 | A and D were both WT |
| 452-E11 | 24038 | 2 | 2.43 | >2 | 2.36 | 2 | Not tested | | 0.00 | 0 | 0.00 | 0 | not sequenced |
| 452-F11 | 24038 | 2 | 2.12 | 2 | 2.21 | 2 | Not tested | | 0.00 | 0 | 0.00 | 0 | not sequenced |
| 452-G11 | 24038 | 2 | 2.38 | 2 | 1.99 | 2 | Not tested | | 0.00 | 0 | 0.00 | 0 | not sequenced |
| 452-H11 | 24038 | 2 | 1.82 | 2 | 1.83 | 2 | Not tested | | 0.00 | 0 | 0.00 | 0 | not sequenced |

TABLE 7-continued

Sequencing data from edited wheat haploids.

| Plant ID | Construct ID | copy # | TAV_2A 3332 Raw Copy # | TAV_2A 3332 Copy # level | TAV_2D 3333 Raw Copy # | TAV_2D 3333 Copy # level | TAV_2B 3255 Raw Copy # | TAV_2B 3255 Copy # level | PMI 1750 Raw Copy # | PMI 1750 Copy # level | Cas9 2540 Raw Copy # | Cas9 2540 Copy # level | Sequencing result |
|---|---|---|---|---|---|---|---|---|---|---|---|---|---|
| NANDA | | | | | | | | | | | | | |
| 425-A2 | WT | N/A | 2.30 | 2 | 2.62 | >2 | 1.908 | 2 | 0.00 | 0 | 0.00 | 0 | not sequenced |
| 425-B2 | WT | N/A | 2.28 | 2 | 2.41 | >2 | 2.274 | 2 | 0.00 | 0 | 0.00 | 0 | not sequenced |
| 425-C2 | WT | N/A | 2.47 | >2 | 1.92 | 2 | 1.962 | 2 | 0.00 | 0 | 0.00 | 0 | not sequenced |
| 425-D2 | WT | N/A | 2.10 | 2 | 2.11 | 2 | 1.772 | 2 | 0.00 | 0 | 0.00 | 0 | not sequenced |
| 447-A12 | 24038 | 2 | 1.72 | 2 | 1.90 | 2 | 2.02 | 2 | 0.00 | 0 | 0.00 | 0 | not sequenced |
| 447-B12 | 24039 | 2 | 2.18 | 2 | 1.62 | 2 | 1.47 | 1 or 2 | 0.00 | 0 | 0.00 | 0 | not sequenced |
| 447-C12 | 24039 | 2 | 1.78 | 2 | 2.40 | 2 | 1.90 | 2 | 0.00 | 0 | 0.00 | 0 | not sequenced |
| 447-D12 | 24039 | 2 | 1.58 | 1 or 2 | 1.70 | 2 | 2.18 | 2 | 0.00 | 0 | 0.00 | 0 | not sequenced |
| 447-E12 | 24039 | 2 | 2.13 | 2 | 1.82 | 2 | 2.14 | 2 | 0.00 | 0 | 0.00 | 0 | not sequenced |
| 447-F12 | 24039 | 2 | 2.25 | 2 | 1.78 | 2 | 2.15 | 2 | 0.00 | 0 | 0.00 | 0 | not sequenced |
| 447-G12 | 24039 | 2 | 1.90 | 2 | 2.30 | 2 | 2.23 | 2 | 0.00 | 0 | 0.00 | 0 | not sequenced |
| 447-H12 | 24039 | 1 | 2.34 | 2 | 1.95 | 2 | 0.89 | 1 | 0.00 | 0 | 0.00 | 0 | A, B, and D were all WT |
| 440-A2 | 24039 | 1 | 1.72 | 2 | 1.71 | 2 | 1.24 | 1 | 0.00 | 0 | 0.00 | 0 | not sequenced |
| 440-B2 | 24039 | 1 | 2.30 | 2 | 2.56 | >2 | 1.77 | 2 | 0.00 | 0 | 0.00 | 0 | not sequenced |
| 440-C2 | 24039 | 1 | 3.05 | >2 | 1.85 | 2 | 2.01 | 2 | 0.00 | 0 | 0.00 | 0 | not sequenced |
| 440-D2 | 24039 | 1 | 1.66 | 2 | 1.70 | 2 | 1.44 | 1 or 2 | 0.00 | 0 | 0.00 | 0 | not sequenced |
| 440-E2 | 24039 | 1 | 2.23 | 2 | 1.91 | 2 | 2.04 | 2 | 0.00 | 0 | 0.00 | 0 | not sequenced |
| 440-F2 | 24039 | 1 | 2.63 | >2 | 2.07 | 2 | 2.28 | 2 | 0.00 | 0 | 0.00 | 0 | not sequenced |
| 440-G2 | 24038 | 11 | 1.91 | 2 | 1.87 | 2 | 2.10 | 2 | 0.00 | 0 | 0.00 | 0 | not sequenced |
| 440-H2 | 24038 | 1 | 1.85 | 2 | 1.80 | 2 | 1.97 | 2 | 0.00 | 0 | 0.00 | 0 | not sequenced |
| 440-A3 | 24038 | 1 | 2.52 | >2 | 2.05 | 2 | 1.99 | 2 | 0.00 | 0 | 0.00 | 0 | not sequenced |
| 440-B3 | 24038 | 1 | 2.16 | 2 | 2.19 | 2 | 0.00 | 0 | 0.00 | 0 | 0.00 | 0 | A & D were WT; B failed |
| 440-C3 | 24038 | 1 | 2.58 | >2 | 2.02 | 2 | 2.78 | >2 | 0.00 | 0 | 0.00 | 0 | not sequenced |
| 440-D3 | 24038 | 1 | 2.34 | 2 | 2.32 | 2 | 0.00 | 0 | 0.00 | 0 | 0.00 | 0 | A & D were WT; B failed |
| 440-E3 | 24038 | 1 | 2.49 | >2 | 2.23 | 2 | 2.47 | >2 | 0.00 | 0 | 0.00 | 0 | not sequenced |
| 440-F3 | 24038 | 1 | 2.08 | 2 | 2.10 | 2 | 2.17 | 2 | 0.00 | 0 | 0.00 | 0 | not sequenced |
| 440-F4 | 24038 | 1 | 1.73 | 2 | 1.47 | 1 or 2 | 1.41 | 1 or 2 | 0.00 | 0 | 0.00 | 0 | not sequenced |
| 440-G4 | 24038 | 1 | 1.53 | 1 or 2 | 2.02 | 2 | 1.99 | 2 | 0.00 | 0 | 0.00 | 0 | not sequenced |
| 440-H4 | 24038 | 1 | 2.22 | 2 | 1.90 | 2 | 0.00 | 0 | 0.00 | 0 | 0.00 | 0 | not sequenced |
| 440-A5 | 24038 | 1 | 2.22 | 2 | 1.90 | | | | | | | | A & D were WT; B failed |
| 440-A6 | 24039 | 2 | 2.49 | >2 | 2.32 | 2 | 1.84 | 2 | 0.00 | 0 | 0.00 | 0 | not sequenced |
| 440-B6 | 24039 | 2 | 2.12 | 2 | 2.03 | 2 | 2.21 | 2 | 0.00 | 0 | 0.00 | 0 | not sequenced |
| 440-C6 | 24039 | 2 | 2.63 | >2 | 2.07 | 2 | 2.28 | 2 | 0.00 | 0 | 0.00 | 0 | not sequenced |
| 440-D6 | 24039 | 2 | 2.49 | >2 | 2.23 | 2 | 2.47 | >2 | 0.00 | 0 | 0.00 | 0 | not sequenced |
| 440-E6 | 24039 | 2 | 2.45 | >2 | 2.20 | 2 | 2.32 | 2 | 0.00 | 0 | 0.00 | 0 | not sequenced |
| 440-F6 | 24039 | 2 | 2.10 | 2 | 1.92 | 2 | 1.91 | 2 | 0.00 | 0 | 0.00 | 0 | not sequenced |
| 440-G6 | 24039 | 2 | 0.57 | 1 | 0.66 | 1 | 0.53 | 1 | 0.00 | 0 | 0.00 | 0 | A, B & D were all WT |
| 440-H6 | 24039 | 2 | 1.81 | 2 | 1.96 | 2 | 2.51 | >2 | 0.00 | 0 | 0.00 | 0 | not sequenced |
| 447-A8 | 24038 | 1 | 2.42 | >2 | 2.21 | 2 | 2.10 | 2 | 0.00 | 0 | 0.00 | 0 | not sequenced |
| 447-B8 | 24038 | 1 | 2.46 | >2 | 2.32 | 2 | 2.09 | 2 | 0.00 | 0 | 0.00 | 0 | not sequenced |
| 447-C8 | 24038 | 1 | 2.09 | 2 | 2.08 | 2 | 2.29 | 2 | 0.00 | 0 | 0.00 | 0 | not sequenced |
| 447-D8 | 24038 | 1 | 2.13 | 2 | 2.14 | 2 | 2.34 | 2 | 0.00 | 0 | 0.00 | 0 | not sequenced |
| 447-E8 | 24038 | 11 | 2.36 | 2 | 2.31 | 2 | 2.44 | >2 | 0.00 | 0 | 0.00 | 0 | not sequenced |
| 447-F8 | 24038 | 1 | 2.72 | >2 | 2.28 | 2 | 2.00 | 2 | 0.00 | 0 | 0.00 | 0 | not sequenced |
| 447-G8 | 24038 | 1 | 0.71 | 1 | 1.34 | 1 or 2 | 2.33 | 2 | 0.00 | 0 | 0.00 | 0 | B & D were WT; A failed |
| 447-H8 | 24038 | 1 | 2.25 | 2 | 2.29 | 2 | 2.01 | 2 | 0.00 | 0 | 0.00 | 0 | not sequenced |
| 456-A9 | 24038 | 2 | 2.19 | 2 | 1.59 | 1 or 2 | 2.03 | 2 | 0.00 | 0 | 0.00 | 0 | not sequenced |
| 456-B9 | 24038 | 2 | 2.13 | 2 | 2.11 | 2 | 2.02 | 2 | 0.00 | 0 | 0.00 | 0 | not sequenced |
| 456-C9 | 24038 | 2 | 2.16 | 2 | 1.85 | 2 | 1.45 | 1 or 2 | 0.00 | 0 | 0.00 | 0 | not sequenced |
| 456-D9 | 24038 | 2 | 2.56 | >2 | 2.18 | 2 | 1.76 | 2 | 0.00 | 0 | 0.00 | 0 | not sequenced |
| 456-E9 | 24038 | 2 | 2.29 | 2 | 2.03 | 2 | 1.65 | 2 | 0.00 | 0 | 0.00 | 0 | not sequenced |
| 456-F9 | 24038 | 2 | 2.24 | 2 | 2.02 | 2 | 2.05 | 2 | 0.00 | 0 | 0.00 | 0 | not sequenced |

TABLE 7-continued

Sequencing data from edited wheat haploids.

| Plant ID | Construct ID | copy # | TAV_2A 3332 | | TAV_2D 3333 | | TAV_2B 3255 | | PMI 1750 | | Cas9 2540 | | Sequencing result |
|---|---|---|---|---|---|---|---|---|---|---|---|---|---|
| | | | Raw Copy # | Copy # level | Raw Copy # | Copy # level | Raw Copy # | Copy # level | Raw Copy # | Copy # level | Raw Copy # | Copy # level | |
| 456-G9 | 24038 | 2 | 2.49 | >2 | 2.03 | 2 | 0.00 | 0 | 0.00 | 0 | 0.00 | 0 | A & D were WT; B failed |
| 456-H9 | 24038 | 2 | 1.78 | 2 | 1.62 | 2 | 1.38 | 1 or 2 | 0.00 | 0 | 0.00 | 0 | not sequenced |
| 459-A2 | 24038 | 2 | 1.38 | 1 or 2 | 1.11 | 1 | 0.94 | 1 | 0.00 | 0 | 0.00 | 0 | A & B were WT; D failed |
| 459-B2 | 24038 | 2 | 1.86 | 2 | 1.91 | 2 | 2.12 | 2 | 0.00 | 0 | 0.00 | 0 | not sequenced |
| 459-C2 | 24038 | 2 | 1.94 | 2 | 2.09 | 2 | 1.42 | 1 or 2 | 0.00 | 0 | 0.00 | 0 | not sequenced |
| 459-D2 | 24038 | 2 | 2.09 | 2 | 2.05 | 2 | 1.91 | 2 | 0.00 | 0 | 0.00 | 0 | not sequenced |
| 459-E2 | 24038 | 2 | 2.18 | 2 | 2.12 | 2 | 2.12 | 2 | 0.00 | 0 | 0.00 | 0 | not sequenced |

Overall, we found that the editing frequency (number of edited haploids identified divided by the total number of haploids) for construct 24038 was 0.79%; for construct 24039 it was 0%; for construct 24091 it was 0%, and for construct 24094 it was 0.75%. However, this editing rate is certainly an under-estimate because we did not have assays to detect edits at many of the guide RNA target sites. Additionally, because we used T0 pollen that was either 1 or 2 copy, we know that with the 1-copy pollen, only 50% of the fertilizing pollen grains will contain the Cas9, and so only half of the embryos have the opportunity to be edited; similarly, for 2 copy parents, assuming random segregation of the transgenes in the male meiosis, we would expect about 75% of the pollen to contain Cas9, so 25% of the embryos cannot be edited. It is reasonable to conclude that, when one is trying to use this simultaneous editing plus haploid induction technology with the editing machinery carried by the pollen, it may in some cases be more optimal to use a promoter that express specifically or highly in pollen and in sperm cells, so that the Cas9 can be expressed at a higher level. In cases where the gene target might impact development of the haploid inducer plant, having a pollen or sperm-preferred promoter that does not express in leaves might be useful because it would avoid editing the target gene in the haploid inducer plant during development—perhaps editing it for the first time in pollen.

Because the sperm cells fertilize the egg, they have the potential to deliver Cas9 RNA and protein (as well as the transgene DNA itself, integrated into one of the male chromosomes that will be eliminated). As we demonstrated in the wide-cross work in this example, it may work well to have the Cas9 and/or guide RNA under the control of a promoter that specifically or highly expresses in pollen, and in particular in sperm cells, when using a haploid inducer as the male to edit elite lines. We do not know exactly whether MATRILINEAL, EXPB1, EXPB2, and PRF3 express in the vegetative nucleus, the sperm cells, or both, and whether there might be any expression in a zygote cell type, but these were chosen because they are supposedly highly and/or specifically expressed in pollen. The PRF3 promoter has a DUO1 binding motif in the promoter, which may indicate it expresses in sperm cells. This is consistent with that promoter having higher editing frequency. The fact that we found many edited wheat haploids after the wide cross makes it clear that when there is high expression of Cas9 in pollen, using these or any other promoter, that expression can lead to editing in the wheat embryos after the wide cross. There is a strong possibility that these promoters, as well as other promoters that drive expression in pollen, or in particular in the sperm cells, might increase the efficiency of the editing process during corn haploid induction, or rice haploid induction.

Similarly, in the next example below, we show haploid editing in a dicot using a CENH3-modified-haploid inducer line, and we use constitutive promoter to drive the Cas9. But in an attempt to increase the efficiency of the haploid editing, we could opt to use a promoter that drives high and/or specific expression in egg cells, such as the EGG APPARATUS1 gene's promoter ("prEA1") (see, e.g., Gray-Mitsumune, M. and Matton, D. P., *The Egg apparatus 1 gene from maize is a member of a large gene family found in both monocots and dicots*, PLANTA 223(3):618-625 (February 2006)) or EGG CELL1 (EC1) (see, e.g., Sprunck S, et al., *Egg cell-secreted EC1 triggers sperm cell activation during double fertilization.* Science 2012; 338:1093-97; PMID: 23180860; http://dx.doi.org/10.1126/science.1223944).

As an example of this, one could use a sperm-cell expressed promoter, such as the *Arabidopsis* sperm-specific DUO1 promoter (see, e.g., Engel, et al., *Green Sperm. Identification of Male Gamete Promoters in Arabidopsis*, PLANT PHYSIOLOGY August 2005, 138 (4) 2124-2133; DOI: 10.1104/pp. 104.054213), or homologs of DUO1 from other species (for instance, the maize genes GRMZM2G105137 and GRMZM2G046443 are both DUO1 homologs that share a similar pollen-specific expression pattern). If one used any of these to drive Cas9 expression in the sperm cells of a haploid inducer line like RWK, NP2222-HI, or an matl mutant, it might make a highly efficient haploid editor line for use in editing diverse elite maize or wheat germplasm, via intraspecific or wide cross, respectively.

Other suitable sperm-expressed promoters for this concept of driving high Cas9 expression in sperm cells would include the DUO1 homologs in wheat, rice, barley, tomato, sunflower, or other monocots or dicots. Other suitable promoters for this concept are shown in Table 8 below. These promoters, or their homologs in crop species—might be very useful for this concept. The principal at work is that gamete cell expression of the editing machinery can increase the rate or efficiency of this invention because it means that there will be abundant editing protein or RNA present or delivered to the embryo during fertilization so that editing can happen rapidly.

TABLE 8

Promoters List: promoters one can use in a transgene to drive high sperm cell expression of editing machinery to boost the efficiency of simultaneous editing and doubled-haploid induction ("SEDHI").

| Gene Name | Gene ID | Maize Ortholog | Rice Ortholog |
|---|---|---|---|
| DUO1 | At3G60460 | GRMZM2G105137, GRMZM2G046443 | LOC_Os04g46384 |
| MGH3 | At1G19890 | NA | NA |
| GEX1 | At5G55490 | GRMZM2G388045 | LOC_Os09g27040, LOC_Os07g47194 |
| GEX2 | At5G49150 | GRMZM2G036832 | LOC_Os09g25650 |
| GEX3 | At5G16020 | GRMZM2G458159 | LOC_Os01g42060 |
| HAP2/GSC1 | At4G11720 | GRMZM2G412911 | LOC_Os05g18730 |
| CycB1 | At4G37490 | NA | NA |
| DAZ1 | At2G17180 | GRMZM2G132057 | NA |
| DAZ2 | At4G35280 | NA | LOC_Os02g19180 |
| DAZ 3 | At4G35700 | NA | NA |
| PCR11 | At1G68610 | NA | NA |
| DAN1 | At3G04620 | NA | NA |
| TIP1 | AT3G47440 | NA | LOC_Os04g46490 |
| MKKK20 | AT3G50310 | NA | NA |
| DAF1 | At3G62230 | NA | NA |
| DAW1 | At4G35560 | GRMZM2G176647 | NA |
| DAU2/DMP9 | At5G39650 | NA | NA |

VII. Simultaneous Haploid Induction and Editing in Dicots Via Wide Cross or Via Crosses to CENH3-Altered Lines or Other Haploid Inducing Lines.

In vivo haploid induction can also be achieved using interspecific or intergeneric wide crosses on dicot plant species, for example, in cotton (Turcotte et al. 1969, Semigametic production of haploids in pima cotton. Crop Sci. 9:653-655) and tobacco (Burke et al, 1979, Maternal haploids of *Nicotiana tabacum* L. Science 206:585; Wernsman et al. 1989, Androgenetic vs. gynogenetic doubled haploids of tobacco. Crop Sci. 29:1151-1155). Haploid *Arabidopsis* plants can be obtained by crossing with pollen from mutant CENH3 plant, or by crossing said plants as females to wild type pollen (Ravi and Chan, 2010, Haploid plants produced by centromere-mediated genome elimination. Nature 464: 615-618). Other candidate genes which may be modified to generate a haploid inducer and SEDHI editing line include KNL2 and CENPC (both of which may operate via centromere-mediated uniparental genome elimination) as well as MSI2 and sunflower PLA2. In this case, the haploid-inducing genome (be it the male or female in the cross) also contains the editing machinery, so that the editing can be achieved during the haploid induction process, with the result being an edited maternal or paternal haploid progeny plant without altered CENH3 or editing transgenes. See, e.g., WO 2017/004375, incorporated herein by reference in its entirety. Transgenic locus expressing editing machinery can be introduced into any dicot crops or their wild relatives of *Brassica*, tomato, pepper, lettuce, eggplant, soybean, sunflower, sugar beet, cotton, alfalfa, tobacco, and others. The transgenic lines expressing editing machinery are then used as pollen donors, or in the case of CENH3, either pollen donors or acceptors, in interspecific or intergeneric wide crosses for haploid induction and simultaneous genome editing. For example, *N. africana* transgenic CRISPR-Cas9 lines expressing sgRNA targeting tobacco gibberellin 20-oxidase are created through *Agrobacterium*-mediated transformation and used to pollinate emasculated tobacco flowers to induce haploid plants with their genome edited at the gibberellin 20-oxidase locus. Preferably, an easily transformable line with large number of pollen is used as pollen donor for haploid induction and to provide the editing machinery transiently. The recipient plant for haploid production has flowers that are easy to emasculate or is male sterile. More preferably, a color or other visual marker is present in the induction line or is included in the editing locus to easily differentiate haploid embryos or plants from diploids resulted from normal zygote development.

We exemplified this by utilizing an *Arabidopsis* haploid inducer line in the Columbia ecotype, and transforming it with a construct encoding expression of Cas9 and a single guide RNA targeting the GLABROUS1 gene (GL1) which, when knocked out, gives a trichome-less phenotype. We crossed the T0s as females by Landsberg Erecta (Ler) ecotype pollen, and recovered gl1 edited haploid progeny.

The haploid inducer materials were obtained from the Comai lab at UC Davis. These materials are typically utilized as paternal haploid inducer lines (causing androgenesis, when crossed as females to wild-type males) but can also act as maternal haploid inducers (causing gynogenesis, when crossed as males to wild-type females). These lines have been altered to become haploid inducers by replacing the native CENH3 gene with a *Zea mays* CENH3 transgene as reported in (Maheshwari, et al, 2017, Centromere location in *Arabidopsis* is unaltered by extreme divergence in CENH3 protein sequence. Genome Research 27(3)).

In particular, both copies of the native AtCENH3 gene was knocked out and complemented with the stably inserted ZmCENH3 transgene, which did not impact normal plant development, and did not produce haploids upon self-pollination, but did produce about 10% haploids upon outcross. This is a modification to the original concept of CENH3-tailswap described in detail in (Ravi and Chan, 2010, Haploid plants produced by centromere-mediated genome elimination. Nature 464: 615-618) and many subsequent publications.

After we obtained the CENH3* lines from UC Davis, we grew them up, confirmed that they had the ZmCENH3 transgene and were homozygous "null" for the native AtCENH3 gene. We did this by designing a taqman qPCR assay for ZmCENH3 (assay #2298) and by using PCR and gel electrophoresis to test 183 seedlings for the zygosity of the AtCENH3 genotype by running PCR using the Xbal forward and reverse primers (SEQ NO TKX and TKY) and Reddy mix at 60° C. annealing temperature and cutting with the Xbal restriction enzyme overnight at 37° C. The wild-type allele would be cut by this enzyme and produce two bands (189 bp, 25 bp) while the mutant would remain at 215 bp. These tests showed that all of the seed that UC Davis sent were homozygous for the mutant allele Atcenh3-1, and that there were multiple copies of the ZmCENH3 transgene present.

Confident that these acquired seeds were indeed haploid inducers, we kept 100 plants and initiated floral dip transformation with binary vector 24075 (SEQ ID NO: 98) containing a sgRNA cassette targeting the *Arabidopsis* (GL1) gene (AT3G27920) at two target sites. The target sequences are 5'-GGAAAAGTTGTAGACTGAGA-3', and 5'-GCAGTGATGAACAATGACGG-3' (complementary strand). The disruption of the GL1 gene produces visible phenotypes of partially or completely glabrous plants (glabrous plants lack trichomes). The Cas9 gene (cCas9-05) in this vector was driven by the *Arabidopsis thaliana* elongation factor promoter. The vector also contains two selectable marker cassettes conferring Kan resistance and AmCyan florescence driven by the CMP-02 promoter and *Glycine max* UBI-01 promoter respectively. The vector was moved into the *agrobacterium* strain EHA101 and then floral dip transformed into the haploid inducer *Arabidopsis* plants.

The transformation protocol was as follows: In the morning we spread 24075 EHA101 RecA *Agrobacterium* obtained from plates to YPSpec100Kan50 plates. We cultured these in 28° C. dark for 24 hours. We prepared infiltration medium (4L): ½ XMS salts (8.66 g), 1λGamborg's B5 vitamins (4 ml), 5% (W/V) sucrose (200 g), 0.044 μM BAP (12.5 mg - - - 12.5 mlDMSO) 40 μL, followed by filter sterilization. We then added 250 μl 40 mg/ml AS (20 mg/L) and 25 μl SIlwet L-77 (50 μl/L) to 500 ml Infiltration media. Using a loop to collect the *Agrobacterium* and put in 50 ml tube with ~10 ml o the filter sterilization, we suspended the *Agrobacterium* until it produced 1 L with an optical density 600 of 0.54. We dipped the inflorescence shoot in to the suspension medium for 20-30 seconds and used the lid to cover the tray. We repeated this for a second time with another suspension of OD600 of 0.552.

About 4 weeks after transformation, approximately 100,000 self-pollinated seeds were harvested and incubated at 4° C. for two days vernalization, and then the seeds were sterilized by soaking in 70% ethanol for 1 minute and then soaking in 50% (V/V) bleach with 0.05% (v/v) Triton X-100 for a further 10 minutes, then washing the seeds in four changes of sterile water. The seeds were then placed on kanamycin (50 μg/ml) plates for germination-screening/selection in a plant tissue culture room (23° C. day, 24° C. night, 16 hours lighting). 38 positive transformants were identified because they were resistant to the kanamycin selection, and they were grown into seedlings before being transferred onto soil and sampled to test for the presence of the Cas9 T-DNA (assay #3049) as well as the status of the two guide RNA cut sites (assays #3321 and #3322). 10 single copy and 15 2-copy events were identified that had both alleles of GL1 mutated and that had a trichomeless phenotype. These plants were prioritized because they had shown evidence of Cas9 activity (by virtue of the mutated GL1 and the glabrous phenotype), they had the Cas9 transgene and they had the ZmCENH3 transgene by qPCR assay. These plants were induced to flower for a long period of time by keeping them in the following growth conditions: 16 hours light, 23° C. Day 20° C. night temperature, not >60% relative humidity.

At the same time as these haploid inducer plants that were transformed with the Cas9 construct were being identified, we were sowing and growing a population of Landsberg Erecta (Ler) seed obtained from the *Arabidopsis* Biological Resource Center at Ohio State University (line #CS20). These are wild type seed and the sequence of the GL1 guide RNA target sites in CS20 match that of the guide RNA in our construct. We allowed both populations to flower and made about 2000 controlled crosses, using the wild-type Ler plants as the male pollen-donor, crossing onto the approximately 25 haploid inducers with the Cas9 construct, which was used as the female. We made up to 100 crosses per female, marking the crossed flowers with a black marker and removing flowers that we did not cross so as to limit the potential of harvesting self-pollinated siliques. In most cases, we emasculated the female flowers prior to pollination by removing the anthers with forceps, again to avoid contamination with self-pollinated seed, but in some cases this was not necessary because the anthers were young or mal-developed.

About 15 days we harvested the siliques which had developed a light brown color. Then we opened the siliques and planted the seeds in the soil. Then put them in the 6° C. (day and light), 8 hours day length, 200 umal/m²s lighting, 60% relative humidity growth chamber for 4 days. Then we transferred them to 16 hours light, 23° C. Day, 20° C. night temperature, not >60% humidity growth chamber for 7-10 days. We observed a high frequency of aborted seed in almost all of the siliques, averaging about 40-50% of the total seeds. This number of aborted embryos is very consistent with the performance of this haploid inducer material in published reports. Without wishing to be constrained by this theory, it has been speculated that the aborted seed is most likely caused by partial or complete genome elimination in the endosperm leading to endosperm imbalance and failure. This is a natural phenomenon in CENH3-type haploid inducer lines during outcross and is likely not connected with the presence of the Cas9 transgene. These aborted embryos do not germinate. Because of the steady and reliable rate of embryo abortion in every outcrossed silique, we ended up using the absence of that phenotype to screen away siliques that were accidental self-pollinations. That way we germinated siliques that had been outcrossed.

In total we recovered approximately 2000 germinated progeny, the majority of which were outcrossed. We identified the edited haploids via a combination of qPCR marker assays and/or phenotypic screening. The markers that we used to detect the edited haploids were as follows.

First, we looked for a "0" score for the ZmCENH3 assay. This indicates that the plant is a haploid because the maternal genome has been lost, and so the ZmCENH3 transgene, which is present in multiple copies of the mother haploid inducer plant, has also been lost. The diploids, in contrast, will be hybrids between the maternal and paternal genome, and will have a "1" or "2" or higher Taqman score for this assay, depending on the copy number of the mother plant. The key is that all diploids will show evidence of this transgene, but paternal haploids, having only the Ler genome, will not and will thus be a "0."

Second, we looked for a "0" score for the Cas9 assay, which indicates that it is non-transgenic. This can also be seen visually by using a fluorescent light and looking for the CFP fluorescent marker.

Third, we looked for a "0" score for one of the GL1 target site assays, which indicates that the plant has been edited. The diploid plants might show a "0," "1" or "2" for those assays, but the haploids either showed a "2" or a "0." The first of the two GL1 guide RNAs apparently had a much higher editing efficiency than the second, because assay 3321 had a high preponderance of "0"s and "1"s in the haploid inducer T0s, but 3322 had mostly "2"s.

Using these assays, we were able to identify unedited haploids (which were "0" for ZmCENH3 and Cas9, but had "2" scores for both GL1 target sites) and also edited haploids (which had a "0" for the ZmCENH3, Cas9 and GL1 (3321) assays). We were also able to identify diploid hybrids that had Cas9 (and often were edited at the GL1 sites) and diploid hybrids that did not have Cas9 (and often had one copy of GL1 edited (from the maternal parent) but not the other, and thus had a score of "1" for the GL1 assay. We were also able to identify several putative edited haploids because they had a score of "0" for the target site assay (3321), the ZmCENH3 (2298) and the Cas9 (3049). See Table 9 below for an example of progeny Taqman data from parent USR01424136 containing three putative edited haploids (plant 254 in well F2, plant 260 in well D3, and plant 261 in plant E3).

TABLE 9

Progeny analysis from parent USR01424136.

| PLATE 1045 HI parent was single copy Cas9 | | AtGL1-1 cut site 3321 | | AtGL1-2 cut site 3322 | | ZmCENH3 2298 | | Cas9 3049 | | | |
|---|---|---|---|---|---|---|---|---|---|---|---|
| Well | Plant ID | Raw Copy # | Copy # level | Raw Copy # | Copy # level | Raw Copy # | Copy # level | Raw Copy # | Copy # level | Putative Haploid | Putative Edited |
| E2 | USR01424136 X Ler-253 | 0.06 | 0 | 0.87 | 1 | 4.30 | >2 | 2.93 | >2 | | x |
| F2 | USR01424136 X Ler-254 | 0.00 | 0 | 0.32 | 0 or 1 | 0.00 | 0 | 0.00 | 0 | x | x |
| G2 | USR01424136 X Ler-255 | 1.32 | 1 or 2 | 2.06 | 2 | 3.16 | >2 | 0.00 | 0 | | |
| H2 | USR01424136 X Ler-256 | 0.02 | 0 | 0.99 | 1 | 2.51 | >2 | 2.99 | >2 | | x |
| A3 | USR01424136 X Ler-257 | 0.04 | 0 | 0.87 | 1 | 2.40 | 2 | 2.84 | >2 | | x |
| B3 | USR01424136 X Ler-258 | 0.03 | 0 | 1.64 | 2 | 2.99 | >2 | 3.17 | >2 | | x |
| C3 | USR01424136 X Ler-259 | 0.03 | 0 | 1.21 | 1 | 5.28 | >2 | 5.28 | >2 | | x |
| D3 | USR01424136 X Ler-260 | 0.06 | 0 | 2.01 | 2 | 0.00 | 0 | 0.00 | 0 | x | x |
| E3 | USR01424136 X Ler-261 | 0.00 | 0 | 2.01 | 2 | 0.01 | 0 | 0.00 | 0 | x | x |
| F3 | USR01424136 X Ler-262 | 2.04 | 2 | 2.10 | 2 | 0.00 | 0 | 0.00 | 0 | x | |
| G3 | USR01424136 X Ler-263 | 1.36 | 1 or 2 | 1.25 | 1 | 0.00 | 0 | 0.00 | 0 | x | |
| H3 | USR01424136 X Ler-264 | 1.75 | 2 | 1.71 | 2 | 0.00 | 0 | 0.00 | 0 | x | |
| A4 | USR01424136 X Ler-265 | 0.00 | 0 | 1.67 | 2 | 3.06 | >2 | 3.16 | >2 | | x |
| B4 | USR01424136 X Ler-266 | 1.66 | 2 | 2.32 | 2 | 0.00 | 0 | 0.00 | 0 | x | |
| C4 | USR01424136 X Ler-267 | 2.09 | 2 | 1.94 | 2 | 3.99 | >2 | 0.00 | 0 | | |
| D4 | USR01424136 X Ler-268 | 1.47 | 1 or 2 | 2.08 | 2 | 6.34 | >2 | 1.51 | 1 or 2 | | |
| E4 | USR01424136 X Ler-269 | 1.95 | 2 | 1.76 | 2 | 3.19 | >2 | 0.00 | 0 | | |
| F4 | USR01424136 X Ler-270 | 1.92 | 2 | 2.17 | 2 | 4.28 | >2 | 0.02 | 0 | | |
| G4 | USR01424136 X Ler-271 | 2.02 | 2 | 1.85 | 2 | 4.31 | >2 | 0.00 | 0 | | |
| H4 | USR01424136 X Ler-272 | 0.00 | 0 | 1.71 | 2 | 1.65 | 2 | 1.12 | 1 | | x |

Simply by germinating seeds and sampling for qPCR Taqman analysis, we were able to identify 8 putative edited haploids. Edited haploids were also identified by phenotypic visual screening, and then confirmed later by Taqman assay. We screened for the edited haploids by looking for trichome-less, or glabrous, plants, which indicated that they did not have any wild-type alleles for the GL1 gene, and by looking for a lack of cyan fluorescent protein ("CFP") expression in the embryo or seedling root. This indicated that they lacked the Cas9 T-DNA. We observed several of these plants, and submitted them for Taqman assays. For three such plants that we identified phenotypically, we were able to confirm that they were truly edited haploids by the Taqman assays. We were aware of the fact that it is possible that some of these glabrous plants that lack CFP were false positives, either because the CFP was silent or because of self-pollination of the fully-edited mother plant and production of null segregant, fully edited (and thus glabrous) progeny. The Taqman assays were able to detect and screen out these false positives, because they directly tested for the presence of not only the Cas9 transgene, but also the ZmCENH3 allele, which would certainly be present in any self-pollinated contaminating seed. We found several examples of self-pollinated seed that all came from one mother plant. The pollination notes for that mother indicated that there was highly abundant pollen that may have resulted in some self-pollination. We excluded these progeny from the total analysis.

Figure 24:
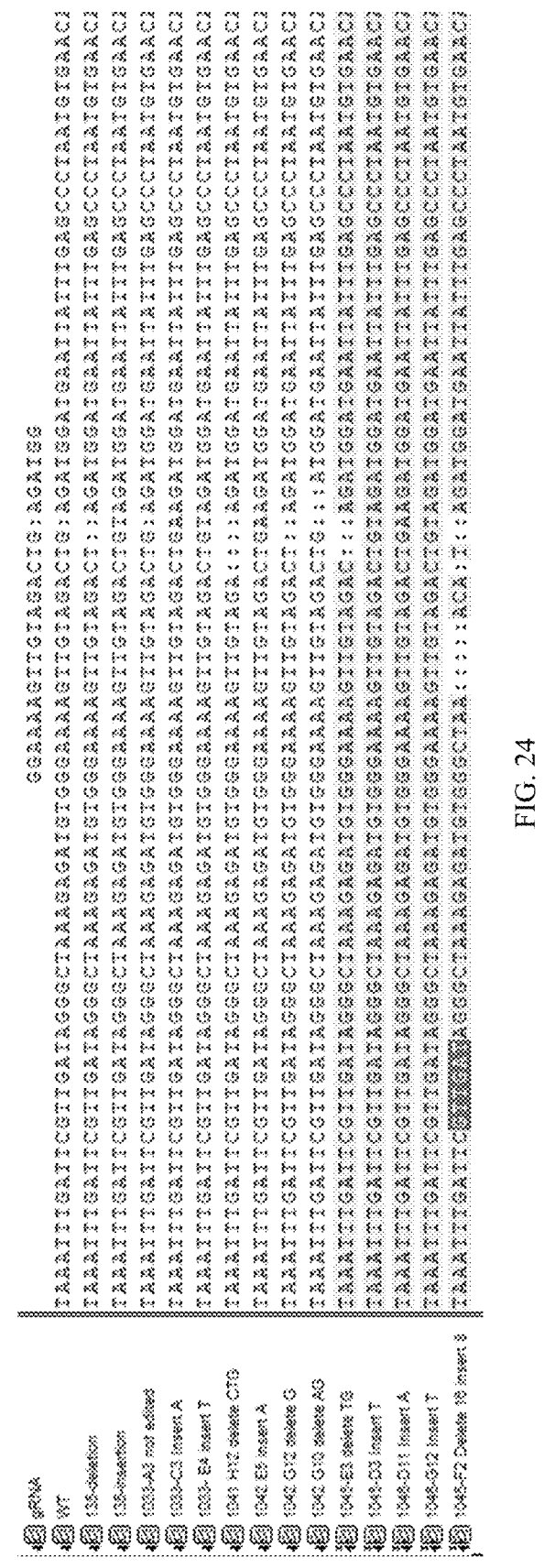

All of the putative edited haploids identified by Taqman assay were sequenced. We used PCR to amplify the edited alleles, and then subcloned and sequenced at least 8 colonies for each putative edited allele. See Table 10 for the sequence changes we found in the edited haploids at the first guide RNA (assay #3321) target site, as well as the Taqman data from the TO parents. In total, we found 19 putative edited haploids, and we confirmed that the 3321 target sites had mutations in 11 of the 12 edited haploids that we attempted to sequence. Whether the other 7 would also have mutations will be confirmed upon sequencing. See the sequence alignment for these edits in FIG. 24.

TABLE 10

Taqman and sequence data from 19 edited haploids.

| | | | AtGL1-1 cut site 3321 | | AtGL1-2 cut site 3322 | | ZmCENH3 2298 | | Cas9 3049 | | Target site mutation | PA confirm? |
|---|---|---|---|---|---|---|---|---|---|---|---|---|
| Plate | Well | Plant ID | Raw Copy # | Copy # level | Raw Copy # | Copy # level | Raw Copy # | Copy # level | Raw Copy # | Copy # level | | |
| 1033 | A3 | USR01424135 X Ler-425 | 0.00 | 0 | 1.67 | 2 | 0.04 | 0 | 0.00 | 0 | wild type | Not done |
| 1033 | C3 | USR01424135 X Ler-427 | 0.21 | 0 | 2.43 | >2 | 0.01 | 0 | 0.00 | 0 | insert A | Yes |
| 1033 | E4 | USR01424135 X Ler-437 | 0.08 | 0 | 2.04 | 2 | 0.00 | 0 | 0.00 | 0 | insert T | Yes |
| 1042 | E5 | USR01424136 X Ler-25 | 0.16 | 0 | 2.95 | >2 | 0.00 | 0 | 0.00 | 0 | insert A | Not done |
| 1042 | G10 | USR01424136 X Ler-67 | 0.00 | 0 | 2.19 | 2 | 0.00 | 0 | 0.00 | 0 | delete AG | Not done |
| 1042 | G12 | USR01424136 X Ler-83 | 0.00 | 0 | 1.86 | 2 | 0.00 | 0 | 0.00 | 0 | delete G | Not done |

TABLE 10-continued

Taqman and sequence data from 19 edited haploids.

| Plate | Well | Plant ID | AtGL1-1 cut site 3321 Raw Copy # | AtGL1-1 cut site 3321 Copy # level | AtGL1-2 cut site 3322 Raw Copy # | AtGL1-2 cut site 3322 Copy # level | ZmCENH3 2298 Raw Copy # | ZmCENH3 2298 Copy # level | Cas9 3049 Raw Copy # | Cas9 3049 Copy # level | Target site mutation | PA confirm? |
|---|---|---|---|---|---|---|---|---|---|---|---|---|
| 1043 | B11 | USR01424136 X Ler-154 | 0.16 | 0 | 1.59 | 1 or 2 | 0.01 | 0 | 0.00 | 0 | Not done | Not done |
| 1045 | F2 | USR01424136 X Ler-254 | 0.00 | 0 | 0.32 | 0 or 1 | 0.00 | 0 | 0.00 | 0 | delete 8nt* | Not done |
| 1045 | D3 | USR01424136 X Ler-260 | 0.06 | 0 | 2.01 | 2 | 0.00 | 0 | 0.00 | 0 | insert T | Not done |
| 1045 | E3 | USR01424136 X Ler-261 | 0.00 | 0 | 2.01 | 2 | 0.01 | 0 | 0.00 | 0 | delete TG | Not done |
| 1046 | D11 | USR01431609 X Ler-111 | 0.09 | 0 | 1.59 | 1 or 2 | 0.02 | 0 | 0.01 | 0 | insert A | Not done |
| 1046 | G12 | USR01431609 X Ler-122 | 0.02 | 0 | 1.62 | 2 | 0.00 | 0 | 0.00 | 0 | insert T | Not done |
| 1046 | H12 | USR01431609 X Ler-123 | 0.00 | 0 | 0.00 | 0 | 0.00 | 0 | 0.00 | 0 | delete CTG | Yes |
| 0583 | D12 | USR01431603 X Ler-80 | 0.00 | 0 | 1.50 | 1 or 2 | 0.00 | 0 | 0.00 | 0 | Not done | Not done |
| 0584 | A9 | USR01431603 X Ler-137 | 0.00 | 0 | 1.87 | 2 | 0.00 | 0 | 0.00 | 0 | Not done | Not done |
| 0584 | C11 | USR01431603 X Ler-155 | 0.05 | 0 | 2.06 | 2 | 0.00 | 0 | 0.17 | 0 | Not done | Not done |
| 0584 | G11 | USR01431603 X Ler-159 | 0.09 | 0 | 2.15 | 2 | 0.00 | 0 | 0.00 | 0 | Not done | Not done |
| 0584 | C12 | USR01431603 X Ler-163 | 0.00 | 0 | 1.35 | 1 or 2 | 0.00 | 0 | 0.11 | 0 | Not done | Not done |
| 0584 | F12 | USR01431603 X Ler-166 | 0.00 | 0 | 1.65 | 2 | 0.00 | 0 | 0.00 | 0 | Not done | Not done |
| 0585 | H7 | USR01431603 X Ler-212 | 0.06 | 0 | 2.05 | 2 | 0.00 | 0 | 0.01 | 0 | ΔG, +T chimera | Not done |
| Female | | USR01424135 | 0.03 | 0 | 1.42 | 1 or 2 | 4.46 | >2 | 2.98 | >2 | | Diploid |
| Parent T0 Plants | | USR01424136 | 0.03 | 0 | 1.13 | 1 | 3.59 | >2 | 2.76 | >2 | Not done | Diploid |
| | | USR01431603 | 0.14 | 0 | 1.25 | 1 | 2.48 | >2 | 3.42 | >2 | Not done | Diploid |
| | | USR01431609 | 0.18 | 0 | 1.1 | 1 | 4.75 | >2 | 5.57 | >2 | Not done | Diploid |

*delete 16 nt insert CTAAACAT

We further ran leaf samples from three edited haploid plants through ploidy analysis, along with three diploid controls (tissue sampled from the maternal parent plants), which showed that they were true haploids (FIGS. 18-23). This served to reconfirm their status as edited haploids.

In three parental lines where we were confident that there was no self-pollination contamination, we did not do any phenotypic pre-screening, but instead sampled all germinated progeny for Taqman analysis (Table 11). The three female parents for these progeny were USR01431603, USR01431609, and USR01431604. We found a haploid induction rate of about 9.7% calculated by dividing the number of progeny that lack the ZmCENH3 and Cas9 transgenes (59) by the total number of progeny sampled (605). Of the 59 haploids we found that 10 were edited. That means 16.9% of haploids, on average, were edited by the maternal Cas9, prior to elimination of the maternal genome. Without wishing to be constrained by this final number, this means that, using this system, as a percentage of total progeny, 9.7%*16.9%=1.64% of all germinated progeny were edited haploids.

The rate of CENH3* type haploid editing or other paternal haploid editing (using a maternal haploid inducer line) might be increased through the use of a promoter that drives the expression of Cas9 and/or the guide RNA to a higher level in the egg cell before fertilization and/or in the zygote cell during or after fertilization. An example of such a promoter would the promoter for EA1 (EGG APPARATUS1) (GRMZM2G456746), although there are many other examples. One could also express the Cas9 in the context of an egg apparatus-specific enhancer (EASE), which is a 77-bp sequence that stimulates expression of adjoining genes in the egg cell or the very early zygote (see, e.g., Yang, et al. *An Egg Apparatus-Specific Enhancer of Arabidopsis, Identified by Enhancer Detection*, PLANT PHYSIOLOGY November 2005, 139 (3) 1421-1432; DOI: https://doi.org/10.1104/pp. 105.068262).

VIII. Simultaneous Haploid Induction and Editing by Directly Modifying a Target Base in Genomic DNA Sequence.

Targeted mutagenesis of DNA sequence can also be achieved through direct conversion of one DNA base to

TABLE 11

Haploid induction rate and editing rate data from three sets of progeny, each derived from a different SEDHI inducer female parent crossed by *Landsberg erecta* pollen.

| ID | Patent plant Cas9-05 | Parent plant cNpt2-10 | Total samples | Haploid number | Haploid rate | Edited Haploid | Edited Haploid rate |
|---|---|---|---|---|---|---|---|
| USR01431603 X Landsberg erecta | >2 | >2 | 230 | 36 | 15.65 | 7 | 19.44 |
| USR01431609X Landsberg erecta | >2 | >2 | 123 | 14 | 11.38 | 3 | 21.43 |
| USR01431604 X Landsberg erecta | 2 | 1 | 252 | 9 | 3.57 | 0 | 0.00 | another without requiring double stranded breaks (DSBs). For example, cytidine deaminase APOBEC1, adenine deaminase, and other enhancing components like Uracil DNA glycosylase (UDG) can be fused to Cas9 (A840H) nickase or nuclease-inactivated dead Cas9 (dCa9) to direct editing of DNA sequence without introducing double strand DNA breaks (Komor et al. 2016. Programmable editing of a target base in genomic DNA without double-stranded DNA cleavage. Nature doi:10.1038/nature17946; Gaudelli et al. 2017. Programmable base editing of A:T to G:C in genomic DNA without DNA cleavage. Nature doi:10.1038/nature24644; Komor et al. 2017. Improved base excision repair inhibition and bacteriophage Mu Gam protein yields C:G-to-T:A base editors with higher efficiency and product purity. *Science Advances*, Vol. 3, no. 8, eaao4774, DOI: 10.1126/sciadv.aao4774). This kind of base editor machinery can also be delivered through haploid induction line to induce base editing in target sequences directly in other varieties. For example, a guide RNA sequence, xZmVLHP-03 (5'-AGGCGTCGAGCAGCGAGGTG-3', SEQ ID NO: 28) is designed to target the cytidine deaminase base editor system to convert ZmVLHP gene exon 2 genomic sequence 5'-AGGCGTCGAGCAGCGAGGTG-3' (SEQ ID NO: 28) into 5'-AGGCGTTGAGCAGCGAGGTG-3' (SEQ ID NO: 29), thus changing the arginine codon CGA into a stop codon (TGA) in the coding sequence and causing premature termination of the protein sequence and functional gene knockout. The C to T mutation is underlined. Similarly, chimeric nCas9- or dCas9-adenine deaminase base editing system can be used to mutate the coding region, splicing junction or promoter sequence of ZmVLHP or other genes to generate variants that have altered gene activity. Both cytidine and adenine deaminase are particularly useful for altering transcript splicing site since canonical splicing junction has 5'- . . . AG/GT . . . 3' sequence (or 5'- . . . AC/CT . . . 3' in the opposite strand).

IX. Simultaneous Haploid Induction and Editing by Allele Replacement with DNA Template Not only can in vivo haploid induction system be used to introduce protein, RNA or DNA for cleavage or conversion of target sequence, it can also be used to deliver DNA template for homology-dependent repair for precise sequence replacement in the target region in the form of transgenic DNA. The template DNA can be inserted into the inducer line genome carrying genome editing machinery such as CRISPR-Cas9 system, either in the same transgenic locus or different locus. When both Cas9-sgRNA and template DNA are present in the induced haploid embryos, cleavage of the target sequence will result in repair of the chromosomal break with the homologous transgenic DNA sequence as template. For example, for creating E149L mutation in ZmPYL-D gene (GRMZM2G048733_P02) (see WO16033230, incorporated herein by reference), DNA fragment containing donor sequence (5'-CCTTGGTGTTGCCGTCGGGGACGTCGACGACGAAT GACAGGATGACGAGCGTCC CTGGCCGGCCGTC-GATGACCT-3', SEQ ID NO: 30) is used as repair donor. It should be noted that additional homology sequences can be added to flank this core repair donor sequence. One or more copies of this repair donor sequence are inserted into Cas9-sgRNA expression vector 23136 (SEQ ID NO: 31) which expresses guide RNA 5'-GTCGGGGACGTCGACGACGA-3' (SEQ ID NO: 32) to form allele modification vector pBSC23136-AMD. It should be noted that the potential PAM site has been removed from the donor DNA sequences so that the integrated donor sequence will not be cleaved by the Cas9-sgRNA complex expressed from pBSC23136-AMD. pBSC23136-AMD is transformed into haploid inducer line NP2222-HI to generate transgenic editing line. Transgenic editing-haploid induction lines are selfed to produce progeny lines homozygous editing loci. These homozygous lines are used to pollinate target elite maize inbred lines to induce haploid formation and also introduce modified alleles by expressed Cas9-sgRNA using donor DNA present transiently before pollen donor chromosomes are eliminated.

X. Inducing Haploids and Simultaneous Gene Editing in Rice

A HI-rice line is obtained. For example, the rice MATL ortholog, Os03g27610 (SEQ ID NO: 33, is mutated to create a new rice HI line. This line is transformed with a vector comprising a site-directed mutagenesis system for editing the rice genome, for example the CRISPR/Cas9 system.

The rice HI line is crossed with a different rice line, preferably an elite line, to produce at least one progeny haploid embryo. During the cross to produce at least one progeny haploid embryo, the HI parent rice plant also causes the genome editing machinery, e.g., Cas9 plus a guide RNA, to be delivered to the embryo. At that point, the editing machinery operates to edit the genome of the haploid embryo, and thus an edited, haploid progeny plant is obtained.

XI. Taqman Assays and Conditions.

Several assays are mentioned by number or by target name. Provided below is a table of assays mentioned above and the sequences of the relevant primers and probes. Conditions for PCR are standard for all assays and are as follows: Denature at 98° C. for 2 minutes; followed by 35 cycles of (i) denature at 98° C. for 30 seconds, (ii) anneal at 60° C. for 30 seconds, (iii) extension at 72° C. for 1 minute; followed by final extension at 72° C. for 10 minutes with a hold at 4° C. until ready. Assays are carried out at these conditions unless otherwise noted below.

TABLE 11

Assay primers and probes.

| Target Assay No. | Cas9-in corn 2540 | Sequence | SEQ ID NO: |
|---|---|---|---|
| Forward Primer | FE09340 | TTGTGCTGCTCCACGAACA | 39 |
| Reverse Primer | FE09341 | GCCAGCCACTACGAGAAGCT | 40 |
| Probe | FE09342 | CTGCTTCTGCTCGTTGTCCTCCGG | 41 |

TABLE 11-continued

Assay primers and probes.

| Target Assay No. | mat1 2827 | Sequence | SEQ ID NO: |
|---|---|---|---|
| Forward Primer | FE10299 | GCGGATGCTGGCACAGC | 42 |
| Reverse Primer | FE10300 | GGCATTGCTTCCTTCTCCG | 43 |
| Probe | FE10301 | CAGGGAGCGAGGTAC | 44 |
| Target Assay No. | PMI 1750 | Sequence | SEQ ID NO: |
| Forward Primer | FE07390 | CTGGTGGCCAACGTGAAGTT | 45 |
| Reverse Primer | FE07391 | GCTTCACGGGCTGGGTC | 46 |
| Probe | FE07392 | AGGCCAAGCCCGCCAACCAG | 47 |
| Target Assay No. | MATL-WT 2826 | Sequence | SEQ ID NO: |
| Forward Primer | FE10297 | GCGGATGCTGGCACAGA | 48 |
| Reverse Primer | FE10298 | GCATTGCTTCCTTCGCCA | 49 |
| Probe | FE10299 | CAGGGAGGTACGAACC | 50 |
| Target Assay No. | TAV_4A 3252 | Sequence | SEQ ID NO: |
| Forward Primer | FE11306 | GCGGCGAAGAAGCGAA | 51 |
| Reverse Primer | FE11307 | GCGGCGTCTCCAGCTTC | 52 |
| Probe | FE11308 | CCAGGAACTGCG | 53 |
| Target Assay No. | TAV_4B 3253 | Sequence | SEQ ID NO: |
| Forward Primer | FE11309 | AAGAAACGCCGGCTGAGT | 54 |
| Reverse Primer | FE11310 | ACCTTGCGGGGCGTT | 55 |
| Probe | FE11308 | CCAGGAACTGCG | 56 |
| Target Assay No. | TAV_4D 3254 | Sequence | SEQ ID NO: |
| Forward Primer | FE11309 | AAGAAACGCCGGCTGAGT | 57 |
| Reverse Primer | FE11311 | CCTTGCGCGGCGTC | 58 |
| Probe | FE11308 | CCAGGAACTGCG | 59 |
| Target Assay No. | GW2-01 3065 | Sequence | SEQ ID NO: |
| Forward Primer | FE10799 | TGATCCTCGAGGCCAAGCT | 60 |
| Reverse Primer | FE10800 | AGGTCGAGGTCCCCTCCA | 61 |
| Probe | FE10801 | CCTGCTACCCGGGC | 62 |

TABLE 11-continued

Assay primers and probes.

| Target Assay No. | GW2-02 3095 | Sequence | SEQ ID NO: |
|---|---|---|---|
| Forward Primer | FE10991 | CGCGCCCTGCTACCC | 63 |
| Reverse Primer | FE10992 | GCGCGTGCTTACCAGGA | 64 |
| Probe | FE10993 | TCGAGGAGTGCCC | 65 |
| Target Assay No. | TaVHLP2-2A 3332 | Sequence | SEQ ID NO: |
| Forward Primer | FE11312 | CACCGATGAGCAGGCG | 66 |
| Reverse Primer | FE11313 | AGATACACCTTCCGGCCG | 67 |
| Probe | FE11314 | TTCCTCCCGGAAGC | 68 |
| Target Assay No. | TaVHLP2-2D 3333 | Sequence | SEQ ID NO: |
| Forward Primer | FE11312 | CACCGATGAGCAGGCG | 69 |
| Reverse Primer | FE11313 | AGATACACCTTCCGGCCAGT | 70 |
| Probe | FE11314 | CTCCTCCCGGAAGC | 71 |
| Target Assay No. | 3049 | Sequence | SEQ ID NO: |
| Forward Primer | FE10730 | CAAGTTTCTGGACAAGGAGATTCTC | 72 |
| Reverse Primer | FE10731 | AAGAATTCCCTTCTTAATAGCTGGAGA | 73 |
| Probe | FE10732 | CACGAGCACATTGCTAACCTTGCTGG | 74 |
| Target Assay No. | TaVHLP2-2B 3255 | Sequence | SEQ ID NO: |
| Forward Primer | FE11315 | TCACCGATGAGCAGGCA | 75 |
| Reverse Primer | FE11316 | ATACACCTTCCGGCCAGC | 76 |
| Probe | FE11317 | TTCCTCCCGGAAGC | 77 |
| Target Assay No. | 3321 | Sequence | SEQ ID NO: |
| Forward Primer | FE11540 | GATAGGGCTAAAGAGATGTGGGAA | 78 |
| Reverse Primer | FE11541 | CTTTGTTCACATTAGGGCTCAAATAA | 79 |
| Probe | FE11542 | TAGACTGAGATGGATG | 80 |

TABLE 11-continued

Assay primers and probes.

| | Target Assay No. | 3322 | Sequence | SEQ ID NO: |
|---|---|---|---|---|
| Forward Primer | FE11543 | | AAAACCACCGGAGAAGACGA | 81 |
| Reverse Primer | FE11544 | | AGGTGTGGCGGCAGTGA | 82 |
| Probe | FE11545 | | CACCGTCATTGTTC | 83 |

| | Target Assay No. | Cas9-in Arabidopsis 3049 | Sequence | SEQ ID NO: |
|---|---|---|---|---|
| Forward Primer | FE10730 | | CAAGTTTCTGGACAAGGAGATTCTC | 84 |
| Reverse Primer | FE10731 | | AAGAATTCCCTTCTTAATAGCTGGAGA | 85 |
| Probe | FE10732 | | CACGAGCACATTGCTAACCTTGCTGG | 86 |

| | Target Assay No. | ZmCENH3 2298 | Sequence | SEQ ID NO: |
|---|---|---|---|---|
| Forward Primer | FE08737 | | GCGACGCCGGAAAGG | 87 |
| Reverse Primer | FE08738 | | TGGCGTGGTTTCGTCTTCTTA | 88 |
| Probe | FE08739 | | AAGAGCGGCGTCTGGAGGTGACTCA | 89 |

| | Target | GL1 3321 target site (PCR) | Sequence | SEQ ID NO: |
|---|---|---|---|---|
| Forward Primer | 3321F | | AACCGCATCGTCAGAAAAAC | 90 |
| Reverse Primer | 3321R | | TCAACTTAACCGGCCAAATC | 91 |
| Annealing Temp. | 60° C. | | | |

| | Target | VLHP2-2A target site (PCR) | Sequence | SEQ ID NO: |
|---|---|---|---|---|
| Forward Primer | FE4117 | | CATCCCTTCTCTTCCCTCCTG | 92 |
| Reverse Primer | FE4118 | | GCCAGTGTGAGTGTGTATGAGCA | 93 |
| Annealing Temp. | 61° C. | | | |

| | Target | VLHP2-2B target site (PCR) | Sequence | SEQ ID NO: |
|---|---|---|---|---|
| Forward Primer | FE4120 | | CATCGTTTTCTCCCCTCCTCA | 94 |
| Reverse Primer | FE4121 | | ACTGATATGCACGGCGCCA | 95 |
| Annealing Temp. | 62° C. | | | |

| | Target | VLHP2-2D target site (PCR) | Sequence | SEQ ID NO: |
|---|---|---|---|---|
| Forward Primer | FE4121 | | TGCAGTAGCTTCATTTTCACCG | 96 |
| Reverse Primer | FE4122 | | AGGAATTGATATGTACGCCCGT | 97 |
| Annealing Temp. | 61° C. | | | |

What is claimed is:

1. A method of editing maize genomic DNA, comprising:
   a) obtaining a first maize plant comprising a loss-of-function mutation in a wildtype patatin-like phospholipase A2α gene having a cDNA sequence as represented by SEQ ID NO: 19, wherein said first maize plant expresses a DNA modification enzyme and at least one guide nucleic acid;
   b) obtaining a second maize plant, wherein the second maize plant comprises the plant genomic DNA which is to be edited;
   c) pollinating the second maize plant with pollen from the first maize plant; and
   d) selecting at least one haploid progeny produced by the pollination of step (c) wherein the haploid progeny comprises the genome of the second maize plant but not the first maize plant, and the genome of the haploid progeny has been modified by the DNA modification enzyme and at least one guide nucleic acid delivered by the first maize plant;

wherein the DNA modification enzyme is a base editor.

2. The method of claim 1, wherein the DNA modification enzyme comprises a site-directed nuclease selected from the group consisting of a Cas9 nuclease, Cpf1 nuclease, dCas9-FokI, dCpf1-FokI, chimeric Cas9-cytidine deaminase, chimeric Cas9-adenine deaminase, a nickase Cas9 (nCas9), chimeric dCas9 non-FokI nuclease and dCpf1 non-FokI nuclease.

3. The method of claim 1, wherein the at least one guide nucleic acid is a guide RNA.

4. The method of claim 1, wherein the edited haploid progeny is treated with a chromosome doubling agent, thereby creating an edited doubled haploid progeny.

5. The method of claim 4, wherein the chromosome doubling agent is colchicine, pronamide, dithipyr, trifluralin, or another known anti-microtubule agent.

6. The method of claim 1, wherein the optional guide RNA is an 18-21 nucleotide sequence and is homologous to a sequence selected from the group consisting of SEQ ID NOs: 2, 4, 8, 21, 23, 25, 29, 32, and 33.

7. The method of claim 1, wherein the first plant expresses a marker gene.

8. The method of claim 7, wherein the marker gene is selected from the group consisting of GUS, PMI, PAT, GFP, RFP, CFP, B1, C1, R-nj, and anthocyanin pigments.

9. The method of claim 1, wherein the first plant is a transformable maize plant selected and/or derived from the group consisting of Stock 6, RWK, RWS, UH400, AX5707RS, and NP2222-matl.

10. The method of claim 1, wherein the base editor comprises a cytidine deaminase fused to a Cas polypeptide.

11. The method of claim 10, wherein the cytidine deaminase is an APOBEC deaminase.

12. The method of claim 1, wherein the base editor comprises an adenine deaminase fused to a Cas polypeptide.

13. The method of claim 1, wherein the base editor comprises a uracil DNA glycosylase fused to a Cas polypeptide.

* * * * *

SEQUENCE LISTING

```
Sequence total quantity: 117
SEQ ID NO: 1             moltype = DNA   length = 15722
FEATURE                  Location/Qualifiers
misc_feature             1..15722
                         note = vector 23396
misc_feature             4..259
                         note = bNRB-05
regulatory               304..2100
                         note = promoter - prSoUbi4-04
                         regulatory_class = promoter
gene                     2117..6286
                         note = cCas9-01
variation                5606..5608
                         note = mutation - L to V mutation
variation                5651..5653
                         note = mutation - I to V mutation
regulatory               6292..6544
                         note = terminator - tNOS-05-01
                         regulatory_class = terminator
regulatory               6551..6925
                         note = promoter - prOsU3-01
                         regulatory_class = promoter
misc_feature             6927..6946
                         note = xZmVLHP
misc_feature             6927..7032
                         note = rsgRNAZmVLHP-01
regulatory               7042..9033
                         note = promoter - prUbi1-04
                         regulatory_class = promoter
gene                     9050..10228
                         note = cPMI-09
regulatory               10251..10503
                         note = terminator - tNOS-05-01
                         regulatory_class = terminator
misc_feature             10547..10676
                         note = bNLB-03
gene                     10956..11744
                         note = cSpec-03
regulatory               11839..11969
                         note = promoter - prVirG-01
                         regulatory_class = promoter
gene                     12706..13779
                         note = cRepA-01
source                   1..15722
                         mol_type = other DNA
                         organism = synthetic construct
SEQUENCE: 1
attcctgtgg ttggcatgca catacaaatg gacgaacgga taaaccttt cacgcccttt    60
taaatatccg attattctaa taaacgctct tttctcttag gtttaccgc caatatatcc    120
tgtcaaacac tgatagttta aactgaaggc gggaaacgac aatctgatca tgagcggaga   180
attaagggag tcacgttatg acccccgccg atgacgcggg acaagccgtt ttacgtttgg   240
aactgacaga accgcaacgc tgcaggaatt ggccgcagcg tgcatttaaa caaagcttgg   300
taccattatg tggtctaggt aggttctata tataagaaaa cttgaaatgt tctaaaaaaa   360
aattcaagcc catgcatgat tgaagcaaac ggtatagcaa cggtgttaac ctgatctagt   420
gatctcttgc aatccttaac ggccacctac cgcaggtagc aaacggcgtc cccctcctcg   480
atatctccgc ggcgacctct ggcttttcc gcggaattgc gcggtgggga cggattccac    540
gagaccgcga cgcaaccgcc tctcgccgct gggccccaca ccgctcggtg ccgtagcctc   600
acgggactct ttctccctcc tccccgtta taaattggct tcatccctc cttgcctcat    660
ccatccaaat cccagtcccc aatcccatcc cttcgtagga gaaattcatc gaagctaagc   720
gaatcctcgc gatcctctca aggtactgcg agttttcgat ccccctctcg acccctcgta   780
tgtttgtgtt tgtcgtagcg tttgattagg tatgcttttc ctgtttgtgt tcgtcgtagc   840
gtttgattag gtatgctttc cctgttcgtg ttcatcgtag tgtttggatta ggtcgtgtga   900
ggcgatggcc tgctcgcgtc cttcgatctg tagtcgattt gcgggtcgtg gtgtagatct   960
gcgggctgtg atgaagttat ttggtgtgat ctgctcgcct gattctgcgg gttggctcga  1020
gtagatatga tggttggacc ggttggttcg tttaccgcgt taggggtggg ctgggatgat  1080
gttgcatgcg ccgttgcgcg tgatcccgca gcaggacttg cgtttgattg ccagatctcg  1140
ttacgattat gtgatttggt ttggactttt tagatctgta gcttctgctt atgtgccaga  1200
tgcgcctact gctcatatgc ctgatgataa tcataaatgg ctgtggaact aactagttga  1260
ttgcggagtc atgtatcagc tacaggtgta gggactagct acaggtgtag ggacttcttg  1320
ctaattgttt ggtcctttac tcatgttgca attatgcaat ttagtttaga ttgtttgttc  1380
cactcatcta ggctgtaaaa gggacactgc ttagattgct gtttaatctt tttagtagat  1440
tatattatat tggtaactta ttaccccctat tacatgccat acgtgacttc tgctcatgcc  1500
tgatgataat catagatcac tgtggaatta attagttgat tgtggaatca tgtttcatgt  1560
acataccacg gcacaattgc ttagttcctt aacaaatgca aatttttactg atccatgtat  1620
gatttgcgtg gttctctaat gtgaaatact atagctactt gttagtaaga atcaggttcg  1680
tatgcttaat gctgtatgtg ccttctgctc atgcctgatg ataatcatat atcactggaa  1740
ttaattagtt gatcgtttaa tcatatatca agtcatacc atgccacaat ttttagtcac   1800
ttaacccatg cagattgaac tggtccctgc atgttttgct aaattgttct attctgatta  1860
```

-continued

```
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag cttttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgaggg   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
ccccgacaac agcgacgtgg acaagctgtt catccagctg gtgcagacct acaaccagct   2700
gttcgaggag aacccgatca cgcagcggc cgtggacgcc aaggccatcc tgagcgccta   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacacctacg acgacgacct   2940
ggacaacctg ctgcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggg ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggaa aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga aaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
gctgaagacc tacgcccacc tgttcgacga caaggtgatg aagcagctga gaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg caggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag caccgggtgg agaaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actgaggca gctgctgaac gccaagctga tcacccagag   4800
gaagttcgac aacctgacca aggccgagag ggggcggctg agcgagctgg acaaggccgg   4860
cttcattaaa aggcagctgg tggagaccag gcagatcacc aagcacgtgg cccagatcct   4920
ggacagcagg atgaacacca gtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
cagcccgacc gtgcctaca gcgtgctggt ggtggccaag gtgagaaagg gcaagagcaa   5580
gaagctgaag agcgtgaagg agctggtggg catcaccatc atggagagga gcagcttcga   5640
gaagaaccca gtggacttcc tggaggccaa gggctacaag gaggtgaaaa aggcctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca cgagcagaa   5880
gcagctgttc gtggagcagc acaagcacta cctggacgag atcatcgagc agatcagcga   5940
gttcagcaag aggtgatcc aactgtga aaggtgctga gcgcctacaa   6000
caagcacagg gacaagccga tcagggagca ggccgagaac atcatccacc tgttcaccct   6060
gaccaacctg ggcgcccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagaac atgtgaagct tgatcgttca   6300
aacatttggc aataaagttt cttaagattg aatcctgttg ccggtcttgc gatgattatc   6360
atataattc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatctta aacatacgaa cagatcactt aaagttcttc tgaagcaact   6600
```

```
taaagttatc aggcatgcat ggatcttgga ggaatcagat gtgcagtcag ggaccatagc    6660
acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcagcag gaggcgtcga gcagcggttt tagagctaga    6960
aatagcaagt taaaataagg ctagtccgtt atcaacttga aaaagtggca ccgagtcggt    7020
gcttttttt tcggaccgcg cctgcagtgc agcgtgaccc ggtcgtgccc ctctctagag    7080
ataatgagca ttgcatgtct aagttataaa aaattaccac atatttttt tgtcacactt    7140
gtttgaagtg cagtttatct atctttatac atatatttaa actttactct acgaataata    7200
taatctatag tactacaata atatcagtgt tttagagaat catataaatg aacagttaga    7260
catggtctaa aggacaattg agtatttga caacaggact ctacagtttt atcttttag    7320
tgtgcatgtg ttctcctttt tttttgcaaa tagcttcacc tatataatac ttcatccatt    7380
ttattagtac atccatttag ggtttagggt taatggtttt tatagactaa tttttttagt    7440
acatctattt tattctattt tagcctctaa attaagaaaa ctaaaactct atttttagttt   7500
ttttatttaa taatttagat ataaaataga ataaaataaa gtgactaaaa attaaacaaa    7560
tacccttta gaaattaaaa aaactaagga aacatttttc ttgtttcgag tagataatgc    7620
cagcctgtta aacgccgtcg acgagtctaa cggacaccaa ccagcgaacc agcagcgtcg    7680
cgtcgggcca agcgaagcag acggcacggc atctctgtcg ctgcctctgg acccctctcg    7740
agagttccgc tccaccgttg gacttgctcc gctgtcggca tccagaaatt gcgtggcgga    7800
gcggcagacg tgagccggca cggcaggcgg cctcctcctc ctctcacggc accggcagct    7860
acgggggatt cctttcccac cgctccttcg cttttcccttc ctcgcccgcc gtaataaata    7920
gacaccccct ccacccctc ttttcccaac ctcgtgttgt tcggagcgca cacacacaca    7980
accagatctc cccaaatcc acccgtcggc acctccgctt caaggtacgc cgctcgtcct    8040
ccccccccc cctctctacc ttctctagat cggcgttccg gtccatggtt agggcccggt    8100
agttctactt ctgttcatgt ttgtgttaga tccgtgtttg tgttagatcc gtgctgctag    8160
cgttcgtaca cggatgcgac tctgtacgtca gacacgttct gattgctaac ttgcagtgt    8220
ttctctttgg ggaatcctgg gatgctcta gccgttccgc agacgggatc gatttcatga    8280
ttttttttgt ttcgttgcat aggggttggt ttgcccttt cctttattc aatatatgcc    8340
gtgcacttgt ttgtcgggtc atcttttcat gcttttttt gtcttggttg tgatgatgtg    8400
gtctggttgg gcggtcgttc tagatcggag tagaattctg tttcaaacta cctggtggat    8460
ttattaattt tggatctgta tgtgtgtgcc atacatattc atagttacga attgaagatg    8520
atggatggaa atatcgatct aggataggta tacatgttga tgcggttttt actgatgcat    8580
atacagagat gctttttgtt cgcttggttg tgatgatgtg gtgtggttgg gcggtcgttc    8640
attcgttcta gatcggagta gaatactgtt tcaaactacc tggtgtattt attaattttg    8700
gaactgtatg tgtgtgtcat acatcttcat agttacgagt ttaagatgga tggaaatatc    8760
gatctaggat aggtatacat gttgatgtgg gttttactga tgcatataca tgatggcata    8820
tgcagcatct attcatatgc tctaaccttg agtacctatc tattataata aacaagtatg    8880
ttttataatt atttttgatct tgatatactt ggatgatggc atatgcagca gctatatgtg   8940
gattttttta gccctgcctt catacgctat ttatttgctt ggtactgttt cttttgtcga    9000
tgctcaccct gttgtttggt gttacttctg cagggatccg gcagcagcca tgcagaagct    9060
gatcaacagc gtgcagaact acgcctgggg cagcaagacc gccctgaccg agctgtacgg    9120
catggagaac cccagcagcc agcccatggc cgagctgtgg atgggcgcc accccaagag    9180
cagcagccgc gtgcagaacg ccgcggcga catcgtgagc ctgcgcgacg tgatcgagag    9240
cgacaagagc accctgctgg gcgaggccgt ggccaagcgc ttcggcgagc tgcccttcct    9300
gttcaaggtg ctgtgcgccg cccagcccct gagcatccag gtgcacccca acaagcacaa    9360
cagcagatc ggcttcgcca aggagaacgc cgccggcatc cccatggacg ccgcgagcg    9420
caactacaag gaccccaacc acaagcccga gctggtgttc gccctgaccc ccttcctggc    9480
catgaacgcc ttccgcgagt tcagcgagat cgtgagcctg ctgcagcccg tggccggcgc    9540
ccaccccgcc atcgcccact tcctgcagca gcccgacgcc gagcgcctga gcgagctgtt    9600
cgccagcctg ctgaacatgc agggcagga gaagaagccc gcctggcca tcctgaagag    9660
cgccctggac agccagcagg gcgagccctg gcagaccatc cgcctgatca gcgagttcta    9720
ccccgaggac agcggcctgt tcagcccct gctgctgaac gtggtgaagc tgaacccggg    9780
cgaggccatg ttcctgttcg ccgagacccc ccacgcctac ctgcagggcg tggccctgga    9840
ggtgatggcc aacagcgaca acgtgctgcg cgccggcctg accccccaagt acatcgacat    9900
ccccgagctg gtgcccaacg tgaagttcga ggccaagccc gccaaccagc tgctgaccca    9960
gccccgtgaag cagggcgccg agctggactt ccccatcccc gtgacgact cgccttcag   10020
cctgcacgac ctgagcgaca aggagaccac catcagccag cagagcgccg ccatcctgtt   10080
ctgcgtggag ggcgacgcca cccctgtgaa gggcagccag cagtgcagcc ctgaagcccgg   10140
cgagagcgcc ttcatcgccg ccaacgagag cccccgtgacc gtgaagggcc acggccgcct   10200
ggcccgcgtg tacaacaagc tgtgatagga gctcgatccg tcgacctgca gatcgttcaa   10260
acatttggca ataaagtttc ttaagattga atcctgttgc cggtcttgcg atgattatca   10320
tataaatttct gttgaattac gttaagcatg taataattaa catgtaatgc atgacgttat   10380
ttatgagatg ggttttatg catttagagtcc cgcaattaa catttaatac ggtagtttaa   10440
acaaaatata gcgcgcaaac taggataaat tatcgcgcgc ggtgtcatct atgttactag   10500
atcggcgcgc cgcaattgaa gtttgggcgg ccagcatggc cgtatccgca atgtgttatt   10560
aagttgtcta agcgtcaatt tgtttacacc acaatatatc ctgccaccag ccagccaaca   10620
gctccccgac cggcagctcg gcacaaaatc accactcgat acaggcagcc catcagaatt   10680
aattctcatg tttgacagct tatcatcgac tgcacggtgc accaatgctt ctggcgtcag   10740
gcagccatcg gaagctgtgg tatggctgtg caggtcgtaa atcactgcat aattcgtgtc   10800
gctcaaggcg cactcccgtt ctggataatg ttttttgcgc cgacatcata acggttctgg   10860
caaatattct gaaatgagct gttgacaatt aatcatccgg ctcgtataat gtgtggaatt   10920
gtgagcggat aacaatttca cacaggaaac agaccatgag ggaagcgttg atcgccgaag   10980
tatcgactca actatcagag gtagttgcg tcatcgagcg ccatctcgaa ccgacgttgg   11040
tggccgtaca tttgtacggc tccgcagtgg atgccggcct gaagcacac agtgatattg   11100
atttgctggt tacggtgacc gtaaggcttg atgaaacaac gcggcgagct ttgatcaacg   11160
accttttgga aacttcggct tcccctggag agagcgagat tctccgcgct gtagaagtca   11220
ccattgttgt gcacgacgac atcattccgt ggcgttatcc agctaagcgc gaactgcaat   11280
ttggagaatg gcagcgcaat gacattcttg caggtatctt cgagccagcc acgatcgaca   11340
```

```
ttgatctggc tatcttgctg acaaaagcaa gagaacatag cgttgccttg gtaggtccag 11400
cggcggagga actctttgat ccggttcctg aacaggatct atttgaggcg ctaaatgaaa 11460
ccttaacgct atggaactcg ccgcccgact gggctggcga tgagcgaaat gtagtgctta 11520
cgttgtcccg catttggtac agcgcagtaa ccggcaaaat cgcgccgaag gatgtcgctg 11580
ccgactgggc aatggagcgc ctgccggccc agtatcgacc cgtcatactt gaagctaggc 11640
aggcttatct tggacaagaa gatcgcttgg cctcgcgcgc agatcagttg gaagaatttg 11700
ttcactacgt gaaaggcgag atcaccaaag tagtcggcaa ataaagctct agtggatctc 11760
cgtacccggg gatctggctc gcggcggacg cacgacgccg gggcgagacc ataggcgatc 11820
tcctaaatca atagtagctg taacctcgaa gcgtttcact tgtaacaacg attgagaatt 11880
tttgtcataa aattgaaata cttggttcgc atttttgtca tccgcggtca gccgcaattc 11940
tgacgaactg cccatttagc tggagatgat tgtacatcct tcacgtgaaa atttctcaag 12000
cgctgtgaac aagggttcag attttagatt gaaaggtgag ccgttgaaac acgttcttct 12060
tgtcgatgac gacgtcgcta tgcggcatct tattattgaa taccttacga tccacgcctt 12120
caaagtgacc gcggtagccg acagcaccca gttcacaaga gtactctctt ccgcgacggt 12180
cgatgtcgtg gttgttgatc tagatttagg tcgtgaagat gggctcgagc taggagcaag 12240
tgattttatc gctaagccgt tcagtatcag agagtttcta gcacgcattc gggttgcctt 12300
gcgcgtcgcg cccaacgttg tccgctccaa agaccgacgg tcttttttgtt ttactgactg 12360
gacacttaat ctcaggcaac gtcgcttgat gtccgaagct ggcggtgagg tgaaacttac 12420
ggcaggtgag ttcaatcttc tcctcgcgtt tttagaaaaa ccccgcgacg ttctatcgcg 12480
cgagcaactt ctcattgcca gtcgagtacg cgacgaggag gtttatgaca ggagtataga 12540
tgttctcatt ttgaggctgc gccgcaaact tgaggcagat ccgtcaagcc ctcaactgat 12600
aaaaacagca agaggtgccg gttatttctt tgacgcggac gtgcaggttt cgcacgggcg 12660
gacgatggca gcctgagcca attcccagat ccccgaggaa tcggcgtgag cggtcgcaaa 12720
ccatccggcc cggtacaaat cggcgcggcg ctgggtgatg acctggtgga gaagttgaag 12780
gccgcgcagg ccgcccagcg gcaacgcatc gaggcagaag cacgcccggg tgaatcgtgg 12840
caagccgccg ctgatcgaat ccgcaaagaa tcccggcaac cgccggcagc cggtgcgccg 12900
tcgattagga agccgcccaa gggcgacgag caaccagatt ttttcgttcc gatgctctat 12960
gacgtgggca cccgcgatag tcgcagcatc atggacgtgg ccgttttccg tctgtcgaag 13020
cgtgaccgac gagctggcga ggtgatccgc tacgagcttc cagacgggca cgtagaggtt 13080
tccgcagagt cggccggcat ggccagtgtg tgggattacg acctggtact gatggcgggtt 13140
tcccatctaa ccgaatccat gaaccgatac cgggaaggga agggagacaa gccggccgc 13200
gtgttccgtc cacacgttgc ggacgtactc aagttctgcc ggcgagccga tggcggaaag 13260
cagaaagacg acctggtaga aacctgcatt cggttaaaca ccacgcacgt tgccatgcag 13320
cgtacgaaga aggccaagaa cggccgcctg gtgacggtat ccgagggtga agccttgatt 13380
agccgctaca agatcgtaaa gagcgaaacc gggcggccgg agtacatcga gatcgagcta 13440
gctgattgga tgtaccgcga gatcacagaa ggcaagaacc cggacgtgct gacggttcac 13500
cccgattact ttttgatcga tcccggcatc ggccgttttc tctaccgcct ggcacgccgc 13560
gccgcaggca aggcagaagc cagatggttg ttcaagacga tctacgaacg cagtggcagc 13620
gccggagagt tcaagaagtt ctgtttcacc gtgcgcaagc tgatcgggtc aaatgacctg 13680
ccggagtacg atttgaagga ggaggcgggg caggctggcc cgatcctagt catgcgctac 13740
cgcaacctga tcgagggcga agcatccgcc ggttcctaat gtacgagca gatgctaggg 13800
caaattgccc tagcaggga aaaaggtcga aaaggtctct ttcctgtgga tagcacgtac 13860
attgggaacc caaagccgta cattgggaac cggaacccgt acattgggaa cccaaagccg 13920
tacattggga accggtcaca catgtaagtg actgatataa aagagaaaaa aggcgatttt 13980
tccgcctaaa actcttaaa acttattaaa actcttaaaa cccgcctggc ctgtgcataa 14040
ctgtctggcc agcgcacagc cgaagagctg caaaaagcgc ctacccttcg gtcgctgcgc 14100
tccctacgcc ccgccgcttc gcgtcggcct atcgcggccg ctggccgtc aaaaatggct 14160
ggcctacggc caggcaatct accagggcgc ggacaagccg cgccgtcgcc actcgaccgc 14220
cggcgctgag gtctgcctcg tgaagaaggt gttgctgact cataccaggc ctgaatcgcc 14280
ccatcatcca gccagaaagt gagggagcca cggttgatga gagctttgtt gtaggtggac 14340
cagttggtga ttttgaactt ttgctttgcc acggaacggt ctgcgttgtc gggaagatga 14400
gtgatctgat ccttcaactc agcaaaagtt cgatttattc aacaaagccg ccgtcccgtc 14460
aagtcagcgt aatgctctgc cagtgttaca accaattaac caattctgat tagaaaaact 14520
catcgagcat caaatgaaac tgcaatttat tcatatcagg attatcaata ccatatttt 14580
gaaaaagccg tttctgtaat gaaggagaaa actcaccgag gcagttccat aggatggcaa 14640
gatcctggta tcggtctgcg attccgactc gtccaacatc aatacaacct attaatttcc 14700
cctcgtcaaa aataaggtta tcaagtgaga atcaccatg agtgacgact gaatccggtg 14760
agaatgccaa aagctctgca ttaatgaatc ggccaacgcg cggggagagg cggtttgcgt 14820
attgggcgct cttccgcttc ctcgctcact gactcgctgc gctcggtcgt tcggctgcgg 14880
cgagcggtat cagctcactc aaaggcggta atacggttat ccacagaatc aggggataac 14940
gcaggaaaga acatgtgagc aaaaggccag caaaaggcca ggaaccgtaa aaaggccgcg 15000
ttgctggcgt ttttccatag gctccgcccc cctgacgagc atcacaaaaa tcgacgctca 15060
agtcagaggt ggcgaaaccc gacaggacta taaagatacc aggcgtttcc ccctggaagc 15120
tccctcgtgc gctctcctgt tccgaccctg ccgcttaccg gatacctgtc cgcctttctc 15180
ccttcgggaa gcgtggcgct ttctcatagc tcacgctgta ggtatctcag ttcggtgtag 15240
gtcgttcgct ccaagctggg ctgtgtgcac gaaccccccg ttcagcccga ccgctgcgcc 15300
ttatccggta actatcgtct tgagtccaac ccggtaagac acgacttatc gccactggca 15360
gcagccactg gtaacaggat tagcagagcg aggtatgtag gcggtgctac agagttcttg 15420
aagtggtggc ctaactacgg ctacactaga agaacagtat ttggtatctg cgctctgctg 15480
aagccagtta ccttcggaaa aagagttggt agctcttgat ccggcaaaca accaccgct 15540
ggtagcggtg gtttttttgt ttgcaagcag cagattacgc gcagaaaaaa aggatctcaa 15600
gaagatcctt tgatcttttc tacggggtct gacgctcagt ggaacgaaaa ctcacgttaa 15660
gggattttgg tcatgagatt atcaaaaagg atcttcacct agatcctttt gatccggaat 15720
ta                                                                 15722

SEQ ID NO: 2          moltype = DNA   length = 20
FEATURE               Location/Qualifiers
misc_feature          1..20
                      note = gRNA sequence for editing VLHP1
```

```
source                  1..20
                        mol_type = other DNA
                        organism = synthetic construct
SEQUENCE: 2
gcaggaggcg tcgagcagcg                                                     20

SEQ ID NO: 3            moltype = DNA  length = 15722
FEATURE                 Location/Qualifiers
misc_feature            1..15722
                        note = vector 23399
misc_feature            4..259
                        note = bNRB-05
regulatory              304..2100
                        note = promoter - prSoUbi4-04
                        regulatory_class = promoter
gene                    2117..6286
                        note = cCas9-01
variation               5606..5608
                        note = mutation - L to V mutation
variation               5651..5653
                        note = mutation - I to V mutation
regulatory              6292..6544
                        note = terminator - tNOS-05-01
                        regulatory_class = terminator
regulatory              6551..6925
                        note = promoter - prOsU3-01
                        regulatory_class = promoter
misc_feature            6927..6946
                        note = xZmGW2
misc_feature            6927..7031
                        note = rsgRNAZmGW2-02
regulatory              7042..9033
                        note = promoter - prUbi1-04
                        regulatory_class = promoter
gene                    9050..10228
                        note = cPMI-09
regulatory              10251..10503
                        note = terminator - tNOS-05-01
                        regulatory_class = terminator
misc_feature            10547..10676
                        note = bNLB-03
gene                    10956..11744
                        note = cSpec-03
regulatory              11839..11969
                        note = promoter - prVirG-01
                        regulatory_class = promoter
gene                    12706..13779
                        note = cRepA-01
misc_feature            13822..14226
                        note = oVS1-02
misc_feature            14904..15710
                        note = oCOLE-06
source                  1..15722
                        mol_type = other DNA
                        organism = synthetic construct
SEQUENCE: 3
attcctgtgg ttggcatgca catacaaatg gacgaacgga taaaccttt cacgcccttt        60
taaatatccg attattctaa taaacgctct tttctcttag gtttacccgc caatatatcc       120
tgtcaaacac tgatagttta aactgaaggc gggaaacgac aatcgatca tgagcggaga       180
attaagggag tcacgttatg acccccgccg atgacgcggg acaagccgtt ttacgtttga       240
aactgacaga accgcaacgc tgcaggaatt ggccgcagcg gccatttaaa caaagcttgg       300
taccattatg tggtctaggt aggttctata tataagaaaa cttgaaatgt tctaaaaaaa       360
aattcaagcc catgcatgat tgaagcaaac ggtatagcaa cggtgttaac ctgatctagt       420
gatctcttgc aatccttaac ggccacctac cgcaggtagc aaacggcgtc cccctcctcg       480
atatctccgc ggcgacctct ggcttttcc gcggaattgc gcggtgggga cggattccac        540
gagaccgcga cgcaaccgcc tctcgccgct gggcccaca ccgctcggtg ccgtagcctc        600
acgggactct ttctccctcc tccccgtta taaattggct tcatccctc cttgcctcat         660
ccatccaaat cccagtcccc aatcccatcc cttcgtagga gaaattcatc gaagctaagc       720
gaatcctcgc gatcctctca aggtactgcg agttttcgat cccctctcg accctcgta         780
tgtttgtgtt tgtcgtagcg tttgattagg tatgcttttcc ctgtttgtgt tcgtcgtagc      840
gtttgattag gtatgctttc cctgttcgtg ttcatcgtag tgtttgatta ggtcgtgtga       900
ggcgatggcc tgctcgcgtc cttcgatctg tagtcgattt gcgggtcgtg gtgtagatct       960
gcgggctgtg atgaagttat ttggtgtgat ctgctcgcct gattctgcgg gttggctcga      1020
gtagatatga tggttggacc ggttggttcg tttaccgcgc tagggtttggg ctgggatgat     1080
gttgcatgcg ccgttgcgcg tgatcccgca gcaggacttg cgtttgattg ccagatctcg      1140
ttacgattat gtgatttggt ttggactttt tagatctgta gcttctgctt atgtgccaga      1200
tgcgcctact gctcatatgc ctgatgataa tcataaatgg ctgtgaact aactagttga       1260
ttgcggagtc atgtatcagc tacaggtgta gggactagct acaggtgtag ggacttgcgt      1320
ctaattgttt ggtcctttac tcatgttgca attatgcaat ttagtttaga ttgtttgttc      1380
```

```
cactcatcta ggctgtaaaa gggacactgc ttagattgct gtttaatctt tttagtagat   1440
tatattatat tggtaactta ttaccccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt ttttggtaa tggttctctt attttaaatg ctatatagtt     1920
ctggtacttg ttagaaagat ctgcttcata gtttagttgc ctatccctcg aattaggatg   1980
ctgagcagct gatccctatag cttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg caccaacag    2160
cgtgggctgg gccgtgatca ccgacgagta caaggtccgg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca acgcagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacaccctacg agcagacct   2940
ggacaacctg ctgggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcaga agctgccgga gaagtacaaag gagatcttct tcgaccagag   3180
caagaacggc tacgcggct acatcgacgg cggcgccagc caggaggagt ctctacaagtt   3240
catcaagccg atcctggaga agatggacgg caccgaggag ctgctggtga agctgaacag   3300
gaggaccctg ctgaggaagc agaggaccttt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg cgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
gctgaagacc tacgcccacc tgttcgacga caaggtgatg aagcagctga gaggaggag    4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagccggg ccatcaagaa   4320
gggcatcctg cagaccgtga aggtggtgga cgagctggtg aaggtgatgg gcaggcacaa   4380
gccggagaac atcgtgatcg agatggcgag ggagaaccag accacccaga agggccagaa   4440
gaacagcagg gagaggatga agaggatcga ggagggcatc aaggagctgg gcagccagat   4500
cctgaaggag caccccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actggaggca gctgctgaac gccaagctga tcacccagag   4800
gaagttcgac aacctgacca aggccgagag ggcggcctg agcgagctgg acaaggccgg   4860
cttcattaaa aggcagctgg tggagaacgg gcagatcacc aagcacgtgg cccagatcct   4920
ggacagcagg atgaacacca atgacgacga gaacgacaag ctgatcaggg aggtgaaggt   4980
gatcacccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacgcg actacaaggt   5160
gtacgacgtg aggaagatga tcgccaagag cgagcaggaa gtcaccggcca ccatcgccaa  5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca gaagaagga ctgggaccg aagaagtcgc gggccttcga    5520
cagcccgacc gtggcctaca gcgtgctggt ggtggccaag gtggagaagg caagagcaa    5580
gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaaactg ccgaagtaca gcctgttcga gctgagaaac ggcaggaaga gatgctggc    5760
cagcgcggc gagctgcaga agggccaacga gctgccctg ccagcagt acgtgaactt     5820
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcacccct   6060
gaccaacctg ggcgcccgg ccgccttcaa gtacttcgac accaccatcg acaggaagag   6120
```

```
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactggta   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcaaagc tcgcgccctg ctacccgttt tagagctaga   6960
aatagcaagt taaataagg ctagtccgtt atcaacttga aaaagtggca ccgagtcggt    7020
gcttttttt tcggaccgcg cctgcagtgc agcgtgaccc ggtcgtgccc ctctctagag    7080
ataatgagca ttgcatgtct aagttataaa aaattaccac atattttttt tgtcacactt   7140
gtttgaagtg cagtttatct atcttttatac atatatttaa actttactct acgaataata  7200
taatctatag tactacaata atatcagtgt tttagagaat catataaatg aacagttaga   7260
catggtctaa aggacaattg agtatttga caacaggact ctacagtttt atctttttag    7320
tgtgcatgtg ttctcctttt tttttgcaaa tagcttcacc tatataatac ttcatccatt   7380
ttattagtac atccatttag ggtttagggt taatggttt tatagactaa ttttttttagt   7440
acatctattt tattctattt tagcctctaa attaagaaaa ctaaaactct attttagtttt  7500
ttttatttaa taatttagat ataaaataga ataaaataaa gtgactaaaa attaaacaaa   7560
tacccttta gaaattaaaa aaactaagga aacattttc ttgtttcgag tagataatgc     7620
cagcctgtta aacgcctcg acgagtctaa cggacaccaa ccagcgaacc agcagcgtcg    7680
cgtcgggcca agcgaagcag acggcacggc atctctgtcg ctgcctctgg accccctctcg  7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acggggggatt ccttttcccac cgctccttcg ctttcccttc ctcgccccgcc gtaataaata  7920
gacaccccct ccacccctc tttcccaaac ctcgtgttgt tcggagcgca cacacacaca   7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
tttttttgt ttcgttgcat aggggtttgg ttgcccttt cctttatttc aatatatgcc     8340
gtgcacttgt ttgtcgggtc atctttcat gcttttttt gtcttggttg tgatgatgtg     8400
gtctggttgg gcggtcgttc tagatcggag tagaattcgt tttcaaacta cctggtagtt   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gcttttgttt cgcttggttg tgatgatgtg gtgtgttgg gcggtcgttc   8640
attcgttcta gatcggagta gaatactgtt tcaaactact tgttgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatgc atcagca gctatatgtg      8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcaccca acaagcacaa    9360
cagcagatc ggcttcgcca aggagaacgc cgccggcatc cccatggccg ccgcgagcg     9420
caactacaag gacccccaacc acaagcccga gctggtgttc gccctgaccc cttcctggc    9480
catgaacgcc ttccgcgagt tcagcgagat cgtgagcctg ctgcagcccg tggcggcgc    9540
ccaccccgcc atcgcccact tcctgcagca gcccgacgcc gagcgcctga gcagctgtt    9600
cgccagcctg ctgaacatgc agggcgagga aagagccgc gcctggcca tcctgaagag    9660
cgcctggac agccagcagg gcgagccctg gcagaccatc gcctgatca gcgagttcta    9720
ccccgaggac agcggcctgt tcagccccct gctgctgaac gtggtgaagc tgaaccccgg    9780
cgaggccatg ttcctgttcg ccgagacccc ccacgcctac ctgcagggcg tggccctgga    9840
ggtgatggcc aacagcgaca acgtgctgcg cgccggcctg acccccaagt acatccgcat    9900
cccccagcgtg gtggccaacg tgaagttcga gccaagccc gccaaccagc tgctgaccca    9960
gcccgtgaag cagggcgccg agctggactt ccccatcccc gtggacgact cgccttcag   10020
cctgcacgac ctgagcgaca aggagaccac catccagcag cagagcgccg ccatcctgtt   10080
ctgcgtggag ggcgacgcca ccctgtgaa gggcagccag cagctgcagc tgaagccccg   10140
cgagagcgcc ttcatcgccg ccaacgagag ccccgtgacc gtgaagggcc acggccgcct   10200
ggccccgctg tacaacaagc tgtgataggga gtcgatccg tcgacctgca gcgttcaa    10260
acatttggca ataaagtttc ttaagattga atcctgttgc cggtcttgcg atgattatca   10320
tataatttct gttgaattac gttaagcatg taataattaa catgtaatgc atgacgttat   10380
ttatgagatg gttttttatg attagagtcc cgcaattata catttaatac gcgatagaaa   10440
acaaaatata gcgcgcaaac taggataaat tatcgcgcg ggtgtcatct atgttactag    10500
atcggccggc cgcaattgaa gtttgggcgg cagcagctgcc cgtatccgca atgttggtatt   10560
aagttgtcta agcgtcaatt tgtttacacc acaatatatc ctgccaccag ccagccaaca   10620
gctcccgac cggcagctcg gcacaaaatc accactcgat acaggcagcc atcagaatt     10680
aattctcatg tttgacagct tatcatcgac tgcacggtgc accaatgctt ctggcgtcag   10740
gcagccatcg gaagctgtgg tatggctgtg caggtcgtaa atcactgcat aattcgtgtc   10800
gctcaaggcg cactcccgtt ctggataatg ttttttgcgc cgacatcata acggttctgg   10860
```

```
caaatattct gaaatgagct gttgacaatt aatcatccgg ctcgtataat gtgtggaatt    10920
gtgagcggat aacaatttca cacaggaaac agaccatgag ggaagcgttg atcgccgaag    10980
tatcgactca actatcagag gtagttggcg tcatcgagcg ccatctcgaa ccgacgttgc    11040
tggccgtaca tttgtacggc tccgcagtgg atggcggcct gaagccacac agtgatattg    11100
atttgctggt tacggtgacc gtaaggcttg atgaaacaac ggcgcgagct ttgatcaacg    11160
accttttgga aacttcggct tccctggag agagcgagat tctccgcgct gtagaagtca    11220
ccattgttgt gcacgacgac atcattccgt ggcgttatcc agctaagcgc gaactgcaat    11280
ttggagaatg gcagcgcaat gacattcttg caggtatctt cgagccagcc acgatcgaca    11340
ttgatctggc tatcttgctg acaaaagcaa gagaacatag cgttgccttg gtaggtccag    11400
cggcggagga actctttgat ccggttcctg aacaggatct atttgaggcg ctaaatgaaa    11460
ccttaacgct atggaactcg ccgcccgact gggctggcga tgagcgaaat gtagtgctta    11520
cgttgtcccg catttggtac agcgcagtaa ccggcaaaat cgcgccgaag gatgtcgctg    11580
ccgactgggc aatggagcgc ctgccggccc agtatcagcc cgtcatactt gaagctaggc    11640
aggcttatct tggacaagaa gatcgcttgg cctcgcgcga agatcagttg gaagaatttg    11700
ttcactacgt gaaaggcgag atcaccaaag tagtcggcaa ataaagctct agtggatctc    11760
cgtacccggg gatctggctc gcggcggacg cacgacgccg gggcgagacc ataggcgatc    11820
tcctaaaatca atagtagctg taacctcgaa gctttcact tgtaacaacg attgagaatt    11880
tttgtcataa aattgaaata cttggttcgc atttttgtca tccgcggtca gccgcaattc    11940
tgacgaactg cccatttagc tggagatgat tgtacatcct tcacgtgaaa atttctcaag    12000
cgctgtgaac aagggttcag attttagatt gaaaggtgag ccgttgaaac acgttcttct    12060
tgtcgatgac gacgtcgcta tgcggcatct tattattgaa taccttacga tccacgcctt    12120
caaagtgacc gcggtagccg acagccaccca gttcacaaga gtactctctt ccgcgacggt    12180
cgatgtcgtg gttgttgatc tagatttagg tcgtgaagat gggctcgagc taggagcaag    12240
tgattttatc gctaagccgt tcagtatcag agagtttcta gcacgcattc gggttgcctt    12300
gcgcgtcgcg cccaacgttg tccgctccaa agaccgacgg tctttttgtt ttactgactg    12360
gacacttaat ctcaggcaac gtccgcttgat gtccgaacgt ggcggtgagg tgaaacttac    12420
ggcaggtgag ttcaatcttc tcctcgcgtt tttagagaaa ccccgcgacg ttctatcgcg    12480
cgagcaactt ctcattgcca gtcgagtacg cgacgaggag gtttatgaca ggagtataga    12540
tgttctcatt ttgaggctgc gccgcaaact tgaggcagat ccgtcaagcc ctcaactgat    12600
aaaaacagca agaggtgccg gttatttctt tgacgcggac gtgcaggttt cgcacggggg    12660
gacgatggca gcctgagcca attcccagat ccccgaggaa tcggcgtgag cggtcgcaaa    12720
ccatccggcc cggtacaaat cggcgcggcg ctgggtgatg acctggtgga gaagttgaag    12780
gccgcgcagg ccgcccagcg gcaacgcatc gaggcagaag cacgcccgg tgaatcgtgg    12840
caagcggccg ctgatcgaat ccgcaaagaa tcccggcaac cgcggcgcagc cggtgcgcg    12900
tcgattagga agccgcccaa gggcgacgag caaccagatt ttttcgttcc gatgctctat    12960
gacgtgggca cccgcgatag tcgcagcatc atggacgtgg ccgttttccg tctgtcgaag    13020
cgtgaccgac gagctggcga ggtgatccgc tacgagcttc cagacgggca cgtagaggtt    13080
tccgcagggc cggccggcat ggccagtgtg tgggattacg acctggtact gatgcgcgtt    13140
tcccatctaa ccgaatccat gaaccgatac cgggaaggga agagagacaa gcccggccgc    13200
gtgttccgtc cacacgttgc ggacgtactc aagttctgcc ggcgagccga tggcggaaag    13260
cagaaagacg acctggtaga aacctgcatt cggttaaaca ccacgcacgt tgccatgcag    13320
cgtacgaaga aggccaagaa cggccgcctg gtgacggtat ccgagggtga agccttgatt    13380
agccgctaca agatcgtaaa gagcgaaacc gggcggccgg agtacatcga gatcgagcta    13440
gctgattgga tgtaccgcga gatcacagaa ggcaagaacc cggacgtgct gacggttcac    13500
cccgattact ttttgatcga tcccggcatc ggccgttttc tctaccgcct ggcacgcgcc    13560
gccgcaggca aggcagaagc cagatggttg ttcaagacga tctacgaacg cagtggcagc    13620
gccggagagt tcaagaagtt ctgtttcacc gtgcgcaagc tgatcgggtc aaatgacctg    13680
ccggagtacg atttgaagga ggaggcgggg caggctggcc cgatcctagt catgcgctac    13740
cgcaacctga tcgagggcga agcatccgcc ggttcctaat gtacgagcca gatgctaggg    13800
caaattgccc tagcagggga aaaggtcga aaggtctct ttcctgtgga tagcacgtac    13860
attgggaacc caaagccgta cattgggaac cggaacccgt acattgggaa cccaaagccg    13920
tacattggga accggtcaca catgtaagtg actgatataa aagagaaaaa aggcgatttt    13980
tccgcctaaa actctttaaa acttattaaa actcttaaaa cccgcctggc ctgtgcataa    14040
ctgtctggcc agcgcacagc cgaagagctg caaaaagcgc ctacccttcg gtcgctcgcg    14100
tccctacgcc ccgccgcttc gcgtcggcct atcgcggccg ctggccgctc aaaaatggct    14160
ggcctacggc caggcaatct accagggcgc ggacaagccg cgccgtcgcc actcgaccgt    14220
cggcgctgag gtctgcctcg tgaagaaggt gttgctgact cataccaggc ctgaatcgcc    14280
ccatcatcca gccagaaagt gagggagcca cggttgatga gagctttgtt gtaggtggac    14340
cagttggtga ttttgaactt ttgcttttgcc acggaacggt ctgcgttgtc gggaagatgc    14400
gtgatctgat ccttcaactc agcaaaagtt cgatttattc aacaaagccg ccgtcccgtc    14460
aagtcagcgt aatgctctgc cagtgttaca accaattaac caattctgat tagaaaaact    14520
catcgagcat caaatgaaac tgcaatttat tcatatcagg attatcaata ccatattttt    14580
gaaaaagccg tttctgtaat gaaggagaaa actcaccgag gcagttccat aggatggcaa    14640
gatcctggta tcggtctgcg attccgactc gtccaactat aatacaacct attaatttcc    14700
cctcgtcaaa aataaggtta tcaagtgaga atcaccatg agtgacgact gaatccggta    14760
agaatggcaa aagctctgca ttaatgaatc ggccaacgcg cggggagagg cggtttgcgt    14820
attgggcgct cttccgcttc ctcgctcact gactcgctgc gctcggtcgt tcggctgcgg    14880
cgagcggtat cagctcactc aaaggcggta atacggttat ccacagaatc aggggataac    14940
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc cgcctttctc    15180
ccttcgggaa gcgtggcgct ttctcatagc tcacgctgta ggtatctcag ttcggtgtag    15240
gtcgttcgct ccaagctggg ctgtgtgcac gaaccccccg ttcagcccga ccgctgcgcc    15300
ttatccggta actatcgtct tgagtccaac ccggtaagac acgacttatc gccactggca    15360
gcagccactg gtaacaggat tagcagagcg aggtatgtag cggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gtttttttgt ttgcaagcag cagattacgc gcagaaaaaa aggatctcaa    15600
```

```
gaagatccttt tgatcttttc tacggggtct gacgctcagt ggaacgaaaa ctcacgttaa    15660
gggattttgg tcatgagatt atcaaaaagg atcttcacct agatccttt gatccggaat     15720
ta                                                                   15722

SEQ ID NO: 4              moltype = DNA  length = 20
FEATURE                   Location/Qualifiers
misc_feature              1..20
                          note = for editing GW2-2
source                    1..20
                          mol_type = other DNA
                          organism = synthetic construct
SEQUENCE: 4
aagctcgcgc cctgctaccc                                                 20

SEQ ID NO: 5              moltype = DNA  length = 19617
FEATURE                   Location/Qualifiers
misc_feature              1..19617
                          note = vector 22808
misc_feature              4..259
                          note = bNRB-05
regulatory                304..2100
                          note = promoter - prSoUbi4-04
                          regulatory_class = promoter
gene                      2119..5193
                          note = cTNPLAIIAFw-01
regulatory                5200..5452
                          note = terminator - tNOS-05-01
                          regulatory_class = terminator
regulatory                5486..7478
                          note = promoter - prUbi1-10
                          regulatory_class = promoter
gene                      7492..10566
                          note = cTNPLAIIARv-01
regulatory                10573..10825
                          note = terminator - tNOS-05-01
                          regulatory_class = terminator
regulatory                10844..12835
                          note = promoter - prUbi1-04
                          regulatory_class = promoter
gene                      12852..14030
                          note = cPMI-09
regulatory                14053..14305
                          note = terminator - tNOS-05-01
                          regulatory_class = terminator
misc_feature              14349..14478
                          note = bNLB-03
gene                      14758..15546
                          note = cSpec-03
regulatory                15641..15771
                          note = promoter - prVirG-01
                          regulatory_class = promoter
gene                      15846..16571
                          note = cVirG-01
gene                      16601..17674
                          note = cRepA-01
misc_feature              17717..18121
                          note = oVS1-02
misc_feature              18799..19605
                          note = oCOLE-06
source                    1..19617
                          mol_type = other DNA
                          organism = synthetic construct
SEQUENCE: 5
attcctgtgg ttggcatgca catacaaatg gacgaacgga taaaccttt cacgcccttt      60
taaatatccg attattctaa taaacgctct tttctcttag gtttaccgc caatatatcc     120
tgtcaaacac tgatagttta aactgaaggc gggaaacgac aatctgatca tgagcggaga    180
attaaggag tcacgttatg acccccgccg atgacgcggg acaagccgtt ttacgtttgg     240
aactgacaga accgcaacgc tgcaggaatt ggccgcagcg gccatttaaa caaagcttgg    300
taccattatg tggtctaggt aggttctata tataagaaaa cttgaaatgt tctaaaaaaa    360
aattcaagcc catgcatgat tgaagcaaac ggtatagcaa cggtgttaac ctgatctagt    420
gatctcttgc aatccttaac ggccacctac cgcaggtagc aaacggcgtc cccctcctcg    480
atatctccgc ggcgacctct ggcttttcc gcggaattgc gcgtggggga cggattccac    540
gagaccgcga cgcaaccgcc tctcgccgct gggcccaca ccgtcggtg ccgtagcctc     600
acgggactct ttctcctcc tcccccgtta taaattggct tcatccctc cttgcctcat     660
ccatccaaat cccagtcccc aatcccatcc cttcgtagga gaaattcatc gaagctaagc   720
gaatcctcgc gatcctctca aggtactgcg agttttcgat cccctctcg acccctcgta    780
tgtttgtgtt tgtcgtagcg tttgattagg tatgctttcc ctgtttgtgt tcgtcgtagc   840
gtttgattag gtatgctttc cctgtttgtg ttcatcgtag tgtttgatta ggtcgtgtga   900
ggcgatggcc tgctcgcgtc cttcgatctg tagtcgattt gcgggtcgtg gtgtagatct   960
```

-continued

```
gcgggctgtg atgaagttat ttggtgtgat ctgctcgcct gattctgcgg gttggctcga   1020
gtagatatga tggttggacc ggttggttcg tttaccgcgc tagggttggg ctgggatgat   1080
gttgcatgcc ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgc ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
tatattatat tggtaactta ttaccccctat tacatgccat acgtgacttc tgctcatgat   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacataca atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag cttttgtttca tgtatcaatt cttttgtgtt caacagtcag   2040
tttttgttag attcattgta acttatggtc gcttactctt ctggtcctca atgcttgcag   2100
gatcgcggcc gcgccaccat gggaaaacct attcctaatc ctctgctggg cctggattct   2160
accgaggca tggcccctaa gaaaagcgg aaggtggacg cgcgagtgga cctgagaaca    2220
ctgggatatt ctcagcagca gcaggagaag atcaagccca aggtgagatc tacagtggcc   2280
cagcaccacg aagccctggt gggacacgga tttacacacg cccacattgt ggccctgtct   2340
cagcaccctg ccgccctggg aacagtggcc gtgaaatatc aggatatgat tgccgccctg   2400
cctgaggcca cacacgaagc cattgtggga gtgggaaaac agtggtctgg agccagagcc   2460
ctggaagccc tgctgacagt ggccggagaa ctgagaggac ctcctctgca gctggataca   2520
ggacagctgc tgaagattgc caaaagggc ggagtgaccg cggtggaagc cgtgcacgcc    2580
tggagaaatg ccctgacagg agcccctctg aacctgaccc ccgaacaggt ggtggccatt   2640
gccagccacg acggcggcaa gcaggccctg gaaaccgtgc agagactgct gcccgtgctg   2700
tgccagccc atggcctgac acctgaacag gtggtgccta tcgcctctca cgacggagga   2760
aaacaggctc tggaaacagt gcagcggctg ctgcctgtgc tgtgtcaggc tcacggcttg   2820
actcagaac aggtggtggc tattgcttcc aatattgggg ggaaacaggc cctgaaact    2880
gtgcagcgcc tgctgccagt gctgtgccag gctcacggac tgaccccga acaggtggtg   2940
gccattgcca gcaacaacgg cggcaagcag gccctgaaa ccgtgcagag actgctgccc   3000
gtgctgtgcc aggcccatgg cctgacacct gaacaggtgg tggctatcgc ctctaacaac   3060
ggaggaaaac aggctctgga aacagtgcag cggctgctgc ctgtgctgtg tcaggctcac   3120
ggcttgactc cagaacaggt ggtggctatt gcttccaaca acgggggaa acaggccctg    3180
gaaactgtgc agcgcctgct gccagtgctg tgccaggctc acgggctgac cccgaacag    3240
gtggtgcca ttgccagcaa cggcggcggc aagcaggccc tggaaccgt gcagagactg     3300
ctgcccgtgc tgtgccaggc ccatggcctg cacctgaac aggtggtggc tatcgcctct    3360
cacgacggag gaaaacaggc tctgaaaca gtgcagcggc tgctgcctgt gctgtgtcag    3420
gctcacggct tgactccaga acaggtggtg gctattgctt ccaatattgg ggggaaacag   3480
gccctggaaa ctgtgcagcg cctgctgcca gtgctgtgcc aggctcacgg cctcactccc   3540
gaacaggtgg tggccattgc cagcaacatc ggcggcaagc aggccctgga aaccgtgcag   3600
agactgctgc ccgtgctgtg ccaggcccat ggcctgacac tgaacaggt ggtggctatc    3660
gcctctcacg acggaggaaa acaggctctg aaacagtgc agcggctgct gcctgtgctg    3720
tgtcaggcc acggcttgac tccagaacag gtggtgcta ttgcttccaa caacggggg     3780
aaacaggccc tggaaactgt gcagcgcctg ctgccagtgc tgtgccaggc tcacggactg   3840
accccccgaac aggtggtggc cattgccagc aacggcggcg gcaagcaggc cctgaaacc   3900
gtgcagagac tgctgcccgt gctgtgccag gcccatggcc tgacacctga acaggtggtg   3960
gctatcgcct ctaacaacgg aggaaaacaa gcactcgaga cagtgcagcg gctgctgcct   4020
gtgctgtgtc aggctcacgg cttgactcca gaacaggtgg tggctattgc ttccaacaac   4080
gggggaaaac aggccctgga aactgtgcag cgcctgctgc cagtgctgtg ccaggctcac   4140
gggctgaccc ccgaacaggt ggtggccatt gccagcaaca tcggcggcaa gcaggccctg   4200
gaaaccgtgc agagactgct gcccgtgctg tgccaggccc atggcctgac acctgaacag   4260
gtggtggcta tcgcctctaa caacggagga aaacaggctc tggaaacagt gcagcggctg   4320
ctgcctgtgc tgtgtcaggc tcacggcttg actccacagc aggtcgtggc aattgctagc   4380
aatatcggcg gacggcccgc cctggagagc attgtggccc agctgtctag acctgatcct   4440
gccctggccg ccctgacaaa tgatcacctg tgggcccctc ctgtctggg aggcagacct    4500
gccctggatg ccgtgaaaaa aggactgcct cacgcccctg ccctgattaa aagaacaaat   4560
agaagaatcc ccgagcggac ctctcacaga gtggccggat cccagctggt gaaatctgag   4620
ctggaggaga agaagtctga gctgagacac aagctgaagt acgtgcctca cgagtacatc   4680
gagctgatcg agatcgccag aaatagcacc caggataaa tcctggagat gaaggtgatg   4740
gagttcttca tgaaagtgta cggctacaga ggaaagcatc tggaggaga cagaaaacct   4800
gacgagccca tttatacagt gggcagccct atcgattatg gcgtgatcgt ggatacaaag   4860
gcctacagcg gaggctacaa tctgcctatt ggacaggccg atgagatgca gagatacgtg   4920
gaggagaacc aaaccaggaa caagcatatc aaccctaacg agtggtggaa ggtgtacct    4980
tctagcgtga ccgagttcaa gttcctgttt gtgagcggcc acttcaaggg caattataag   5040
gcccagctga ccaggctgaa ccacatcaca aattgtaatg gcgccgtgct gtctgtggga   5100
gaactgctga ttggaggaga gatgattaag gccggaacac tgacactgga ggaggtgaga   5160
agaaagttca caacggcga gatcaacttc tgaaagcttg atcgttcaaa catttggcaa   5220
taaagtttct taagattgaa tcctgttgcc ggtcttgcga tgattatcat ataatttctg   5280
ttgaattacg ttaagcatgt aataattaac atgtaatgca tgacgttatt tatgagatgg   5340
gttttatga ttagagtccc gcaattatac atttaatgcca cgatagaaaa caaaatatag   5400
cgcgcaaact aggataaatt atcgcgcgcg gtgtcatcta tgttactaga tcttcgaacc   5460
ctagtcgaag acaaccggtg catgcctgca gtgcagcgtg accggtcgt gcccctctct   5520
agagataatg agcattgcat gtctaagtta taaaaaatta ccacatattt ttttgtcac    5580
acttgtttga agtgcagttt atctatcttt atacatatat ttaaacttta ctctacgaat   5640
aatataatct atagtactac aataatatca gtgttttaga gaatcatata aatgaacagt   5700
```

```
tagacatggt ctaaaggaca attgagtatt ttgacaacag gactctacag tttttatcttt    5760
ttagtgtgca tgtgttctcc tttttttttg caaatagctt cacctatata atacttcatc    5820
cattttatta gtacatccat ttagggttta gggttaatgg ttttttataga ctaattttttt   5880
tagtacatct atttttattct attttagcct ctaaattaag aaaactaaaa ctctatttta    5940
gttttttat ttaataattt agatatataa tagaataaaa taaagtgact aaaaattaaa    6000
caaatacccct ttaagaaatt aaaaaaacta aggaaacatt tttcttgttt cgagtagata   6060
atgccagcct gttaaacgcc gtcgacgagt caacggaca ccaaccagcg aaccagcagc    6120
gtcgcgtcgg gccaagcgaa gcagacggca cggcatctct gtcgctgcct ctggaccct    6180
ctcgagagtt ccgctccacc gttggacttg ctccgctgtc ggcatccaga aattgcgtgg    6240
cggagcggca gacgtgagcc ggcacggcag gcggcctcct cctcctctca cggcaccggc    6300
agctacgggg gattccttc ccaccgctcc ttcgctttcc cttcctcgcc cgccgtaata    6360
aatagacacc ccctccacac cctctttccc caacctcgtg ttgttcggag cgcacacaca    6420
cacaaccaga tctcccccaa atccaccccgt cggcacctcc gcttcaaggt acgccgctcg    6480
tcctcccccc cccccctct ctaccttctc tagatcggcg ttccggtcca tggttagggc    6540
ccggtagttc tacttctgtt catgtttgtg ttagatccgt gtttgtgtta gatccgtgct    6600
gctagcgttc gtacacggat gcgacctgta cgtcagacac gttctgattg ctaacttgcc    6660
agtgtttctc tttggggaat cctgggatgg ctctagccgt tccgcagacg ggatcgattt    6720
catgattttt tttgtttcgt tgcataggt ttggtttgcc ctttcctttt atttcaatat    6780
atgccgtgca cttgtttgtc gggtcatctt ttcatgcttt ttttttgtctt ggttgtgatg    6840
atgtggtctg gttgggcggt cgttctagat cggagtagaa ttctgtttca aactacctgg    6900
tggatttatt aattttggat ctgtatgtgt gtgccataca tattcatagt tacgaattga    6960
agatgatgga tggaaatatc gatctaggat aggtatacat tttgatgcgg gttttactga    7020
tgcatataca gagatgcttt ttgttcgctt ggttgtgatg atgtggtgtg ttgggcggt    7080
cgttcattcg ttctagatcg gagtagaata ctgtttcaaa ctaccggtg tatttattaa    7140
ttttggaact gtatgtgtgt gtcatacatc ttcatagtta cgagtttaag atggatggaa    7200
atatcgatct aggataggta tacatgttga tgtgggtttt actgatgcat atacatgatg    7260
gcatatgcag catctattca tatgctctaa ccttgagtac ctatctatta taataaaacaa   7320
gtatgtttta taattatttt gatcttgata tacttggatg atggcatatg cagcagctat    7380
atgtggattt ttttagccct gccttcatac gctatttatt tgcttggtac tgtttctttt    7440
gtcgatgctc accctgttgt ttggtgttac ttctgcagca gccgcgccac catgggaaaa    7500
cctattccta atcctctgct gggcctggat tctaccggag gcatggcccc taagaaaaag    7560
cggaaggtgg acgcggagt ggacctgaga acactgggat attctcagca gcagcaggag    7620
aagatcaagc ccaaggtgag atctacagtg gcccagcacc acgaagccct ggtgggacac    7680
ggatttacac acgcccacat tgtggccctg tctcagcacc ctgccgcct gggaacagtg    7740
gccgtgaaat atcaggatat gattgccgcc ccacacacga agccattgtg    7800
ggagtgggaa aacagtggtc tggagccaga gccctggaag ccctgctgac agtgccggaa   7860
gaactgagag gacctcctct gcagctggat acaggacagc tgctgaagat tgccaaaagg    7920
ggcggagtga ccgcggtgga agccgtgcac gcctggagaa atgcccctgac aggagcccct    7980
ctgaacctga ccccccgaaca ggtggtggcc attgccagca acaacggcgg caagcaggcc    8040
ctggaaaccg tgcagagact gctgcccgtg ctgtgccagg cccatggcct gacacctgaa    8100
caggtggtgg ctatcgcctc tcacgacgga ggaaaacagg ctctgaaac agtgcagcgg    8160
ctgctgcctg tgctgtgtca ggctcacggc ttgactccag aacaggtggt ggctattgct    8220
tccaacgccg gggggaaaca ggccctggaa actgtgcagc gcctgctgcc agtgctgtgc    8280
caggctcacg gactgacccc cgaacaggtg gtgccattg ccagcaacgg cggcggcaag    8340
caggccctgg aaaccgtgca gagactgctg cccgtgctgt gccaggccca tggcctgaca    8400
cctgaacagg tggtggctat cgcctctcac gacgaggaa acaggctct ggaaacagtg    8460
cagcggctgc tgcctgtgct gtgtcaggct cacggcttga ctccagagaa ggtggtggct    8520
attgcttccc acgacggggg gaaacaggcc ctgaaactg tgcagcgcct gctgccagtg    8580
ctgtgccagg ctcacgggct gaccccgaa caggtggtgg ccattgccag caacggcggc    8640
ggcaagcagg ccctggaaac cgtgcagaga ctgctgcccg tgctgtgcca ggcccatggc    8700
ctgacacctg aacaggtggt ggctatcgcc tctaacggca gaggaaaaca ggctctgaa    8760
acagtgcagc ggctgctgcc tgtgctgtgt caggctcacg gcttgactcc agaacaggtg    8820
gtggctattg cttcccacga cgggggaaa caggccctgg aaactgtgca gcgcctgctg    8880
ccagtgctgt gccaggctca cggcctcact cccgaacagg tggtggccat tgccagcaac    8940
aacggcggca agcaggccct ggaaaccgtg cagagactgc tgcccgtgct gtgccaggcc    9000
catggcctga cacctgaaca ggtggtggcc atcgcctctc acgacggagg aaaaacaggct    9060
ctggaaacag tgcagcggct gctgcctgtg ctgtgtcagg ctcacggctt gactccagaa    9120
caggtggtgg ctattgcttc ccacgacggg gggaaacagg ccctgaaaac tgtgcagcgc    9180
ctgctgccag tgctgtgcca ggctcacgga ctgacccccg aacaggtggt ggccattgcc    9240
agcaacatcg gcggcaagca ggccctgaa accgtgcaga gactgctgcc cgtgctgtgc    9300
caggcccatg gcctgacacc tgaacaggtg gtggctatcg cctctaacaa cggaggaaaa    9360
caagcactcg agacagtgca gcggctgctg cctgtgctgt gtcaggctca cggcttgact    9420
ccagaacagg tggtggctat tgcttccaac ggcgggggga acaggccct ggaaactgtg    9480
cagcgcctgc tgccagtgct gtgccaggct cacgggctga ccccgaaca ggtggtggcc    9540
attgccagcc acgacggcgg caagcaggcc ctgaaaccg tgcagagact gctgcccgtg    9600
ctgtgccagg cccatggcct gacacctgaa caggtggtgg ctatcgcctc taatatcgga    9660
ggaaaacagg ctctggaaac agtgcagcgg ctgctgcctg tgctgtgtca ggctcacggc    9720
ttgactccac agcaggtcgt ggcaattgct agccacgacg gcggacggcc cgccctggag    9780
agcattgtgg cccagctgtc tagacctgat cctgcccgga ccgccctgac aaatgatcac    9840
ctggtggccc tggcctgtct gggaggcaga cctgccctgg atgccgtgaa aaaaggactg    9900
cctcacgccc ctgccctgat taaagaaaca aatagaagaa tccccgagcg gacctctcac    9960
agagtggccc gatcccagct ggtgaaatct gagctggagg agaagaagtc tgagctgaga   10020
cacaagctga agtacgtgcc tcacgagtac atcgagctga tcgagatcgc cagaaatagc   10080
acccaggata gaatcctgga gatgaaggtg tacggagttct tcatgaaagt gtacggctac   10140
agaggaaagc atctgggagg aagcagaaaa cctgacggag ccattttatac agtgggcagc   10200
cctatcgatt atggcgtgat cgtggataca aaggcctaca gcgaggcta caatctgcct   10260
attgacagg ccgatgagat gcagagatac gtggaggaga accaaaccag gaacaagcat   10320
atcaacccta cgagtggtg gaaggtgtac ccttctagcg tgaccgagtt caagttcctg   10380
tttgtgagcg gccacttcaa gggcaattat aaggcccagc tgaccaggct gaaccacatc   10440
```

```
acaaattgta atggcgccgt gctgtctgtg gaggaactgc tgattggagg agagatgatt   10500
aaggccggaa cactgacact ggaggaggtg agaagaaagt tcaacaacgg cgagatcaac   10560
ttctgaaagc ttgatcgttc aaacatttgg caataaagtt tcttaagatt gaatcctgtt   10620
gccggtcttg cgatgattat catataattt ctgttgaatt acgttaagca tgtaataatt   10680
aacatgtaat gcatgacgtt atttatgaga tgggttttta tgattagagt cccgcaatta   10740
tacatttaat acgcgataga aaacaaaata tagcgcgcaa actaggataa attatcgcgc   10800
gcggtgtcat ctatgttact agatcttcga agacggaccg cgcctgcagt gcagcgtgac   10860
ccggtcgtgc ccctctctag agataatgag cattgcatgt ctaagttata aaaaattacc   10920
acatatttt tttgtcacac ttgtttgaag tgcagtttat ctatctttat acatatattt    10980
aaactttact ctacgaataa tataatctat agtactacaa taatatcagt gttttagaga   11040
atcatataaa tgaacagtta gacatggtct aaaggacaat tgagtatttt gacaacagga   11100
ctctacagtt ttatcttttt agtgtgcatg tgttctcctt tttttttgca aatagcttca   11160
cctatataat acttcatcca tttattagt acatccattt aggtttagg gttaatggtt      11220
tttatagact aatttttta gtacatctat tttattctat tttagcctct aaattaagaa     11280
aactaaaact ctatttagt tttttttattt aataatttag atataaaata gaataaaata    11340
aagtgactaa aaattaaaca aatacccttt aagaaattaa aaaaactaag gaaacatttt    11400
tcttgtttcg agtagataat gccagcctgt taaacgccgt cgacgagtct aacggacacc   11460
aaccagcgaa ccagcagcgt cgcgtcgggc caagcagagc agacggcacg gcatctctgt    11520
cgctgcctct ggaccctct cgagagttcc gctccaccgt tggacttgct ccgctgtcgg    11580
catccagaaa ttgcgtggcg gagcggcaga cgtgagccgg cacggcaggc ggcctcctcc   11640
tcctctcacg gcaccggcag ctacggggga ttcctttccc accgctcctt cgcttcccct    11700
tcctcgcccg ccgtaataaa tagacacccc ctccacaccc tctttcccca acctcgtgt    11760
gttcggagcg cacacacaca caaccagatc tccccccaaat ccaccccgtcg cgacctccgc   11820
ttcaaggtac gccgctcgtc ctcccccccc ccctctcta ccttctctag atcggcgttc    11880
cggtccatgg ttagggcccg gtagttctac ttctgttcat gtttgtgtta gatccgtgtt    11940
tgtgttagat ccgtgctgct agcgttcgta cacggatgcg acctgtacgt cagacacgtt   12000
ctgattgcta acttgccagt gtttctcttt ggggaatcct gggatggctc tagccgttcc   12060
gcagacggga tcgatttcat gatttttttt gtttcgttgc atagggtttg gtttgccctt    12120
ttcctttatt tcaatatatg ccgtgcactt gtttgtcggg tcatcttttc atgctttttt    12180
ttgtcttgt tgtgatgatg tggtctggtt gggcggtcgt tctagatcgg agtagaattc     12240
tgtttcaaac tacctggtgg atttattaat tttggatctg tatgtgtgtg ccatacatat   12300
tcatagttac gaattgaaga tgatggatgg aaatatcgat ctaggatagg tatacatgtt   12360
gatgcgggtt ttactgatgc atatacgag atgcttttg ttcgcttggt tgtgatgatg      12420
tggtgtggtt gggcggtcgt tcattcgttc tagatcggag tagaatactg tttcaaacta   12480
cctggtgtat ttattaattt tggaactgta tgtgtgtgtc atacatcttc atagttacga    12540
gtttaagatg gatggaaata tcgatctagg ataggtatac atgttgatgt gggttttact   12600
gatgcatata catgatggca tatgcagcat ctattcatat gctctaacct tgagtaccta   12660
tctattataa taaacaagta tgttttataa ttattttgat cttgatatac ttggatgatg   12720
gcatatgcag cagctatatg tggattttt tagccctgcc ttcatacgct atttatttgc    12780
ttggtactgt ttcttttgtc gatgctcacc ctgttgtttg gtgttacttc tgcagggatc   12840
cggcagcagc catgcagaag ctgatcaaca gcgtgcagaa ctacgcctgg ggcagcaaga   12900
ccgccctgac cgagctgtac ggcatggaga accccagcag ccagcccatg gccgagctgt   12960
ggatgggcgc ccaccccaag agcagcagcc gcgtgcagaa cgcgccggcc gacatcgtga   13020
gcctgcgcga cgtgatcgag agcgacaaga gcaccctgct gggcgaggcc gtggccaagc   13080
gcttcggcga gctgccctc ctgttcaagg tgctgtgcgc cgcccagccc ctgagcatcc    13140
aggtgcaccc caacaagcac aacagcgaga tcggcttcgc caaggagaac gccgccggca   13200
tccccatgga cgccgccgag cgcaactaca aggacccccaa ccacaagccc gagctggtgt   13260
tcgccctgac cccccttcctg gccatgaacg ccttccgcga gttcagcgag atcgtgagcc    13320
tgctgcagcc cgtggccggc gcccacccg ccatcgccca cttcctgcag cagcccgacg    13380
ccgagcgcct gagcgagctg ttcgccagcc tgctgaacat gcagggcgag gagaagagcc   13440
gcgccctggc catcctgaag agcgccctgg acagccagca gggcgagcc tggcagacca    13500
tccgcctgat cagcgagttc taccccgagg acagcggcct gttcagcccc ctgctgctga   13560
acgtggtgaa gctgaacccc ggcgaggcca tgttcctgtt cgccgagacc ccccacgcct   13620
acctgcaggg cgtggccctg gaggtgatgg ccaacagcga caacgtgctg cgcgccggcc   13680
tgaccccaa gtacatcgac atccccgagc tggtggccaa cgtgaagttc gaggccaagc    13740
ccgccaacca gctgctgacc cagcccgtga agcagggcc cgagctggac ttccccatcc    13800
ccgtggacga cttcgccttc agcctgcacg acctgagcga caaggagacc accatcagcc   13860
agcagagcgc cgccatcctg ttctgcgtgg agggcgacgc caccctgtgg aagggcagcc   13920
agcagctgca gctgaagccc ggcgagagcg ccttcatccg cgccaacgag agccccgtga   13980
ccgtgaaggg ccacgccgc ctggcccgcg tgtacaacga gctgtgatag gagctcgatc    14040
cgtcgacctg cagatcgttc aaacatttgg caataaagtt tcttaagatt gaatcctgtt   14100
gccggtcttg cgatgattat catataattt ctgttgaatt acgttaagca tgtaataatt   14160
aacatgtaat gcatgacgtt atttatgaga tgggttttta tgattagagt cccgcaatta   14220
tacatttaat acgcgataga aaacaaaata tagcgcgcaa actaggataa attatcgcgc   14280
gcggtgtcat ctatgttact agatcggcgc gccgcaattg aagtttggc ggccagcatg    14340
gccgtatccg caatgtgtta ttaagttgtc taagcgtcaa tttgtttaca ccacaatata   14400
tcctgccacc agccagccaa cagctccccg accggcagct cggcacaaaa tcaccactcg   14460
atacaggcag cccatcagaa ttaattctca tgtttgacag cttatcatcg actgcacggt   14520
gcaccaatgc ttctggcgtc aggcagccat cggaagctgt ggtatgcgtg tgcaggtcgt   14580
aaatcactgc ataattcgtg tcgctcaagg cgcactcccg ttctggataa tgttttttgc   14640
gccgacatca taacggttct ggcaaatatt ctgaaatgag ctgttgacaa ttaatcatcc   14700
ggctcgtata atgtgtggaa ttgtgagcgg ataacaattt cacacaggaa acagaccatg   14760
agggaagcgt tgatcgccga agtatcgact caactatcag aggtagttgg cgtcatcgag   14820
cgccatctcg aaccgacgtt gctggccgta catttgtacg gctccgcagt ggatggcggc   14880
ctgaagccac acagtgatat tgatttgctg ttacggtga ccgtaaggct tgatgaaaca    14940
acgcggcgag ctttgatcaa cgaccttttg gaaacttcgg cttcccctgg agagagcgag   15000
attctccgcg ctgtagaagt caccattgtt gtgcacgacg acatcattcc gtggcgttat   15060
ccagctaagc gcgaactgca atttggagaa tggcagcgca atgacattct tgcaggtatc    15120
ttcgagccag ccacgatcga cattgatctg gctatccttg tgacaaaagc aagagaacat   15180
```

```
agcgttgcct tggtaggtcc agcggcggag gaactctttg atccggttcc tgaacaggat   15240
ctatttgagg cgctaaatga aaccttaacg ctatggaact cgccgcccga ctgggctggc   15300
gatgagcgaa atgtagtgct tacgttgtcc cgcatttggt acagcgcagt aaccggcaaa   15360
atcgcgccga aggatgtcgc tgccgactgg gcaatggagc gcctgccggc ccagtatcag   15420
cccgtcatac ttgaagctag gcaggcttat ctttggacaag aagatcgctt ggcctcgcgc   15480
gcagatcagt tggaagaatt tgttcactac gtgaaaggcg agatcaccaa agtagtcggc   15540
aaataaagct ctagtggatc tccgtacccg gggatctggc tcgcggcgga cgcacgacgc   15600
cggggcgaga ccataggcga tctcctaaat caatagtagc tgtaacctcg aagcgtttca   15660
cttgtaacaa cgattgagaa ttttttgtcat aaaattgaaa tacttggttc gcattttgt   15720
catccgcggt cagccgcaat tctgacgaac tgcccattta gctggagatg attgtacatc   15780
cttcacgtga aaatttctca agcgctgtga acaagggttc agattttaga ttgaaaggtg   15840
agccgttgaa acacgttctt cttgtcgatg acgacgtcgc tatgcggcat cttattattg   15900
aataccttac gatccacgcc ttcaaagtga ccgcggtagc cgacagcacc cagttcacaa   15960
gagtactctc ttccgcgacg gtcgatgtcg tggttgttga tctagattta ggtcgtgaag   16020
atgggctcga gatcgttcgt aatctggcgg caaagtctga tattccaatc ataattatca   16080
gtggcgaccg ccttgaggag acggataaag ttgttgcact cgagctagga gcaagtgatt   16140
ttatcgctaa gccgttcagt atcagagagt ttctagcacg cattcgggtt gccttgcgcg   16200
tgcgcccaa cgttgtccgc tccaaagacc gacggtcttt ttgtttttact gactggacac   16260
ttaatctcag gcaacgtcgc ttgatgtccg aagctggcgg tgaggtgaaa cttacggcag   16320
gtgagttcaa tcttctcctc gcgtttttag agaaacccccg cgacgttcta tcgcgcgagc   16380
aacttctcat tgccagtcga gtacgcgacg aggaggttta tgacaggagt atagatgttc   16440
tcattttgag gctgcgccgc aaacttgagg cagatccgtc aagccctcaa ctgataaaaa   16500
cagcaagagg tgccggttat ttctttgacg cggacgtgca ggtttcgcac gggggggacga   16560
tggcagcctg agccaattcc cagatccccg aggaatcggc gtgagcggtc gcaaaccatc   16620
cggcccggta caaatcggcg cggcgctggg tgatgacctg gtggagaagt tgaaggccgc   16680
gcaggccgcc cagcggcaac gcatcgaggc agaagccgac cccggtgaat cgtggcaagc   16740
ggccgctgat cgaatccgca aagaatcccg gcaaccgccg gcagccggtg cgccgtcgat   16800
taggaagccg cccaagggcg acgagcaacc agattttttc gttccgatgc tctatgacgt   16860
gggcacccgc gatagtcgca gcatcatgga cgtggccgtt ttccgtctgt cgaagcgtga   16920
ccgacgagct ggcgaggtga tccgctacga gcttccagac gggcacgtag aggtttccgc   16980
agggccgcc ggcatggcca gtgtgtggga ttacgacctg gtactgatgg cggtttccca   17040
tctaaccgaa tccatgaacc gataccggga agggaaggga gacaagcccg gccgcgtgtt   17100
ccgtccacac gttgcggacg tactcaagtt ctgccggcga gccgatggcg gaaagcagaa   17160
agacgacctg gtagaaacct gcattcggtt aaacaccacg cacgttgcca tgcagcgtac   17220
gaagaaggcc aagaacggcc gcctggtgac ggtatccgga ggtgaagcct tgattagccg   17280
ctacaagatc gtaaagagcg aaaccgggcg gccggagtac atcgagatcg agctagctga   17340
ttggatgtac cgcgagatca cagaaggcaa gaacccggac gtgctgacgg ttcacccccga   17400
ttactttttg atcgatcccg gcatcggccg ttttctctac cgcctggcac gccgcgccgc   17460
aggcaggca gaagccagat ggttgttcaa gacgatctac gaacgcagtg gcagcgccgg   17520
agagttcaag aagttctgtt tcaccgtgcg caagctgatc gggtcaaatg acctgccgga   17580
gtacgatttg aaggaggagg cggggcaggc tggcccgatc ctagtcatgc gctaccgcaa   17640
cctgatcgag ggcgaagcat ccgccggttc ctaatgtacg gagcagatgc tagggcaaat   17700
tgccctagca ggggaaaaag gtcgaaaagg tctcttttcct gtggatagca cgtacattgg   17760
gaacccaaag ccgtacattg ggaaccggaa cccgtacatt gggaacccaa agccgtacat   17820
tgggaaccgg tcacacatgt aagtgactga tataaaagag aaaaaaggcg attttttccgc   17880
ctaaaactct ttaaaactta ttaaaactct taaaacccgc ctggcctgtg cataactgtc   17940
tggccagcgac acagccgaag agctgcaaaa agcgcctacc cttcggtcgc tgcgctccct   18000
acgccccgcc gcttcgcgtc ggcctatcgc ggccgctagcc cgctcaaaaa tggctggcct   18060
acggccaggc aatctaccag ggcgcggaca agccgcgccg tcgccactcg accgccggcg   18120
ctgaggtctg cctcgtgaag aaggtgttgc tgactcatac caggcctgaa tcgcccatc   18180
atccagccag aaagtgaggg agccacggtt gatgagagct ttgttgtagg tggaccagtt   18240
ggtgattttg aacttttgct ttgccacgga acggtctgcg ttgtcgggaa gatgcgtgat   18300
ctgatccttc aactcagcaa aagttcgatt tattcaacaa agccgccgtc ccgtcaagtc   18360
agcgtaatgc tctgccagtg ttacaaccaa ttaaccaatt ctgattagaa aaactcatcg   18420
agcatcaaat gaaactgcaa tttattcata tcaggattat caataccata tttttgaaaa   18480
agccgtttct gtaatgaagg agaaaactca ccgaggcagt tccataggat ggcaagatcc   18540
tggtatcggt ctgcgattcc gactcgtcca acatcaatac aacctattaa tttcccctcg   18600
tcaaaaataa ggttatcaag tgagaaatca ccatgagtga cgactgaatc cggtgagaat   18660
ggcaaaagct ctgcattaat gaatcggcca acgcgcgggg agagcggtt tgcgtattgg   18720
gcgctcttcc gcttcctcgc tcactgactc gctgcgctcg gtcgttcggc tgcggcgagc   18780
ggtatcagct cactcaaagg cggtaatacg gttatccaca gaatcagggg ataacgcagg   18840
aaagaacatg tgagcaaaag gccagcaaaa ggccaggaac cgtaaaaagg ccgcgttgct   18900
ggcgtttttc cataggctcc gcccccctga cgagcatcac aaaaatcgac gctcaagtca   18960
gaggtggcga aacccgacag gactataaag ataccaggcg tttccccctg gaagctcccct   19020
cgtgcgctct cctgttccga ccctgccgct taccggatac ctgtccgcct ttctcccttc   19080
gggaagcgtg gcgctttctc atagctcacg ctgtaggtat ctcagttcgg tgtaggtcgt   19140
tcgctccaag ctgggctgtg tgcacgaacc ccccgttcag cccgaccgct gcgccttatc   19200
cggtaactat cgtcttgagt ccaacccggt aagacacgac ttatcgccac tggcagcagc   19260
cactggtaac aggattagca gagcgaggta tgtaggcggt gctacagagt tcttgaagtg   19320
gtggcctaac tacggctaca ctagaagaac agtatttggt atctgcgctc tgctgaagcc   19380
agttaccttc ggaaaaagag ttggtagctc ttgatccggc aaacaaacca ccgctggtag   19440
cggtggtttt tttgtttgca agcagcagat tacgcgcaga aaaaaaggat ctcaagaaga   19500
tcctttgatc ttttctacgg ggtctgacgc tcagtggaac gaaaactcac gttaagggat   19560
tttggtcatg agattatcaa aaaggatctt cacctagatc cttttgatcc ggaatta     19617
```

| SEQ ID NO: 6 | moltype = DNA   length = 55 |
|---|---|
| FEATURE | Location/Qualifiers |
| misc_feature | 1..55 |
| | note = target sequence for the TALEN of 22808 |

```
                    source          1..55
                                    mol_type = other DNA
                                    organism = synthetic construct
SEQUENCE: 6
tccagggtca acgtggagac agggaggtac gaaccggtga ctggcgaagg aagca       55

SEQ ID NO: 7           moltype = DNA  length = 15722
FEATURE                Location/Qualifiers
misc_feature           1..15722
                       note = vector 23123
misc_feature           4..259
                       note = bNRB-05
regulatory             304..2100
                       note = promoter - prSoUbi4-04
                       regulatory_class = promoter
gene                   2117..6286
                       note = cCas9-01
variation              5606..5608
                       note = mutation - L to V mutation
variation              5651..5653
                       note = mutation - I to V mutation
regulatory             6292..6544
                       note = terminator - tNOS-05-01
                       regulatory_class = terminator
regulatory             6551..6925
                       note = promoter - prOsU3-01
                       regulatory_class = promoter
misc_feature           6927..6946
                       note = xZmPLAIIA
misc_feature           6927..7031
                       note = rsgRNAZmPLAIIA02
regulatory             7042..9033
                       note = promoter - prUbi1-04
                       regulatory_class = promoter
gene                   9050..10228
                       note = cPMI-09
regulatory             10251..10503
                       note = terminator - tNOS-05-01
                       regulatory_class = terminator
misc_feature           10547..10676
                       note = bNLB-03
gene                   10956..11744
                       note = cSpec-03
regulatory             11839..11969
                       note = promoter - prVirG-01
                       regulatory_class = promoter
gene                   12706..13779
                       note = cRepA-01
misc_feature           13822..14226
                       note = oVS1-02
misc_feature           14904..15710
                       note = oCOLE-06
source                 1..15722
                       mol_type = other DNA
                       organism = synthetic construct
SEQUENCE: 7
attcctgtgg ttggcatgca catacaaatg gacgaacgga taaaccttt cacgcccttt    60
taaatatccg attattctaa taaacgctct tttctcttag gtttacccgc caatatatcc  120
tgtcaaacac tgatagttta aactgaaggc gggaaacgac aatgatca tgagcggaga   180
attaagggag tcacgttatg accccgccg atgacgcggg acaagccgtt ttacgtttg  240
aactgacaga accgcaacgc tgcaggaatt ggccgcagcg gccatttaaa caaagcttgg  300
taccattatg tggtctaggt aggttctata tataagaaaa cttgaaatgt tctaaaaaaa  360
aattcaagcc catgcatgat tgaagcaaac ggtatagcaa cggtgttaac ctgatctagt  420
gatctcttgc aatccttaac ggccacctac cgcaggtagc aaacggcgtc ccctcctcg   480
atatctccgc ggcgacctct ggcttttcc gcggaattgc gcggtgggga cggattccac  540
gagaccgcga cgcaaccgcc tctcgccgct gggccccaca ccgctcggtg ccgtagcctc  600
acgggactct ttctccctcc tccccgtta taaattggct tcatccctc cttgcctcat   660
ccatccaaat cccagtcccc aatcccatcc cttcgtagga gaaattcatc gaagctaagc  720
gaatcctcgc gatcctctca aggtactgcg agtttcgat cccctctcg acccctcgta   780
tgtttgtgtt tgtcgtagcg tttgattagg tatgctttcc ctgtttgtgt tcgtcgtagc  840
gtttgattag gtatgctttc cctgttcgtg ttcatcgtag tgtttgatta ggtcgtgtga  900
ggcgatggcc tgctcgcgtc cttcgatctg tagtcgattt gcgggtcgtg gtgtagatct  960
gcgggctgtg atgaagttat ttggtgtgat ctgctcgcct gattctgcgg gttggctcga 1020
gtagatatga tggtttggacc ggttggttcg tttaccgcgt taggggttggg ctgggatgat 1080
gttgcatgcg ccgttgcgcg tgatcccgca gcaggacttg cgtttgattg ccagatctcg 1140
ttacgattat gtgatttggt ttggactttt tagatctgta gcttctgctt atgtgccaga 1200
tgcgcctact gctcatatgc ctgatgataa tcataaatgg ctgtgaact aactagttga  1260
ttgcggagtc atgtatcagc tacaggtgta gggactagct acaggtgtag ggacttgcgt 1320
ctaattgttt ggtcctttac tcatgttgca attatgcaat ttagtttaga ttgtttgttc  1380
```

```
cactcatcta ggctgtaaaa gggacactgc ttagattgct gtttaatctt tttagtagat   1440
tatattatat tggtaactta ttaccccstat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatccctatag ctttgttttca tgtatcaatt cttttgtgtt caacagtcag   2040
ttttttgttag attcattgta acttatggtc gcttactctt ctggtcctca atgcttgcag   2100
gatcgcggcc gctcatatgg acaagaagta cagcatcggc ctggacatcg caccaacag   2160
cgtgggctgg gccgtgatca ccgacgagta caaggtgccg agcaagaagt tcaaggtgct   2220
gggcaacacc gacaggcaca gcatcaagaa gaacctgatc ggcgcccgtgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggga ggacaagaa agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg cgacctgaa   2640
cccggacaac agcgacgtgg acaagctgtt catccagctg gtgcagacct acaaccagct   2700
gttcgaggag aacccgatca acgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg acccgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcaga gctgccgga gaagtacaag gagatcttct tcgaccagag   3180
caagaacggc tacgcggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggaccctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gctgctgta   3660
cgagtacttc accgtgtaca acgagctgac caaggtgaag tacgtgaccg agggcatgag   3720
gaagccggcc ttcctgagcg gcgagcagaa aaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
gctgaagacc tacgcccacc tgttcgacga caaggtgatg aagcagctga gaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagccggg ccatcaagaa   4320
gggcatcctg cagaccgtga aggtggtgga cgagctggtg aaggtgatgg caggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag caccccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actggaggca gctgctgaac gccaagctga tcacccagag   4800
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca agtacgacga gaacgacaag ctgatcaggg aggtgaaggt   4980
gatcacccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacgcg actacaaggt   5160
gtacgacgtg aggaagatga tcgccaagag cgagcaggaa cccaccgcca gcaagagcaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggaccccg aagaagtac gcggcttcga   5520
cagccgacc gtggcctaca gcgtgctggt ggtggccaag gtggagaagg caagagcaa   5580
gaagctgaag agcgtgaagg agctggtggg catcaccatc atggagagga gcagcttcga   5640
gaagaaccca gtgacttcc tggaggccaa gggctacaag gaggtgaaga aggaccgat   5700
cattaaactg ccgaagtaca gcctgttcga gctggagaac ggcaggaaga ggatgctggc   5760
cagcgcgggc gagctgcaga agggcaacga gctggccctg ccgagcaagt acgtgaactt   5820
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
```

```
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactggtt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagggt caacgtggga acaggggttt tagagctaga   6960
aatagcaagt taaaataagg ctagtccgtt atcaacttga aaaagtggca ccgagtcggt   7020
gcttttttt tcggaccgcg cctgcagtgc agcgtgaccc ggtcgtgccc ctctctagag   7080
ataatgagca ttgcatgtct aagttataaa aaattaccac atattttttt tgtcacactt   7140
gtttgaagtg cagttttatc atctttatac atatatttaa actttactct acgaataata   7200
taatctatag tactacaata atatcagtgt tttagagaat catataaatg aacagttaga   7260
catggtctaa aggacaattg agtatttga caacaggact ctacagtttt atcttttag   7320
tgtgcatgtg ttctcctttt tttttgcaaa tagcttcacc tatataatac ttcatccatt   7380
ttattagtac atccatttag ggtttagggt taatggtttt atagactaa tttttttagt   7440
acatctattt tattctattt tagcctctaa attaagaaaa ctaaaactct atttagtttt   7500
ttttatttaa taatttagat ataaaataga ataaataaa gtgactaaaa attaaacaaa   7560
tacccttaa gaaattaaaa aaactaagga aacattttc ttgtttcgag tagataatgc   7620
cagcctgtta aacgcctcg acgagtctaa cggacaccaa ccagcgaacc agcagcgtgc   7680
cgtcgggcca agcgaagcag acggcacggc atctctgtcg ctgcctctgg acccctctcg   7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acggggatt cctttcccac cgctccttcg cttttcccttc ctcgcccgcc gtaataaata   7920
gacacccct ccacccctc tttccccaac ctcgtgttgt tcggagcgca cacacacaca   7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
tttttttgt ttcgttgcat agggtttggt ttgccctttt cctttattc aatatatgcc   8340
gtgcacttgt ttgtcgggtc atcttttcat gctttttttt gtcttggttg tgatgatgtg   8400
gtctggttgg gcggtcgttc tagatcggag tagaattcgt tttcaaacta cctggtggtt   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gcttttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtaccatc tattataata aacaagtatg   8880
ttttataatt attttgatct tgatatactt ggatgatgc atatcagca gctatatgtg   8940
gatttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc acccccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcaccca caagcacaa   9360
cagcagagtc ggcttcgcca aggagaacgc cgccggcatc cccatggacc ccgccgagcg   9420
caactacaag gaccccaacc acaagcccga gctggtgttc gccctgaccc cttcctggc   9480
catgaacgcc ttccgcgagt tcagcgagat cgtgagcctg ctgcagcccg tggcggcgc   9540
ccaccccgcc atcgcccact tcctgcagca gcccgacgcc gagcgcctga gcagctgtt   9600
cgccagcctg ctgaacatgc agggcgagga gaagaaccgc gccctggcca tcctgaagag   9660
cgccctggac agccagcagg gcgagcccct gcagaccatc cgcctgatca gcgagttcta   9720
ccccgaggac agccggcctgt tcagccccct gctgctgaac gtggtgaagc tgaacccgg   9780
cgaggccatg ttcctgttcg ccgagacccc cacgcctac ctgcagggcg tggccctgga   9840
ggtgatggcc aacagcgaca acgtgctgcg cgccggcctg accccaagt acatcgacat   9900
ccccgagctg gtggccaacg tgaagttcga ggccaagccc gccaaccagc tgctgaccca   9960
gcccgtgaag cagggcgccg agctggactt ccccatcccc gtggacgact cgccttcag  10020
cctgcacgac ctgagcgaca aggagaccac catccaccag cagagcgccg ccatcctgtt  10080
ctgcgtggag ggcgacgcca ccctgtgaa gggcagccag cagctgcagc tgaagcccgg  10140
cgagagcgcc ttcatcgccg ccaacgagag ccccgtgacc gtgaagggcc acggccgcct  10200
ggcccgctgg tacaacaagc tgtgtgatagga gtcgatccg tcgacctgca gcgttcaa   10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg gttttttatg attagagtcc cgcaattata catttaatac gcgatagaaa  10440
acaaaatata gcgcgcaaac taggataaat tatcgcgcg ggtgtcatct atgttactag  10500
atcggcggc cgcaattgaa gtttgggcgg ccagcatgcg tatccgcca atgtgttatt  10560
aagttgtcta agcgtcaatt tgtttacacc acaatatatc ctgccaccag ccagccaaca  10620
gctcccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg ttttttgcgc cgacatcata acggttctgg  10860
```

```
caaatattct gaaatgagct gttgacaatt aatcatccgg ctcgtataat gtgtggaatt   10920
gtgagcggat aacaatttca cacaggaaac agaccatgag ggaagcgttg atcgccgaag   10980
tatcgactca actatcagag gtagttggcg tcatcgagcg ccatctcgaa ccgacgttgc   11040
tggccgtaca tttgtacggc tccgcagtgg atggcggcct gaagccacac agtgatattg   11100
atttgctggt tacggtgacc gtaaggcttg atgaaacaac gcggcgagct ttgatcaacg   11160
acctttggga aacttcggct tccctggag agagcgagat tctccgcgct gtagaagtca   11220
ccattgttgt gcacgacgac atcattccgt ggcgttatcc agctaagcgc gaactgcaat   11280
ttggagaatg gcagcgcaat gacattcttg caggtatctt cgagccagcc acgatcgaca   11340
ttgatctggc tatcttgctg acaaaagcaa gagaacatag cgttgccttg gtaggtccag   11400
cggcggagga actctttgat ccggttcctg aacaggatct atttgaggcg ctaaatgaaa   11460
ccttaacgct atggaactcg ccgcccgact gggctggcga tgagcgaaat gtagtgctta   11520
cgttgtcccg catttggtac agcgcagtaa ccggcaaaat cgcgccgaag gatgtcgctg   11580
ccgactgggc aatggagcgc ctgccggccc agtatcagcc cgtcatactt gaagctaggc   11640
aggcttatct tggacaagaa gatcgcttgg cctcgcgcga agatcagttg gaagaatttg   11700
ttcactacgt gaaaggcgag atcaccaaag tagtcggcaa ataaagctct agtggatctc   11760
cgtacccggg gatctggctc gcggcggacg cacgacgccg gggcgagacc ataggcgatc   11820
tcctaaatca atagtagctg taacctcgaa gcgtttcact tgtaacaacg attgagaatt   11880
tttgtcataa aattgaaata cttggttcgc attttttgtca tccgcggtca gccgcaattc   11940
tgacgaactg cccatttagc tggagatgat tgtacatcct tcacgtgaaa atttctcaag   12000
cgctgtgaac aagggttcag attttagatt gaaaggtgag ccgttgaaac acgttcttct   12060
tgtcgatgac gacgtcgcta tgcggcatct tattattgaa taccttacga tccacgcctt   12120
caaagtgacc gcggtagccg acagccaccca gttcacaaga gtactctctt ccgcgacggt   12180
cgatgtcgtg gttgttgatc tagatttagg tcgtgaagat gggctcgagc taggagcaag   12240
tgattttatc gctaagccgt tcagtatcag agagtttcta gcacgcattc gggttgcctt   12300
gcgcgtcgcc cccaacgttg tccgctccaa agaccgacgg tctttttgtt ttactgactg   12360
gacacttaat ctcaggcaac gtccgcttgat gtccgaaget ggcggtgagg tgaaacttac   12420
ggcaggtgag ttcaatcttc tcctcgcgtt tttagaaaa ccccgcgacg ttctatcgcg   12480
cgagcaactt ctcattgcca gtcgagtacg cgacgaggag gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacgggg   12660
gacgatggca gcctgagcca attcccagat ccccgaggaa tcggcgtgag cggtcgcaaa   12720
ccatccggcc cggtacaaat cggcgcggcg ctgggtgatg acctggtgga gaagttgaag   12780
gccgcgcagg ccgcccagcg gcaacgcatc gaggcagaag cacgcccegg tgaatcgtgg   12840
caagcggccg ctgatcgaat ccgcaaagaa tcccggcaac cgccgccgac cggtgcgcg   12900
tcgattagga agccgcccaa gggcgacgag caaccagatt ttttcgttcc gatgctctat   12960
gacgtgggca cccgcgatag tcgcagcatc atggacgtgg ccgttttccg tctgtcgaag   13020
cgtgaccgac gagctggcga ggtgatccgc tacgagcttc cagacgggca cgtagaggtt   13080
tccgcagggc cggccggcat ggccagtgtg tgggattacg acctggtact gatgcgcgtt   13140
tcccatctaa ccgaatccat gaaccgatac cgggaaggga agggagacaa gcccggccgc   13200
gtgttccgtc cacacgttgc ggacgtactc aagttctgcc ggcgagccga tgcggaaag   13260
cagaaagacg acctggtaga aacctgcatt cggttaaaca ccacgcacgt tgccatgcag   13320
cgtacgaaga aggccaagaa cggccgcctg gtgacggtat ccgagggtga agccttgatt   13380
agccgctaca agatcgtaaa gagcgaaacc gggcggccgg agtacatcga gatcgagcta   13440
gctgattgga tgtaccgcga gatcacagaa ggcaagaacc cggacgtgct gacgttcac   13500
cccgattact ttttgatcga tcccggcatc ggccgttttc tctaccgcct ggcacgccgc   13560
gccgcaggca aggcagaagc cagatggttg ttcaagacga tctacgaacg cagtggcagc   13620
gccggagagt tcaagaagtt ctgtttcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacgagca gatgctaggg   13800
caaattgccc tagcagggga aaaaggtcga aaggtctct ttcctgtgga tagcacgtac   13860
attgggaacc caaagccgta cattgggaac cggaacccgt acattgggaa cccaaagccg   13920
tacattggga accggtcaca catgtaagtg actgatataa aagagaaaaa aggcgattt   13980
tccgcctaaa actctttaaa acttattaaa actcttaaaa cccgcctggc ctgtgcataa   14040
ctgtctggcc agcgcacagc cgaagagctg caaaagcgc ctacccttcg gtcgctgcg   14100
tcctacgcc ccgccgcttc gcgtcggcct atcgcggccg ctggccgctc aaaaatggct   14160
ggcctacggc caggcaatct accagggcgc ggacaagccg cgccgtcgcc actcgaccgt   14220
cggcgctgag gtctgcctcg tgaagaaggt gttgctgact cataccaggc ctgaatcgcc   14280
ccatcatcca gccagaaagt gagggagcca cggttgatga gagctttgtt gtaggtggac   14340
cagttggtga tttttgaactt ttgctttgcc acggaacggt ctgcgttgtc gggaagatga   14400
gtgatctgat ccttcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaatttat tcatatcagg attatcaata ccatattttt   14580
gaaaaagccg tttctgtaat gaaggagaaa actcaccgag gcagttccat aggatggcaa   14640
gatcctggta tcggtctgcg attccgactc gtccaactat aatacaacct attaatttcc   14700
cctcgtcaaa aataaggtta tcaagtgaga atcaccatg agtgacgact gaatccggta   14760
agaatggcaa aagctctgca ttaatgaatc ggccaacgcg cggggagagg cggtttgcgt   14820
attgggcgct cttccgcttc ctcgctcact gactcgctgc gctcggtcgt tcggctgcgg   14880
cgagcggtat cagctcactc aaaggcggta atacggttat ccacagaatc aggggataac   14940
gcaggaaaga acatgtgagc aaaaggccag caaaaggcca ggaaccgtaa aaaggccgcg   15000
ttgctggcgt ttttccatag gctccgcccc cctgacgagc atcacaaaaa tcgacgctca   15060
agtcagaggt ggcgaaaccc gacaggacta taaagatacc aggcgtttcc cctggaagc   15120
tccctcgtgc gctctcctgt tccgaccctg ccgcttaccg gatacctgtc cgcctttctc   15180
ccttcgggaa gcgtggcgct ttctcatagc tcacgctgta ggtatctcag ttcggtgtag   15240
gtcgttcgct ccaagctggg ctgtgtgcac gaaccccccg ttcagcccga ccgctgcgcc   15300
ttatccggta actatcgtct tgagtccaac ccggtaagac acgacttatc gccactggca   15360
gcagccactg gtaacaggat tagcagagcg aggtatgtag cgtgctac agagttcttg   15420
aagtggtggc ctaactacgg ctacactaga agaacagtat ttggtatctg cgctctgctg   15480
aagccagtta ccttcggaaa aagagttggt agctcttgat ccggcaaaca aaccaccgct   15540
ggtagcggtg gttttttgt ttgcaagcag cagattacgc gcagaaaaaa aggatctcaa   15600
```

```
gaagatcctt tgatcttttc tacggggtct gacgctcagt ggaacgaaaa ctcacgttaa   15660
gggattttgg tcatgagatt atcaaaaagg atcttcacct agatccttttt gatccggaat   15720
ta                                                                    15722
```

```
SEQ ID NO: 8              moltype = DNA   length = 20
FEATURE                   Location/Qualifiers
misc_feature              1..20
                          note = for editing MTL
source                    1..20
                          mol_type = other DNA
                          organism = synthetic construct
SEQUENCE: 8
gggtcaacgt ggagacaggg                                                 20

SEQ ID NO: 9              moltype = DNA   length = 41
FEATURE                   Location/Qualifiers
source                    1..41
                          mol_type = genomic DNA
                          organism = Zea mays
SEQUENCE: 9
agggtcaacg tggagacagg gaggtacgaa ccggtgactg g                         41

SEQ ID NO: 10             moltype = DNA   length = 45
FEATURE                   Location/Qualifiers
source                    1..45
                          mol_type = genomic DNA
                          organism = Zea mays
SEQUENCE: 10
agggtcaacg tggagacagg cgaggaggta cgaaccggtg actgg                     45

SEQ ID NO: 11             moltype = DNA   length = 42
FEATURE                   Location/Qualifiers
misc_feature              1..42
                          note = mutated MTL
source                    1..42
                          mol_type = other DNA
                          organism = synthetic construct
SEQUENCE: 11
agggtcaacg tggagacaag ggaggtacga accggtgact gg                        42

SEQ ID NO: 12             moltype = DNA   length = 28
FEATURE                   Location/Qualifiers
misc_feature              1..28
                          note = mutated MTL portion
source                    1..28
                          mol_type = other DNA
                          organism = synthetic construct
SEQUENCE: 12
agggtcaacg tggagaaccg gtgactgg                                        28

SEQ ID NO: 13             moltype = DNA   length = 40
FEATURE                   Location/Qualifiers
misc_feature              1..40
                          note = mutated MTL portion
source                    1..40
                          mol_type = other DNA
                          organism = synthetic construct
SEQUENCE: 13
agggtcaacg tggagacggg aggtacgaac cggtgactgg                           40

SEQ ID NO: 14             moltype = DNA   length = 28
FEATURE                   Location/Qualifiers
misc_feature              1..28
                          note = mutated MTL portion
source                    1..28
                          mol_type = other DNA
                          organism = synthetic construct
SEQUENCE: 14
agggtcaacg tggagaaccg gtgactgg                                        28

SEQ ID NO: 15             moltype = DNA   length = 42
FEATURE                   Location/Qualifiers
misc_feature              1..42
                          note = mutated MTL portion
source                    1..42
                          mol_type = other DNA
                          organism = synthetic construct
SEQUENCE: 15
agggtcaacg tggagacaag ggaggtacga accggtgact gg                        42
```

```
SEQ ID NO: 16           moltype = DNA  length = 40
FEATURE                 Location/Qualifiers
misc_feature            1..40
                        note = mutated MTL portion
source                  1..40
                        mol_type = other DNA
                        organism = synthetic construct
SEQUENCE: 16
agggtcaacg tggagacggg aggtacgaac cggtgactgg                              40

SEQ ID NO: 17           moltype = DNA  length = 41
FEATURE                 Location/Qualifiers
misc_feature            1..41
                        note = unmutated MTL portion
source                  1..41
                        mol_type = other DNA
                        organism = synthetic construct
SEQUENCE: 17
agggtcaacg tggagacagg gaggtacgaa ccggtgactg g                            41

SEQ ID NO: 18           moltype = DNA  length = 28
FEATURE                 Location/Qualifiers
misc_feature            1..28
                        note = mutated MTL portion
source                  1..28
                        mol_type = other DNA
                        organism = synthetic construct
SEQUENCE: 18
agggtcaacg tggagaaccg gtgactgg                                           28

SEQ ID NO: 19           moltype = DNA  length = 1371
FEATURE                 Location/Qualifiers
source                  1..1371
                        mol_type = genomic DNA
                        organism = Zea mays
SEQUENCE: 19
agttcatcac taatcacact tattgttccc tcgacgagta tctagctagc tcattaatcg        60
atcaatcggg gtgtgcggtc gaaggcggca atggcgagct actcgtcgcg gcgtccatgc       120
aatacctgta gcacgaaggc gatggccggg agcgtggtcg gcgagcccgt cgtgctgggg       180
cagagggtga cggtgctgac ggtggacggg ggcggcgtcc ggggtctcat cccgggaacc       240
atcctcgcct tcctcgaggc caggctgcag gagctggacg gaccggaggc gaggctggcg       300
gactacttcg actacatcgc cggaaccagc accggcagtc tcatcaccgc catgctcacc       360
gcgcccggca aggacaagcg gcctctctac gctgccaagg acatcaacca cttttacatg       420
gagaactgcc cgcgcatctt ccctcagaag agcaggcttg cggccgccat gtccgcgctg       480
aggaagccaa agtacaacgg caagtgcatg cgcagcctga ttaggagcat cctcggcgag       540
acgagggcca agagcacgcc tctgaagaac gctctgctct cggacgtgtg cattggcacg       600
tccgccgcgc cgacctacct cccggcgcac tacttccaga ctgaagacgc caacggcaag       660
gagcgcgaat acaacctcat cgacggcggt gtggcggcca acaacccgac gatggttgcg       720
atgacgcaga tcaccaaaaa gatgcttgcc agcaaggaca aggccgagga gctgtaccca       780
gtgaagccgt cgaactgccg caggttcctg gtgctgtcca tcgggacggg gtcgacgtcc       840
gagcagggcc tctacacggc gcggcagtgc tcccggtggg gtatctgccg gtggctccgc       900
aacaacggca tggcccccat catcgacatc ttcatggcgg ccagctcgga cctggtggac       960
atccacgtcg ccgcgatgtt ccagtcgctc cacagcgacg cgactacct gcgcatccag       1020
gacaactcgc tccgtggcgc cgcggccacc gtggacgcgg cgacgccgga gaacatgcgg      1080
acgctcgtcg ggatcgggga gcggatgctg gcacagaggg tgtccagggt caacgtggag      1140
acagggaggt acgaaccggt gactggcgaa ggaagcaatg ccgatgccct cggtgggctc      1200
gctaggcagc tctccgagga gaggagaaca aggctcgcgc gccgcgtgtc tgccatcaac      1260
ccaagaggct ctagatgtgc gtcgtacgat atctaagaca agtggcttta ctgtcagtca      1320
catgcttgta aataagtaga ctttatttta ataaacata aaaatatata t                1371

SEQ ID NO: 20           moltype = DNA  length = 15722
FEATURE                 Location/Qualifiers
misc_feature            1..15722
                        note = vector 23397
misc_feature            4..259
                        note = bNRB-05
regulatory              304..2100
                        note = promoter - prSoUbi4-04
                        regulatory_class = promoter
gene                    2117..6286
                        note = cCas9-01
variation               5606..5608
                        note = mutation - L to V mutation
variation               5651..5653
                        note = mutation - I to V mutation
regulatory              6292..6544
                        note = terminator - tNOS-05-01
                        regulatory_class = terminator
```

| | | |
|---|---|---|
| regulatory | 6551..6925 | |
| | note = promoter - prOsU3-01 | |
| | regulatory_class = promoter | |
| misc_feature | 6927..6946 | |
| | note = xZmVLHP | |
| misc_feature | 6927..7031 | |
| | note = rsgRNAZmVLHP-02 | |
| regulatory | 7042..9033 | |
| | note = promoter - prUbi1-04 | |
| | regulatory_class = promoter | |
| gene | 9050..10228 | |
| | note = cPMI-09 | |
| regulatory | 10251..10503 | |
| | note = terminator - tNOS-05-01 | |
| | regulatory_class = terminator | |
| misc_feature | 10547..10676 | |
| | note = bNLB-03 | |
| gene | 10956..11744 | |
| | note = cSpec-03 | |
| regulatory | 11839..11969 | |
| | note = promoter - prVirG-01 | |
| | regulatory_class = promoter | |
| gene | 12706..13779 | |
| | note = cRepA-01 | |
| misc_feature | 13822..14226 | |
| | note = oVS1-02 | |
| misc_feature | 14904..15710 | |
| | note = oCOLE-06 | |
| source | 1..15722 | |
| | mol_type = other DNA | |
| | organism = synthetic construct | |

```
SEQUENCE: 20
attcctgtgg ttggcatgca catacaaatg gacgaacgga taaaccttt  cacgcccttt    60
taaatatccg attattctaa taaacgctct tttctcttag gtttacccgc caatatatcc   120
tgtcaaacac tgatagttta aactgaaggc gggaaacgac aatctgatca tgagcggaga   180
attaagggag tcacgttatg accccgccg atgacgcggg acaagccgtt ttacgtttgg   240
aactgacaga accgcaacgc tgcaggaatt ggccgcagcg gccattttaa caaagcttgg   300
taccattatg tggtctaggt aggttctata tataagaaaa cttgaaatgt tctaaaaaaa   360
aattcaagcc catgcatgat tgaagcaaac ggtatagcaa cggtgttaac ctgatctagt   420
gatctcttgc aatccttaac ggccacctac cgcaggtagc aaacggcgtc ccctcctcg    480
atatctccgc ggcgacctct ggctttttcc gcggaattgc gcggtgggga cggattccac   540
gagaccgcga cgcaaccgcc tctcgccgct gggcccacca ccgctcggtg ccgtagcctc   600
acgggactct ttctccctcc tcccccgtta taaattgcgt tcatccctc cttgcctcat   660
ccatccaaat cccagtcccc aatcccatcc cttcgtagga gaaattcatc gaagctaagc   720
gaatcctcgc gatcctctca aggtactgcg agttttcgat ccccctctcg acccctcgta   780
tgtttgtgtt tgtcgtagcg tttgattagg tatgcttcc ctgtttgtgt tcgtcgtagc   840
gtttgattag gtatgctttc cctgttcgtg ttcatcgtag tgtttgatta ggtcgtgtga   900
ggcgatggcc tgctcgcgtc cttcgatctg tagtcgattt gcgggtcgtg gtgtagatct   960
gcgggctgtg atgaagttat ttggtgtgat ctgctcgcct gattctgcgg gttggctcga  1020
gtagatatga tggttggacc ggttggtcg tttaccgcgc tagggttggg ctgggatgat  1080
gttgcatgcg ccgttgcgcg tgatcccgca gcaggacttg cgtttgattg ccagatctcg  1140
ttacgattat gtgatttggt ttggactttt tagatctgta gcttctgctt atgtgccaga  1200
tgcgcctact gctcatatgc ctgatgataa tcataaatgg ctgtggaact aactagttga  1260
ttgcggagtc atgtatcagc tacaggtgta gggactagct acaggtgtag ggacttgcgt  1320
ctaattgttt ggtcctttac tcatgttgca attatgcaat ttagttaga ttgttgttc   1380
cactcatcta ggctgtaaaa gggacactgc ttagattgct gttaatctt tttagtagat   1440
tatattat tggtaactta ttaccccat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat  1620
gatttgcgtg gttctctaat gtgaaatact atagctactt gttagtaaga atcaggttcg  1680
tatgcttaat gctgtatgtg ccttctgctc atgcctgatg ataatcatat atcactggaa  1740
ttaattagtt gatcgtttaa tcatatatca agtacatacc atgccacaat ttttagtcac  1800
ttaacccatg cagattgaac tggtccctgc atgttttgct aaattgttct attctgatta  1860
gaccatatat catgtatttt tttttggtaa tggttctctt atttaaatg ctatatagtt  1920
ctggtacttg ttagaaagat ctgcttcata gtttagttgc ctatccctcg aattaggatg  1980
ctgagcagct gatcctatag cttttgtttca tgtatcaatt cttttgtgtt caacagtcag  2040
tttttgttag attcattgta acttatggtc gcttactctt ctggtcctca atgcttgcag  2100
gatcgcggcc gctcatatgg acaagaagta cagcatcggc ctggacatcg gcaccaacag  2160
cgtgggctgg gccgtgatca ccgacgagta caaggtgccg agcaagaagt tcaaggtgct  2220
gggcaacacc gacaggcaca gcatcaagaa gaacctgatc ggcgccctgc tgttcgacag  2280
cggcgagacc gccgaggcca ccaggctgaa gaggaccgcc aggaggaggt acaccaggag  2340
gaagaacagg atctgctacc tgcaggagat cttcagcaac gagatggcca aggtggacga  2400
cagcttcttc cacaggctgg aggagagctt cctggtggag gaggacaaga agcacgagag  2460
gcaaccgatc ttcggcaaca tcgtggacga ggtggcctac catgagaagt acccgaccat  2520
ctaccacctg aggaagaagc tggtggacag caccgacaag gccgacctga ggctgatcta  2580
cctggccctg gcccacatga tcaagttcag gggccacttc ctgatcgagg gcgacctgaa  2640
cccggacaac agcgacgtgg acaagctgtt catccagctg gtgcagacct acaaccagct  2700
gttcgaggag aacccgatca cgccagcgg cgtggacgcc aaggccatcc tgagcgccag  2760
gctgagcaag agcaggaggc tggagaacct gatcgcccag ctgccgggcg agaagaagaa  2820
```

```
cggcctgttc ggcaacctga tcgccctgag cctgggcctg accccgaact tcaagagcaa  2880
cttcgacctg gccgaggacg ccaagctgca gctgagcaag gacacctacg acgacgacct  2940
ggacaacctg ctggcccaga tcggcgacca gtacgccgac ctgttcctgg ccgccaagaa  3000
cctgagcgac gccatcctgc tgagcgacat cctgagggtg aacaccgaga tcaccaaggc  3060
cccgctgagc gccagcatga tcaagaggta cgacgagcac caccaggacc tgaccctgct  3120
gaaggccctg gtgaggcagc agctgccgga gaagtacaag gagatcttct tcgaccagag  3180
caagaacggc tacgccggct acatcgacgg cggcgccagc caggaggagt tctacaagtt  3240
catcaagccg atcctggaga gatggacgg caccgaggac ctgctggtga agctgaacag  3300
ggaggacctg ctgaggaagc agaggacctt cgacaacggc agcatcccgc accagatcca  3360
cctgggcgag ctgcacgcca tcctgaggag gcaggaggac ttctacccgt tcctgaagga  3420
caacagggag aagatcgaga agatcctgac cttccgcatc ccgtactacg tgggcccgct  3480
ggccaggggc aacagcaggt tcgcctggat gaccaggaag agcgaggaga ccatcacccc  3540
gtggaacttc gaggaggtgg tggacaaggg cgccagcgcc cagagcttca tcgagaggat  3600
gaccaacttc gacaagaacc tgccgaacga aaggtgctg ccgaagcaca gcctgctgta  3660
cgagtacttc accgtgtaca acgagctgac caaggtgaag tacgtgaccg agggcatgag  3720
gaagccggcc ttcctgagcg gcgagcagaa gaaggccatc gtggacctgc tgttcaagac  3780
caacaggaag gtgaccgtga agcagctgaa ggaggactac ttcaagaaga tcgagtgctt  3840
cgacagcgtg gagatcagcg gcgtggagga caggttcaac gccagcctgg gcacctacca  3900
cgacctgctg aagatcatca aggacaagga cttcctggac aacgaggaga acgaggacat  3960
cctggaggac atcgtgctga ccctgaccct gttcgaggac agggagatga tcgaggagag  4020
gctgaagacc tacgccacc tgttcgacga caaggtgatg aagcagctga gaggaggag  4080
gtacaccggc tggggcaggc tgagcaggaa gctgatcaac ggcatcaggg acaagcagag  4140
cggcaagacc atcctggact tcctgaagag cgacggcttc gccaacagga acttcatgca  4200
gctgatccac gacgacagcc tgaccttcaa ggaggacatc cagaaggccc aggtgagcgg  4260
ccagggcgac agcctgcacg agcacatcgc caacctggcc ggcagccggg ccatcaagaa  4320
gggcatcctg cagaccgtga aggtggtgga cgagctgggt aaggtgatgg gcaggcaaga  4380
gccggagaac atcgtgatcg agatggccag ggagaaccag accacccaga agggccagaa  4440
gaacagcagg gagaggatga gaggatcga ggagggcatc aaggagctgg gcagccagat  4500
cctgaaggag caccccggtgg agaacaccca gctgcagaac gagaagctgt acctgtacta  4560
cctgcagaac ggcagggaca tgtacgtgga ccaggagctg gacatcaaca ggctgagcga  4620
ctacgacgtg gaccacatcg tgccgcagag cttcctgaag gacgacagca tcgacaacaa  4680
ggtgctgacc aggagcgaca agaacagggg caagagcgac aacgtgccga gcgaggaggt  4740
ggtgaagaag atgaaaaact actggaggca gctgctgaac gccaagctga tcacccagag  4800
gaagttcgac aacctgacca aggccgagag gggcggcctg agcgagctgg acaaggccgg  4860
cttcattaaa aggcagctgg tggagcacag gcagatcacc aagcacgtgg cccagatcct  4920
ggacagcagg atgaacacca agtacgacga aaacgacaag ctgatcaggg aggtgaaggt  4980
gatcaccctg aagagcaagc tggtgagcga cttcaggaag gacttccagt tctacaaggt  5040
gagggagatc aataattacc accacgccca cgacgcctac ctgaacgccg tggtgggcac  5100
cgcccctgatt aaaaagtacc cgaagctgga gagcgagttc gtgtacggcg actacaaggt  5160
gtacgacgtg aggaagatga tcgccaagag cgagcaggag atcggcaagg ccaccgccaa  5220
gtacttcttc tacagcaaca tcatgaactt cttcaagacc gagatcaccc tggccaacgg  5280
cgagatcagg aagaggccgc tgatcgagac caacggcgag accggcgaga tcgtgtggga  5340
caagggcagg gacttcgcca ccgtgaggaa ggtgctgtcc atgccgcagg tgaacatcgt  5400
gaagaagacc gaggtgcaga ccggcggctt cagcaaggag agcatcctgc cgaagaggaa  5460
cagcgacaag ctgatcgcca ggaagaagga ctgggacccg aagaagtacg gcggcttcga  5520
cagcccgacc gtggcctaca gcgtgctggt ggtggccaag gtggagaagg gcaagagcaa  5580
gaagctgaag agcgtgaagg agctggtggg catcaccaag agcgtcttcga  5640
gaagaaccca gtggacttcc tggaggccaa gggctacaag gaggtgaaga aggacctgat  5700
cattaaactg ccgaagtaca gcctgttcga gctggagaac ggcaggaaga gatgctggc  5760
cagcgccggc gagctgcaga agggcaacga gctggcccctg ccgagcaagt acgtgaactt  5820
cctgtacctg gccagccact acgagaagct gaagggcagc ccggaggaca acgagcagaa  5880
gcagctgttc gtggagcagc acaagcacta cctggacgag atcatcgagc agatcagcga  5940
gttcagcaag agggtgatcc tggccgacgc caacctggac aaggtgctga gcgcctacaa  6000
caagcacagg gacaagccga tcagggagca ggccgagaac atcatccacc tgttcaccct  6060
gaccaacctg ggcgccccgg ccgccttcaa gtacttcgac accaccatcg acaggaagag  6120
gtacaccagc accaaggagg tgctggacgc caccctgatc caccagagca tcaccggcct  6180
gtacgagacc aggatcgacc tgagccagct gggcggcgac agcagccgc cgaagaagaa  6240
gaggaaggtg agctggaagg acgccagcgg ctggagcagg atgtgaagct gatcgttca  6300
aacatttggc aataaagttt cttaagattg aatcctgttg ccggtcttgc gatgattatc  6360
atataatttc tgttgaatta cgttaagcat gtaataatta acatgtaatg catgacgtta  6420
tttatgagat gggtttttat gattagagtc ccgcaattat acatttaata cgcgatagaa  6480
aacaaaatat agcgcgcaaa ctaggataaa ttatcgcgcg cggtgtcatc tatgttacta  6540
gatcttcgaa gggatcttta aacatacgaa cagatcactt aaagttcttc tgaagcaact  6600
taaagttatc aggcatgcat ggatcttgga gaatcagatt gtgcagtcag ggaccatagc  6660
acaggacagg cgtcttctac tggtgctacc agcaaatgct ggaagccggg aacactgggt  6720
acgttggaaa ccacgtgatg tggagtaaga taaactgtag gagaaaagca tttcgtagtg  6780
ggccatgaag cctttcagga catgtattgc agtatgggcc ggcccattac gcaattggac  6840
gacaacaaag actagtatta gtaccactc ggctatccac atagatcaaa gctggtttaa  6900
aagagttgtg cagatgatcc gtggcagctg gagctgagct tccggggttt tagagctaga  6960
aatagcaagt taaaataagg ctagtccgtt atcaacttga aaaagtggca ccgagtcggt  7020
gcttttttt tcggaccgcg cctgcagtgc agcgtgaccc ggtcgtgccc ctctctagag  7080
ataatgcaga ttgcatgtct aagttataaa aaattaccac atatttttt tgtcacactt  7140
gtttgaagtg cagtttatct atcttttac atatatttaa actttactct acgaataata  7200
taatctatag tactacaata ttagagaat catataaatg aacagttaga  7260
catggtctaa aggacaattg agtatttga caacaggact ctacagtttt atctttttag  7320
tgtgcatgtg ttctccttt ttttttgcaaa tagcttcacc tatataatac ttcatcccatt  7380
ttattagtac atccatttag ggtttagggt taatggtttt tatagactaa tttttttagt  7440
acatctattt tattctattt tagcctctaa attaagaaaa ctaaaactct attttagttt  7500
ttttattaa taatttagat ataaaataga ataaaataaa gtgactaaaa attaaacaaa  7560
```

```
taccctttaa gaaattaaaa aaactaagga aacattttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg acccctctcg   7740
agagttccgc tccaccgttg gacttgctcc gctgtcggca tccagaaatt gcgtggcgga   7800
gcggcagacg tgagccggca cggcaggcgg cctcctcctc ctctcacggg accggcagct   7860
acggggatt cctttcccac cgctccttcg ctttccttc ctcgcccgcc gtaataaata   7920
gacaccccct ccacaccctc tttcccaac ctcgtgttgt tcggagcgca cacacacaca   7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
ttttttttgt ttcgttgcat agggtttggt ttgcccttt cctttattc aatatatgcc   8340
gtgcacttgt ttgtcgggtc atctttcat gcttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gcttttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gatttttta gccctgcctt catacgctat ttatttgctt ggtactgttt cttttgtcga   9000
tgctcaccct gttgttggt gttacttctg cagggatccg gcagcagcca tgcagaagct   9060
gatcaacagc gtgcagaact acgcctgggg cagcaagacc gcctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagccccc gagcatccag gtgcacccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc cttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga gaagagccgc gccctggcca tcctgaagag   9660
cgccctggac agccagcagg gcgagccctg cagaccatc cgcctgatca gcgagttcta   9720
ccccgaggac agcggcctgt tcagccccct gctgctgaac gtggtgaagc tgaaccccgg   9780
cgaggccatg ttcctgttcg ccgagacccc ccacgcctac ctgcagggcg tggccctgga   9840
ggtgatgcc aacagcgaca acgtgctgcg cgccggcctg acccccaagt acatcgacat   9900
ccccgagctg gtggcaacg tgaagttcga ggccaagccc gccaaccagc tgctgaccca   9960
gcccgtgaag cagggcgccg agctggactt ccccatcccc gtggacgact cgccttcag  10020
cctgcacgac ctgagcgaca aggagaccac catcagccag cagagcgccg ccatcctgtt  10080
ctgcgtggag ggcgacgcca ccctgtgaa gggcagccag cagctgacgc tgaagcccgg  10140
cgagagcgcc ttcatcgccc caacgagag cccgtgacc gtgaagggcc acggccgcct  10200
ggcccgcgtg tacaacaagc tgtgatagga gctcgatccg tcgacctgca gatcgttcaa  10260
acatttggca ataaagttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttggggcg gccagcatgg cgtatccgca atgtgttatt  10560
aagttgtcta agcgtcaatt tgtttacacc acaatatctg ccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg tttttgcgc cgacatcata acggttctgg  10860
caaatattct gaaatgagct gttgacaatt aatcatccgg ctcgtataat gtgtggaatt  10920
gtgagcggat aacaatttca caggaaac agaccatgag ggaagcgttg atcgccgaag  10980
tatcgactca actatcagag gtagttggcg tcatcgagcg ccatctcgaa ccgacgttgc  11040
tggccgtaca tttgtacggc tccgcagtgg atggcggcct gaagccacac agtgatattg  11100
atttgctggt tacggtgacc gtaaggcttg atgaaacaac gcggcgagct ttgatcaacg  11160
accttttgga aacttcggct tcccctggag agagcgagat tctccgcgct gtagaagtca  11220
ccattgttgt gcacgacgac atcattccgt ggcgttatcc agctaagcgc gaactgcaat  11280
ttggagaatg gcagcgcaat gacattcttg caggtatctt cgagccagcc acgatcgaca  11340
ttgatctggc tatcttgctg acaaaagcaa gagaacatag cgttgccttg gtaggtccag  11400
cggcggagga actctttgat ccggttcctg aacaggatct atttgaggcg ctaaatgaaa  11460
ccttaacgct atggaactcg ccgcccgact gggctggcga tgagcgaaat gtagtgctta  11520
cgttgtcccg catttggtac agcgcagtaa ccggcaaaat cgcgccgaag gatgtcgctg  11580
ccgactggc aatggagcgc ctgccggccc agtatcagcc cgtcatactt gaagctaggc  11640
aggcttatct tggacaagaa gatcgcttgg cctcgcgcgc agatcagttg gaagaatttg  11700
ttcactacgt gaaaggcgag atcaccaaag tagtcggcaa ataaagctct agtggatctc  11760
cgtacccggg gatctggctc gcggcggacg cacgacgccg gggcgagacc ataggcgatc  11820
tcctaaatca atagtagctg taacctcgaa gcgtttcact tgtaacaacg attgagaatt  11880
tttgtcataa aattgaaata cttggttcgc attttgtca tccgcggtca gccgcaattc  11940
tgacgtactg cccatttagc tggagatgat tgtacatcct tcacgtgaaa atttctcaag  12000
cgctgtgaac aagggttcag atttagatt gaaggtgag ccgttgaaac acgttcttct  12060
tgtcgatgac gacgtcgcta tgcggcatct tattattgaa tacctacga tccacgcctt  12120
caaagtgacc gcggtagccg acagcaccca gttcacaaga gtactctctt ccgcgacggt  12180
cgatgtcgtg gttgttgatc tagatttagg tcgtgaagat gggctcgagc taggagcaag  12240
tgatttatc gctaagccgt tcagtatcag agagtttcta gcacgcattc gggttgcctt  12300
```

```
gcgcgtgcgc cccaacgttg tccgctccaa agaccgacgg tcttttgtt ttactgactg   12360
gacacttaat ctcaggcaac gtcgcttgat gtccgaagct ggcggtgagg tgaaacttac   12420
ggcaggtgag ttcaatcttc tcctcgcgtt tttagagaaa ccccgcgacg ttctatcgcg   12480
cgagcaactt ctcattgcca gtcgagtacg cgacgaggag gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacggggg   12660
gacgatggca gcctgagcca attcccagat ccccgaggaa tcggcgtgag cggtcgcaaa   12720
ccatccggcc cggtacaaat cggcgcggcg ctgggtgatg acctggtgga gaagttgaag   12780
gccgcgcagg ccgcccagcg gcaacgcatc gaggcagaag cacgccccgg tgaatcgtgg   12840
caagcggccg ctgatcgaat ccgcaaagaa tcccgcgcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgttttccg tctgtcgaag   13020
cgtgaccgac gagctggcga ggtgatccgc tacgagcttc cagacgggca cgtagaggtt   13080
tccgcagggc cggccgcat ggccagtgtg tgggattacg acctggtact ggcttgatt   13140
tcccatctaa ccgaatccat gaaccgatac cgggaaggga agggagacaa gcccggccgc   13200
gtgttccgtc cacacgttgc ggacgtactc aagttctgcc ggcgagccga tggcggaaag   13260
cagaaagacg acctggtaga aacctgcatt cggttaaaca ccacgcacgt tgccatgcag   13320
cgtacgaaga aggccaagaa cggccgcctg gtgacggtat ccgagggtga agccttgatt   13380
agccgctaca agatcgtaaa gagcgaaacc gggcggccgg agtacatcga gatcgagcta   13440
gctgattgga tgtaccgcga gatcacagaa ggcaagaacc cggacgtgct gacggttcac   13500
cccgattact ttttgatcga tcccggcatc ggccgttttc tctaccgcct ggcacgccgc   13560
gccgcaggca aggcagaagc cagatggttg ttcaagacga tctacgaacg cagtggcagc   13620
gccgagagt tcaagaagtt ctgttcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacgagca gatgctaggg   13800
caaattgccc tagcagggga aaaaggtcga aaaggtctct ttcctgtgga tagcacgtac   13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actctttaaa acttattaaa actcttaaaa cccgcctggc ctgtgcataa   14040
ctgtctggcc agcgcacagc cgaagagctg caaaaagcgc ctacccttcg gtcgctgcgg   14100
tccctacgcc ccgccgcttc gcgtcggcct atcgcggccg ctggccgctc aaaaatggct   14160
ggcctacgg caggcaatct accgggcgc ggacaagccg cgccgtcgcc actcgaccgc   14220
cggcgctgag gtctgcctcg tgaagaaggt gttgctgact cataccaggc ctgaatcgcc   14280
ccatcatcca gccagaaagt gagggagcca cggttgatga gagctttgtt gtaggtggac   14340
cagttggtga ttttgaactt ttgctttgcc acggaacggt ctgcgttgtc gggaagatgc   14400
gtgatctgat cctcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaattat tcatatcagg attatcaata ccatattttt   14580
gaaaaagccg tttctgtaat gaaggagaaa actcaccgag gcagttccat aggatggcaa   14640
gatcctggta tcggtctgcg attccgactc gtccaacatc aatacaacct attaatttcc   14700
cctcgtcaaa aataaggtta tcaagtgaga atcaccatg agtgacgact gaatccggtg   14760
agaatggcaa aagctctgca ttaatgaatc ggccaacgcg cggggagagg cggtttgcgt   14820
attggcgcgt cttccgcttc ctcgctcact gactcgctgc gctcggtcgt tcggctgcgg   14880
cgagcggtat cagctcactc aaaggcggta atacgttat ccacagaatc aggggataac   14940
gcaggaaaga acatgtgagc aaaaggccag caaaaggcca ggaaccgtaa aaaggccgcg   15000
ttgctggcgt ttttccatag gctccgcccc cctgacgagc atcacaaaaa tcgacgctca   15060
agtcagaggt ggcgaaaccc gacaggacta taaagatacc aggcgtttcc ccctggaagc   15120
tccctcgtgc gctctcctgt tccgaccctg ccgcttaccg gatacctgtc cgcctttctc   15180
ccttcgggaa gcgtggcgct ttctcatagc tcacgctgta ggtatctcag ttcggtgtag   15240
gtcgttcgct ccaagctggg ctgtgtgcac gaaccccccg ttcagcccga ccgctgcgcc   15300
ttatccggta actatcgtct tgagtccaac ccggtaagac acgacttatc gccactggca   15360
gcagccactg gtaacaggat tagcagagcg aggtatgtag gcggtgctac agagttcttg   15420
aagtggtggc ctaactacgg ctacactaga agaacagtat ttggtatctg cgctctgctg   15480
aagccagtta ccttcggaaa aagagttggt agctcttgat ccggcaaaca aaccaccgct   15540
ggtagcggtg gtttttttgt ttgcaagcag cagattacgc gcagaaaaaa aggatctcaa   15600
gaagatcctt tgatcttttc tacggggtct gacgctcagt ggaacgaaaa ctcacgttaa   15660
gggattttgg tcatgagatt atcaaaaagg atcttcacct agatccttt gatccggaat   15720
ta                                                                 15722
```

```
SEQ ID NO: 21           moltype = DNA  length = 20
FEATURE                 Location/Qualifiers
misc_feature            1..20
                        note = for editing VLHP2
source                  1..20
                        mol_type = other DNA
                        organism = synthetic construct
SEQUENCE: 21
gctggagctg agcttccggg                                                  20

SEQ ID NO: 22           moltype = DNA  length = 15722
FEATURE                 Location/Qualifiers
misc_feature            1..15722
                        note = vector 23398
misc_feature            4..259
                        note = bNRB-05
regulatory              304..2100
                        note = promoter - prSoUbi4-04
                        regulatory_class = promoter
gene                    2117..6286
```

```
                        note = cCas9-01
misc_feature            5606..5608
                        note = L to V mutation
misc_feature            5651..5653
                        note = I to V mutation
regulatory              6292..6544
                        note = terminator - tNOS-05-01
                        regulatory_class = terminator
regulatory              6551..6925
                        note = promoter - prOsU3-01
                        regulatory_class = promoter
misc_feature            6927..6946
                        note = xZmGW2
misc_feature            6927..7031
                        note = rsgRNAZmGW2-01
regulatory              7042..9033
                        note = promoter - prUbi1-04
                        regulatory_class = promoter
gene                    9050..10228
                        note = cPMI-09
regulatory              10251..10503
                        note = terminator - tNOS-05-01
                        regulatory_class = terminator
misc_feature            10547..10676
                        note = bNLB-03
gene                    10956..11744
                        note = cSpec-03
regulatory              11839..11969
                        note = promoter - prVirG-01
                        regulatory_class = promoter
gene                    12706..13779
                        note = cRepA-01
misc_feature            13822..14226
                        note = oVS1-02
misc_feature            14904..15710
                        note = oCOLE-06
source                  1..15722
                        mol_type = other DNA
                        organism = synthetic construct SEQUENCE: 22
attcctgtgg ttggcatgca catacaaatg gacgaacgga taaaccttt cacgcccttt     60
taaatatccg attattctaa taaacgctct tttctcttag gttacccgc caatatatcc    120
tgtcaaacac tgatagttta aactgaaggc gggaaacgac aatctgatca tgagcggaga   180
attaagggag tcacgttatg acccccgccg atgacgcggg acaagccgtt ttacgtttgg   240
aactgacaga accgcaacgc tgcaggaatt ggccgcagcg gccatttaaa caaagcttgg   300
taccattatg tggtctaggt aggttctata tataagaaaa cttgaaatgt tctaaaaaaa   360
aattcaagcc catgcatgat tgaagcaaac ggtatagcaa ggtgttaac ctgatctagt    420
gatctcttgc aatccttaac ggccacctac cgcaggtagc aaacggcgtc ccctcctcg    480
atatctccgc ggcgacctct ggcttttcc gcggaattgc gcggtgggga cggattccac    540
gagaccgcga cgcaaccgcc tctcgccgct gggccccaca ccgctcggtg ccgtagcctc   600
acgggactct ttctccctcc tccccgtta taaattggct tcatcccctc cttgcctcat    660
ccatccaaat cccagtcccc aatcccatcc cttcgtagga gaaattcatc gaagctaagc   720
gaatcctcgc gatcctctca aggtactgcg agttttcgat ccccctctcg accctcgta    780
tgtttgtgtt tgtcgtagcg tttgattagg tatgcttcc ctgtttgtgt tcgtcgtagc    840
gtttgattag gtatgctttc cctgttcgtg ttcatcgtag tgtttgatta ggtcgtgtga   900
ggcgatggcc tgctcgcgtc cttcgatctg tagtcgattt gcgggtcgtg gtgtagatct   960
gcgggctgtg atgaagttat ttggtgtgat ctgctcgcct gattctgcgg gttggctcga  1020
gtagatatga tggttggacc ggttggttcg tttaccgcgc tagggttggg ctgggatgat  1080
gttgcatgcg ccgttgcgcg tgatcccgca gcaggacttg cgtttgattg ccagatctcg  1140
ttacgattat gtgatttggt ttggacttt tagatctgta gcttctgctt atgtgccaga   1200
tgcgcctact gctcatatgc ctgatgataa tcataaatgg ctgtggaact aactagttga  1260
ttgcggagtc atgtatcagc tacaggtgta gggactagct acaggtgtag ggacttgcgt  1320
ctaattgttt ggtcctttac tcatgttgca attatgcaat ttagtttaga ttgtttgttc  1380
cactcatcta ggctgtaaaa gggacactgc ttagattgct gtttaatctt tttagtagat  1440
tatattatat tggtaactta ttaccccctat tacatgccat acgtgacttc tgctcatgcc  1500
tgatgataat catagatcac tgtggaatta attagttgat tgttgaatca tgtttcatgt  1560
acataccacg gcacaattgc ttagttcctt aacaaatgca aattttactg atccatgtat  1620
gatttgcgtg gttctctaat gtgaaatact atagctactt gttagtaaga atcaggttgc  1680
tatgcttaat gctgtatgtg ccttctgctc atgcctgatg ataatcatat atcactggaa  1740
ttaattagtt gatcgtttaa tcatatatca agtacatacc atgccacaat ttttagtcac  1800
ttaacccatg cagattgaac tggtccctgc atgttttgct aaattgttct attctgatta  1860
gaccatatat catgtatttt tttttggtaa tggttctctt attttaaatg ctatatagtt  1920
ctggtacttg ttagaaagat ctgcttcata gtttagttgc ctatccctcg aattaggatg  1980
ctgagcagct gatcctatag cttttgtttca tgtatcaatt cttttgtgtt caacagtcag  2040
tttttgttag attcattgta acttatggtc gcttactctt ctggtcctca atgcttgcag  2100
gatcgcggcc gctcatatgg acaagaagta cagcatcggc ctggacatcg gcaccaacag  2160
cgtgggctgg gccgtgatca ccgacgagta caaggtgccg agcaagaagt tcaaggtgct  2220
gggcaacacc gacaggcaca gcatcaagaa gaacctgatc ggcgccctgc tgttcgacag  2280
cggcgagacc gccgaggcca ccaggctgaa gaggaccgcc aggaggaggt acaccaggag  2340
```

-continued

```
gaagaacagg atctgctacc tgcaggagat cttcagcaac gagatggcca aggtggacga 2400
cagcttcttc cacaggctgg aggagagctt cctggtggag gaggacaaga agcacgagag 2460
gcacccgatc ttcggcaaca tcgtggacga ggtggcctac cacgagaagt acccgaccat 2520
ctaccacctg aggaagaagc tggtggacag caccgacaag gccgacctga ggctgatcta 2580
cctggccctg gcccacatga tcaagttcag gggccacttc ctgatcgagg gcgacctgaa 2640
cccggacaac agcgacgtgg acaagctgtt catccagctg gtgcagacct acaaccagct 2700
gttcgaggag aacccgatca acgccagcgg cgtggacgcc aaggccatcc tgagcgccag 2760
gctgagcaag agcaggaggc tggagaacct gatcgcccag ctgccgggcg agaagaagaa 2820
cggcctgttc ggcaacctga tcgccctgag cctgggcctg accccgaact tcaagagcaa 2880
cttcgacctg gccgaggacg ccaagctgca gctgagcaag gacacctacg acgacgacct 2940
ggacaacctg ctggcccaga tcggcgacca gtacgccgac ctgttcctgg ccgcaagaa 3000
cctgagcgac gccatcctgc tgagcgacat cctgagggtg aacaccgaga tcaccaaggc 3060
cccgctgagc gccagcatga tcaagaggta cgacgagcac caccaggacc tgaccctgct 3120
gaaggccctg gtgaggcagc agctgccgga gaagtacaag gagatcttct tcgaccagag 3180
caagaacggc tacgccggct acatcgacgg cggcgccagc caggaggagt tctacaagtt 3240
catcaagcc atcctggaga agatggacgg caccgaggag ctgctggtga agctgaacag 3300
ggaggacctg ctgaggaagc agaggacctt cgacaacgga agcatcccgc accagatcca 3360
cctgggcgag ctgcacgcca tcctgaggag gcaggaggac ttctacccgt tcctgaagga 3420
caacagggag aagatcgaga agatcctgac cttccgcatc ccgtactacg tgggcccgct 3480
ggccagggc aacagcaggt tcgcctggat gaccaggaag agcgaggaga ccatcacccc 3540
gtggaacttc gaggaggtgg tggacaaggg cgccagcgcc cagagcttca tcgagaggat 3600
gaccaacttc gacaagaacc tgccgaacga aaggtgctg gccaagcagc gctgctgta 3660
cgagtacttc accgtgtaca acgagctgac caaggtgaag tacgtgaccg agggcatgag 3720
gaagccggcc ttcctgagcg gcgagcagaa gaaggccatc gtggacctgc tgttcaagac 3780
caacaggaag gtgaccgtga agcagctgaa ggaggactac ttcaagaaga tcgagtgctt 3840
cgacagcgtg gagatcaagg gcgtggagga caggttcaac gccagcctgg gcacctacca 3900
cgacctgctg aagatcatca aggacaagga cttcctggac aacgaggaga acgaggacat 3960
cctggaggac atcgtgctga ccctgaccct gttcgaggac agggagatga tcgaggagag 4020
gctgaagacc tacgcccacc tgttcgacga caaggtgatg aagcagctga agaggaggag 4080
gtacaccggc tggggcaggc tgagcaggaa gctgatcaac ggcatcaggg acaagcagg 4140
cggcaagacc atcctggact tcctgaagag cgacggcttc gccaacagga acttcatgca 4200
gctgatccac gacgacagcc tgaccttcaa ggaggacatc cagaaggccc aggtgagcgg 4260
ccagggcgac agcctgcacg agcacatcgc caacctggcc ggcagcccgg ccatcaagaa 4320
gggcatcctg cagaccgtga aggtggtgga cgagctggtg aaggtgatgg gcaggcacaa 4380
gccggagaac atcgtgatcg agatggccag ggagaaccag accacccaga agggccaaa 4440
gaacagcagg gagaggatga agaggatcga ggagggcatc aaggagctgg gcagccagat 4500
cctgaaggag cacccggtgg agaacaccca gctgcagaac gagaagctgt acctgtacta 4560
cctgcagaac ggcagggaca tgtacgtgga ccaggagctg gacatcaaca ggctgagcga 4620
ctacgacgtg gaccacatcg tgccgcagag cttcctgaag gacgacagca tcgacaacaa 4680
ggtgctgacc aggagcgaca gaacaggggc aagagcgaa aacgtgccga gcgaggaggt 4740
ggtgaagaag atgaaaaact actggaggca gctgctgaac gccaagctga tcacccagag 4800
gaagttcgac aacctgacca aggccgagag gggcggcctg agcgagctgg acaaggccgg 4860
cttcattaaa aggcagctgg tggagaccag gcagatccat aacacgtgg cccagatcct 4920
ggacagcagg atgaacacca gtacgacga gaacgacaag ctgatcaggg aggtgaaggt 4980
gatcaccctg aagagcaagc tggtgagcga cttcaggaag gacttccagt tctacaaggt 5040
gagggagatc aataattacc accacgccca cgacgcctac ctgaacgcc tggtgggcac 5100
cgccctgatt aaaagtacc cgaagctgga gagcgagttc gtgtacggca actacaaggt 5160
gtacgacgtg aggaagatga tcgccaagag cgagcaggga atcggcaagg ccaccgccaa 5220
gtacttcttc tacagcaaca tcatgaactt cttcaagacc gagatcaccc tggccaacgg 5280
cgagatcagg aagaggccgc tgatcgagac caacggcgag accggcgaga tcgtgtggga 5340
caagggcagg gacttcgcca ccgtgaggaa ggtgctgtcc atgccgcagg tgaacatcgt 5400
gaagaagacc gaggtgcaga ccggcggctt cagcaaggag agcatcctgc cgaagaggaa 5460
cagcgacaag ctgatcgcca ggaagaagga ctgggacccg aagaagtacg gcggcttcga 5520
cagcccgacc gtggcctaca gcgtgctggt ggtggccaag gtggagaagg gcaagagcaa 5580
gaagctgaag agcgtgaagg agctggtggg catcaccatc atggagagga gcagcttcga 5640
gaagaaccca gtggacttcc tggaggcaa gggctacaag gaggtgaaga aggacctgat 5700
cattaaactg ccgaagtaca gcctgttcga gctggagaac ggcaggaaga ggatgctggc 5760
cagcgccggc gagctgcaga agggcaacga gctggcctg ccgagcaagt acgtgaactt 5820
cctgtacctg gccagccact acgagaagct gaagggcagc ccggaggaca acgagcagaa 5880
gcagctgttc gtggagcagc acaagcacta cctggacgag atcatcgagc agatcagcga 5940
gttcagcaag agggtgatcc tggccgacgc caacctggac aaggtgctga gcgcctacaa 6000
caagcacagg gacaagccga tcagggcagca ggccgagaac atcatccacc tgttcacct 6060
gaccaacctg ggcgccccgg ccgccttcaa gtacttcgac accaccatcg acaggaagag 6120
gtacaccagc accaaggagg tgctggacgc caccctgatc caccagagca tcaccggcct 6180
gtacgagacc aggatcgacc tgagccagct gggcggcgac agcagccgc cgaagaagaa 6240
gaggaaggtg agctggaagg acgccagcgg ctggagcagg atgtgaagct tgatcgttca 6300
aacatttggc aataaagttt cttaagatta atcctgttg ccggtcttgc gatgattatc 6360
atataatttc tgttgaatta cgttaagcat gtaataatta acatgtaatg catgacgtta 6420
tttatgagat gggttttttat gattagagtc ccgcaattat acatttaata cgcgatagaa 6480
aacaaaatat agcgcgcaaa ctaggataaa ttatcgcgcg cggtgtcatc tatgttacta 6540
gatcttcgaa gggatcttta aacatacgaa cagatcactt aaagttcttc tgaagcaact 6600
taaagttatc aggcatgcat ggatcttgga ggaatcagat gtgcagtcag gaccatagc 6660
acaggacagg cgtcttctac tggtgctacc agcaaatgct ggaagccggg aacactgggt 6720
acgttggaaa ccacgtgatg tggagtaaga taactgtag tttcgtagtg 6780
ggccatgaag cctttcagga catgtattgc agtatgggcc ggccattac gcaattggac 6840
gacaacaaag actagtatta gtaccactc ggctatccac atagatcaaa gctgtttaa 6900
aagagttgtg cagatgatcc gtggcagagc ggttcacgcg ccgcagttt tagagctaga 6960
aatagcaagt taaaataagg ctagtccgtt atcaacttga aaaagtggca ccgagtcggt 7020
gcttttttt tcggaccgcg cctgcagtgc agcgtgaccc ggtcgtgccc ctctctagag 7080
```

```
ataatgagca ttgcatgtct aagttataaa aaattaccac atattttttt tgtcacactt   7140
gtttgaagtg cagtttatct atctttatac atatatttaa actttactct acgaataata   7200
taatctatag tactacaata atatcagtgt tttagagaat catataaatg aacagttaga   7260
catggtctaa aggacaattg agtatttga caacaggact ctacagtttt atctttttag    7320
tgtgcatgtg ttctccttt ttttgcaaa tagcttcacc tatataatac ttcatccatt     7380
ttattagtac atccatttag ggtttagggt taatggtttt tatagactaa tttttttagt   7440
acatctattt tattctattt tagcctctaa attaagaaaa ctaaaactct attttagttt   7500
ttttattaa taatttagat ataaaataga ataaaataaa gtgactaaaa attaaacaaa    7560
taccctttaa gaaattaaaa aaactaagga aacattttc ttgtttcgag tagataatgc    7620
cagcctgtta aacgccgtcg acgagtctaa cggacaccaa ccagcgaacc agcagcgtcg   7680
cgtcgggcca agcgaagcag acggcacggc atctctgtcg ctgcctctgg accctctcg    7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acggggatt cctttcccac cgctccttcg cttttccctc ctccgcccgcc gtaataaata   7920
gacaccccct ccacccctc tttccccaac ctcgtgttgt tcggagcgca cacacacaca   7980
accagatctc ccccaaatcc acccgtcggc acctccgctt caaggtacgc cgctcgtcct   8040
ccccccccc cctctctacc ttctctagat cggcgttccg gtccatggtt agggcccggt    8100
agttctactt ctgttcatgt ttgtgttaga tccgtgtttg tgttagatcc tgctgctag    8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
ttttttttgt ttcgttgcat agggtttggt ttgccctttt cctttatttc aatatatgcc   8340
gtgcacttgt ttgtcgggtc atctttttcat gcttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gcttttttgtt cgcttggttg tgatgatgtg gtgggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagcag gccctgaccg agctgtacg    9120
catggagaac cccagcagcc agcccatggc cgagctgtgg atgggcgccc acccccaagag  9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcaccccca acaagcacaa  9360
cagcagagtc ggcttcgcca aggagaacgc cgccggcatc cccatggacg tcgccggcgc   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgccactt tcctgcagca gcccgacgcc gagcgcctga gcgagctgtt   9600
cgccagcctg ctgaacatgc agggcaggga aagagccgca tcctgaagag tcctgaagag   9660
cgccctggac agccagcagg gcgagccctg gcagaccatc cgcctgatca gcgagttcta   9720
ccccgaggac agcggcctgt tcagccccct gctgctgaac gtggtgaagc tgaaccccgg   9780
cgaggccatg ttcctgttcg ccgagacccc ccacgcctac ctgcagggcg tggccctgga   9840
ggtgatgacc aacagcgaca acgtgctgcg cgccggcctg accccccaagt acatccgacat  9900
ccccgagctg gtggccaacg tgaagttcga ggccaagccc gccaaccagc tgctgaccca   9960
gcccgtgaag cagggcgccg agctggactt ccccatcccc gtgacgact tcgccttcag   10020
cctgcacgac ctgagcgaca aggagaccac catcagccag cagagcgccg ccatcctgtt   10080
ctgcgtggag ggcgaccgca ccctgtgaa gggcagccag cagctgcgca tgaagcccga  10140
cgagagcgcc ttcatcgccc caacgagag ccccgtgacc gtgaagggcc acggccgcct   10200
ggcccgcgtg tacaacaagc tgtgataggg gctcgatccg tcgacctgca gatcgttcaa   10260
acatttggca ataaagtttc ttaagattga atcctgttgc cggtcttgcg atgattatca   10320
tataattct gttgaattac gttaagcatg taataattaa catgtaatgc atgacgttat    10380
ttatgagatg ggtttttatg attagagtcc cgcaattata catttaatac gcgatagaaa   10440
acaaaatata gcgcgcaaac taggataaat tatcgcgcgc ggtgtcatct atgttactag   10500
atcggcgcgc cgcaattgaa gtttgggcgg ccagcatggc cgtatccgca atgtgttatt   10560
aagttgtcta agcgtcaatt tgtttacacc acaatatatc ctgccaccag ccaaccaaca   10620
gctccccgac cggcagctcg gcacaaaatc accactcgat acaggcagcc atcagaatt    10680
aattctcatg tttgacagct tatcatcgac tgcacggtgc accaatgctt ctggcgtcag   10740
gcagccatcg gaagctgtgg tatggctgtg caggtcgtaa atcactgcat aattcgtgtc   10800
gctcaaggcg cactcccgtt ctggataatg ttttttgcgc cgacatcata acggttctgg   10860
caaatattct gaaatgagct gttgacaatt aatcatccgg ctcgtataat gtgtggaatt   10920
gtgagcggat aacaatttca cacaggaaac agaccatgga gaagcgttg atcgccaag    10980
tatcgactca actatcagag gtagttggcg tcatcgagcg ccatctcgaa ccgacgttgc   11040
tggccgtaca tttgtacggc tccgcagtgg atggcggcct gaagccacac agtgatattg   11100
atttgctggt tacggtgacc gtaaggcttg atgaaacaac gcggcgagct ttgatcaacg   11160
accttttgga aacttcggct tcccctggag agagcgagat tctccgcgct gtagaagtca   11220
ccattgttgt gcacgacgac atcattccgt ggcgttatcc agctaagcgc gaactgcaat   11280
ttggagaatg gcagcgcaat gacattcttg caggtatctt cgagccagcc acgatcgaca   11340
ttgatctggc tatcttgctg acaaaagcaa gagaacatag cgttgccttg gtaggtccag   11400
cggcggagga actctttgat ccggttcctg aacaggatct atttgaggcg ctaaatgaaa   11460
ccttaacgct atggaactcg ccgcccgact gggctggcga tgagcgaaat gtagtgctta   11520
cgttgtcccg catttggtac agcgcagtaa ccggcaaaat cgcgccgaag gatgtcgctg   11580
ccgactgggc aatggagcgc ctgccggccc agtatcagcc cgtcatactt gaagctaggc   11640
aggcttatct tggacaagaa gatcgcttgg cctcgcgcgc agatcagttg gaagaatttg   11700
ttcactacgt gaaaggcgag atcaccaaag tagtcggcaa ataaagctct agtggatctc   11760
cgtacccggg gatctggctc gcggcggacg cacgacgccg ggcgagacc ataggcgatc    11820
```

```
tcctaaatca atagtagctg taacctcgaa gcgtttcact tgtaacaacg attgagaatt    11880
tttgtcataa aattgaaata cttggttcgc atttttgtca tccgcggtca gccgcaattc    11940
tgacgaactg cccatttagc tggagatgat tgtacatcct tcacgtgaaa atttctcaag    12000
cgctgtgaac aagggttcag attttagatt gaaaggtgag ccgttgaaac acgttcttct    12060
tgtcgatgac gacgtcgcta tgcggcatct tattattgaa taccttacga tccacgcctt    12120
caaagtgacc gcggtagccg acagcaccca gttcacaaga gtactctctt ccgcgacggt    12180
cgatgtcgtg gttgttgatc tagatttagg tcgtgaagat gggctcgagc taggagcaag    12240
tgatttatc gctaagccgt tcagtatcag agagtttcta gcacgcattc gggttgcctt     12300
gcgcgtgcgc cccaacgttg tccgctccaa agaccgacgg tcttttttgtt ttactgactg   12360
gacacttaat ctcaggcaac gtcgcttgat gtccgaagct ggcggtgagg tgaaacttac    12420
ggcaggtgag ttcaatcttc tcctcgcgtt tttagagaaa ccccgcgacg ttctatcgcg    12480
cgagcaactt ctcattgcca gtcgagtacg cgacgaggag gtttatgaca ggagtataga    12540
tgttctcatt ttgaggctgc gccgcaaact tgaggcagat ccgtcaagcc ctcaactgat    12600
aaaaacagca agaggtgccg gttatttctt tgacgcgaac gtgcaggttt cgcacggggg    12660
gacgatggca gcctgagcca attcccagat ccccgaggaa tcggcgtgag cggtcgcaaa    12720
ccatccggcc cggtacaaat cggcgcggcg ctgggtgatg acctggtgga gaagttgaag    12780
gccgcgcagg ccgcccagcg gcaacgcatc gaggcagaag cacgcccgg tgaatcgtgg     12840
caagcggccg ctgatcgaat ccgcaaagaa tcccggcaac cgccggcagc cggtgcgccg    12900
tcgattagga agccgcccaa gggcgacgag caaccagatt ttttcgttcc gatgctctat    12960
gacgtgggca cccgcgatag tcgcagcatc atggacgtgg ccgttttccg tctgtcgaag    13020
cgtgaccgac gagctggcga ggtgatccgc tacgagcttc cagacgggca cgtagaggtt    13080
tccgcaggca cggccggcat ggccagtgtg tgggattacg acctggtact gatgcgcggt    13140
tcccatctaa ccgaatccat gaaccgatac cgggaaggga agggagacaa gcccggccgc    13200
gtgttccgtc cacacgttgc ggacgtactc aagttctgcc ggcgagccga tggcggaaag    13260
cagaaagacg acctggtaga aacctgcatt cggttaaaca ccacgcacgt tgccatgcag    13320
cgtacgaaga aggccaagaa cggccgcctg gtgacggtat ccgagggtga agccttgatt    13380
agccgctaca agatcgtaaa gagcgaaacc gggcggccgg agtacatcga gatcgagcta    13440
gctgattgga tgtaccgcga gatcacgaaa ggcaagaacc cggacgtgct gacggttcac    13500
cccgattact ttttgatcga tcccggcatc ggccgttttc tctaccgcct ggcacgccgc    13560
gccgcaggca aggcagaagc cagatggttg ttcaagacga tctacgaacg cagtggcagc    13620
gccggagagt tcaagaagtt ctgtttcacc gtgcgcaagc tgatcgggtc aaatgacctg    13680
ccggagtacg atttgaagga ggaggcgggg caggctggcc cgatcctagt catgcgctac    13740
cgcaacctga tcgagggcga agcatccgcc ggttcctaat gtacggagca gatgctaggg    13800
caaattgccc tagcagggga aaaaggtcga aaaggtctct ttcctgtgga tagcacgtac    13860
attgggaacc caaagccgta cattgggaac cggaacccgt acattgggaa cccaaagccg    13920
tacattggga accggtcaca catgtaagtg actgatataa aagagaaaaa aggcgatttt    13980
tccgcctaaa actctttaaa acttattaaa actcttaaaa cccgcctggc ctgtgcataa    14040
ctgtctggcc agcgcacagc cgaagagctg caaaaagcgc ctaccctttcg gtcgctgcgc   14100
tccctacgcc ccgccgcttc gcgtcggcct atcgcggccg ctggccgctc aaaaatggct    14160
ggcctacggc caggcaatct accagggcgc ggacaagccg cgccgtcgcc actcgaccgc    14220
cggcgctgag gtctgcctcg tgaagaaggt gttgctgact cataccaggc ctgaatcgcc    14280
ccatcatcca gccagaaagt gagggagcca cggttgatga gagcttttgtt gtaggtggac    14340
cagttggtga ttttgaactt ttgctttgcc acggaacggt ctgcgttgca gggaagatgc    14400
gtgatctgat ccttcaactc agcaaaagtg cgatttattc aacaaagccg ccgtcccgtc    14460
aagtcagcgt aatgctctgc cagtgttaca accaattaac caattctgat tagaaaaact    14520
catcgagcat caaatgaaac tgcaatttat tcatatcagg attatcaata ccatattttt    14580
gaaaaagccg tttctgtaat gaaggagaaa actcaccgag gcagttccat aggatggcaa    14640
gatcctggta tcggtctgcg attccgactc gtccaacatc aatacaacct attaatttcc    14700
cctcgtcaaa aataaggtta tcaagtgaga atcaccatg agtgacgact gaatccggtg    14760
agaatggcaa aagctctgca ttaatgaatc ggccaacgcg cggggagagg cggtttgcgt    14820
attggcgcgt cttccgcttc ctcgctcact gactcgctgc gctcggtcgt tcggctgcgg    14880
cgagcggtat cagctcactc aaaggcggta atacgttat ccacagaatc aggggataac     14940
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc gcctttctc     15180
ccttcgggaa gcgtggcgct ttctcatagc tcacgctgta ggtatctcag ttcggtgtag    15240
gtcgttcgct ccaagctggg ctgtgtgcac gaaccccccg ttcagcccga ccgctgcgcc    15300
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gtttttttgt ttgcaagcag cagattacgc gcagaaaaaa aggatctcaa    15600
gaagatcctt tgatcttttc tacggggtct gacgctcagt ggaacgaaaa ctcacgttaa    15660
gggattttgg tcatgagatt atcaaaaagg atcttcacct agatcctttt gatccggaat    15720
ta                                                                   15722

SEQ ID NO: 23         moltype = DNA  length = 20
FEATURE               Location/Qualifiers
misc_feature          1..20
                      note = for editing GW2-1
source                1..20
                      mol_type = other DNA
                      organism = synthetic construct
SEQUENCE: 23
gagcggttca cgcggccgca                                                20

SEQ ID NO: 24         moltype = DNA  length = 15721
FEATURE               Location/Qualifiers
```

```
misc_feature          1..15721
                      note = vector 23763
misc_feature          4..259
                      note = bNRB-05
regulatory            304..2100
                      note = promoter - prSoUbi4-04
                      regulatory_class = promoter
gene                  2117..6286
                      note = cCas9-01
variation             5606..5608
                      note = mutation - L to V mutation
variation             5651..5653
                      note = mutation - I to V mutation
misc_feature          6221..6283
                      note = xSV40NLS-03
regulatory            6292..6544
                      note = terminator - tNOS-05-01
                      regulatory_class = terminator
regulatory            6551..6925
                      note = promoter - prOsU3-01
                      regulatory_class = promoter
misc_feature          6927..6945
                      note = xTaVLHP1
misc_feature          6927..7030
                      note = rsgRNA TaVLHP1-01
regulatory            7041..9032
                      note = promoter - prUbi1-04
                      regulatory_class = promoter
gene                  9049..10227
                      note = cPMI-09
regulatory            10250..10502
                      note = terminator - tNOS-05-01
                      regulatory_class = terminator
misc_feature          10546..10675
                      note = bNLB-03
gene                  10955..11743
                      note = cSpec-03
regulatory            11838..11968
                      note = promoter - prVirG-01
                      regulatory_class = promoter
gene                  12705..13778
                      note = cRepA-01
misc_feature          13821..14225
                      note = oVS1-02
misc_feature          14903..15709
                      note = oCOLE-06
source                1..15721
                      mol_type = other DNA
                      organism = synthetic construct
SEQUENCE: 24
attcctgtgg ttggcatgca catacaaatg gacgaacgga taaacctttt cacgcccttt      60
taaatatccg attattctaa taaacgctct tttctcttag gtttaccgc caatatatcc     120
tgtcaaacac tgatagttta aactgaaggc gggaaacgac aatctgatca tgagcggaga    180
attaaggag tcacgttatg accccgccg atgacgcggg acaagccgtt ttacgtttgg      240
aactgacaga accgcaacgc tgcaggaatt ggccgacgg gccatttaaa caaagcttg     300
taccattatg tggtctaggt aggttctata tataagaaaa cttgaaatgt tctaaaaaa    360
aattcaagcc catgcatgat tgaagcaaac ggtatagcaa cggtgttaac ctgatctagt   420
gatctcttgc aatccttaac ggccacctac cgcaggtagc aaacggcgtc ccctcctcg    480
atatctccgc ggcgacctct ggcttttcc gcggaattgc gcggtgggga cggattccac   540
gagaccgcga cgcaaccgcc tctcgccgct gggcccaca ccgctcggtg ccgtagcctc    600
acgggactct ttctccctcc tccccgtta taaattggct tcatccctc cttgcctcat     660
ccatccaaat cccagtcccc aatcccatcc cttcgtagga gaaattcatc gaagctaagc   720
gaatcctcgc gatcctctca aggtactgcg agttttcgat cccctctcg accctcgta     780
tgtttgtgtt tgtcgtagcg tttgattagg tatgcttcc ctgtttgtg tcgtcgtagc    840
gtttgattag gtatgctttc cctgttcgtg ttcatcgtag tgtttgatta ggtcgtgtga   900
ggcgatggcc tgctcgcgtc cttcgatctg tagtcgattt gcgggtcgtg tgtagatct    960
gcgggctgtg atgaagttat ttggtgtgat ctgctcgcct gattctgcgg gttggctcga  1020
gtagatatga tggttggacc ggttggttcg tttaccgcgc tagggttggg ctgggatgat  1080
gttgcatgcg ccgttgcgcg tgatcccgca gcaggacttg cgtttgattg ccagatctcg  1140
ttacgattat gtgatttggt ttggactttt tagatctgta gcttctgctt atgtgccaga  1200
tgcgcctact gctcatatgc ctgatgataa tcataaatgg ctgtgaaact aactagttga  1260
ttgcggagtc atgtatcagc tacaggtgta gggactagct acaggtgtag ggacttgcgt  1320
ctaattgttt ggtcctttac tcatgttgca attatgcaat ttagtttaga ttgtttgttc  1380
cactcatcta ggctgtaaaa gggacactgc ttagattgct gtttaatctt tttagtagat  1440
tatattatat tggtaactta ttaccccta tacatgccat acgtgacttc tgctcatgcc   1500
tgatgataat catagatcac tgtggaatta attagttgat tgttgaatca tgtttcatgt  1560
acataccacg gcacaattgc ttagttcctt aacaaatgca aattttactg atccatgtat  1620
gatttgcgtg gttctctaat gtgaaatact atagctactt gttagtaaga atcaggttcg  1680
tatgcttaat gctgtatgtg ccttctgctc atgcctgatg ataatcatat atcactggaa  1740
```

```
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgacgagct gatcctatag cttttgtttca tgtatcaatt ctttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg caccaacag    2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcaccccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca cgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg acccccgaact tcaagagcaa   2880
cttcgacctg gccgaggacg ccaagctgca gctgagcaag gacacctacg acgacgacct   2940
ggacaacctg ctgcccagat cggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga aagtacaag gagatcttct cgaccagag    3180
caagaacggc tacgccggct acatcgacgg cggcgccagc caggaggagt tctacaagtt   3240
catcaagccg atcctggaga agatgacgag cacccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga gatcctgac cttccgcatc ccgtactacg tgggcccgct   3480
ggccagggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga aaggtgctg ccgaagcaca gcctgctgta   3660
cgagtacttc accgtgtaca acgagctgac caaggtgaag tacgtgaccg aggggcatgag   3720
gaagccggcc ttcctgagcg gcgagcagaa aaggccatc gtggcaccgc tgttcaagac   3780
caacaggaag gtgaccgtga agcagctgaa ggaggactac ttcaagaaga tcgagtgctt   3840
cgacaggcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac agggagatga tcgaggagag   4020
gctgaagacc tacgcccacc tgttcgacga caaggtgatg aagcagctga agagaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga agtggtgga cgagctggtg aaggtgatgg gcaggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag caccccggtgg agaacacccca ctgcagaac gaaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actgaggca gctgctgaac gccaagctga tcacccgagag   4800
gaagttcgac aacctgacca ggcgagag gggcggcctg agcgagctgg acaaggccgg   4860
cttcattaaa aggcagctgg tggagaccag gcagatcacc aagcacgtgg cccagatcct   4920
ggacagcagg atgaacacca agtacgacga aacgacaag ctgatcaggg aggtgaaggt   4980
gatcacctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaagtacc gaagctgga gagcgagttc gtgtacgcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccacagg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
cagcccgacc gtggcctaca gcgtgctggt ggtggccagg gtggagggca gaagggcaa   5580
gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaaga cgtgaacttt   5820
cctgtacctg gccagccact acgagaagct gaagggcagc cggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgcccggg ccgccttcaa gtacttcgac accaccatcg acaggaagag   6120
gtacaccagc accaaggagg tgctggacgc caccctgatc caccagagca tcaccgggctg   6180
gtacgagacc aggatcgacc tgagccagct gggcggcgac agcagcccgc cgaagaagaa   6240
gaggaaggtg agctggaagg acgccagcgg ctggagcagg atgtgaagct gatcgttca    6300
aacatttggc aataaagttt cttaagattg aatcctgttg ccggtcttgc gatgattatc   6360
atataattc tgttgaatta cgttaagcat gtaataatta acatgtaatg catgacgtta   6420
tttatgagat gggttttat gattagagtc ccgcaattat acatttaata cgcgatagaa   6480
```

```
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagacg agcaggcgca gttccgtttt agagctagaa   6960
atagcaagtt aaaataaggc tagtccgtta tcaacttgaa aaagtggcac cgatcggtg    7020
cttttttttt cggaccgcgc ctgcagtgca gcgtgacccg gtcgtgcccc tctctagaga   7080
taatgagcat tgcatgtcta agttataaaa aattaccaca tatttttttt gtcacacttg   7140
tttgaagtgc agtttatcta tctttataca tatatttaaa ctttactcta cgaataatat   7200
aatctatagt actacaataa tatcagtgtt ttagagaatc atataaatga acagttagac   7260
atggtctaaa ggacaattga gtatttttgac aacaggactc tacagttta tcttttttagt   7320
gtgcatgtgt tctccttttt ttttgcaaat agcttcacct atataatact tcatccattt   7380
tattagtaca tccatttagg gtttagggtt aatggttttt atagactaat ttttttagta   7440
catctatttt attctatttt agcctctaaa ttaagaaaac taaaactcta ttttagtttt   7500
tttatttaat aattagata taaaatagaa taaaataaag tgactaaaaa ttaaacaaat   7560
acccttttaag aaattaaaaa aactaaggaa acattttttct tgtttcgagt agataatgcc   7620
agcctgttaa acgccgtcga cgagtctaac ggacaccaac cagcgaacca gcagcgtcgc   7680
gtcgggccaa gcgaagcaga cggcacggca tctctgtcgc tgcctctgga cccctctcga   7740
gagttccgct ccaccgttgg acttgctccg ctgtcggcat ccagaaattg cgtggcggag   7800
cggcagacgt gagccggcac ggcaggcggc ctcctcctcc tctcacggca ccggcagcta   7860
cgggggattc ctttcccacc gctccttcgc tttcccttcc tcgcccgccg taataaatag   7920
acaccccctc cacaccctct ttccccaacc tcgtgttgtt cggagcgcac acacacacaa   7980
ccagatctcc cccaaatcca cccgtcggca cctccgcttc aaggtacgcc gctcgtcctc   8040
cccccccccc ctctctacct tctctagatc ggcgttccgg tccatggtta gggcccggta   8100
gttctacttc tgttcatgtt tgtgttagat ccgtgtttgt gttagatccg tgctgctagc   8160
gttcgtacac ggatgcgacc tgtacgtcag acacgttctg attgctaact tgccagtgtt   8220
tctctttggg gaatcctggg atggctctag ccgttccgca gacgggatcg atttcatgat   8280
ttttttttgtt tcgttgcata gggtttggtt tgccctttct ctttatttca atatatgccg   8340
tgcacttgtt tgtcgggtca tcttttcatg ctttttttttg tcttggttgt gatgatgtgg   8400
tctggttggg cggtcgttct agatcggagt agaattctgt ttcaaactac ctggtggatt   8460
tattaattttt ggatctgtat gtgtgtgcca tacatattca tagttacgaa ttgaagatga   8520
tggatggaaa tatcgatcta ggataggtat acatgttgat gcgggttttta ctgatgcata   8580
tacagagatg ctttttgttc gcttggttgt gatgatgtgg tgtggttggg cggtcgttca   8640
ttcgttctag atcggagtag aatactgttt caaactacct ggtgtattta ttaattttgg   8700
aactgtatgt gtgtgtcata catcttcata gttacgagtt taagatggat ggaaatatcg   8760
atctaggata ggtatacatg ttgatgtggg ttttactgat gcatatacat gatgcatat    8820
gcagcatcta ttcatatgct ctaaccttga gtacctatct attataataa acaagtatgt   8880
tttataatta ttttgatctt gatatacttg gatgatggca tatgcagcag ctatatgtgg   8940
atttttttag ccctgccttc atacgctatt tatttgcttg gtactgtttc ttttgtcgat   9000
gctcaccctg ttgtttggtg ttacttctgc agggatccgg gacagccat gcagaagctg    9060
atcaacagcg tgcagaacta cgcctggggc agcaagaccg ccctgaccga gctgtacgcc   9120
atggagaacc ccagcagcca gcccatggcc gagctgtgga tgggcgccca ccccaagagc   9180
agcagccgcg tgcagaacgc cgccggcgac atcgtgagcc tgcgcgacgt gatcgagagc   9240
gacaagagca ccctgctggg cgaggccgtg gccaagcgct tcggcgagct gcccttcctg   9300
ttcaaggtgc tgtgcgccgc ccagcccctg agcatccagg tgcacccca caagcacaac    9360
agcgagatcg gcttcgccaa ggagaacgcc gccggcatcc ccatgacgc cgccgagcgc    9420
aactacaagg accccaacca caagcccgag ctggtgttcg ccctgacccc cttcctggcc   9480
atgaacgcct tccgcgagtt cagcgaggcc gtgagcctgc tgggcccggt ggccggcgcc   9540
caccccgcca tcgcccactt cctgcagcag cccgacgccg agcgcctgag cgagctgttc   9600
gccagcctgc tgaacatgca gggcgaggag aagagccgcg ccctggccat cctgaagagc   9660
gccctggaca gccagcaggg cgagccctgg cagaccatcc gcctgatcag cgagttctac   9720
cccgaggaca gcggcgcctgtt cagccccctg ctgctgaacg tggtgaagct gaacccgcgc   9780
gaggccatgt tcctgttcgc cgagaccccc cacgccacc tgcagggcgt ggccctggag    9840
gtgatggcca acagcgacaa cgtgctgcgc gccggcctga ccccaagta catcgacatc    9900
cccgagctgg tggccaacgt gaagttcgag gccaagcccg ccaaccagct gctgaccag    9960
cccgtgaagc agggcgccga gctggactt cccatccccg tggacgactt cgcctcagc    10020
ctgcacgacc tgagcgacaa ggagaccacc atcagccagc agagcgccgc catcctgttc   10080
tgcgtggagg cgacgccac cctgtggaag ggcagcagc agctgcagct gaagcccggc     10140
gagagcgcct tcatcgccgc caacgagagc ccgtgaccg tgaagggcca cggccgcctg    10200
gcccgcgtgt acaacaagct gtgataggag ctcgatccgt cgacctgcag atcgttcaaa   10260
catttggcaa taaagtttct taagattgaa tcctgttgcc ggtcttgcga tgattatcat   10320
ataatttctg ttgaattacg ttaagcatgt aataattaac atgtaatgca tgacgttatt   10380
tatgagatgg gttttatga ttagagtccc gcaattatac atttaatacg cgatagaaaa   10440
caaaatatag cgcgcaaact aggataaatt atcgcgcgcg tgtcatcta tgttactaga    10500
tcggcgcgcc gcaattgaag tttgggcggc cagcatatcc gtatccgcac tgtgttatta   10560
agttgtctaa cgtcaatttt gtttacacca caatatatcc tgccaccagc cagccaacag   10620
ctccccgacc ggcagctcgg cacaaaatca ccactcgata caggcagccc atcagaatta   10680
attctcatgt ttgacagctt atcatcgact gcacggtgca ccaatgcttc tggcgtcagg   10740
cagccatcgg aagctgtggt atggctgtgc aggtcgtaaa tcactgcata attcgtgtcg   10800
ctcaaggcgc actcccgttc tggataatgt ttttttgcgcc gacatcataa cggttctggc   10860
aaatgaaatg cgaggctacc aaacgtcttc atgtgaatct ctcactctat gcagagataa   10920
tgagcggata acaatttcac acaggaaaca gaccatgagg gaagcgttga tcgccgaagt   10980
atcgactcaa ctatcagagg tagttggcgt catcgagcgc catctcgaac cgacgttgct   11040
ggccgtacat ttgtacggct ccgcagtgga tggcggcctg aagccacaca gtgatattga   11100
tttgctggtt acggtgaccg taaggcttga tgaaacaacg cggcgagctt tgatcaacga   11160
ccttttggaa acttcggctt cccctggaga gagcgagatt ctccgcgctg tagaagtcac   11220
```

```
cattgttgtg cacgacgaca tcattccgtg gcgttatcca gctaagcgcg aactgcaatt   11280
tggagaatgg cagcgcaatg acattcttgc aggtatcttc gagccagcca cgatcgacat   11340
tgatctggct atcttgctga caaaagcaag agaacatagc gttgccttgg taggtccagc   11400
ggcggaggaa ctctttgatc cggttcctga acaggatcta tttgaggcgc taaatgaaac   11460
cttaacgcta tggaactcgc cgcccgactg ggctggcgat ggcgaaatg tagtgcttac    11520
gttgtcccgc atttggtaca gcgcagtaac cggcaaaatc gcgccgaagg atgtcgctgc   11580
cgactgggca atggagcgcc tgccggccca gtatcagccc gtcatacttg aagctaggca   11640
ggcttatctt ggacaagaag atcgcttggc ctcgcgcgca gatcagttgg aagaatttgt   11700
tcactacgtg aaaggcgaga tcaccaaagt agtcggcaaa taaagctcta gtggatctcc   11760
gtacccgggg atctggctcg cggcggacgc acgacgccgg ggcgagacca taggcgatct   11820
cctaaatcaa tagtagctgt aacctcgaag cgtttcactt gtaacaacga ttgagaattt   11880
ttgtcataaa attgaaatac ttggttcgca tttttgtcat ccgcggtcag ccgcaattct   11940
gacgaactgc ccatttagct ggagatgatt gtacatcctt cacgtgaaaa tttctcaagc   12000
gctgtgaaca agggttcaga ttttagattg aaaggtgagc cgttgaaaca cgttcttctt   12060
gtcgatgacg acgtcgctat gcggcatctt attattgaat accttacgat ccacgccttc   12120
aaagtgaccg cggtagccga cagcacccag ttcacaagag tactctcttc cgcgacggtc   12180
gatgtcgtgg ttgttgatct agatttaggt cgtgaagatg ggctcgagct aggagcaagt   12240
gattttatcg ctaagccgtt cagtatcaga gagtttctag cacgcattcg ggttgccttg   12300
cgcgtgcgcc ccaacgttgt ccgctccaaa gaccgacggt cttttgtttt tactgactgg   12360
acacttaatc tcaggcaacg tcgcttgatg tccgaagctg gcggtgaggt gaaacttacg   12420
gcaggtgagt tcaatcttct cctcgcgttt ttagagaaac cccgcgacgt tctatcgcgc   12480
gagcaacttc tcattgccag tcgagtacgc gacgagagg tttatgacag gagtatagat    12540
gttctcattt tgaggctgcg ccgcaaactt gaggcagatc cgtcaagccc tcaactgata   12600
aaaacagcaa gaggtgccgg ttatttcttt gacgcggacg tgcaggtttc gcacgggggg   12660
acgatggcag cctgagccaa ttcccagatc cccgaggaat cggcgtgagc ggtcgcaaac   12720
catccggccc ggtacaaatc ggcgcggcgc tgggtgatga cctggtggag aagttgaagg   12780
ccgcgcaggc cgcccagcgg caacgcatcg aggcagaagc acgccccggt gaatcgtggc   12840
aagcggccgc tgatcgaatc cgcaaagaat cccggcaacc gccggcagcc ggtgcgccgt   12900
cgattaggaa gccgcccaag ggcgacgagc aaccagattt tttcgttccg atgctctatg   12960
acgtgggcac ccgcgatagt cgcagcatca tggacgtggc cgtttttccgt ctgtcgaagc   13020
gtgaccgacg agctggcgag gtgatccgct acgagcttcc agacgggcac gtagaggttt   13080
ccgcagggcc ggccggcatg gccagtgtgt gggattacga cctggtactg atggcggttt   13140
cccatctaac cgaatccatg aaccgatacc gggaagggaa gggagacaag cccggccgcg   13200
tgttccgtcc acacgttgcg gacgtactca agttctgccg gcgagccgat ggcggaaagc   13260
agaaagacga cctggtagaa acctgccattc ggttaaacac cacgcacgtt ggccatgcagc   13320
gtacgaagaa ggccaagaac ggccgcctgg tgacggtatc cgagggtgaa gccttgatta   13380
gccgctacaa gatcgtaaag agcgaaaccg ggcggccgga gtacatcgag atcgagctag   13440
ctgattggat gtaccgcgag atcacagaag gcaagaaccc ggacgtgctg acggttcacc   13500
ccgattactt tttgatcgat cccggcatcg gccgttttct ctaccgcctg gcacgccgcg   13560
ccgcaggcaa ggcagaagcc agatggttgt tcaagacgat ctacgaacgc agtgcgcagcg   13620
ccggagagtt caagaagttc tgtttcaccg tgcgcaagct gatcgggtca aatgacctgc   13680
cggagtacga tttgaaggag gaggcgggc aggctggccc gatcctagtc atgcgctacc    13740
gcaacctgat cgaggcgaa gcatccgccg gttcctaatg tacggagcag atgctagggc    13800
aaattgccct agcaggggaa aaaggtcgaa aaggtctctt tcctgtggat agcacgtaca   13860
ttgggaaccc aaagccgtac attgggaacc ggaacccgta cattgggaac ccaaagccgt   13920
acattgggaa ccgtcacac atgtaagtga ctgatataaa agagaaaaaa ggcgattttt    13980
ccgcctaaaa ctcttttaaaa cttattaaaa ctcttaaaac ccgcctggcc tgtgcataac   14040
tgtctggcca gcgcacagcc gaagagctgc aaaaagcgcc taccccttcgg tcgctgcgct   14100
ccctacgccc cgccgcttcg cgtcggccta tcgcggccgc tggccgctca aaaatggctg   14160
gcctacggcc aggcaatcta ccagggcgcg gacaagccgc gccgtcgcca ctcgaccgcc   14220
ggcgctgagg tctgcctcgt gaagaaggtg ttgctgctca ataccaggcc tgaatcgccc   14280
catcatccag ccagaaagtg aggagccac ggttgatgag agctttgttg taggtggacc    14340
agttggtgat tttgaacttt tgctttgcca cggaacggtc tgcgttgtcg ggaagatgcg   14400
tgatctgatc cttcaactca gcaaaagttc gatttattca acaaagccgc cgtcccgtca   14460
agtcagcgta atgctctgcc agtgttacaa ccaattaacc aattctgatt agaaaaactc   14520
atcgagcatc aaatgaaact gcaatttatt catatcagga ttatcaatac cattttttg   14580
aaaaagccgt ttctgtaatg aaggagaaaa ctcaccgagg cagttccata ggatggcaag   14640
atcctggtat cggtctgcga ttccgactcg tccaacatca atacaaccta ttaatttccc   14700
ctcgtcaaaa ataaggttat caagtgagaa atcaccatga gtgacgactg aatccggtga   14760
gaatggcaaa agctctgcat taatgaatcg gccaacgcgc ggggagaggc ggtttgcgta   14820
ttgggcgctc ttccgcttcc tcgctcactg actcgctgcg ctcggtcgtt cggctgcggc   14880
gagcggtatc agctcactca aaggcggtaa tacggttatc cacagaatca ggggataacg   14940
caggaaagaa catgtgagca aaaggccagc aaaaggccag gaaccgtaaa aaggccgcgt   15000
tgctggcgtt tttccatagg ctccgcccc ctgacgagca tcacaaaaat cgacgctcaa    15060
gtcagaggtg gcgaaacccg acaggactat aaagatacca ggcgtttccc cctggaagct   15120
ccctcgtgcg ctctcctgtt ccgaccctgc cgcttaccgg atacctgtcc gcctttctcc   15180
cttcgggaag cgtggcgctt tctcatagct cacgctgtag gtatctcagt tcggtgtagg   15240
tcgttcgctc caagctgggc tgtgtgcacg aaccccccgt tcagcccgac cgctgcgcct   15300
tatccggtaa ctatcgtctt gagtccaacc cggtaagaca cgacttatcg ccactggcag   15360
cagccactgg taacaggatt agcagagcga ggtatgtagg cggtgctaca gagttcttga   15420
agtggtggcc taactacggc tacactagaa gaacagtatt tggtatctgc gctctgctga   15480
agccagttac cttcggaaaa agagttggta gctcttgatc cggcaaacaa accaccgctg   15540
gtagcggtgg tttttttgtt tgcaagcagc agattacgcg cagaaaaaaa ggatctcaag   15600
aagatccttt gatcttttct acggggtctg acgctcagtg gaacgaaaac tcacgttaag   15660
ggattttggt catgagatta tcaaaaagga tcttcaccta gatcctttg atccggaatt    15720
a                                                                   15721

SEQ ID NO: 25        moltype = DNA   length = 19
FEATURE              Location/Qualifiers
```

```
misc_feature            1..19
                        note = for editing VLHP1 in wheat
source                  1..19
                        mol_type = other DNA
                        organism = synthetic construct
SEQUENCE: 25
gacgagcagg cgcagttcc                                                        19

SEQ ID NO: 26           moltype = DNA  length = 20
FEATURE                 Location/Qualifiers
source                  1..20
                        mol_type = genomic DNA
                        organism = Triticum aestivum
SEQUENCE: 26
gctggagctg agcttccggg                                                       20

SEQ ID NO: 27           moltype = DNA  length = 20
FEATURE                 Location/Qualifiers
source                  1..20
                        mol_type = genomic DNA
                        organism = Triticum aestivum
SEQUENCE: 27
tctggagctg agcttccggg                                                       20

SEQ ID NO: 28           moltype = DNA  length = 20
FEATURE                 Location/Qualifiers
source                  1..20
                        mol_type = genomic DNA
                        organism = Zea mays
SEQUENCE: 28
aggcgtcgag cagcgaggtg                                                       20

SEQ ID NO: 29           moltype = DNA  length = 20
FEATURE                 Location/Qualifiers
misc_feature            1..20
                        note = edited ZmVLHP-03 portion
source                  1..20
                        mol_type = other DNA
                        organism = synthetic construct
SEQUENCE: 29
aggcgttgag cagcgaggtg                                                       20

SEQ ID NO: 30           moltype = DNA  length = 75
FEATURE                 Location/Qualifiers
misc_feature            1..75
                        note = repair donor template for creating E149L mutation in
                        ZmPYL-D
source                  1..75
                        mol_type = other DNA
                        organism = synthetic construct
SEQUENCE: 30
ccttggtgtt gccgtcgggg acgtcgacga cgaatgacag gatgacgagc gtccctggcc           60
ggccgtcgat gacct                                                            75

SEQ ID NO: 31           moltype = DNA  length = 15722
FEATURE                 Location/Qualifiers
misc_feature            1..15722
                        note = vector 23136
misc_feature            4..259
                        note = bNRB-05
regulatory              304..2100
                        note = promoter - prSoUbi4-04
                        regulatory_class = promoter
gene                    2117..6286
                        note = cCas9-01
variation               5606..5608
                        note = mutation - L to V mutation
variation               5651..5653
                        note = mutation - I to V mutation
regulatory              6292..6544
                        note = terminator - tNOS-05-01
                        regulatory_class = terminator
regulatory              6551..6925
                        note = promoter - prOsU3-01
                        regulatory_class = promoter
misc_feature            6927..6946
                        note = xZmPYL-D
misc_feature            6927..7031
                        note = rsgRBAZmPYLd-02
```

| | | |
|---|---|---|
| regulatory | 7042..9033<br>note = promoter - prUbi1-04<br>regulatory_class = promoter | |
| gene | 9050..10228<br>note = cPMI-09 | |
| regulatory | 10251..10503<br>note = terminator - tNOS-05-01<br>regulatory_class = terminator | |
| misc_feature | 10547..10676<br>note = bNLB-03 | |
| gene | 10956..11744<br>note = cSpec-03 | |
| regulatory | 11839..11969<br>note = promoter - prVirG-01<br>regulatory_class = promoter | |
| gene | 12706..13779<br>note = cRepA-01 | |
| misc_feature | 13822..14226<br>note = oVS1-02 | |
| misc_feature | 14904..15710<br>note = oCOLE-06 | |
| source | 1..15722<br>mol_type = other DNA<br>organism = synthetic construct | |

SEQUENCE: 31

```
attcctgtgg ttggcatgca catacaaatg gacgaacgga taaacctttt cacgcccttt      60
taaatatccg attattctaa taaacgctct tttctcttag gtttaccgc caatatatcc     120
tgtcaaacac tgatagttta aactgaaggc gggaaacgac aatctgatca tgagcggaga     180
attaaggag tcacgttatg accccgccg atgacgcggg acaagccgtt ttacgtttgg      240
aactgacaga accgcaacgc tgcaggaatt ggccgcagcg gccattttaaa caaagcttgt    300
taccattatg tggtctaggt aggttctata tataagaaaa cttgaaatgt tctaaaaaaa    360
aattcaagcc catgcatgat tgaagcaaac ggtatagcaa cggtgttaac ctgatcagt     420
gatctcttgc aatccttaac ggccacctac cgcaggtagc aaacggcgtc ccctcctcg     480
atatctccgc ggcgacctct ggctttttcc gcggaattgc gcggtgggga cggattccac    540
gagaccgcga cgcaaccgcc tctcgccgct gggcccacca ccgctcggtg ccgtagcgtc    600
acggactct ttctccctcc tccccgtta taaattggct tcatcccctc cttgcctcat      660
ccatccaaat cccagtcccc aatcccatcc cttcgtagga gaaattcatc gaagctaagc    720
gaatcctcgc gatcctctca aggtactgcg agttttcgat ccccctctcg acccctgta    780
tgtttgtgtt tgtcgtagcg tttgattagg tatgctttc ctgtttgtgt tcgtcgtagc    840
gtttgattag gtatgcttc cctgttcgtg ttcatcgtag tgtttgatta ggtcgtgtga    900
ggcgatggcc tgctcgcgtc cttcgatctg tagtcgattt gcgggtcgtg gtgtagatct    960
gcgggctgtg atgaagttat ttggtgtgat ctgctcgcct gattctgcgg gttggctcga   1020
gtagatatga tggttggacc ggttggttcg tttaccgcgc tagggtttggg ctgggatgat   1080
gttgcatgcg ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgg ctgtgaact aactagttga    1260
ttgcggagtc atgtatcagc tacaggtgta gggactagct acaggtgtag ggacttgcgt    1320
ctaattgttt ggtcctttac tcatgttgca attatgcaat ttagtttaga ttgttttgttc   1380
cactcatcta ggctgtaaaa gggacactgc ttagattgct gtttaatctt tttagtagat   1440
tatattatat tggtaactta ttaccccat tacatgccat acgtgacttc tgctcatgcc     1500
tgatgataat catagatcac tgtggaatta attagttgat tgttgaatca tgtttcaatt    1560
acataccacg gcacaattgc ttagttcctt aacaaatgca aatttactg atccatgtat    1620
gatttgcgtg gttctctaat gtgaaatact atagctactt gttagtaaga atcaggttcg    1680
tatgcttaat gctgtatgtg ccttctgctc atgcctgatg ataatcatat atcactggaa    1740
ttaattagtt gatcgtttaa tcatatatca agtacatacc atgccacaat tttagtcac    1800
ttaacccatg cagattgaac tggtccctgc atgttttgct aaattgttct attctgatta    1860
gaccatatat catgtatttt ttttttggtaa tggttctctt atttttaaatg ctatatagtt   1920
ctggtacttg ttagaaagat ctgcttcata gtttagttgc ctatccctcg aattaggatg    1980
ctgagcagct gatcctatag cttttgtttca tgtatcaatt cttttgtgtt caacagtcag    2040
tttttgttag attcattgta acttatggtc gcttactctt ctggtcctca atgcttgcag    2100
gatcgcggcc gctcatatgg acaagaagta cagcatcggc ctggacatcg gcaccaacag    2160
cgtgggctgg gccgtgatca ccgacgagta caaggtgccg agcaagaagt tcaaggtgct    2220
gggcaacacc gacaggcaca gcatcaagaa gaacctgatc ggcgccctgc tgttcgacag    2280
cggcgagacc gccgaggcca ccaggctgaa gaggaccgcc aggaggaggt acaccaggag    2340
gaagaacagg atctgctacc tgcaggagat cttcagcaac gagatggcca aggtggacga    2400
cagcttcttc cacaggctgg aggagagctt cctggtggag gaggcaga agcacgagag     2460
gcacccgatc ttcggcaaca tcgtggacga ggtggcctac cacgagaagt acccgaccat    2520
ctaccacctg aggaagaagc tggtgacag caccgacaag gccgacctga gctgatcta     2580
cctgggccctg ccccacttca tcaagttcag gggccacttc ctgatcgagg gcgacctgaa   2640
cccggacaac agcgacgtgg acaagctgtt catccagctg gtgcagacct acaaccagct    2700
gttcgaggag aacccgatca cgcagcggc cgtggacgcc aaggccatcc tgagcgccag    2760
gctgagcaag agcaggaggc tggagaacct gatcgcccag ctgccgggcg agaagaagaa    2820
cggcctgttc ggcaacctga tcgccctgag cctgggcctg acccgaact tcaagagcaa    2880
cttcgacctg gccgaggacg ccaagctgca gctgagcaag gacacctacg acgacgacct    2940
ggacaacctg ctggcccaga tcggcgacca gtacgccgac ctgttcctgg ccgccaagaa    3000
cctgagcgac gccatcctgc tgagcgacat cctgagggtg aacaccgaga tcaccaaggc    3060
ccgctgagc gccagcatga tcaagaggta cgacgagcac caccaggacc tgaccctgct    3120
gaaggccctg gtgaggcagc agctgccgga gaagtacaag gagatcttct cgaccgagag    3180
caagaacggc tacgccggct acatcgacgg cggcgccagc caggaggagt tctacaagtt    3240
```

```
catcaagccg atcctggaga agatggacgg caccgaggag ctgctggtga agctgaacag 3300
ggaggacctg ctgaggaagc agaggacctt cgacaacggc agcatcccgc accagatcca 3360
cctgggcgag ctgcacgcca tcctgaggag gcaggaggac ttctacccgt tcctgaagga 3420
caacaggag aagatcgaga agatcctgac cttccgcatc ccgtactacg tgggcccgct 3480
ggccaggggc aacagcaggt tcgcctggat gaccaggaag agcgaggaga ccatcacccc 3540
gtggaacttc gaggaggtgg tggacaaggg cgccagcgcc cagagcttca tcgagaggat 3600
gaccaacttc gacaagaacc tgccgaacga aaggtgctg ccgaagcaca gcctgctgta 3660
cgagtacttc accgtgtaca acgagctgac caaggtgaag tacgtgaccg agggcatgag 3720
gaagccggcc ttcctgagcg gcgagcagaa aaggccatc gtggacctgc tgttcaagac 3780
caacaggaag gtgaccgtga agcagcgtaa ggaggactac ttcaagaaga tcgagtgctt 3840
cgacagcgtg gagatcagcg gcgtggagga caggttcaac gccagcctgg gcacctacca 3900
cgacctgctg aagatcatca aggacaagga cttcctggac aacgaggaga acgaggacat 3960
cctggaggac atcgtgctga ccctgaccct gttcgaggac agggagatga tcgaggagag 4020
gctgaagacc tacgcccacc tgttcgacga caaggtgatg aagcagctga agaggaggag 4080
gtacaccggc tggggcaggc tgagcaggaa gctgatcaac ggcatcaggg acaagcagag 4140
cggcaagacc atcctggact tcctgaagag cgacggcttc gccaacagga cttcatgca 4200
gctgatccac gacgacagcc tgaccttcaa ggaggacatc cagaaggccc aggtgagcgg 4260
ccaggggac agcctgcacg agcacatcgc caacctggcc ggcagcccgg ccatcaagaa 4320
gggcatcctg cagaccgtga agtggtggga cgagctggtg aaggtgatgg gcaggcacaa 4380
gccggagaac atcgtgatcg agatggccag ggagaaccag accacccaga agggccagaa 4440
gaacagcagg gagaggatga agaggatcga ggagggcatc aaggagctgg gcagccagat 4500
cctgaaggag caccccggtgg agaacaccca gctgcagaac gagaagctgt acctgctacta 4560
cctgcagaac ggcagggaca tgtacgtgga ccaggagctg gacatcaaca ggctgagcga 4620
ctacgacgtg gaccacatcg tgccgcagag cttcctgaag gacgacagca tcgacaacaa 4680
ggtgctgacc aggagcgaca gaacagggg caagagcgac aacgtgccga gcgaggaggt 4740
ggtgaagaag atgaaaaact actgaggca gctgctgaac gccaagctga tcacccagag 4800
gaagttcgac aacctgacca aggccgagag gggcggcctg agcgagctgg acaaggccgg 4860
cttcattaaa aggcagctgg tggagaccag gcagatcacc aagcacgtgg cccagatcct 4920
ggacagcagg atgaacacca agtacgacga gaacgacaag ctgatcaggg aggtgaaggt 4980
gatcaccctg aagagcaagc tggtgagcga cttccagt tctacaaggt 5040
gagggagatc aataattacc accacgccca cgacgcctac ctgaacgccg tggtgggcac 5100
cgccctgatt aaaaagtacc cgaagctgga gagcgagttc gtgtacgcg actacaaggt 5160
gtacgacgtg aggaagatga tcgccaagag cgagcaggga atcggcaagg ccaccgccaa 5220
gtacttcttc tacagcaaca tcatgaactt cttcaagacc gagatcaccc tggccacggg 5280
cgagatcagg aagaggccgc tgatcgagac caacggcgag accggcgaga tcgtgtggga 5340
caagggcagg gacttcgcca ccgtgaggaa ggtgctgtcc atgccgcagg tgaacatcgt 5400
gaagaagacc gaggtgcaga ccggcggctt cagcaaggag agcatcctgc cgaagaggaa 5460
cagcgacaag ctgatcgcca ggaagaagga ctgggacccg aagaagtacg gcggcttcga 5520
cagcccgacc gtggcctaca gcgtgctggt ggtggccaag gtggagaagg gcaagggcaa 5580
gaagctgaag agcgtgaagg agctggtggg catcaccatc atggagagga gcagcttcga 5640
gaagaacccca gtggacttcc tggaggccaa gggctacaag gaggtgaaga aggacctgat 5700
cattaaactg ccgaagtaca gcctgttcga gctggagaac ggcaggaaga ggatgctggc 5760
cagcgccggc gagctgcaga agggcaacga gctggccctg ccgagcaagt acgtgaactt 5820
cctgtacctg gccagccact acgagaagct gaagggcagc ccggaggaca acgagcagaa 5880
gcagctgttc gtggagcagc acaagcacta cctggacgag atcatcgagc agatcagcga 5940
gttcagcaag agggtgatcc tggccgacgc caacctggac aaggtgctga gcgcctacaa 6000
caagcacagg gacaagccga tcagggagca ggccgaagac atcatccacc tgttcaccct 6060
gaccaacctg ggcgccccgg ccgccttcaa gtacttcgac accaccatcg acaggaagag 6120
gtacaccagc accaaggagg tgctggacgc caccctgatc caccagagca tcaccggcct 6180
gtacgagacc aggatcgacc tgagccagct gggcggcgac agcagcccgc cgaagaagaa 6240
gagaaggtg agctggaagg acgccagcgg ctggagcagg atgtgaagct tgatcgttca 6300
aacatttggc aataaagttt cttaagattg aatcctgttg ccggtcttgc gatgattatc 6360
atataaatttc tgttgaatta cgttaagcat gtaataatta acatgtaatg catgacgtta 6420
tttatgagat gggtttttat gattagagtc ccgcaattat acatttaata cgcgatagaa 6480
aacaaaatat agcgcgcaaa ctaggataaa ttatcgcgcg cggtgtcatc tatgttacta 6540
gatcttcgaa gggatcttta aacatacgaa cagatcactt aaagttcttc tgaagcaact 6600
taaagttatc aggcatcat ggatcttgga ggaatcagat gtgcagtcag gaccatagc 6660
acaggacagg cgtcttctac tggtgctacc agcaaatgct ggaagccggg aacactgggg 6720
acgttggaaa ccacgtgatg tggagtaaga taaactgtag gagaaaagca tttcgtagtg 6780
ggccatgaag cctttcagga catgtattgc agtatgggcc ggccattac gcaattggac 6840
gacaacaaag actagtatta gtaccactc ggctatccac atagatcaaa gctggtttaa 6900
aagagttgtg cagatgatcc gtggcagtcg ggacgtcga cgacgagttt tagagctaga 6960
aatagcaagt taaataagg ctagtccgtt atcaacttga aaagtggca ccgagtcggt 7020
gcttttttt tcggaccgcg cctgcagtgc agcgtgaccg ggtcgtgccc ctctctagag 7080
ataatgagca ttgcatgtct aagttataaa aaattaccac atattttttt tgtcacactt 7140
gtttgaagtg cagtttatct atctttatac atatatttaa actttactct acgaataata 7200
taatctatag tactacaata atatcagtgt tttagagaat catataaatg aacagttaga 7260
catggtctaa aggacaattg agtattttga caacaggact ctacagtttt atcttttag 7320
tgtgcatgtg ttctcctttt tttttgcaaa tagcttcacc tatataatac ttcatccatt 7380
ttattagtac atccattag ggtttagggt taatggtttt tatagactaa ttttttttag 7440
acatctattt tattctattt tagcctctaa attaagaaaa ctaaaactct attttagttt 7500
ttttatttaa taatttagat ataaaataga ataaaataaa gtgactaaaa attaaacaaa 7560
taccctttaa gaaattaaaa aaactaagga aacatttttc ttgtttcgag tagataatgc 7620
cagcctgta aacgccgtcg cagagtctaa cggacaccaa ccagcgaacc agcagcgtcg 7680
cgtcgggcca agcgaagcag acggcacggc atctctgtcg ctgcctctgg acccctctcg 7740
agagttccgc tccaccgttg gacttgctcc gctgtcggca tccagaaatt gcgtggcgga 7800
gcggcagacg tgagccggca cggcaggcgg cctcctcctc ctctcacggc accggcagct 7860
acggggggat ccttcccac cgctccttcg ctttcccttc ctcgcccgcc gtaataaata 7920
gacacccct ccacaccctc tttccccaac ctcgtgttgt tcggagcgca cacacacaca 7980
```

```
accagatctc ccccaaatcc acccgtcggc acctccgctt caaggtacgc cgctcgtcct  8040
cccccccccc cctctctacc ttctctagat cggcgttccg gtccatggtt agggcccggt  8100
agttctactt ctgttcatgt ttgtgttaga tccgtgtttg tgttagatcc gtgctgctag  8160
cgttcgtaca cggatgcgac ctgtacgtca gacacgttct gattgctaac ttgccagtgt  8220
ttctctttgg ggaatcctgg gatggctcta gccgttccgc agacgggtgc gatttcatga  8280
ttttttttgt ttcgttgcat agggtttggt ttgcccttt cctttattc aatatatgcc  8340
gtgcacttgt ttgtcgggtc atcttttcat gctttttttt gtcttggttg tgatgatgtg  8400
gtctggttgg gcggtcgttc tagatcgag tagaattctg tttcaaacta cctggtggat  8460
ttattaattt tggatctgta tgtgtgtgcc atacatattc atagttacga attgaagatg  8520
atggatggaa atatcgatct aggataggta tacatgttga tgcgggtttt actgatgcat  8580
atacagagat gcttttgtt cgcttggttg tgatgatgtg gtgtggttgg gcggtcgttc  8640
attcgttcta gatcggagta gaatactgtt tcaaactacc tggtgtattt attaattttg  8700
gaactgtatg tgtgtgtcat acatcttcat agttacgagt ttaagatgga tggaaatatc  8760
gatctaggat aggtatacat gttgatgtgg gttttactga tgcatataca tgatggcata  8820
tgcagcatct attcatatgc tctaaccttg agtacctatc tattataata aacaagtatg  8880
ttttataatt attttgatct tgatatactt ggatgatggc atatgcagca gctatatgtg  8940
gatttttta gccctgcctt catacgctat ttatttgctt ggtactgttt cttttgtcga  9000
tgctcaccct gttgtttggt gttacttctg cagggatccg gcagcagcca tgcagaagct  9060
gatcaacagc gtgcagaact acgcctgggg cagcaagacc gccctgaccg agctgtacgg  9120
catggagaac cccagcagcc agcccatggc cgagctgtgg atgggcgccc accccaagag  9180
cagcagccgc gtgcagaacg ccgccggcga catcgtgagc ctgcgcacg tgatcgagag  9240
cgacaagagc accctgctgg gcgaggccgt ggccaagcgc ttcggcgagc tgcccttcct  9300
gttcaaggtg ctgtgcgccc ccagcccct gagcatccag gtgcacccca acaagcacaa  9360
cagcgagatc ggcttcgcca aggagaacgc cgccggcatc cccatggacg ccgccgagcg  9420
caactacaag gaccccaacc acaagcccga gctggtgttc gccctgaccc ccttcctggc  9480
catgaacgcc ttccgcgagt tcagcgagat cgtgagcctg ctgcagcgca tggccgacgc  9540
ccaccccgcc atcgcccact tcctgcagca gccgacgcc gagcgcctga gcgagctgtt  9600
cgccagcctg ctgaacatgc agggcgagga agagccgc gccctggcca tcctgaagag  9660
cgccctggac agccagcagg gcgagccctg gcagaccatc cgcctgatca gcgagttcta  9720
ccccgaggac agcggcctgt tcagccccct gctgctgaac gtggtgaagc tgaacccgga  9780
cgaggccatg ttcctgttcg ccgagacccc ccacgcctac ctgcagggcg tggccctgga  9840
ggtgatggcc aacagcgaca acgtgctgcg cgccggcctg accccaagt acatcgacat  9900
ccccgagctg gtgccaacg tgaagttcga ggccaagccc gccaaccagc tgctgaccca  9960
gcccgtgaag cagggcgccg agctggactt cccccatccg gtggacgact tcgccttcag 10020
cctgcacgac ctgagcgaca aggagaccac cagagcgccg ccatcctgt 10080
ctgcgtggag ggcgacgcca ccctgtgaa gggcagccag cagctgcagc tgaagcccgg 10140
cgagagcgcc ttcatcgccg ccaacgagg cccgtgacc gtgaagggcc acggccgcct 10200
ggcccgcgtg tacaacaagc tgtgataga gctcgatccg tcgacctgca gatcgttcaa 10260
acatttggca ataaagtttc ttaagattga atcctgttgc cggtcttgcg atgattatca 10320
tataatttct gttgaattac gttaagcatg taataattaa catgtaatgc atgacgttat 10380
ttatgagatg ggtttttatg attagagtcc cgcaattata catttaatac gcgatagaaa 10440
acaaaatata gcgcgcaaac taggataaat tatcgcgcgc ggtgtcatct atgttactag 10500
atcggcgcgc cgcaattgaa gttgggcgg ccagcatgc cgtatccgca atgtgttatt 10560
aagttgtcta agcgtcaatt tgtttacacc acaatatatc ctgccaccag ccagccaaca 10620
gctcccgac cggcagctcg gcacaaaatc accactcgat acaggcagcc catcagaatt 10680
aattctcatg tttgacagct tatcatcgac tgcacggtgc accaatgctt ctggcgtcag 10740
gcagccatcg gaagctgtgg tatggctgtg caggtcgtaa atcactgcat aattcgtgtc 10800
gctcaaggcg cactcccgtt ctggataatg tttttgcgc cgacatcata acggttctgg 10860
caaatattct gaaatgagct gttgacaatt aatcatccgg ctcgtataat gtgtggaatt 10920
gtgagcggat aacaatttca cacaggaaac agaccatgag ggaagcgttg atcgccgaag 10980
tatcgactca atatcagag gtagttggcg tcatcgagcg ccatctcgaa ccgacgttgg 11040
tggccgtaca tttgtacggc tccgcagtgg atgcgggcct gaagccacac agtgatattg 11100
atttgctggt tacggtgacc gtaaggcttg atgaaacaac gcggcgagct ttgatcaacg 11160
acctttgga aacttcggct tcccctggag agagcgagat tctccgcgct gtagaagtca 11220
ccattgttgt gcacgacgac atcattccgt ggcgttatcc agctaagcgc gaactgcaat 11280
ttggagaatg gcagcgcaat gacattcttg caggtatctt cgagccagcc acgatcgaca 11340
ttgatctggc tatcttgctg acaaaagcaa gagaacatag cgttgccttg gtaggtccag 11400
cggcggagga actctttgat ccggttcctg aacaggatct atttgaggcg ctaaatgaaa 11460
ccttaacgct atggaactcg ccgcccgact gggctggcga tgagcgaaat gtagtgctta 11520
cgttgtcccg catttggtac agcgcagtaa ccggcaaaat cgcgccgaag gatgtcgctg 11580
ccgactgggc aatggagcgc ctgccggccc agtatcagcc cgtcatactt gaagctaggc 11640
aggcttatct tggacaagaa gatcgcttgg cctcgcgcgc agatcagttg gaagaatttg 11700
ttcactacgt gaaaggcgag atcaccaaag tagtcggcaa ataaagctct agtggatctc 11760
cgtacccggg gatctggctc gcggcggacg cacgacgcg gagagacc ataggcgatc 11820
tcctaaatca atagtagctg taacctcgaa gcgtttcact tgtaacaacg attgagaatt 11880
tttgtcataa aattgaaata cttggttcgc attttgtca tccgcggtca gccgcaattc 11940
tgacgaactg cccatttagc tggagatgat tgtacatcct tcacgtgaaa atttctcaag 12000
cgctgtgaac aagggttcag atttagatt gaaaggtgag ccgtgaaac acgttcttct 12060
tctgatgac acgtcgcta tgcggcatct tattattgaa taccttacga tccacgcctt 12120
caaagtgacc gcggtagccg acagcaccca gttcacaaga gtactctctt ccgcgacggt 12180
cgatgtcgtg gttgttgatc tagatttagg tcgtgaagat gggctcgagc taggagcaag 12240
tgattttatc gctaagccgt tcagtatcag agagtttcta gcacgcattc gggttgcctt 12300
gcgcgtcgcc ccaacgttg tccgctccaa agaccgacgg tcttttttgtt ttactgactg 12360
gacacttaat ctcaggcaac gtcgcttgat gtccgaagct ggggtgagg tgaaacttac 12420
ggcaggtgag ttcaatcttc tcctcgcgtt tttagagaaa cccgcgacg ttctatcgcg 12480
cgagcaactt ctcattgcca gtcgagtacg cgacgaggag gtttatgaca ggagtataga 12540
tgttctcatt tgaggctgc gccgcaaact tgaggcagat ccgtcaagcc ctcaactgat 12600
aaaaacagca agaggtgccg gttatttctt tgacgcggac gtgcaggttt cgcacggggg 12660
gacgatggca gcctgagcca attcccagat ccccgaggaa tcggcgtgag cggtcgcaaa 12720
```

```
ccatccggcc cggtacaaat cggcgcggcg ctgggtgatg acctggtgga gaagttgaag   12780
gccgcgcagg ccgcccagcg gcaacgcatc gaggcagaag cacgcccgg tgaatcgtgg    12840
caagcggccg ctgatcgaat ccgcaaagaa tcccggcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgtttttcg tctgtcgaag   13020
cgtgaccgac gagctggcga ggtgatccgc tacgagcttc cagacgggca cgtagaggtt   13080
tccgcagggc cggccggcat ggccagtgtg tgggattacg acctggtact gatggcggtt   13140
tcccatctaa ccgaatccat gaaccgatac cgggaaggga agggagacaa gcccggccgc   13200
gtgttccgtc cacacgttgc ggacgtactc aagttctgcc ggcgagccga tggcggaaag   13260
cagaaagacg acctggtaga aacctgcatt cggttaaaca ccacgcacgt tgccatgcag   13320
cgtacgaaga aggccaagaa cggccgcctg tgacggtat ccgagggtga agccttgatt    13380
agccgctaca agatcgtaaa gagcgaaacc gggcggccgg agtacatcga gatcgagcta   13440
gctgattgga tgtaccgcga gatcacagaa ggcaagaacc cggacgtgct gacggttcac   13500
cccgattact ttttgatcga tcccggcatc ggccgttttc tctaccgacc ggcacgccgc   13560
gccgcaggca aggcagaagc cagatgggtt ttcaagacga tctacgaacg cagtggcagc   13620
gccggagagt tcaagaagtt ctgtttcacc gtgcgcaagc tgatcgggtc aaatgacctg   13680
ccggagtacg atttgaagga ggaggcgggg caggctggcc cgatcctagt catgcgctac   13740
cgcaacctga tcgaggggca agcatccgcc ggttcctaat gtacggagca gatgctaggg   13800
caaattgccc tagcagggga aaaggtcga aaaggtctct ttcctgtgga tagcacgtac    13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actcttttaaa acttattaaa actcttaaaa cccgcctgtc ctgtgcataa   14040
ctgtctggcc agcgcacagc cgaagagctg caaaaagcgc ctaccttcg gtcgctgcgc    14100
tccctacgcc ccgccgcttc gcgtcggcct atcgcggccg ctggccgctc aaaaatggct   14160
ggcctacggc caggcaatct accagggcgc ggacaagccg cgccgtcgcc actcgaccgc   14220
cggcgctgag gtctgcctcg tgaagaaggt gttgctgact cataccaggc tcgaatcgcc   14280
ccatcatcca gccagaaagt gagggagcca cggttgatga gagctttgtt gtaggtggac   14340
cagttggtga ttttgaactt ttgctttgcc acggaacggt ctgcgttgtc gggaagatgc   14400
gtgatctgat ccttcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaatttat tcatatcagg attatcaata ccatattttt   14580
gaaaagccg tttctgtaat gaaggagaaa actcaccgag gcagttccat aggatggcaa   14640
gatcctggta tcggtctgcg attccgactc gtccaacatc aatacaacct attaatttcc   14700
cctcgtcaaa aataaggtta tcaagtgaga aatcaccatg agtgacgact gaatccggtg   14760
agaatggcaa aagctctgca ttaatgaatc ggccaacgcg cggggagagg cggtttgcgt   14820
attgggcgct cttccgcttc ctcgctcact gactcgctgc gctcggtcgt tcggctgcgg   14880
cgagcggtat cagctcactc aaaggcggta atacggttat ccacagaatc aggggataac   14940
gcaggaaaga acatgtgagc aaaaggccag caaaaggcca ggaaccgtaa aaaggccgcg   15000
ttgctgcgt ttttccatag gctccgcccc cctgacgagc atcacaaaaa tcgacgctca    15060
agtcagaggt ggcgaaaccc gacaggacta taaagatacc aggcgtttcc ccctggaagc   15120
tccctcgtgc gctctcctgt tccgaccctg ccgcttaccg gatacctgtc cgcctttctc   15180
ccttcggaa gcgtggcgct ttctcatagc tcacgctgta ggtatctcag ttcggtgtag    15240
gtcgttcgct ccaagctggg ctgtgtgcac gaaccccccg ttcagcccga ccgctgcgcc   15300
ttatccggta actatcgtct tgagtccaac ccggtaagac acgacttatc gccactggca   15360
gcagccactg gtaacaggat tagcagagcg aggtatgtag cggtgctac agagttcttg    15420
aagtggtggc ctaactacgg ctacactaga agaacagtat ttggtatctg cgctctgctg   15480
aagccagtta ccttcggaaa aagagttggt agctcttgat ccggcaaaca aaccaccgct   15540
ggtagcggtg ttttttttgt ttgcaagcag cagattacgc gcagaaaaaa aggatctcaa   15600
gaagatcctt tgatcttttc tacggggtct gacgctcagt ggaacgaaaa ctcacgttaa   15660
gggattttgg tcatgagatt atcaaaaagg atcttcacct agatcctttt gatccggaat   15720
ta                                                                  15722

SEQ ID NO: 32        moltype = DNA  length = 20
FEATURE              Location/Qualifiers
misc_feature         1..20
                     note = encoding gRNA for vector 23136
source               1..20
                     mol_type = other DNA
                     organism = synthetic construct
SEQUENCE: 32
gtcggggacg tcgacgacga                                               20

SEQ ID NO: 33        moltype = DNA  length = 1823
FEATURE              Location/Qualifiers
source               1..1823
                     mol_type = genomic DNA
                     organism = Oryza sativa
SEQUENCE: 33
acagtgacta gtgacaaacg atcgatcgat ccctccatcc acaaaccctc ctcgatctca   60
tcttccttcg tctcgtcaat ggcggcgagc tactcgtgcc ggcggacatg cgaggcgtgc   120
agcacgaggg cgatggccgg gtgcgtggtg gcgagccgg cgtcggcgcc ggggcagcgg    180
gtgacgttgc tggcgatcga cggcggcggc atcaggggcc tcatcccggg caccatcctc   240
gccttcctcg aggccaggct gcaggagctg gatggccccg acgcgcgcct cgccgattac   300
ttcgactgca tcgcccggac cagcaccggc ggcctcatca ccgccatgct cgccgcgccc   360
ggcgaccacg gccgcccgct cttcgccgcc agcacatca accgcttcta cctcgacaac   420
ggcccactca tcttcccaca aaagtaactg atcacctcga attcgatctc ctctcttcga   480
tctctgcatt atttgatttg attggggatt gtggcggcg tggcgtggcg tccaggaggt    540
gcggcatggc ggcggccatg gcgcggctga cgaggccgag gtacaacggc aagtacctgc   600
agggaagat caggaagatg ctgggcgaga cgagggtgcg cgacacgctg acgaacgtcg    660
```

-continued

```
tcatccccac gttcgacgtc aggctgctcc agccaaccat cttctccaca tacgacgtgc    720
gtgcgttgat tccatccgca ttggcgttgg aatcagctga ttgtttgatt gatcgaacaa    780
ttgatcggtt aaaattttgc aggcgaagag catgccgctc aagaacgcgc tcctctccga    840
catctgcatc agcacatccg cggcgccgac ctacctcccc gcgcactgct ccagaccac     900
cgacgacgcc accggcaagg tccgcgagtt cgacctcatc gacggcgggc tcgccgccaa    960
caacccggta actaatcaat caagcaatcc atcaaacgaa gatccacatg tgcattcctg   1020
tggtacaaat gctgatcgat cgatggatgg atcgattttc gcgagaacgt acagacgatg   1080
gtggccatga cgcagatcac caagaagata atggtgaagg acaaggagga gctgtacccg   1140
gtaaagccgt cggactgcgg taagttcctg gtgctgtccg tgggcaccgg gtcgacgtcg   1200
gaccaggaga tgtacacggc gaggcagtgc tcgcggtggg ggatcgtccg gtggctgcgc   1260
aacaagggga tggcgcccat catcgacatc ttcatggcgg ccagctccga cctcgtcgac   1320
atccacgccg ccgtcatgtt ccagtcgctg cacagcgacg gcgactacct ccgcatccag   1380
gacaacacgc tccacggcga cgccgccacg gtggacgccg ccaccaggga caacatgcgg   1440
gcgctcgtcg ggatcggcga gcggatgctg gcgcagcggg tgtcgagggt caacgtcgga   1500
accggcaggt acgtcgaggt gcccggcgcc ggcagcaacg ccgacgcgct gaggggcttc   1560
gccaggcagc tctccgagga gaggaggcg aggctaggtc ggcgaaacgc ctgccggcggc   1620
ggcggcgaag gagagcccag cggcgtggcg tgcaagcgtt agtaactgta cacgcatcat   1680
gctgacgcga tcttttttat ttttcttttt tttttttac ctttctagcg gacatgggga   1740
ataacaagac gtgacagtag tgcaatcggt ttgtaacgtg cgtataccaa cattgatcca   1800
tttcttcatc acagtttcag ttc                                           1823
```

```
SEQ ID NO: 34              moltype = DNA   length = 15921
FEATURE                    Location/Qualifiers
misc_feature               1..15921
                           note = Vector 24038
misc_feature               4..259
                           note = bNRB-05
regulatory                 313..1149
                           note = promoter - prZmGRMZM5G876285-01
                           regulatory_class = promoter
gene                       1152..5412
                           note = cCas9-12
regulatory                 5419..6736
                           note = terminator - tZmGRMZM5G876285-01
                           regulatory_class = terminator
regulatory                 6750..7124
                           note = promoter - prOsU3-01
                           regulatory_class = promoter
misc_feature               7126..7145
                           note = xZmVLHP2
misc_feature               7126..7230
                           note = rsgRNAZmVLHP-02
misc_feature               7146..7157
                           note = rCrRNA-01
misc_feature               7146..7230
                           note = rsgRNAbase-01
misc_feature               7162..7230
                           note = rTracrRNA-01
regulatory                 7241..9232
                           note = promoter - prUbi-04
                           regulatory_class = promoter
gene                       9249..10427
                           note = cPMI-09
regulatory                 10450..10702
                           note = terminator - tNOS-05-01
                           regulatory_class = terminator
misc_feature               10746..10875
                           note = bNLB-03
gene                       11155..11943
                           note = cSpec-03
regulatory                 12038..12168
                           note = promoter - prVirG-01
                           regulatory_class = promoter
gene                       12243..12875
                           note = cVirG-09
gene                       12905..13978
                           note = cRepA-01
misc_feature               14021..14425
                           note = oVA1-02
misc_feature               15103..15909
                           note = oCOLE-06
source                     1..15921
                           mol_type = other DNA
                           organism = synthetic construct
SEQUENCE: 34
attcctgtgg ttggcatgca catacaaatg gacgaacgga taaaccttt cacgcccttt     60
taaatatccg attattctaa taaacgctct tttctcttag gtttaccgc caatatatcc    120
tgtcaaaac tgatagttta aactgaaggc gggaaacgca aatctgatca tgagcggaga    180
attaagggag tcacgttatg accccgccg atgacgcggg acaagccgtt ttacgtttgg    240
```

```
aactgacaga accgcaacgc tgcaggaatt ggccgcagcg gccatttaaa caaagcttgg    300
taccgggacc ctaagtaatc ttgtgctaca aatttatttt tcagacagaa aaatctattt    360
agctaactaa ttaatacaaa ttaataccaa gcaacgatag atgaacatct agttgtctaa    420
ttagctaact aattaataca aattaagtag aatccttacc gtggggagat ggggcgcgac    480
gaagtgctcg agcttgggc gcggcgaccg gcgacgtgaa gcttggggc gcggggccg     540
gacggcgctg cgggcggcat ggcgggcggc tgcgggcggc ggcgcgggcg caggaaacaa    600
acgacgggag tgggaggaag gagaaagcgg cgcgccggtt tagtcctagc tcggcgccaa    660
gatctgtggc gccgagctag gtgccacgat ggccgccgcg tcagcaaagc tcggcgccaa    720
ggcatgttgc gccgagccgt gttagtcgg cgtcatagct catggtgccg agttttgggt    780
ctaaaattgc gtttaagtat tctagggatc taaacgcaaa tatttttcga aaatagggcc    840
gaaaacaaa aaaaaatcgg tcgtttcgtc gagcacatcg tccagcctat cttgcatgtc    900
catcctctct atggttcgcg agccgcgcgc atggcgctcc aaaggagggg cgaggttgaa    960
tatagacaga tggaatgggt ggttctctat ttatagcgca tgcagtcgtc ccctggcaca   1020
cctatttata tgtgagcgtt cctggcacta gagagatcga tcgatcgagc ttaattgcgc   1080
cactgctcgt tatcctcctc ttgcattgca ttgcaggtcg tagttgagca gcagcaacca   1140
ctgcacaggc catggacaag aagtacagca tcggcctgga catcggcacc aacagcgtgg   1200
gctgggccgt gatcaccgac gagtacaagg tgataccaat ttgcatgatc cttgttcgtt   1260
ctagctcttg catgccgatc agttgaatca cgccgttttcc ttctgcgcat ttgcatccag   1320
gtgccgagca agaagttcaa ggtgctgggc aacaccgaca ggcacagcat caagaagaac   1380
ctgatcggcc ccctgctgtt cgacagcggc gagaccgccg aggccaccag gctgaagagg   1440
accgccagga ggaggtacac caggaggaag aacaggatct gctacctgca ggagatcttc   1500
agcaacgaga tggccaaggt ggacgacagc ttcttccaca ggctggagga gagcttcctg   1560
gtggaggagg acaagaagca cgagaggcac ccgatcttcg gcaacatcgt ggacgaggtg   1620
gcctaccacg agaagtaccc gaccatctac cacctgagga agaagctggt ggacagcacc   1680
gacaaggccg acctgaggct gatctacctg gccctggccc acatgatcaa gttcaggggc   1740
cacttcctga tcgagggcga cctgaacccg gacaacagcg acgtggacaa gctgttcatc   1800
cagctggtgc agacctacaa ccagctgttc gaggagaacc cgatcaacgc cagcggcgtg   1860
gacgccaagg ccatcctgag cgccaggctg agcaagagca ggaggctgga gaacctgatc   1920
gcccagctgc cgggcgagaa gaagaacggc ctgttcggca acctgatcgc cctgagcctg   1980
ggcctgaccc cgaacttcaa gagcaacttc gacctggccg aggacgccaa gctgcagctg   2040
agcaaggaca cctacgacga cgacctggac aacctgctgg cccagatcgg cgaccagtac   2100
gccgacctgt tcctggccgc caagaacctg agcgacgcca tcctgctgag cgacatcctg   2160
agggtgaaca ccgagatcac caaggccccg ctgagcgcca gcatgatcaa gaggtacgac   2220
gagcaccacc aggacctgac cctgctgaag gccctggtga ggcagcagct gccggagaag   2280
tacaaggaga tcttcttcga ccagagcaag aacggctacg ccggctacat cgacggcggc   2340
gccagccagg aggagttcta caagttcatc aagccgatcc tggagaagat ggacggcacc   2400
gaggagctgc tggtgaagct gaacagggag gacctgctga ggaagcagag gaccttcgac   2460
aacggcagca tcccgcacca gatccacctg ggcgagctgc acgccatcct gaggaggcag   2520
gaggacttct acccgttcct gaaggacaac agggagaaga tcgagaagat cctgaccttc   2580
cgcatcccgt actacgtggg cccgctggcc aggggcaaca gcaggttcgc ctggatgacc   2640
aggaagagcg aggagaccat caccccgtgg aacttcgagg aggtggtgga caagggcgcc   2700
agcgcccaga gcttcatcga gaggatgacc aacttcgaca gaacctgcc gaacgagaag   2760
gtgctgccga agcacagcct gctgtacgag tacttcaccg tgtacaacga gctgaccaag   2820
gtgaagtacg tgaccgaggg catgaggaag ccggccttcc tgagcggcga gcagaagaag   2880
gccatcgtgg acctgctgtt caagaccaac aggaaggtga ccgtgaagca gctgaaggag   2940
gactacttca agaagatcga gtgcttcgac agcgtggaga tcagcggcgt ggaggacagg   3000
ttcaacgcca gcctgggcac ctaccacgac ctgctgaaga tcatcaagga caaggacttc   3060
ctggacaacg aggagaacga ggacatcctg gaggacatcg tgctgaccct gaccctgttc   3120
gaggacaggg agatgatcga ggagaggctg aagacctacg cccacctgtt cgacgacaag   3180
gtgatgaagc agctgaagag gaggaggtac accggctggg gcaggctgag caggaagctg   3240
atcaacggca tcagggacaa gcagagcggc aagaccatcc tggacttcct gaagagcgac   3300
ggcttcgcca acaggaactt catgcagctg atccacgacg acagcctgac cttcaaggag   3360
gacatccaga aggcccaggt gagcggccag ggcgacagcc tgcacgagca catcgccaac   3420
ctggccggca gcccggccat caagaagggc atcctgcaga ccgtgaaggt ggtggacgag   3480
ctggtgaagg tgatgggcag gcacaagccg gagaacatcg tgatcgagat ggccagggag   3540
aaccagacca cccagaaggg ccagaagaac agcagggaga ggatgaagag gatcgaggag   3600
ggcatcaagg agctgggcag ccagatcctg aaggagcacc cggtggagaa cacccagctg   3660
cagaacgaga agctgtacct gtactacctg cagaacggca gggacatgta cgtggaccag   3720
gagctggaca tcaacaggct gagcgactac gacgtggacc acatcgtgcc gcagagcttc   3780
ctgaaggacg acagcatcga caacaaggtg ctgaccagga gcgacaagaa caggggcaag   3840
agcgacaacg tgccgagcga ggaggtggtg aagaagatga aaaactactg gaggcagctg   3900
ctgaacgcca agctgatcac ccagaggaag ttcgacaacc tgaccaaggc cgagaggggc   3960
ggcctgagcg agctggacaa ggccggcttc attaaaaggc agctggtgga gaccaggcag   4020
atcaccaagc acgtggccca gatcctggac agcaggatga acaccaagta cgacgagaac   4080
gacaagctga tcagggaggt gaaggtgatc accctgaaga gcaagctggt gagcgacttc   4140
aggaaggact tccagttcta caaggtgagg gagatcaata attaccacca cgcccacgac   4200
gcctacctga acgccgtggt gggcaccgcc ctgattaaaa agtacccgaa gctggagagc   4260
gagttcgtgt acggcgacta caaggtgtac gacgtgagga agatgatcgc caagagcgag   4320
caggagatcg gcaaggccac cgccaagtac ttcttctaca gcaacatcat gaacttcttc   4380
aagaccgaga tcaccctggc caacggcgag atcaggaaga ggccgctgat cgagaccaac   4440
ggcgagaccg gcgagatcgt gtgggacaag gcagggact tcgccaccgt gaggaaggtg   4500
ctgtccatgc cgcaggtgaa catcgtgaag aagaccgagg tgcagaccgg cggcttcagc   4560
aaggagcagca tcctgccgaa gaggaacagc gacaagctga tcgccaggaa gaaggactgg   4620
gacccgaaga gtacgcggg cttcgacgcc cctacagcgc gctggtggta   4680
gccaaggtgg agaagggcaa gagcaagaag ctgaagagcg tgaaggagct ggtgggcatc   4740
accatcatgg agaggagcag cttcgagaag aacccagtgg acttcctgga ggccaagggc   4800
tacaaggagg tgaagaagga cctgatcatt aaactgccga agtacagcct gttcgagctg   4860
gagaacggca ggaagaggat gctggccagc gccggcgagc tgcagaaggg caacgagctg   4920
gccctgccga gcaagtacgt gaacttcctg tacctggcca gccactacga gaagctgaag   4980
```

```
ggcagcccgg aggacaacga gcagaagcag ctgttcgtgg agcagcacaa gcactacctg   5040
gacgagatca tcgagcagat cagcgagttc agcaagaggg tgatcctggc cgacgccaac   5100
ctggacaagg tgctgagcgc ctacaacaag cacaggaca agccgatcag ggagcaggcc    5160
gagaacatca tccacctgtt caccctgacc aacctgggcg ccccggccgc cttcaagtac   5220
ttcgacacca ccatcgacag gaagaggtac accagcacca aggaggtgct ggacgccacc   5280
ctgatccacc agagcatcac cggcctgtac gagaccagga tcgacctgag ccagctgggc   5340
ggcgacagca gcccgccgaa gaagaagagg aaggtgagct ggaaggacgc cagcggctgg   5400
agcaggatgt gagctctaat gcatccaaac aacgacacca acgccaacat taattaatta   5460
gtagtctcca tgccctggga ttgtgcgtgg ccgctccgtt gaacaccacc catccttcgt   5520
tcggcatttt ttccccctt gtttatataa ttttattgta tcgttttggc aaataatttt    5580
gtgattcgac cccaaagcaa gtttggttgt cttacgattt gtaaacctgg aacaatatat   5640
aatgtgattg aactgctttg tctattcttt ttgtagtacg ataatatgta tatgtattcc   5700
atgcgatctc ttctagggcg acgactaatg tgcaagtgtg tgtttgcatg cgctgagcac   5760
ggagtttgta ttcaggggtc aatatcttc gattccttta tctaaaaagg tgttgcatat   5820
atctaaaaaa aagaaaaaaa aggcttacaa ctgttgaaaa aataagcatt tttagttta    5880
atttaattca gaaaatcata gtgatatatg tgacgatatg catgtgcata tgtatcacta   5940
ctcacataaa cagtaaacaa cagtaaaata tgtataaata caaaaataac aaagtgtacc   6000
ctgcggaggg accgatgttc aaggcatctg tggctccatt cacacgagac atctcgtgtg   6060
tatgttcgat gtagtcatac gcagtcgagg cagtcagatg tacgcagtgc agtccctcga   6120
tcggcgccgg cgacgaggaa cttgatcagt gctggtcgag cggacgaagc gagcagtcgc   6180
gagtacgctc ccgaaaaaca tgatcgctcg cacacccatg caagtgtcgc tctgcggacg   6240
acgatttcgg aagcctacgc gtatgagaat gtttgtatgt gtgttctctc gtaaccagaa   6300
gcctcatctc ctccgtatat atacacgcgc agagggaggc caacagatag taacggtgga   6360
aggaatactc ggaccaaggt ccgatctacc atggccacgg cccggcctgg ccagcggcgc   6420
gtgcgtgtgg cagtccttca tccttttatc agcttatcaa tagatgcacc aaagatccac   6480
ctatttaagt tgattgaatt gtctcttgta cttccggtat gttactaaag taataataca   6540
ccgtagcatt aaattgggcc tttagcattg gctattattg aatattaatt tgagccagac   6600
ccaccaccag atgctaagtc acaccaaaat gctctcatca tctcaaacat ttcatatact   6660
ggtgtttcga tggagactat taagttgaac atccacctag aatctagatt acacttgacc   6720
acaactacat aatggacgga ccgttcgaag ggatcttaa acatacgaac agatcactta   6780
aagttcttct gaagcaactt aaagttatca ggcatgcatg gatcttggag gaatcagatg   6840
tgcagtcagg gaccatagca caggacaggc gtcttctact ggtgctacca gcaaatgctg   6900
gaagccggga acactgggta cgttggaaac cacgtgatgt ggagtaagat aaactgtagg   6960
agaaaagcat ttcgtagtgg gccatgaagc cttcaggac atgtattgca gtatgggccg    7020
gcccattacg caattggacg acaacaaaga ctagtattag taccacctcg gctatccaca   7080
tagatcaaag ctggtttaaa agagttgtgc agatgatccg tggcagctgg agctgagctt   7140
ccgggggtttt agctagaa atagcaagtt aaaataaggc tagtccgtta tcaacttgaa    7200
aaagtggcac cgagtcggtg cttttttttt cggaccgcgc ctgcagtgca gcgtgacccg   7260
gtcgtgcccc tctctagaga taatgagcat tgcatgtcta agttataaaa aattaccaca   7320
tatttttttt gtcacacttg tttgaagtgc agtttatcta tctttataca tatatttaaa   7380
ctttactcta cgaataatat aatctatagt actacaataa tatcagtgtt ttagagaatc   7440
atataaatga acagttagac atggtctaaa ggacaattga gtattttgac aacaggactc   7500
tacagttttc tcttttttagt gtgcatgtgt tctcctttt ttttgcaaat agcttcacct    7560
atataatact tcatccattt tattagtaca tccatttagg gtttagggtt aatggttttt   7620
atagactaat ttttttagta catctatttt attctatttt agcctctaaa ttaagaaaac   7680
taaaactcta ttttagttttt tttatttaat aatttagata taaaatagaa taaaataaag   7740
tgactaaaaa ttaaacaaat acccctttaag aaattaaaaa aactaaggaa acatttttct   7800
tgtttcgagt agataatgcc agcctgttaa acgccgtcga cgagtctaac ggacaccaac   7860
cagcgaacca gcagcgtcgc gtcgggccaa gcgaagcaga cggcacggca tctctgtcgc   7920
tgcctctgga cccctctcga gagttccgct ccaccgttgg acttgctccg ctgtcggcat   7980
ccagaaattg cgtggcggag cggcagacgt gagccggcac ggcaggcggc ctcctcctca   8040
tctcacggca ccggcagcta cggggggattc ctttcccacc gctccttcgc tttcccttcc   8100
tcgcccgccg taataaatag acaccccctc cacaccctct ttcccaacc tcgtgttgtt    8160
cggagcgcac acacacacaa ccagatctcc cccaaatcca cccgtcggca cctccgcttc   8220
aaggtacgcc gctcgtcctc cccccccccc tctctagatc tctctagagg ggcgttccgg   8280
tccatggtta gggcccggta gttctacttc tgttcatgtt tgtgttagat ccgtgtttgt   8340
gttagatccg tgctgctagc gttcgtacac ggatgcgacc tgtacgtcag acacgttctg   8400
attgctaact tgccagtgtt tctctttggg gaatcctggg atggctctag ccgttccgca   8460
gacgggatcg atttcatgat tttttttgtt tcgttgcata gggtttggtt tgcccttttc   8520
ctttatttca atatatgccg tgcacttgtt tgtcgggtca tcttttcatg ctttttttg    8580
tcttggttgt gatgatgtgg tctggttggg cggtcgttct agatcggagt agaattctgt   8640
ttcaaactac ctggtggatt tattaatttt ggatctgtat gtgtgtgcca tacatattca   8700
tagttacgaa ttgaagatga tggatggaaa tatcgatcta ggataggtat acatgttgat   8760
gcgggtttta ctgatgcata tacagagatg cttttttgtc gcttggttgt gatgatgtgg   8820
tgtggttggg cggtcgttca ttcgttctag atcggagtag aatactgttt caaactacct   8880
ggtgtattta ttaatttttgg aactgtatgt gtgtgtcata catcttcata gttacgagtt   8940
taagatggat ggaaatatcg atctaggata ggtatacatg ttgatgtggg ttttactgat   9000
gcatatacat gatggcatat gcagcatcta ttcatatgct ctaaccttga gtacctatct   9060
attataataa acaagtatgt tttataatta tttttgatctt gatatactg gatgatgcct   9120
tatgcagcag ctatatgtgg attttttttag ccctgccttc atacgctatt tatttgcttg   9180
gtactgtttc ttttgtcgat gctcaccctg ttgtttggtg ttacttctgc agggatccgg   9240
cagcagccat gcagaagctg atcaacgcgc tgcagaacta cgcctgggc agcaagaccc   9300
ccctgaccga gctgtacggc atggagaacc ccagcagcca gccatgcc gagctgtgga    9360
tgggcgcccc ccaagagc agcagccgcg tgcagaacgc tgcagtcgtgga                  9420
tgcgcgacgt gatcgagagc gacaagagca cctgcgggg cgaggccgtg gccaagcgct   9480
tcggcgagct gcccttcctg ttcaaggtgc tgtgcgccgc ccagcccctg agcatccagg   9540
tgcaccccaa caagcacaac agcgagatcg cttcgccaa ggagaacgcc gccggcatcc   9600
ccatggacgc cgccgagcgc aactacaagg accccaacca caagcccgag ctggtgttcg   9660
ccctgacccc cttcctggcc atgaacgcct tccgcgagtt cagcgagatc gtgagcctgc   9720
```

```
tgcagcccgt ggccggcgcc caccccgcca tcgcccactt cctgcagcag cccgacgccg   9780
agcgcctgag cgagctgttc gccagcctgc tgaacatgca gggcgaggag aagagccgcg   9840
ccctggccat cctgaagagc gccctggaca gccagcaggg cgagccctgg cagaccatcc   9900
gcctgatcag cgagttctac cccgaggaca gcggcctgtt cagcccctg ctgctgaacg   9960
tggtgaagct gaaccccggc gaggccatgt tcctgttcgc cgagacccc cacgcctacc   10020
tgcagggcgt ggccctggag gtgatggcca acagcgacaa cgtgctgcgc gccggcctga   10080
cccccaagta catcgacatc cccgagctgg tggccaacgt gaagttcgag gccaagcccg   10140
ccaaccagct gctgacccag cccgtgaagc agggcgccga gctggacttc cccatccccg   10200
tggacgactt cgccttcagc ctgcacgacc tgagcgacaa ggagaccacc atcagccagc   10260
agagcgccgc catcctgttc tgcgtggagg gcgacgccac cctgtggaag ggcagccagc   10320
agctgcagct gaagcccggc gagagcgcct tcatcgccgc caacgagagc cccgtgaccg   10380
tgaagggcca cggccgcctg gccgcgtgt acaacaagct gtgataggag ctcgatccgt   10440
cgacctgcag atcgttcaaa catttggcaa taaagtttct taagattgaa tcctgttgcc   10500
ggtcttgcga tgattatcat ataatttctg ttgaattacg ttaagcatgt aataattaac   10560
atgtaatgca tgacgttatt tatgagatgg gttttatga ttagagtccc gcaattatac   10620
atttaatacg cgatagaaaa caaaatatag cgcgcaaact aggataaatt atcgcgcgcg   10680
gtgtcatcta tgttactaga tcggcgcgcc gcaattgaag tttgggcggc cagcatggcc   10740
gtatccgcaa tgtgttatta agttgtctaa gcgtcaattt gtttacacca caatatatcc   10800
tgccaccagc cagccaacag ctccccgacc ggcagctcgg cacaaaatca ccactcgata   10860
caggcagccc atcagaatta attctcatgt ttgacagctt atcatcgact gcacggtgca   10920
ccaatgcttc tggcgtcagg cagccatcgg aagctgtggt atggctgtgc aggtcgtaaa   10980
tcactgcata attcgtgtcg ctcaaggcgc actcccgttc tggataatgt tttttgcgtt   11040
gacatcataa cggttctggc aaatattctg aaatgagctg ttgacaatta atcatccggc   11100
tcgtataatg tgtggaattg tgagcggata acaatttcac acaggaaaca gaccatgagg   11160
gaagcgttga tcgccgaagt atcgactcaa ctatcagagg tagttggcgt catcgagcgc   11220
catctcgaac cgacgttgct ggccgtacat ttgtacggct ccgcagtgga tggcggcctg   11280
aagccacaca gtgatattga tttgctggtt acggtgaccg taaggcttga tgaaacaacg   11340
cggcgagctt tgatcaacga ccttttgaa acttcggctt ccctggaga gagcgagatt   11400
ctccgcgctg tagaagtcac cattgttgtg cacgacgaca tcattccgtg gcgttatcca   11460
gctaagcgcg aactgcaatt tggagaatgg cagcgcaatg acattcttgc aggtatcttc   11520
gagccagcca cgatcgacat tgatctggct atcttgctga caaaagcaag agaacatagc   11580
gttgccttgg taggtccagc ggcggaggaa ctctttgatc cggttcctga acaggatcta   11640
tttgaggcgc taaatgaaac cttaacgcta tggaactcgc cgcccgactg gctggcgat   11700
gagcgaaatg tagtgcttac gttgtcccgc atttggtaca gcgcagtaac cggcaaaatc   11760
gcgccgaagg atgtcgctgc cgactgggca atggagcgcc tgccggccca gtatcagccc   11820
gtcatacttg aagctaggca ggcttatctt ggacaagaag atcgcttggc ctcgcgcgca   11880
gatcagttgg aagaatttgt tcactacgtg aaaggcgaga tcaccaaagt agtcggcaaa   11940
taaagctcta gtggatctcc gtacccgggg atctggctcg cggcggacgc acgacgccgg   12000
ggcgagacca taggcgatct cctaaatcaa tagtagctgt aacctcgaag cgtttcactt   12060
gtaacaacga ttgagaattt ttgtcataaa attgaaatac ttggttcgca tttttgtcat   12120
ccgcggtcag ccgcaattct gacgaactgc ccatttagct ggagatgatt gtacatcctt   12180
cacgtgaaaa tttctcaagc gctgtgaaca agggttcaga ttttagattg aaaggtgagc   12240
cgttgaaaca cgttcttctt gtcgatgacg acgtcgctat gcggcatctt attattgaat   12300
accttacgat ccacgccttc aaagtgaccg cggtagccga cagcacccag ttcacaagag   12360
tactctcttc cgcgacggtc gatgtcgtgg ttgttgatct agatttaggt cgtgaagatg   12420
ggctcgagct aggagcaagt gatttttatcg ctaagccgtt cagtatcaga gagtttctag   12480
cacgcattcg ggttgccttg cgcgtgcgcc ccaacgttgt cgctccaaa gaccgacggt   12540
cttttttgttt tactgactgg acacttaatc tcaggcaacg tcgcttgatg tccgaagctg   12600
gcggtgaggt gaaacttacg gcaggtgagt tcaatcttct cctcgcgttt ttagagaaac   12660
cccgcgacgt tctatcgcgc gagcaacttc tcattgccag tcgagtacgc gacgaggagg   12720
tttatgacag gagtatagat gttctcattt tgaggctgcg ccgcaaactt gaggcagatc   12780
cgtcaagccc tcaactgata aaaacagcaa gaggtgccgg ttatttcttt gacgcggacg   12840
tgcaggtttc gcacgggggg acgatggcag cctgagccaa ttcccagatc cccgaggaat   12900
cggcgtgagc ggtcgcaaac catccggccc ggtacaaatc ggcgcggcgc tgggtgatga   12960
cctggtggag aagttgaagg ccgcgcaggc cgcccagcgg caacgcatcg aggcagaagc   13020
acgcccggt gaatcgtggc aagcggccgc tgatcgaatc cgcaaagaat cccggcaacc   13080
gccggcagcc ggtgcgccgt cgattaggaa gccgcccaag ggcgacgagc aaccagattt   13140
tttcgttccg atgctctatg acgtgggcac ccgcgatagt cgcagcatca tggacgtggc   13200
cgttttccgt ctgtcgaagc gtgaccgacg agctggcgag gtgatccgct acgagcttcc   13260
agacgggcac gtagaggttt ccgcagggcc ggccggccatg gccagtgtgt gggattacga   13320
cctggtactg atggcggttt cccatctaac cgaatccatg aaccgatacc gggaagggaa   13380
gggagacaag cccggccgcg tgttccgtcc acacgttgcg gacgtactca agttctgccg   13440
gcgagccgat ggcggaaagc agaaagacga cctggtagaa acctgcattc ggttaaacac   13500
cacgcacgtt gccatgcagc gtacgaagaa ggccaagaac cgcgcctgt tgacggtatc   13560
cgagggtgaa gccttgatta gccgctacaa gatcgtaaag agcgaaaccg gcggccgga   13620
gtacatcgag atcgagctag ctgattggat gtaccgcgag atcacagaag gcaagaaccc   13680
ggacgtgctg acgttcacc ccgattactt tttgatcgat cccggcatcg gccgttttct   13740
ctaccgcctg gcacgccgcg ccgcaggcaa ggcagaagcc agatggttgt tcaagacgat   13800
ctacgaacgc agtggcagcg ccggagagtt caagaagttc tgtttcaccg tgcgcaagtc   13860
gatcgggtca aatgacctgc cggagtacga tttgaaggag gaggcgggc aggctggccc   13920
gatcctagtc atgcgctacc gcaacctgat cgagggcgaa gcatccgccg gttcctaatg   13980
tacgagcag atgctagggc aaattgccct agcaggggaa aaaggtcgaa aagtctctt   14040
tcctgtggat agcacgtaca ttgggaaccc aaagccgtac attgggaacc ggaacccgta   14100
ggaagaac ccaaagcgt acattgggaa ccggtcacac atgtaagtga ctgatataaa   14160
agagaaaaaa ggcgattttt ccgcctaaaa ctctttaaaa cttattaaaa ctcttaaaac   14220
ccgcctggcc tgtgcataac tgtctggcca gcgcacagcc gaagagctgc aaaaagcgcc   14280
tacccttcgg tcgctgcgct ccctacgccc gccgcttcg cgtcggccta tcggccgc   14340
tggccgctca aaaatggctg gcctacgccc aggcaatcta ccaggcgcg acaagccgc   14400
gccgtcgcca ctcgaccgcc ggcgctgagg tctgcctcgt gaagaaggtg ttgctgactc   14460
```

```
ataccaggcc tgaatcgccc catcatccag ccagaaagtg agggagccac ggttgatgag    14520
agctttgttg taggtggacc agttggtgat tttgaacttt tgctttgcca cggaacggtc    14580
tgcgttgtcg ggaagatgcg tgatctgatc cttcaactca gcaaaagttc gatttattca    14640
acaaagccgc cgtcccgtca agtcagcgta atgctctgcc agtgttacaa ccaattaacc    14700
aattctgatt agaaaaactc atcgagcatc aaatgaaact gcaatttatt catatcagga    14760
ttatcaatac catattttg  aaaaagccgt ttctgtaatg aaggagaaaa ctcaccgagg    14820
cagttccata ggatggcaag atcctggtat cggtctgcga ttccgactcg tccaacatca    14880
atacaaccta ttaatttccc ctcgtcaaaa ataaggttat caagtgagaa atcaccatga    14940
gtgacgactg aatccggtga gaatggcaaa agctctgcat taatgaatcg gccaacgcgc    15000
ggggagaggc ggtttgcgta ttgggcgctc ttccgcttcc tcgctcactg actcgctgcg    15060
ctcggtcgtt cggctgcggc gagcggtatc agctcactca aaggcggtaa tacggttatc    15120
cacagaatca ggggataacg caggaaagaa catgtgagca aaaggccagc aaaaggccag    15180
gaaccgtaaa aaggccgcgt tgctggcgtt tttccatagg ctccgccccc ctgacgagca    15240
tcacaaaaat cgacgctcaa gtcagaggtg cgaaacccg acaggactat aaagatacca    15300
ggcgtttccc cctggaagct ccctcgtgcg ctctcctgtt ccgaccctgc cgcttaccgg    15360
atacctgtcc gcctttctcc cttcgggaag cgtggcgctt tctcatagct cacgctgtag    15420
gtatctcagt tcggtgtagg tcgttcgctc caagctgggc tgtgtgcacg aaccccccgt    15480
tcagcccgac cgctgcgcct tatccggtaa ctatcgtctt gagtccaacc cggtaagaca    15540
cgacttatcg ccactggcag cagccactgg taacaggatt agcagagcga ggtatgtagg    15600
cggtgctaca gagttcttga agtggtggcc taactacggc tacactagaa gaacagtatt    15660
tggtatctgc gctctgctga agccagttac cttcggaaaa agagttggta gctcttgatc    15720
cggcaaacaa accaccgctg gtagcggtgg tttttttgtt tgcaagcagc agattacgcg    15780
cagaaaaaaa ggatctcaag aagatccttt gatcttttct acggggtctg acgctcagtg    15840
gaacgaaaac tcacgttaag ggattttggt catgagatta tcaaaaagga tcttcaccta    15900
gatccttttg atccggaatt a                                              15921
```

```
SEQ ID NO: 35            moltype = DNA  length = 17954
FEATURE                  Location/Qualifiers
misc_feature             1..17954
                         note = vector 24039
misc_feature             4..259
                         note = bNRB-05
regulatory               315..1729
                         note = promoter - prZmGRMZM2G020852-01
                         regulatory_class = promoter
gene                     1731..5979
                         note = cCas9-13
regulatory               5989..8769
                         note = terminator - tZmGRMZM2G020852-01
                         regulatory_class = terminator
regulatory               8783..9157
                         note = promoter - prOsU3-01
                         regulatory_class = promoter
misc_feature             9159..9178
                         note = xZmVLHP2
misc_feature             9159..9263
                         note = rsgRNAZmVLHP-02
misc_feature             9179..9190
                         note = rCrRNA-01
misc_feature             9195..9263
                         note = rTracrRNA-01
regulatory               9274..11265
                         note = promoter - prUbi1-04
                         regulatory_class = promoter
gene                     11282..12460
                         note = cPMI-09
regulatory               12483..12735
                         note = terminator - tNOS-05-01
                         regulatory_class = terminator
misc_feature             12779..12908
                         note = bNLB-03
gene                     13188..13976
                         note = cSpec-03
regulatory               14071..14201
                         note = promoter - prVirG-01
                         regulatory_class = promoter
gene                     14276..14908
                         note = cVirG-09
gene                     14938..16011
                         note = cRepA-01
misc_feature             16054..16458
                         note = oVS1-02
misc_feature             17136..17942
                         note = oCOLE-o6
source                   1..17954
                         mol_type = other DNA
                         organism = synthetic construct
SEQUENCE: 35
attcctgtgg ttggcatgca catacaaatg gacgaacgga taaacctttt cacgccctttt   60
```

```
taaatatccg attattctaa taaacgctct tttctcttag gtttacccgc caatatatcc   120
tgtcaaacac tgatagttta aactgaaggc gggaaacgac aatctgatca tgagcggaga   180
attaagggag tcacgttatg accccgccg atgacgcggg acaagccgtt ttacgtttgg    240
aactgacaga accgcaacgc tgcaggaatt ggccgcagcg gccatttaaa caaagcttgg   300
taccggaccg ttataacagt gaatacaaaa atgacattcg tgttatttag cacaagttac   360
gatctatttc aggaacatgc cggaattttc gaacaccatt ctcacaaaac atgaccttga   420
acttgcgatc cagttgtttt aaaattatat aaaacaaaaa caaagtcaga aaatcatgaa   480
acttgtcgac atgtcatgat atcatatgta gagactctaa taaaaagttg agattgtttc   540
atgaaagttg tcacacacta tgtgtagaaa cttagcccgt ctacattgaa gttctatgat   600
ttcatgtgaa ggacacctag gcatcgatgt ttatgataat atcttatgtt tgtttggaca   660
aaatattaaa aacaaataaa aggggtccct gatcactttg acgagcattg cattcagcaa   720
agggtgcctt tgttgagtgc aatggtcata gaactcggta gaaaagacat acataaacat   780
cgggaaactt gctttaccgc acgctatggc caagacactc ggcaaactag gctcctttgt   840
tgagtgccat ctcaagcact cgacattgga actacgacta ggccctcacg aagcttctt    900
tgccgagtgc cactaagcga ggaactcgga cactcagcaa cagctctgtc atcgtcacga   960
tgtcttttct ttgtcgtgta ccagttggca ctcggttaag actttactga gtgcccgata  1020
gaaagtactc ggcaaagaga ccgttgccga cgtttggttc actgagggct ctttgctgcc  1080
ttttggactt gacaaagaag tcatctccag tactgtctcc taggacgcag gatttatgtt  1140
ttttcccgga gctcgatctg tgggacatca cagatggtcc aatctggtga tctaaaatgg  1200
acggtttgcc aagcccacag agaagtcttt aagatcttcc acgatgcacg catgctttaa  1260
ggttagatag tgtttggtcc aaaaaagcgt caacaatcag gaaattagaa ctaaaattat  1320
taaaggacag atcaaaaggc atgcatgttc ttcttctata gtgtgtgttg agcctgagtt  1380
ttgattttag gctttattag gggactcgca gtctagctaa ggagttgtat tgatgttctg  1440
acaaatatta tgttcgatcg tcacagtggt cttgtgcgga tcgattaggc ccgatcatgg  1500
tgaaataaac taaccaccgg taagcccggg cagccctaga gcatgcagcg gcctacgtga  1560
agcccgcgtg tcgcatcgtc gtccgtcaga cgctaacggc aggccgctgc atgcgttgcc  1620
ggcgaactct ctcctgagcc actcgtcatc catataagta gacatcccat cactgtcgtc  1680
tatcaacaac acacagagcg acatttcgaa taacacagtt gagcgcgacc atggacaaga  1740
agtacagcat cggcctggac atcggcacca acagcgtggg ctgggccgtg atcaccgacg  1800
agtacaaggt acgagcggga tacatgttta tactcctcct gtaggtcgct ccttcatgtg  1860
atgtgttgcg attaaaacgg tgcgcaggtg ccgagcaaga agttcaaggt gctgggcaac  1920
accgacaggc acagcatcaa gaagaacctg atcggcgccc tgctgttcga cagcggcgag  1980
accgccgagg ccaccaggct gaagaggacc gccaggagga ggtacaccag gaggaagaac  2040
aggatctgct acctgcagga gatcttcagc aacgagatgg ccaaggtgga cgacagcttc  2100
ttccacaggc tggaggagag cttcctggtg gaggaggaca agaagcacga gaggcacccg  2160
atcttcggca acatcgtgga cgaggtggcc taccacgaga gtacccgac catctaccac  2220
ctgaggaaga agctggtgga cagcaccgac aaggccgacc tgaggctgat ctacctggcc  2280
ctggcccaca tgatcaagtt cagggggcca cttcctgatcg agggcgacct gaacccggac  2340
aacagcgacg tggacaagct gttcatccag ctggtgcaga cctacaacca gctgttcgag  2400
gagaacccga tcaacgccag cggcgtggac gccaaggcca tcctgagcgc caggctgagc  2460
aagagcagga ggctggagaa cctgatcgcc cagctgccgg gcgagaagaa gaacggcctg  2520
ttcggcaacc tgatcgccct gagcctgggc ctgacccga cttcaagag caacttcgac  2580
ctggccgagg acgccaagct gcagctgagc aaggacacct acgacgacga cctggacaac  2640
ctgctggccc agatcggcga ccagtacgcc gacctgttcc tggccgccaa gaacctgagc  2700
gacgccatcc tgctgagcga catcctgagg gtgaacaccg agatcaccaa ggccccgctg  2760
agcgccagca tgatcaagag gtacgacgag caccaccagg acctgaccct gctgaaggcc  2820
ctggtgaggc agcagctgcc ggagaagtac aaggagatct tcttcgacca gagcaagaac  2880
ggctacgccg gctacatcga cggcggcgcc agccaggagg agttctacaa gttcatcaag  2940
ccgatcctgg agaagatgga cggcaccgag gagctgctgg tgaagctgaa cagggaggac  3000
ctgctgagga gcagaggac cttcgacaac ggcagcatcc cgcaccagat ccacctgggc  3060
gagctgcacg ccatcctgag gaggcaggag gacttctacc cgttcctgaa ggacaacgtg  3120
gagaagatcg agaagatcct gaccttccgc atcccgtact acgtgggccc gctggccagg  3180
ggcaacagca ggttcgcctg gatgaccagg aagagcgagg agaccatcac cccgtggaac  3240
ttcgaggagg tggtggacaa gggcgccagc gcccagagct tcatcgagag gatgaccaac  3300
ttcgacaaga acctgccgaa cgagaaggtg ctgccgaagc acagcctgct gtacgagtac  3360
ttcaccgtgt acaacgagct gaccaaggtg aagtacgtga ccgagggcat gaggaagccg  3420
gccttcctga gcggcgagca gaagaaggcc atcgtggacc tgctgttcaa gaccaacagg  3480
aaggtgaccg tgaagcagct gaaggaggac tacttcaaga gatcgagtg cttcgacagc  3540
gtggagatca gcggcgtgga ggacaggttc aacgccagcc tgggcaccta ccacgacctg  3600
ctgaagatca tcaaggacaa ggacttcctg gacaacgagg agaacgagga catcctggag  3660
gacatcgtgc tgaccctgac cctgttcgag gacagggaga tgatcgagga gaggctgaag  3720
acctacgccc acctgttcga cgacaaggtg atgaagcagc tgaagaggag gaggtacacc  3780
ggctgggca ggctgagcag gaagctgatc aacggcatca gggacaagca gagcggcaag  3840
accatcctgg acttcctgaa gagcgacggc ttcgccaaca gaaacttcat gcagctgatc  3900
cacgacgaca gcctgacctt caaggaggac atccagaagg cccaggtgag cggccagggc  3960
gacagcctgc acgagcacat cgccaacctg gccggcagcc cggccatcaa gaagggcatc  4020
ctgcagaccg tgaaggtggt ggacgagctg gtgaaggtga tgggcaggca caagccggag  4080
aacatcgtga tcgagatggc cagggagaac cagaccaccc agaagggcca gaaaacagc  4140
agggagagca tgaagaggat cgaggagggc atcaaggagc tgggcagcca gatcctgaag  4200
gagcaccgg tggagaacac ccagctgcag aacgagaagc tgtacctgta ctacctgcag  4260
aacggcaggg acatgtacgt ggaccaggag ctggacatca caggctgag cgactacgac  4320
gtggaccaca tcgtgccgca gagcttcctg aaggacgaca gcatcgacaa caaggtgctg  4380
accaggagcg acaagaacag gggcaagagc gacaacgtgc cgagcgagga ggtggtgaag  4440
aagatgaaaa actactggag gcagctgctg aacgccaagc tgatcaccca gaggaagttc  4500
gacaacctga ccaaggccga gaggggcggc ctgagcgagc tggacaaggc cggcttcatt  4560
aaaaggcagc tggtggagac caggcagatc accaagcacg tggcccagat cctggacagc  4620
aggatgaaca ccaagtacga cgagaacgac aagctgatca gggaggtgaa ggtgatcacc  4680
ctgaagagca agctggtgag cgacttcagg aaggacttcc agttctacaa ggtgagggag  4740
atcaataatt accaccacgc ccacgacgcc tacctgaacg ccgtggtggg caccgccctg  4800
```

```
attaaaaagt acccgaagct ggagagcgag ttcgtgtacg gcgactacaa ggtgtacgac   4860
gtgaggaaga tgatcgccaa gagcgagcag gagatcggca aggccaccgc caagtacttc   4920
ttctacagca acatcatgaa cttcttcaag accgagatca ccctggccaa cggcgagatc   4980
aggaagaggc cgctgatcga gaccaacggc gagaccggcg agatcgtgtg ggacaagggc   5040
agggacttcg ccaccgtgag gaaggtgctg tccatgccgc aggtgaacat cgtgaagaag   5100
accgaggtgc agaccggcgg cttcagcaag gagagcatcc tgccgaagag gaacagcgac   5160
aagctgatcg ccaggaagaa ggactgggac ccgaagaagt acggcggctt cgacagcccg   5220
accgtggcct acagcgtgct ggtggtggcc aaggtggaga agggcaagag caagaagctg   5280
aagagcgtga aggagctggt gggcatcacc atcatggaga ggagcagctt cgagaagaac   5340
ccagtggact tcctggaggc caagggctac aaggaggtga agaaggacct gatcattaaa   5400
ctgccgaagt acagcctgtt cgagctggag aacggcagga agaggatgct ggccagcgcc   5460
ggcgagctgc agaagggcaa cgagctgccc ctgccgagca agtacgtgaa cttcctgtac   5520
ctggccagcc actacgagaa gctgaagggc agcccggagg acaacgagca gaagcagctg   5580
ttcgtggagc agcacaagca ctacctggac gagatcatcg agcagatcag cgagttcagc   5640
aagagggtga tcctggccga cgccaacctg gacaaggtgc tgagcgccta caacaagcac   5700
agggacaagc cgatcaggga gcaggccgag aacatcatcc acctgttcac cctgaccaac   5760
ctgggcgccc cggccgcctt caagtacttc gacaccacca tcgacaggaa gaggtacacc   5820
agcaccaagg aggtgctgga cgccaccctg atccaccaga gcatcaccgg cctgtacgag   5880
accaggatcg acctgagcca gctgggcggc gacagcagcc cgccgaagaa gaagaggaag   5940
gtgagctgga aggacgccag cggctggagc aggatgtgag ctcaattaac tttgaattcc   6000
cttcgattca tccggcgcgg tgggctatgg acctgcagca gcaagctaat taagtttata   6060
tatattgcat gagagagcat gcaccgctaa ccatatatac tactgagact tctgaattct   6120
agtatatgta atccttttgt ttgggtttag gaggcaattc taatcatgta tgccgaattc   6180
caaagagtgg aaaacaagca aaatgttaaa tatacatgcc attttcggag gcaattttt    6240
tcatgagggc atgttgctat aattccgggg accttggact tcttggagca ccttcctgtg   6300
acttaggcat acatgattag attataatcc aattagttaa gtcatagaaa attacctcat   6360
tctcatctcc atctccattt ctctattct tctcaatcaa ggaccaaaat agcacttttg    6420
ctaaaaaaca agttagattg caaaccaaag tgcacaatac atagtaaaag gtatatgcaa   6480
catatttgaa tactcaaacc tctcatactt acattttcca tcattttgtt ccatttagcc   6540
tgtttgagct cggggttgga ctccaaaacc tcatgtcaac ataacttgat ccttttagca   6600
aactatgagc tctaacacca tacaatggtc aacaagaact attccaaaca taggaatgac   6660
ccaaactaca agtcaaagta tacttagctc tttgggcact tacaggttct aactttgata   6720
attctgtact tcttgtgacc atgactctgc tcgagctagg atcttgagcc ttatgactta   6780
aacaattaaa ccacaaacat tacctcaatg gttgtaagcc acgtccatat atcacagact   6840
tcaatgcatt cagactattc acagcttgac caaccttgac ctcttgcaag aacctcttct   6900
tctttgtgac cttaggtact ttagtcttct tgaccttctc ccttgctctt cataccttga   6960
agtccttctt gccttcacct tagttcaatc agctatctcc aagtcatgca cattgagttc   7020
cacttagtca atgtccatcc ttcaacttga cttgtgatgt ccacaattca tagtcatctc   7080
agtctatggg tccatcatgc ttgactccat gtgatgaacc ttgtaaggtt ttcactaagt   7140
acatgctcag acctttaatt gtgttgccat ccaaaaaaac caaaacctag attgaccat   7200
tcattatatt catcaatcat tgtacttgca agagtgatca aggtcatatt attttctctca  7260
actactccat ttttgttgagg ggtgtcagtt gtggagactt cttgtttgat cccaacctca   7320
tcacaatact catgaatata gttgttgtca aattcatttc cattgtcact tcttatttt    7380
cttgattttg caatcaaact cattttgtac tttcatggta aatttattca atgttgatgc   7440
aactttgac ttttcttgaa gaaagaacac tcaattacat ctagagaaat catcaacaac   7500
gaccaaacaa tacaggtttc ccccaacact agcatattat gtaggaccaa ataaatccat   7560
gtgaagtaac tctagtggtc ttggtgttga cataaaagcg tttgtaggat gtgtattggc   7620
aacttgttt ccagcttgac atgcactata aaagattttc cttttcaaa cacaacatct   7680
ttcaaatctc taaccatttc tttctttgga agcttcttgt tggggaaatg atccccggac   7740
cctaggaccc accggtcaga gagcgcgagg aagagccccc ggtcgctggg acccgttggt   7800
ccgctggaaa atgtggttac gtcaaccctg aaagaacccg cccctggttg agcccctgg    7860
caccgagcct agggtcgagc gcggtggaat ctgacaggag gggccagaca tgttggaggg   7920
gaaccactca agtggatccc gcgcctggcc ccagaatgac ccgtcattaa tacccaacca   7980
cattaaccat gcctggcacc gagccatagc acggacgtcg gtccacttcc cactcatgac   8040
ctacgaacca gttgggctgc atagcactca tgaccgatag gttgaaggct tggcttcgca   8100
gagtgaaagg cgctgcatac atgtgaaggc tcgacttctt tttcttttcc tttcttttct   8160
tttctatttt taggtttcca atttaaattc caatttttt gtggagttca tatttggatc   8220
aaatagacaa attcacctat cagtatgaat agatgcattt attttgttta tatctatttt   8280
cttcatatttt atatagtatt tccctattc tttatatcat tttcaatttg taattggtaa   8340
gtttggtctt aaattcccca tttgggcact aatatatttt tattaatatt attattatta   8400
ttattattat tatttataga tgcacaaaca cataaactcc gacatgatgc atagattatt   8460
ttagatgtca ctagttaatg gttcacttta aatatggtta ttcccatgtt ctaatgagta   8520
gagggcaaag catatattga ggtcaactct ttccttatta tttacaaatt ggggaaattc   8580
tattcataac tcttcttctc tctcccaagt agcttaattc tcaccatggt gatttcattg   8640
cactttgcac atttttgatca ctttattcct tgtaacccga gtcaaagtgt caatgatctt   8700
gataggatac tccgtgcagg ttagatcacc ttgcacactg agttcttcca ttggtaactg   8760
ttcctctggc ggaccgttcg aagggatctt taaacatacg aacagatcac ttaaagttct   8820
tctgaagcaa cttaaagtta tcaggcatgc atggatcttg gaggaatcag atgtgcagtc   8880
agggaccata gcacaggaca ggcgtcttct actggtgctca ccagcaaatg ctggaagccg   8940
ggaacactgg gtacgttgga aaccacgtga tgtggagtaa gataaactgt aggagaaaag   9000
catttcgtag tgggccatga agcctttcag gacatgtatt gcagtatggg ccggcccatt   9060
acgcaattgg acgacaacaa agactagtat tagtaccacc tcggctatcc acatagatca   9120
aagctggttt aaaagagttg tgcagatgat ccgtggcagc tggagctgag cttccggggt   9180
ttagagcta gaaatagcaa gttaaaataa ggctagtccg ttatcaactt gaaaaagtgg   9240
caccgagtcg gtgctttttt tttcggaccg cgcctgcagt gcagcgtgac ccggtcgtgc   9300
ccctctctag agataatgag cattgcatgt ctaagttata aaaaattacc acatatttt    9360
tttgtcacac ttgtttgaag tgcagtttat ctatctttat acatatattt aaactttact   9420
ctacgaataa tataatctat agtactacaa taatatcagt gttttagaga atcatataaa   9480
tgaacagtta gacatggtct aaaggacaat tgagtatttt gacaacagga ctctacagtt   9540
```

```
ttatcttttt agtgtgcatg tgttctcctt ttttttgca aatagcttca cctatataat   9600
acttcatcca ttttattagt acatccattt aggggttagg gttaatggtt tttatagact   9660
aatttttta gtacatctat tttattctat tttagcctct aaattaagaa aactaaaact   9720
ctattttagt ttttttattt aataatttag atataaaata gaataaaata aagtgactaa   9780
aaattaaaca aatacccttt aagaaattaa aaaaactaag gaaacattttt tcttgtttcg   9840
agtagataat gccagcctgt taaacgccgt cgacgagtct aacggacacc aaccagcgaa   9900
ccagcagcgt cgcgtcgggc caagcgaagc agacggcacg gcatctctgt cgctgcctct   9960
ggacccctct cgagagttcc gctccaccgt tggacttgct ccgctgtcgg catccagaaa  10020
ttgcgtggcg gagcggcaga cgtgagcggc cacggcaggc ggcctcctcc tcctctcacg  10080
gcaccggcag ctacggggga ttcctttccc accgctcctt cgctttccct tcctcgcccg  10140
ccgtaataaa tagacacccc ctccacaccc tctttcccca acctcgtgtt gttcggagcg  10200
cacacacaca caaccagatc tcccccaaat ccacccgtcg gcacctccgc ttcaaggtac  10260
gccgctcgtc ctcccccccc ccctctcta ccttctctag atcggcgttc cggtccatgg  10320
ttagggcccg gtagttctac ttctgttcat gtttgtgtta gatccgtgtt tgtgttagat  10380
ccgtgctgct agcgttcgta cacggatgcg acctgtacgt cagacacgtt ctgattgcta  10440
acttgccagt gtttctcttt ggggaatcct gggatggctc tagccgttcc gcagacggga  10500
tcgatttcat gattttttt gtttcgttgc atagggtttg gtttgcccttt ttccttttatt  10560
tcaatatatg ccgtgcactt gttttgtcggg tcatctttttc atgctttttt ttgtcttggt  10620
tgtgatgatg tggtctggtt gggcggtcgt tctagatcgg agtagaattc tgtttcaaac  10680
tacctggtgg atttattaat tttggatctg tatgtgtgtg ccatacatat tcatagttac  10740
gaattgaaga tgatggatgg aaatatcgat ctaggatagg tatacatgtt gatgcgggtt  10800
ttactgatgc atatacagag atgctttttg ttcgcttggt tgtgatgatg tggtgtggtt  10860
gggcggtcgt tcattcgttc tagatcggag tagaatactg tttcaaacta cctggtgtat  10920
ttattaattt tggaactgta tgtgtgtgtc atacatcttc atagttacga gtttaagatg  10980
gatgaaaata tcgatctagg ataggtatac atgttgatgt gggttttact gatgcatata  11040
catgatggca tatgcagcat ctattcatat gctctaacct tgagtaccta tctattataa  11100
taaacaagta tgttttataa ttattttgat cttgatatac ttggatgatg gcatatgcag  11160
cagctatatg tggattttt tagccctgcc ttcatacgct atttatttgc ttggtactgt  11220
ttcttttgtc gatgctcacc ctgttgtttg gtgttacttc tgcagggatc cggcagcagc  11280
catgcagaag ctgatcaaca gcgtgcagaa ctacgcctgg ggcagcaaga ccgccctgac  11340
cgagctgtac ggcatggaga accccagcag ccagcccatg gccgagctgt ggatgggcgc  11400
ccaccccaag agcagcagcc gcgtgcagaa cgccgccggc gacatcgtga gcctgcgcga  11460
cgtgatcgag agcgacaaga gcaccctgct gggcgaggcc gtggccaagc gcttcggcga  11520
gctgccttc ctgttcaagg tgctgtgcgc cgcccgcccc ctgagcatcc aggtgcaccc  11580
caacaagcac aacagcgaga tcggcttcgc caaggagaac gccgccggca tccccatgga  11640
cgccgccgag cgcaactaca aggacccccaa ccacaagccc gagctggtgt tcgccctgac  11700
ccccttcctg gccatgaacg ccttccgcga gttcagcgag atcgtgagcc tgctgcagcc  11760
cgtggccggc gcccacccccg ccatcgccca cttcctgcag cagcccgacg ccgagcgcct  11820
gagcgagcgg ttcgcagcc tgctgaacat gcagggcgag gagaagagcc ggcccctggc  11880
catcctgaag agcgccctgg acagccagca gggcgagccc tggcagacca tccgcctgat  11940
cagcgagttc taccccgagg acagcggcct gttcagcccc ctgctgctga acgtggtgaa  12000
gctgaacccc ggcgaggcca tgttcctgtt cgccgagacc cccacgcct acctgcaggg  12060
cgtggccctg gaggtgatgg ccaacagcga caacgtgctg cgcgccggcc tgaccccgca  12120
gtacatcgac atccccgagc tggtggccaa cgtgaagttc gaggccaagc ccgccaacca  12180
gctgctgacc cagcccgtga agcagggcgc cgagctggac ttcccatcc ccgtggacga  12240
cttcgccttc agcctgcacg acctgagcga caaggagacc accatcagcc agcagagcgc  12300
cgccatcctg ttctgcgtgg aagggcacgc cacctgtgg agggcagcc gcagctgca  12360
gctgaagccc ggcgagagcg ccttcatcgc cgccaacgag agcccgtga ccgtgaaggg  12420
ccacggccgc ctggcccgcg tgtacaacaa gctgtgatag gagctcgatc cgtcgacctg  12480
cagatcgttc aaacatttgg caataaagtt tcttaagatt gaatcctgtt gccggtcttg  12540
cgatgattat catataattt ctgttgaatt acgttaagca tgtaataatt aacatgtaat  12600
gcatgacgtt atttatgaga tgggttttta tgattagagt cccgcaatta tacatttaat  12660
acgcgataga aaacaaaata tagcgcgcaa actaggataa attatcgcgc gcggtgtcat  12720
ctatgttact agatcggcgc gccgcaattg aagtttgggc ggccagcatg gccgtatccg  12780
caatgtgtta ttaagttgtc taagcgtcaa tttgtttaca ccacaatata tcctgccacc  12840
agccagccaa cagctccccg accggcagct cggcacaaaa tcaccactcg ataccaggcag  12900
cccatcagaa ttaattctca tgtttgacag cttatcatcg actgcacggt gcaccaatgc  12960
ttctggcgtc aggcagccat cggaagctgt ggtatggctg tgcaggtcgt aaatcactgc  13020
ataattcgtg tcgctcaagg cgcactcccg ttctggataa tgttttttgc gccgacatca  13080
taacggttct ggcaaatatt ctgaaatgag ctgttgacaa ttaatcatcc ggctcgtata  13140
atgtgtggaa ttgtgagcgg ataacaattt cacacaggaa acagaccatg agggaagcgt  13200
tgatcgccga agtatcgact caactatcag aggtagttgg cgtcatcgag cgccatctcg  13260
aaccgacgtt gctggccgta catttgtacg gctccgcagt ggatgccggc ctgaagccac  13320
acagtgatat tgatttgctg gttacggtga ccgtaaggct tgatgaaaca acgcggcgag  13380
ctttgatcaa cgaccttttg gaaacttcgg cttcccctgg agagagcgag attctccgcg  13440
ctgtagaagt caccattgtt gtgcacgacg acatcattcc gtggcgttat ccagctaagc  13500
gcgaactgca atttggagaa tggcagcgca atgacattct tgcaggtatc ttcgagccag  13560
ccacgatcga cattgatctg gctatcttgc tgacaaaagc aagagaacat agcgttgcct  13620
tggtaggtcc agcggcggag gaactctttg atccggttcc tgaacaggat ctatttgagg  13680
cgctaaatga aaccttaacg ctatggaact cgccgcccga ctgggctggc gatgagcgaa  13740
atgtagtgct tacgttgtcc cgcatttggt acagcgcagt aaccggcaaa atcgcgccga  13800
aggatgtcgc tgccgactgg gcaatggagc gcctgccggc ccagtatcag cccgtcatac  13860
ttgaagctag gcaggcttat cttggacaag aagatcgctt ggcctcgcgc gcagatcagt  13920
tggaagaatt tgttcactac gtgaaaggcg agatcaccaa agtagtaggt caaataaagct  13980
ctagtggatc tccgtacccg gggatctggc tcgcggcgga cgcacgacgc cggggcgaga  14040
ccataggcga tctcctaaat caatagtagc tgtaacctcg aagcgtttca cttgtaacaa  14100
cgattgagaa ttttttgtcat aaaattgaaa tacttggttc gcattttgt catccgcggt  14160
cagccgcaat tctgacgaac tgcccattta gctggagatg attgtacatc cttcacgtga  14220
aaatttctca agcgctgtga acaagggttc agattttaga ttgaaaggtg agccgttgaa  14280
```

```
acacgttctt cttgtcgatg acgacgtcgc tatgcggcat cttattattg aataccttac   14340
gatccacgcc ttcaaagtga ccgcggtagc cgacagcacc cagttcacaa gagtactctc   14400
ttccgcgacg gtcgatgtcg tggttgttga tctagattta ggtcgtgaag atgggctcga   14460
gctaggagca agtgatttta tcgctaagcc gttcagtatc agagagtttc tagcacgcat   14520
tcgggttgcc ttgcgcgtgc gccccaacgt tgtccgctcc aaagaccgac ggtcttttg   14580
ttttactgac tggacactta atctcaggca acgtcgcttg atgtccgaag ctggcggtga   14640
ggtgaaactt acggcaggtg agttcaatct tctcctcgcg ttttagaga aaccccgcga   14700
cgttctatcg cgcgagcaac ttctcattgc cagtcgagta cgcgacgagg aggtttatga   14760
caggagtata gatgttctca ttttgaggct gcgccgcaaa cttgaggcag atccgtcaag   14820
ccctcaactg ataaaaacag caagaggtgc cggttattc tttgacgcgg acgtgcaggt   14880
ttcgcacggg gggacgatgg cagcctgagc caattcccag atcccgagg aatcggcgtg   14940
agcggtcgca aaccatccgg cccggtacaa atcggcgcgg cgctgggtga tgacctggtg   15000
gagaagttga aggccgcgca ggccgcccag cggcaacgca tcgaggcaga agcacgcccc   15060
ggtgaatcgt ggcaagcggc cgctgatcga atccgcaaag aatcccggca accgccggca   15120
gccggtgcgc cgtcgattag gaagccgccc aagggcgacg agcaaccaga tttttttcgtt   15180
ccgatgctct atgacgtggg cacccgcgat agtcgcagca tcatgacgt ggccgttttc   15240
cgtctgtcga agcgtgaccg acgagctggc gaggtgatcc gctacgagct tccagacggg   15300
cacgtagagg tttccgcagg gccggccggc atggccagtg tgtgggatta cgacctggta   15360
ctgatggcgg tttcccatct aaccgaatcc atgaaccgat accggaagg gaagggagac   15420
aagcccggcc gcgtgttccg tccacacgtt gcggacgtac tcaagttctg ccggcgagcc   15480
gatggcggaa agcagaaga cgacctgta gaaacctgca ttcggttaaa caccacgcac   15540
gttgccatgc agcgtacgaa gaaggccaag aacggccgcc tggtgacggt atccgagggt   15600
gaagccttga ttagccgcta caagatcgta aagagcgaaa ccgggcggcc ggagtacatc   15660
gagatcgagc tagctgattg gatgtaccgc gagatcacag aaggcaagaa cccggacgtg   15720
ctgacggttc accccgatta ctttttgatc gatcccggca tcggccgttt tctctaccgc   15780
ctggcacgcc gcgccgcagg caaggcagaa gccagatgct tgttcaagac gatctacgaa   15840
cgcagtggca gcgccggaga gttcaagaag ttctgttca ccgtgcgcaa gctgatcggg   15900
tcaaatgacc tgccggagta cgatttgaag gaggaggcgg ggcaggctgg cccgatccta   15960
gtcatgcgct accgcaacct gatcgagggc gaagcatccg ccgttccta atgtacggag   16020
cagatgctag ggcaaattgc cctagcaggg gaaaaaggtc gaaaaggtct ctttcctgtg   16080
gatagcacgt acattgggaa cccaaagccg tacattggga accggaaccc gtacattggg   16140
aacccaaagc cgtacattgg gaaccggtca cacatgtaag tgactgatat aaaagagaaa   16200
aaaggcgatt tttccgccta aaactctta aaacttatta aaactcttaa aacccgcctg   16260
gcctgtgcat aactgtctgg ccagcgcaca gccgaagagc tgcaaaaagc gcctacccctt   16320
cggtcgctgc gctccctacg ccccgccgct tcgcgtcggc ctatcgcgcc cgctggccgc   16380
tcaaaaatgg ctggcctacg gccaggcaat ctaccagggc gcggacaagc cgcgccgtcg   16440
ccactcgacc gccggcgctg aggtctgcct cgtgaagaag gtgttgctga ctcataccag   16500
gcctgaatcg cccccatcatc cagccagaaa gtgagggagc cacggttgat gagagcttg   16560
ttgtaggtgg accagttggt gattttgaac ttttgcttg ccacggaacg gtctgcgttg   16620
tcgggaagat gcgtgatctg atccttcaac tcagcaaaag ttcgatttat tcaacaaagc   16680
cgccgtcccg tcaagtcagc gtaatgctct gccagtgtta caaccaatta accaattctg   16740
attagaaaaa ctcatcgagc atcaaatgaa actgcaattt attcatatca ggattatcaa   16800
taccatattt ttgaaaaagc cgtttctgta atgaaggaga aaattcaccg aggcagttcc   16860
ataggatggc aagatcctgg tatcggtctg cgattccgac tcgtccaaca tcaataaac   16920
ctattaattt cccctcgtca aaataaggt tatcaagtga gaatcacca tgagtgacga   16980
ctgaatccgg tgagaatggc aaaagctctg cattaatgaa tcgccaacg cgcgggggaga   17040
ggcggtttgc gtattgggcg ctcttccgct tcctcgctca ctgactcgct gcgctcggtc   17100
gttcggctgc ggcgagcggt atcagctcac tcaaaggcgg taatacggtt atccacagaa   17160
tcaggggata acgcaggaaa gaacatgtga gcaaaaggcc agcaaaaggc caggaaccgt   17220
aaaaaggccg cgttgctggc gtttttccat aggctccgcc cccctgacga gcatcacaaa   17280
aatcgacgct caagtcagag gtggcgaaac ccgacaggac tataaagata ccaggcgttt   17340
ccccctggaa gctccctcgt gcgctctcct gttccgaccc tgccgcttac cggatacctg   17400
tccgcctttc tccccttcggg aagcgtggcg ctttctcata gctcacgctg taggtatctc   17460
agttcggtgt aggtcgttcg ctccaagctg ggctgtgtgc acgaacccc cgttcagccc   17520
gaccgctgcg ccttatccgg taactatcgt cttgagtcca acccggtaag acacgactta   17580
tcgccactgg cagcagccac tggtaacagg attagcagag cgaggtatgt aggcggtgct   17640
acagagttct tgaagtggtg gcctaactac ggctacacta gaagaacagt atttggtatc   17700
tgcgctctgc tgaagccagt taccttcgga aaaagagttg gtagctcttg atccggcaaa   17760
caaaccaccg ctggtagcgg tggtttttt gtttgcaagc agcagattac gcgcagaaaa   17820
aaaggatctc aagaagatcc tttgatcttt tctacggggt ctgacgctca gtggaacgaa   17880
aactcacgtt aagggatttt ggtcatgaga ttatcaaaaa ggatcttcac ctagatcctt   17940
ttgatccgga atta                                                      17954
```

| | | |
|---|---|---|
| SEQ ID NO: 36 | moltype = DNA   length = 17045 | |
| FEATURE | Location/Qualifiers | |
| misc_feature | 1..17045 | |
| | note = vector 24079 | |
| misc_feature | 4..259 | |
| regulatory | 312..2356 | |
| | note = promoter - prGRMZM2G146551-01 | |
| | regulatory_class = promoter | |
| gene | 2358..6527 | |
| | note = cCas9-01 | |
| variation | 5847..5849 | |
| | note = mutation - L to V mutation | |
| variation | 5892..5894 | |
| | note = mutation - I to V mutation | |
| regulatory | 6542..7860 | |
| | note = terminator - tGRMZM2G146551-01 | |

| | | |
|---|---|---|
| regulatory | | regulatory_class = terminator |
| | 7874..8248 | |
| | | note = promoter - prOsU3-01 |
| | | regulatory_class = promoter |
| misc_feature | 8249..8354 | |
| | | note = rsgRNAZmVLHP-02 |
| misc_feature | 8250..8269 | |
| | | note = ZmVLHP2 target |
| misc_feature | 8270..8281 | |
| | | note = rCrRNA-01 |
| misc_feature | 8286..8354 | |
| | | note = rTracrRNA-01 |
| regulatory | 8365..10356 | |
| | | note = promoter - prUbi1-04 |
| | | regulatory_class = promoter |
| gene | 10373..11551 | |
| | | note = cPMI-09 |
| regulatory | 11574..11826 | |
| | | note = terminator - tNOS-05-01 |
| | | regulatory_class = terminator |
| misc_feature | 11870..11999 | |
| | | note = bNLB-03 |
| gene | 12279..13067 | |
| | | note = cSpec-03 |
| regulatory | 13162..13292 | |
| | | note = promoter - prVirG-01 |
| | | regulatory_class = promoter |
| gene | 13367..13999 | |
| | | note = cVirG-09 |
| gene | 14029..15102 | |
| | | note = cRepA-01 |
| misc_feature | 15145..15549 | |
| | | note = oVS1-02 |
| misc_feature | 16227..17033 | |
| | | note = oCOLE-06 |
| source | 1..17045 | |
| | | mol_type = other DNA |
| | | organism = synthetic construct |

SEQUENCE: 36

```
attcctgtgg ttggcatgca catacaaatg gacgaacgga taaaccttt cacgccctt    60
taaatatccg attattctaa taaacgctct tttctcttag gtttacccgc caatatatcc  120
tgtcaaaaac tgatagttta aactgaaggc gggaaacgac aatctgatca tgagcggaga  180
attaagggag tcacgttatg accccccgcc gatgacgcgg acaagccgtt ttacgtttgg  240
aactgacaga accgcaacgc tgcaggaatt ggccgcagcg gccattttaa caaagccttgg  300
taccgggacc catgtagtat cacatgagtg agtcaaggac taagtattat gcattttgtt  360
tctcactcac ggattagctc gcaatcatca tagtgaaatc tagctactgg cactatcgaa  420
atctagctct ttgccgagtg cacttttatcg agcactcgac aaagcattct ttatcgagtg  480
ccagtcttgg cgaaataaga ctctcgacaa agaccttgtt taccgaggga gaaacactcg  540
gcgtaaaaag acactcggca agaagacttt gctgagtgt caaaccctca gcgaaatgcg  600
accctcggca aaggaccgtc agcagccatc tatagttgat ggctattaac ttcgcgagtg  660
tcaggcgttg acacacgaca aaatatcttt ttgtcgagt gtcactgggc aaacacttgg  720
taaacctatg ttttgccgag tgtctttcct tgacactcga caaagtatat ttgttttttc  780
tttttcccca aactttttgt ggtgtgtttc tacaatatat agaccttattt gttcaatttt  840
ggcacaatta taaagtgtt tgctataact atcagattta gtttgcttaa ttggatttct  900
ttggataatt cagatttgaa ctacaagcca cttgaaaaat ggaaaacagt gaatacaaaa  960
atgacattca tgttatttag cacaagttat gatctatttc aggaacatgc gagaattttc 1020
gaacaccatt ctcacaaaac atgattgcgc acttgtgatc aagttgtttt aaaattgtat 1080
aaaacaaaaa caaagtcaga aaatcatgaa acttgttgac atgtcatgat atcatatgta 1140
gagactctaa taaaaatttg agattgtttc atgaaagttg tcacgcgcta tgtgtagaaa 1200
cctagcccgt ctacattgag gttctatgat ttcatgtgaa ggacatctag gcatcaatgt 1260
ttatgataat atcttatgtt tgtttggacg aaatattaaa aacaaataaa aaggggtcct 1320
tgatcacttt gacgagcatt gcactcagca aagggtgcct ttgctgagtg caatggtcat 1380
agaactcggt agaaaaacat acatagacat agggaaactt gctttaccgc gtgctatggc 1440
caagacactc ggcaaactag gctcctttgt cgagttccat cccaagcact cgacattgga 1500
actgcgactg ggcctcacag aagctttctt tgccgagtgc cactaagcga ggaactcgga 1560
tgctcagcaa aggctctgtc atcgtcacga tgtcttttgt ttgtcgtgta ccagttggca 1620
ctcggtaaag actttactga gtgcccgata gaaagtactc gacaaagaga ccgttgccaa 1680
cgtttggttc actgagggct ctttgctgcc ttttggactt gacaaagaag ccgtctccag 1740
tagtgtctcc tgggaggcgg gatttatgtt ttttcccgga gctctcgtgg acatcatgga 1800
cggtccagtc tggtgatcta aaatagacgg tttgccaagc tcacagaaa gtctttaaga 1860
tcttccacga tgcacgcatg ctttaaggtt agttagtgtt tggtctgaaa aagcgtcaac 1920
aattaggaaa caagaactaa aattattaaa ggacagatca ggaagcatgc atgttcttct 1980
tctatagtgt gtgttgagcc tgagtttggc cttttaggct ttattagggg gctcacagtc 2040
taactaagga gttgattga tgtgctgaca aatattatgt tcgatcgtca cagtgttctt 2100
atgcggatcg attaggcccg atcatggtga aataaactaa ccaccggtaa gcccgggcag 2160
ccctagcagca tgcagcggcc tacgtggaagc ccgcacatcg catcgtcgtc cgtcaggcgc 2220
taacggccgg ccgctgcatg cgtcgccggc gaactctctg ctgagccacc cgtcctccct 2280
ataagtagct atcccagcac cgtcgtctat caaccacaca cagagcggca tttcgaataa 2340
cacaggtgag cgcgaccatg gacaagaagt acagcatcgg cctggacatc ggcaccaaca 2400
```

-continued

```
gcgtgggctg ggccgtgatc accgacgagt acaaggtgcc gagcaagaag ttcaaggtgc 2460
tgggcaacac cgacaggcac agcatcaaga agaacctgat cggcgccctg ctgttcgaca 2520
gcggcgagac cgccgaggcc accaggctga agaggaccgc caggaggagg tacaccagga 2580
ggaagaacag gatctgctac ctgcaggaga tcttcagcaa cgagatggcc aaggtggacg 2640
acagcttctt ccacaggctg gaggagagct tcctggtgga ggaggacaag aagcacgaga 2700
ggcaccgat cttcggcaac atcgtggacg aggtggccta ccacgagaag tacccgacca 2760
tctaccacct gaggaagaag ctggtggaca gcaccgacaa ggccgacctg aggctgatct 2820
acctggccct ggcccacatg atcaagttca ggggccactt cctgatcgag ggcgacctga 2880
acccggacaa cagcgacgtg gacaagctgt tcatccagct ggtgcagacc tacaaccagc 2940
tgttcgagga aacccgatc aacgccagcg gcgtggacgc caaggccatc ctgagcgcca 3000
ggctgagcaa gagcaggagg ctggagaacc tgatcgccca gctgccgggc gagaagaaga 3060
acggcctgtt cggcaacctg atcgccctga gcctggccct gaccccgaac ttcaagagca 3120
acttcgacct ggccgaggac gccaagctgc agctgagcaa ggacacctac gacgacgacc 3180
tggacaacct gctggcccag atcggcgacc agtacgccga cctgttcctg gccgccaaga 3240
acctgagcga cgccatcctg ctgagcgaca tcctgagggt gaacaccgag atcaccaagg 3300
ccccgctgag cgccagcatg atcaagaggt acgacgagca ccaccaggac ctgaccctgc 3360
tgaaggccct ggtgaggcag cagctgccgg agaagtacaa ggagatcttc ttcgaccaga 3420
gcaagaacgg ctacgccggc tacatcgacg gcggcgccag ccaggaggag ttctacaagt 3480
tcatcaagcc gatcctggag aagatggacg gcaccgagga gctgctggtg aagctgaaca 3540
gggaggacct gctgagaag cagaggacct tcgacaacgg cagcatcccg caccagatcc 3600
acctgggcga gctgcacgcc atcctgagga ggcaggagga cttctacccg ttcctgaagg 3660
acaacaggga gaagatcgag aagatcctga ccttccgcac cccgtactac gtgggcccga 3720
tggccagggg caacagcagg ttcgcctgga tgaccaggaa gagcgaggag accatcaccc 3780
cgtggaactt cgaggaggtg gtggacaagg cgccagcgc ccagagcttc atcgagagga 3840
tgaccaactt cgacaagaac ctgccgaacg agaaggtgct gccgaagcac agcctgctgt 3900
acgagtactt caccgtgtac aacggctga ccaaggtgga gtacgtgacc gagggcatga 3960
ggaagccggc cttcctgagc ggcgagcaga agaaggccat cgtggacctg ctgttcaaga 4020
ccaacaggaa ggtgaccgtg aagcagctga aggaggacta cttcaagaag atcgagtgct 4080
tcgacagcgt ggagatcagc ggcgtggagg acaggttcaa cgccagcctg ggcacctacc 4140
acgacctgct gaagatcatc aaggacaagg acttcctgga caacgaggaa gaccaggaca 4200
tcctggagga catcgtgctg accctgaccc tgttcgagga cagggagatg atcgaggaga 4260
ggctgaagac ctacgcccac ctgttcgacg acaaggtgat gaagcagctg aagaggagga 4320
ggtacaccgg ctggggcagg ctgagcagga agctgatcaa cggcatcagg gacaagcaga 4380
gcggcaagac catcctggac ttcctgaaga gcgacggctt cgccaacagg aacttcatgc 4440
agctgatcca cgacgacagc ctgaccttca aggaggacat ccagaaggcc caggtgagcg 4500
gccagggcga cagcctgcac gagcacatcg ccaacctggc cggcagcccc gccatcaaga 4560
agggcatcct gcagaccgtg aaggtggtgg acgagctggt gaaggtgatg ggcaggcaca 4620
agccggagaa catcgtgatc gagatggcca gggagaacca gaccacccag aagggccaga 4680
agaacagcag ggagaggatg aagaggatcg aggagggcat caaggagctg ggcagccaga 4740
tcctgaagga gcaccggtg gagaacaccc agctggcagaa cgagaagctg tacctgtact 4800
acctgcagaa cggcagggac atgtacgtgg accaggagct ggacatcaac aggctgagcg 4860
actacgacgt ggaccacatc gtgccgcaga gcttcctgaa ggacgacagc atcgacaaca 4920
aggtgctgac caggagcgac aagaacaggg gcaagagcgac caacgtgccg agcgaggagg 4980
tggtgaagaa gatgaaaaac tactggaggc agctgctgaa cgccaagctg atcacccaga 5040
ggaagttcga caacctgacc aaggccgaga ggggcggcct gagcgagctg gacaaggccg 5100
gcttcattaa aaggcagctg gtggagacca ggcagatcac caagcacgtg cccagatcc 5160
tggacagcag gatgaacacc aagtacgacg agaacgacaa gctgatcagg gaggtgaagg 5220
tgatcacccct gaagagcaag ctggtgagcg acttcaggaa ggacttccag ttctacaagg 5280
tgagggagat caataattac caccacgccc acgacgccta cctgaacgcc gtggtgggca 5340
ccgcccctgat taaaaagtac ccgaagctgg agagcgagtt cgtgtacggc gactacaagg 5400
tgtacgacgt gaggaagatg atcgccaaga gcgagcagga gatcggcaag gccaccgcca 5460
agtacttctt ctacagcaac atcatgaact tcttcaagac cgagatcacc ctggccaacg 5520
gcgagatcag gaagaggccg ctgatcgaga ccaacgcga accggcgag atcgtgtggg 5580
acaagggcag ggacttcgcc accgtgagga aggtgctgtc catgccgcag gtgaacatcg 5640
tgaagaagac cgaggtgcag accggcggct tcagcaagga ggcatcctg ccgaagagga 5700
acagcgacaa gctgatcgcc aggaagaagg actgggaccc gaagaagtac ggcggcttcg 5760
acagcccgac cgtggcctac agcgtgctgg tggtggccaa ggtggagaag ggcaagagca 5820
agaagctgaa gagcgtgaag gagctggtgg gcatcaccat catggagagg agcagcttcg 5880
agaagaaccc agtggacttc ctggaggcca agggctacaa ggaggtgaag aaggacctga 5940
tcattaaaact gccgaagtac agcctgttcg agctggagaa cggcaggaag aggatgctga 6000
ccagcgccgg cgagctgcag aagggcaacg agctggcccct gccgagcaag tacgtgaact 6060
tcctgtacct ggccagccac tacgagaagc tgaagggcag cccggaggac aacgagcaga 6120
agcagctgtt cgtggagcag cacaagcact acctggacga gatcatcgag cagatcagcg 6180
agttcagcaa gagggtgatc ctggccgacg ccaacctgga caaggtgctg agcgcctaca 6240
acaagcacag ggacaagccg atcagggagc aggccgagaa catcatccac ctgttcaccc 6300
tgaccaacct gggcgccccg gccgccttca gtacttcga caccaccatc gacaggaaga 6360
ggtacaccag caccaaggag gtgctggacg ccaccctgat ccaccagagc atcaccggcc 6420
tgtacgagac caggatcgac ctgagccagc tgggcggcga cagcgcccg ccgaagaaga 6480
agaggaaggt gagctgaag gacgccagcg gctggagcag gatgtgacca tggagctcta 6540
aactttgaat tcccttcgat tcatccggca cagcgggcta tggaccttca gcagcaagct 6600
aattaagttg gcagcatgca ccgctaacct tatatactac tgagacttcc aaattctagt 6660
atatgtaatc cttttgttcg ggttcatgat cgaattccaa agagtggaaa acaagcaaaa 6720
ggttaaatat acatgccatt tttggaggca ttttttttcat gagggcatgt ttcgatatat 6780
ggaccactaa atatacatat catttacttt cctacaaatt tgctacatcc ttggaaatgc 6840
atagtctgtc tccaagaaaa agatactctg attacatcca tagtacacac agcctctata 6900
gtggcggttc tagagacatt ttcactgcg cttttcagtg ccgccagtgt taggggccag 6960
tggaaatcgc catttccatt caataaccgc cagtggaaaa agcatttcca ctggcggttt 7020
tcttaagcaa ccgccagtgg aaatgtttcc cgtcttttt taaattttcg tactgaaatt 7080
tatatattta cacacacaaa catatatata tatattga tattgataaa catgtagtat 7140
```

```
tgatactaaa agcaacatga aattaaattc tatcatacat ttatatacat caaagtcttg   7200
tttacaacca tgtatgcatc acacattata tacatcaaag ttttcactta agctctaata   7260
actatctcgg ctaagagata gtctactaat ttctgttagt attctaaact ctggcaaagc   7320
taatgttccg gaagcatcgt gatatttccc ttctgcggga atgacctctt tcaatatgaa   7380
tgtgcacagg tcctcaacta tgccatacaa tgcaccttca gtcaagttct ccggcttcc    7440
tttttgaaat tgctgtaaag gaagtttata aacatcatct atttatactc aataataaca   7500
catttgcatc tttaatgaca taaatacata cgtgactatt actaataata ccttgccagg   7560
gttcgtgatg tatcgtccat tcattctcat aaactcgcac acgtagaacc cacataggac   7620
cgatccgggt ggttgcttgt ggcactacat aacgggagt tggttattta gttgcaacat    7680
tgtcctatgt acgtacatgt atgatatgta ttcataaatt cacatactta ctggccagtt   7740
ataatggatg tctagtggca cacctttttt ggacgtgtcg tactttccac catgtagctt   7800
ataaaaccta aatgccctgt gatctcaaat agaatcacca tgttattcta caattctcat   7860
gggacccttc gaagggatct ttaaacatac gaacagatca cttaaagttc ttctgaagca   7920
acttaaagtt atcaggcatg catggatctt ggaggaatca gatgtgcagt cagggaccat   7980
agcacaggac aggcgtcttc tactggtgct accagcaaat gctggaagcc gggaacactg   8040
ggtacgttgg aaaccacgtg atgtggagta agataaactg taggagaaaa gcatttcgta   8100
gtgggccatg aagcctttca ggacatgtat tgcagtatgg gccggcccat tacgcaattg   8160
gacgacaaca aagactagta ttagtaccac ctcggctacc cacatagatc aaagctggtt   8220
taaaagagtt gtgcagatga tccgtggcag ctggagctga gcttccgggg ttttagagct   8280
agaaatagca agttaaaata aggctagtcc gttatcaact tgaaaaagtg gcaccgagtc   8340
ggtgcttttt ttttcggacc gcgcctgcag tgcagcgtga cccggtcgtg ccctctcta    8400
gagataatga gcattgcatg tctaagttat aaaaaattac cacatatttt ttttgtcaca   8460
cttgtttgaa gtgcagttta tctatcttta tacatatatt taaactttac tctacgaata   8520
ataatccta tagtactaca ataatatcag tgttttagag aatcatataa atgaacagtt   8580
agacatggtc taaaggacaa ttgagtattt tgacaacagg actctacagt tttatctttt   8640
tagtgtgcat gtgttctcct ttttttttgc aaatagcttc acctatataa tacttcatcc   8700
attttattag tacatccatt tagggttag ggttaatggt ttttatagac taatttttttt     8760
agtacatcta ttttattcta ttttagcctc taaattaaga aaactaaaac tctattttag   8820
ttttttttatt taataattta gatataaaat agaataaaat aaagtgacta aaaattaaac   8880
aaatacccctt taagaaatta aaaaaactaa ggaaacattt ttcttgtttc gagtagataa   8940
tgccagcctg ttaaacgccg tcgacgagtc taacggacac caaccagcga accagcagcg   9000
tcgcgtcggg ccaagcgaag cagacggcac ggcatctctg tcgctgcctc tggaccccctc   9060
tcgagagttc cgctccaccg ttggacttgc tccgctgtcg gcatccagaa attgcgtggc   9120
ggagcggcag acgtgagccg gcacggcagg cggcctcctc ctcctctcac ggcaccggca   9180
gctacggggg attcctttcc caccgctcct tcgctttccc ttcctcgccc gccgtaataa   9240
atagacaccc cctccacacc ctctttcccc aacctcgtgt tgttcggagc gcacacacac   9300
acaaccagat ctcccccaaa tccacccgtc ggcacctccg cttcaaggta cgccgctcgt   9360
cctcccccc cccctctct accttctcta gatcggcgtt ccggtccatg gttagggccc    9420
ggtagttcta cttctgttca tgtttgtgtt agatccgtgt ttgtgttaga tccgtgctgc   9480
tagcgttcgt acacggatgc gacctgtacg tcagacacgt tctgattgct aacttgccag   9540
tgtttctctt tggggaatcc tgggatggct ctagccgttc cgcagacggg atcgatttca   9600
tgatttttt tgtttcgttg catagggttt ggtttgccct tttccttat ttcaatatat      9660
gccgtgcact tgtttgtcgg gtcatctttt catgctttt tttgtcttgg ttgtgatgat       9720
gtggtctggt tgggcggtcg ttctagatcg gagtagaatt ctgtttcaaa ctacctggtg   9780
gatttattaa ttttggatct gtatgtgtgt gccatacata ttcatagtta cgaattgaag   9840
atgatggatg gaaatatcga tctaggatag gtatacatgt tgatgcgggt tttactgatg   9900
catatacaga atgcttttt gttcgcttgg ttgtgatgat gtggtgtggt tgggcggtcg    9960
ttcattcgtt ctagatcgga gtagaatact gtttcaaact acctggtgta tttattaatt  10020
ttggaactgt atgtgtgtgt catacatctt catagttacg agtttaagat ggatggaaat  10080
atcgatctag gataggtata catgttgatg tgggttttac tgatgcatat acatgatggc  10140
atatgcagca tctattcata tgctctaacc ttgagtacct atctattata ataaacaagt  10200
atgttttata attatttga tcttgatata cttggatgat ggcatatgca gcagctatat    10260
gtggattttt ttagccctgc cttcatacgc tatttatttg cttggtactg tttcttttgt  10320
cgatgctcac cctgttgttt ggtgttactt ctgcagggat ccggcagcag ccatgcagaa  10380
gctgatcaac agcgtgcaga actacgcctg gggcagcaag accgcctga ccgagctgta    10440
cggcatggag aaccccagca gccagcccat ggccgagctg tggatgggcg cccacccaa    10500
gagcagcagc cgcgtgcaga acgccgccgg cgacatcgtg agcctgcgcg acgtgatcga  10560
gagcgacaag agcaccctgc tgggcgaggc cgtggccaag cgcttcggcg agctgccctt  10620
cctgttcaag gtgctgtgcg ccgcccagcc cctgagcatc caggtgcacc ccaacaagca  10680
caacagcgag atcggcttcg ccaaggagaa cgccgccggc atccccatgg acgccgccga  10740
gcgcaactac aaggaccccca accacaagcc cgagctggtg ttcgccctga ccccccttcct  10800
ggccatgaac gccttccgcg agttcagcga gatcgtgagc ctgctgcagc ccgtggccgg  10860
cgcccacccc gccatcgccc acttcctgca gcagcccgac gccgagcgcc tgagcgagct  10920
gttcgccagc ctgctgaaca tgcagggcga ggagaagagc ccccctgg ccatcctgaa     10980
gagcgccctg gacagccagc agggcgagcc ctgcagacc atccgcctga tcagcgagtt  11040
ctaccccgag gacagcggcc tgttcagccc cctgctgctg aacgtggtga agctgaaccc  11100
cggcgaggcc atgttcctgt tcgccgagac ccccacgcc tacctgcagg gcgtggccct     11160
ggaggtgatg gccaacagcg acaacgtgct gcgcgccggc ctgaccccca agtacatcga  11220
catcccgag ctggtggcca acgtgaagtt cgaggccaag cgccaacc agctgctgac     11280
ccagcccgtg aagcagggcg ccgagctgga cttccccatc cccgtggacg acttcgcctt  11340
cagcctgcac gacctgagcg acaaggagac caccatcagc cagcagagcg ccgccatcct  11400
gttctgcgtg gagggcgacg ccaccctgtg aagggcagc cagcagctgc agctgaagcc    11460
cggcgagagc gccttcatcg ccgccaacga gagccccgtg accgtgaagg ccacggccg    11520
cctggccctg gtgtacaaca gctgtgata ggagctcgat ccgtcgacct gcagatcgtt    11580
caaacatttg gcaataaagt ttcttaagat tgaatcctgt tgccggtctt gcgatgatta  11640
tcatataatt tctgttgaat tacgttaagc atgtaataat taacatgtaa tgcatgacgt  11700
tatttatgag atgggttttt atgattagag tcccgcaatt atacatttaa tacgcgatag  11760
aaaacaaaat atagcgcgca aactaggata aattatcgcg cgcggtgtca tctatgttac  11820
tagatcggcg cgccgcaatt gaagtttggg cggccagcat ggccgtatcc gcaatgtgtt  11880
```

```
attaagttgt ctaagcgtca atttgtttac accacaatat atcctgccac cagccagcca  11940
acagctcccc gaccggcagc tcggcacaaa atcaccactc gatacaggca gcccatcaga  12000
attaattctc atgtttgaca gcttatcatc gactgcacgg tgcaccaatg cttctggcgt  12060
caggcagcca tcggaagctg tggtatggct gtgcaggtcg taaatcactg cataattcgt  12120
gtcgtcaag gcgcactccc gttctggata atgtttttg cgccgacatc ataacggttc  12180
tggcaaatat tctgaaatga gctgttgaca attaatcatc cggctcgtat aatgtgtgga  12240
attgtgagcg gataacaatt tcacacagga aacagaccat gagggaagcg ttgatcgccg  12300
aagtatcgac tcaactatca gaggtagttg gcgtcatcga gcgccatctc gaaccgacgt  12360
tgctggccgt acatttgtac ggctccgcag tggatggcgg cctgaagcca cacagtgata  12420
ttgatttgct ggttacggtg accgtaaggc ttgatgaaac aacgcggcga gctttgatca  12480
acgacctttt ggaaacttcg gcttcccctg gagagagcga gattctccgc gctgtagaag  12540
tcaccattgt tgtgcacgac gacatcattc cgtggcgtta tccagctaag cgcgaactgc  12600
aatttggaga atggcagcgc aatgacattc ttgcaggtat cttcgagcca gccacgatcg  12660
acattgatct ggctatcttg ctgacaaaag caagagaaca tagcgttgcc ttggtaggtc  12720
cagcggcgga ggaactcttt gatccggttc ctgaacagga tctatttgag ggcgcaaatg  12780
aaaacttaac gctatggaac tcgccgcccg actgggctgg cgatgagcga aatgtagtgc  12840
ttacgttgtc ccgcatttgg tacagcgcag taaccggcaa aatcgcgccg aaggatgtcg  12900
ctgccgactg ggcaatggag cgcctgccgg cccagtatca gcccgtcata cttgaagcta  12960
ggcaggctta tcttggacaa gaagatcgct tggcctcgcg cgcagatcag ttggaagaat  13020
ttgttcacta cgtgaaaggc gagatcacca aagtagtcgg caaataaagc tctagtggat  13080
ctccgtaccc ggggatctgg ctcgcggcgg acgcacgacg ccggggcgag accataggcg  13140
atctcctaaa tcaatagtag ctgtaacctc gaagcgttca acttgtaaca acgattgaga  13200
attttgtca taaaattgaa atacttggtt cgcattttg tcatccgcgg tcagccgcaa  13260
ttctgacgaa ctgcccattt agctggagat gattgtacat ccttcacgtg aaaatttctc  13320
aagcgctgtg aacaagggtt cagattttag attgaaaggt gagccgttga aacacgttct  13380
tcttgtcgat gacgacgtcg ctatgcggca tcttattatt gaataccta cgatccacgc  13440
cttcaaagtg accgcggtag ccgacagcac ccagttcaca agagtactct cttccgcgac  13500
ggtcgatgtc gtgttgttg atctagattt aggtcgtgaa gatgggctcg agctaggagc  13560
aagtgatttt atcgctaagc cgttcagtat cagagagttt ctagcacgca ttcgggttgc  13620
cttgcgcgtg cgccccaacg ttgtccgctc caaagaccga cggtcttttt gttttactga  13680
ctggacactt aatctcaggc aacgtcgctt gatgtccgaa gctggcggtg aggtgaaact  13740
tacggcaggt gagttcaatc ttctcctcgc gtttttagag aaacccgcg acgttctatc  13800
gcgcgagcaa cttctcattg ccagtcgagt acgcgacgag gaggtttatg acaggagtat  13860
agatgttctc attttgaggc tgcgccgcaa acttgaggca gatccgtcaa gccctcaact  13920
gataaaaaca gcaagaggtg ccggttattt ctttgacgcg gacgtgcagg tttcgcacgg  13980
ggggacgatg gcagcctgag ccaattccca gatcccgag gaatcggcgt gagcggtcgc  14040
aaaccatccg gcccggtaca aatcggcgcg gcgctgggtg atgacctggt ggagaagttg  14100
aaggccgcgc aggccgccca gcggcaacgc atcgaggcag aagcacgccc cggtgaatcg  14160
tggcaagcgg ccgctgatcg aatccgcaaa gaatcccggc aaccgccggc agccggtcgg  14220
ccgtcgatta ggaagccgcc caagggcgac gagcaaccag attttttcgt tccgatgctc  14280
tatgacgtgg gcacccgcga tagtcgcagc atcatggacg tggccgtttt ccgtctgtcg  14340
aagcgtgacc gacgagctgg cgaggtgatc cgctacgagc ttccagacgg gcacgtagag  14400
gtttccgcag ggccggccgg catggccagt gtgtgggatt acgacctggt actgatgcgg  14460
gtttcccatc taaccgaatc catgaaccga taccggggaag ggaagggaga caagcccggc  14520
cgcgtgttcc gtccacacgt tgcggacgta ctcaagttct gccggcgagc cgatggcgga  14580
aagcagaaag acgacctggt agaaacctgc attcggttaa acaccacgca cgttgccatg  14640
cagcgtacga agaaggccaa gaaccgccgc ctggtgacga tatccgaggg tgaagccttg  14700
attagccgct acaagatcgt aaagagcgaa accgggcggc cggagtacat cgagatcgag  14760
ctagctgatt ggatgtaccg cgagatcaca gaaggcaaga accgggacgt gctgacggtt  14820
caccccgatt acttttgat cgatcccggc atcgccgtt ttctctaccg cctggcacgc  14880
cgcgccgcag gcaaggcaga agccagatgg ttgttcaaga cgatctacga acgcagtgga  14940
agcgccggag agttcaagaa gttctgtttc accgtgcgca agctgatcgg gtcaaatgac  15000
ctgccggagt acgatttgaa ggaggaggcg gggcaggctg gcccgatcct agtcatgcgc  15060
taccgcaacc tgatcgaggg cgaagcatcc gccggttcct aatgtacgga gcagatgcta  15120
gggcaaattg ccctagcagg ggaaaaaggt cgaaaaggtc tcttcctggt ggatagcacg  15180
tacattggga acccaaagcc gtacattggg aaccggaacc cgtacattgg gaacccaaag  15240
ccgtacattg gaaccggtc acacatgtaa gtgactgata taaagagaa aaaggcgat  15300
ttttccgcct aaaactcttt aaaacttatt aaaactctta aaacccgcct ggcctgtgca  15360
taactgtctg gccagcgcac agccgaagag ctgcaaaaag cgcctaccct tcggtcgtca  15420
cgctccctac gccccgccgc ttcgctcgg cctatcgcgg ccgctggccg ctcaaaaatg  15480
gctggcctac ggccaggcaa tctaccaggg cgcggacaag ccgcgccgtc gccactcgac  15540
cgccggcgct gaggtctgcc tcgtgaagaa ggtgttgctg actcatacca ggcctgaatc  15600
gccccatcat ccagccagaa agtgagggag ccacggttga tgagagcttt gttgtaggtg  15660
gaccagttgg tgattttgaa cttttgcttt gccacgaagt ctgtcgttt acttggcgag  15720
tgcgtgatct gatccttcaa ctcagcaaaa gttcgattta ttcaacaaag ccgccgtccc  15780
gtcaagtcag cgtaatgctc tgccagtgtt acaaccaatt aaccaattct gattagaaaa  15840
actcatcgag catcaaatga aactgcaatt tattcatatc aggattatca ataccatatt  15900
tttgaaaaag ccgtttctgt aatgaaggag aaaactcacc gaggcagttc cataggatgg  15960
caagatcctg gtatcggtct gcgattccga ctcgtccaac atcaatacaa cctattaatt  16020
tcccctcgtc aaaaataagg ttatcaagtg agaaatcacc atgagtgacg actgaatccg  16080
gtgagaatgg caaaagctct gcattaatga atcggccaac gcgcggggag aggcggtttg  16140
cgtattgggc gctcttccgc ttcctcgctc actgactcgc tgcgctcggt cgttcggctg  16200
cggcgagcgg tatcagctca ctcaaaggcg gtaatacggt tatccacaga atcagggat  16260
aacgcaggaa agaacatgtg agcaaaaggc cagcaaaagg ccaggaaccg taaaaaggcc  16320
gcgttgctgc cgttttccca taggctccgc cccctgacg agcatcacaa aaatcgacgc  16380
tcaagtcaga ggtggcgaaa cccgacagga ctataaagat accaggcgtt cccctctgga  16440
agctccctcg tgcgctctcc tgttccgacc ctgccgctta ccggatacct gtccgccttt  16500
ctcccttcgg gaagcgtggc gctttctcat agctcacgct gtaggtatct cagttcggtg  16560
taggtcgttc gctccaagct gggctgtgtg cacgaacccc ccgttcagcc cgaccgctgc  16620
```

```
gccttatccg gtaactatcg tcttgagtcc aacccggtaa gacacgactt atcgccactg   16680
gcagcagcca ctggtaacag gattagcaga gcgaggtatg taggcggtgc tacagagttc   16740
ttgaagtggt ggcctaacta cggctacact agaagaacag tatttggtat ctgcgctctg   16800
ctgaagccaa ttaccttcgg aaaaagagtt ggtagctctt gatccggcaa acaaaccacc   16860
gctggtagcg gtggtttttt tgtttgcaag cagcagatta cgcgcagaaa aaaaggatct   16920
caagaagatc ctttgatctt ttctacgggg tctgacgctc agtggaacga aaactcacgt   16980
taagggattt tggtcatgag attatcaaaa aggatcttca cctagatcct tttgatccgg   17040
aatta                                                              17045
```

| | | |
|---|---|---|
| SEQ ID NO: 37 | moltype = DNA  length = 16776 | |
| FEATURE | Location/Qualifiers | |
| misc_feature | 1..16776 | |
| | note = vector 24091 | |
| misc_feature | 4..259 | |
| | note = bNRB-05 | |
| regulatory | 330..2417 | |
| | note = promoter - prZmGRMZM2G471240-01 | |
| | regulatory_class = promoter | |
| gene | 2420..6589 | |
| | note = cCas9-01 | |
| variation | 5909..5911 | |
| | note = mutation - L to V mutation | |
| variation | 5954..5956 | |
| | note = mutation - I to V mutation | |
| regulatory | 6596..7591 | |
| | note = terminator - tZmGRMZM2G471240-01 | |
| | regulatory_class = terminator | |
| regulatory | 7605..7979 | |
| | note = promoter - prOsU3-01 | |
| | regulatory_class = promoter | |
| misc_feature | 7981..8085 | |
| | note = rsgRNAZmVLHP-02 | |
| misc_feature | 7981..8000 | |
| | note = xZmVLHP2 | |
| misc_feature | 8001..8012 | |
| | note = rCrRNA-01 | |
| misc_feature | 8017..8085 | |
| | note = rTracrRNA-01 | |
| regulatory | 8096..10087 | |
| | note = promoter - prUbi1-04 | |
| | regulatory_class = promoter | |
| gene | 10104..11282 | |
| | note = cPMI-09 | |
| regulatory | 11305..11557 | |
| | note = terminator - tNOS-05-01 | |
| | regulatory_class = terminator | |
| misc_feature | 11601..11730 | |
| | note = bNLB-03 | |
| gene | 12010..12798 | |
| | note = cSpec-03 | |
| regulatory | 12893..13023 | |
| | note = promoter - prVirG-01 | |
| | regulatory_class = promoter | |
| gene | 13098..13730 | |
| | note = cVirG-09 | |
| gene | 13760..14833 | |
| | note = cRepA-01 | |
| misc_feature | 14876..15280 | |
| | note = oVS1-02 | |
| misc_feature | 15958..16764 | |
| | note = oCOLE-06 | |
| source | 1..16776 | |
| | mol_type = other DNA | |
| | organism = synthetic construct | |

```
SEQUENCE: 37
attcctgtgg ttggcatgca catacaaatg gacgaacgga taaaccttt  cacgcccttt     60
taaatatccg attattctaa taaacgctct tttctcttag gtttacccgc caatatatcc   120
tgtcaaacac tgatagttta aactgaaggc gggaaacgac aatctgatca tgagcggaga   180
attaagggag tcacgttatg accccgccg atgacgcggg acaagccgtt ttacgtttgg    240
aactgacaga accgcaacgc tgcaggaatt ggccgcagcg gccatttaaa caaagcttgg   300
tacctcgcga atgcatctag atgggacccc atttgtactc attccatgtc tcataaactt   360
tgggcaccat ccatccaaca catccaatct aaacacacca aacgatgggg aatgaaagaa   420
gcagtattcg attcaacaat ggcaaacaaa tatcactgaa ttagaccaag aataaaccta   480
attagacaac gacctcccaa ccatcattcg tcaggctgta aagaagataa agctgccttg   540
gggcatggat caagcagaac accagagatg aatccaaaca cacagaaaat cacgcgcgct   600
gtctacaatg acaacaagcc ccacatttca ttgcagtaca ctgggctaca aaggcacgta   660
caacaaagag ctagggaaac attgcggagg cacgagaga gcagctaact tgacaatata   720
gcagactgag cttgcactgt tagcaggcga ggaagggaat catggggacg gagaatgggg   780
tccatgcccg cgaaggagaa ggcggacgcc gccacggtgg caccggcgca cgcgcacaca   840
```

```
gggaacccgc acaggcagcc aaggatgctg cctcgccatt gcgccggtcg tctctgccac   900
gctcctctct ctctcccgct gcatcgccgt ggatggggca agcagagagc agggactgcg   960
acgatctggg cggaggactc gccttggaga gcgcggacgc agacgggatt ctagggagag  1020
agcgaagacg gggcgcgcgc ggcgctcgcg cggcgtggtg gcggcgagat tagcgggggt  1080
gggggagggg cggagccgtg gtgagggtgt ggacgccctc cttaccctct taagtagtag  1140
tagagatata atccgttcca aaatatccat ccgttcaatt tatatttcgt ttgatctttt  1200
tacccctaaa ttgattgact catcttatta aaaaagttca taactattat taatctttat  1260
tgagatatca tttagcatat aatatacttt aagtgtggtt ttagattttt tttaaaaaaa  1320
aaaattcgca aaaattaaat gaaacgaccc aatcaaactt gaaaagtaaa actaattata  1380
aatttgaacg gaaggagtaa gaggatgttt gaatgtacta gagctaatag ttggttgctt  1440
taaaatttgc tagtagaatt agctagctaa taaatatcta gataactatt agctaatttg  1500
ctaaaacagc taatagttga actattagct agattgtttg gatgtattcg gctaattta  1560
atggctaact attagctata gtacaatatt caaacacctc ctaattaaaa tggacaaata  1620
tctcttcttt tggtcccttg cgttagattt ttcatatctc cttatttagt ataaaagaat  1680
catcaaaaag tggacaaccc ctagtggaac accattttag tagtggttgc atgaaacctt  1740
tcgcgcacca gtttctatgt gtcactctaa aaatgggaca gcatgtacgt agtgcctata  1800
tatatacaag tcatctatcg ttgcctcctc agttcatcac taatcacact tattgtgccc  1860
tcgacgagta tctatagcta gctcattaat cgattcgggg gtgtgttgtc gaaggcggca  1920
ttggcgagct actcgtcgcg gcgtccaagc aatacctgta gcacgaaggc gatcgccggg  1980
agcgtggtcg gcgagcccgt cgtgctgggg cagagggtga cggtgctgac ggtggacggc  2040
ggcggcgtcc ggggtctcat cccgggaacc atcctgcct tcctggaggc caggctgcag  2100
gagctggacg caccggaggc gaggctggcg gactacttcg actacatcgc cggaaccagc  2160
accggcggtc tcatcaccgc cttgctgacc gcgcccggca aggacaagcg gcctctctag  2220
gctgccaagg acatcaacca ctttttacatc cataactgcc cgcgcatctt tcctcagaag  2280
tgagtccgat gctgccgcca ttgttcttgc atccatccag catcgtacgt acgtcctcta  2340
tacatctgcg gatcatcatg tgcgcatgtt tgtggcatgc atgcatgcat gtgagcagga  2400
gcaggcttgc gaaaaccccca tggacaagaa gtacagcatc ggcctggaca tcggcaccaa  2460
cagcgtgggc tgggccgtga tcaccgacga gtacaaggtg ccgagcaaga agttcaaggt  2520
gctgggcaac accgacaggc acagcatcaa gaagaacctg atcggcgccc tgctgttcga  2580
cagcggcgaa accgccgagg ccaccaggct gaagaggacc gccaggagga ggtacaccag  2640
gaggaagaac aggatctgct acctgcagga gatcttcagc aacgagatgg ccaaggtgga  2700
cgacagcttc ttccacaggc tggaggagag cttcctggtg gaggaggaca agaagcacga  2760
gaggcacccg atcttcggca acatcgtgga cgaggtggcc taccacgaga gtacccgac   2820
catctaccac ctgaggaaga agctggtgga cagcaccgac aaggccgacc tgaggctgat  2880
ctacctggcc ctggcccaca tgatcaagtt caggggccac ttcctgatcg agggcgacct  2940
gaacccggac aacagcgacg tggacaagct gttcatccag ctggtgcaga cctacaacca  3000
gctgttcgag gagaacccga tcaacgcag cggcgtggac gccaaggca tcctgagcgc  3060
caggctgagc aagagcagga ggctggagaa cctgatcgcc cagctgccgg gcgagaagaa  3120
gaacggcctg ttcggcaacc tgatcgccct gagcctgggc ctgaccccga acttcaagag  3180
caacttcgac ctggccgagg acgccaagct gcagctgagc aaggacacct acgacgacga  3240
cctggacaac ctgctggccc agatcggcga ccagtacgcc gacctgttcc tggccgccaa  3300
gaacctgagc gacgccatcc tgctgagcga catcctgagg gtgaacaccg agatcaccaa  3360
ggccccgctg agcgccagca tgatcaagag gtacgacgag caccaccagg acctgaccct  3420
gctgaaggcc ctggtgaggc agcagctgcc ggagaagtac aaggagatct tcttcgacca  3480
gagcaagaac ggctacgccg gctacatcga cggcggcgcc agcaggagg agttctacaa  3540
gttcatcaag ccgatcctgg agaagatgga cggcaccgag gagctgctgg tgaagctgaa  3600
cagggagacc ctgctgagga agcagaggac cttcgacaac ggcagcatcc cgcaccagat  3660
ccacctgggc gagctgcacg ccatcctgag gaggcaggag gacttctacc cgttcctgaa  3720
ggacaacagg gagaagatcg agaagatcct gaccttccgc atcccgtact acgtgggcc   3780
gctggccagg ggcaacagca ggttcgcctg gatgaccagg aagagcgagg agaccatcac  3840
cccgtggaac ttcgaggagg tggtggacaa gggcgccagc gcccagagct tcatcgagag  3900
gatgaccaac ttcgacaaga acctgccgaa cgagaaggtg ctgccgaagc acagcctgct  3960
gtacgagtac ttcaccgtgt acaacgagct gaccaaggtg aagtacgtga ccgagggcat  4020
gaggaagccg gccttcctga gcggcgagca gaagaaggcc atcgtggacc tgctgttcaa  4080
gaccaacagg aaggtgaccg tgaagcagct gaaggaggac tacttcaaga agatcgagtg  4140
cttcgacagc gtggagatca gcggcgtgga ggacaggttc aacgccagcc tgggcaccta  4200
ccacgacctg ctgaagatca tcaaggacaa ggacttcctg gacaacgagg agaacgagga  4260
catcctggag gacatcgtgc tgaccctgac cctgttcgag gacagggaga tgatcgagga  4320
gaggctgaag acctacgccc acctgttcga cgacaaggtg atgaagcagc tgaagaggag  4380
gaggtacacc ggctggggca ggctgagcag gaagctgatc aacggcatca gggacaagca  4440
gagcggcaag accatcctgg acttcctgaa gagcgacggc ttcgccaaca ggaacttcat  4500
gcagctgatc cacgacgaca gcctgacctt caaggaggac atccagaagg cccaggtgag  4560
cggccagggc gacagcctgc acgagcacat cgccaacctg gccggcagcc cggccatcaa  4620
gaagggcatc ctgcagaccg tgaaggtggt ggacgagctg gtgaaggtga tgggcaggca  4680
caagccggag aacatcgtga tcgagatggc cagggagaac cagaccaccc agaagggcca  4740
gaagaacagc agggagagga tgaagaggat cgaggagggc atcaaggagc tgggcagcca  4800
gatcctgaag gagcacccgg tggagaacac ccagctgcag aacgagaagc tgtacctgta  4860
ctacctgcag aacggcaggg acatgtacgt ggaccaggag ctggacatca caggctgag   4920
cgactacgac gtggaccaca tcgtgccgca gagcttcctg aaggacgaca gcatcgacaa  4980
caaggtgctg accaggagcg acaagaacag gggcaagagc gacaacgtgc cgagcgagga  5040
ggtggtgaag aagatgaaaa actactggag gcagctgctg aacgccaagc tgatcaccca  5100
gaggaagttc gacaacctga ccaaggccga gagggggcgc ctgagcgagc tggacaaggc  5160
cggcttcatt aaaaggcagc tggtggagac caggcagatc accaagcacg tggcccgat   5220
cctggacaag aggatgaaca caagtacga ggaaacgac aagctgatca gggaggtgaa  5280
ggtgatcacc ctgaagagca agctggtgag cgacttcagg aaggacttcc agttctacaa  5340
ggtgagggag atcaataatt accaccacgc ccacgacgcc tacctgaacg ccgtggtggg  5400
caccgccctg attaaaaagt acccgaagct ggagagcgag ttcgtgtacg cgactacaa   5460
ggtgtacgac gtgaggaaga tgatcgccaa gagcgagcag gagatcggca aggccaccgc  5520
caagtacttc ttctacagca acatcatgaa cttcttcaag accgagatca ccctggccaa  5580
```

```
cggcgagatc aggaagaggc cgctgatcga gaccaacggc gagaccggcg agatcgtgtg   5640
ggacaagggc agggacttcg ccaccgtgag gaaggtgctg tccatgccgc aggtgaacat   5700
cgtgaagaag accgaggtgc agaccggcgg cttcagcaag gagagcatcc tgccgaagag   5760
gaacagcgac aagctgatcg ccaggaagaa ggactgggac ccgaagaagt acggcggctt   5820
cgacagcccg accgtggcct acagcgtgct ggtggtggcc aaggtggaga agggcaagag   5880
caagaagctg aagagcgtga aggagctggt gggcatcacc atcatggaga ggagcagctt   5940
cgagaagaac ccagtggact tcctggaggc caagggctac aaggaggtga agaaggacct   6000
gatcattaaa ctgccgaagt acagcctgtt cgagctggaa cggcagga agaggatgct    6060
ggccagcgcc ggcgagctgc agaagggcaa cgagctggcc ctgccgagca agtacgtgaa   6120
cttcctgtac ctggccagcc actacgagaa gctgaagggc agcccggagg acaacgagca   6180
gaagcagctg ttcgtggagc agcacaagca ctacctggac gagatcatcg agcagatcag   6240
cgagttcagc aagagggtga tcctggccga cgccaacctg gacaaggtgc tgagcgccta   6300
caacaagcac agggacaagc cgatcaggga gcaggccgaa aacatcatcc acctgttcac   6360
cctgaccaac ctgggcgccc cggccgcctt caagtacttc gacaccacca tcgacaggaa   6420
gaggtacacc agcaccaagg aggtgctgga cgccaccctg atccaccaga gcatcaccgg   6480
cctgtacgag accaggatcg acctgagcca gctgggcggc gacagcagcc cgccgaagaa   6540
gaagaggaag gtgagctgga aggacgccag cggctggagc aggatgtgac catgggacaa   6600
gtggctttac tgtcagtcac atgcttgtaa ataagtagac tttattttaa taaaacataa   6660
aaatatatat atgttcttga atataaaatt gataaccaaa ttaaaattcg aaccatcact   6720
tatacataat tttactttat tttttataaa acgtgaacgg gaaggactac cgtgaatgac   6780
tatagaacca atcatactag tataaaatat atgatgacac tacgggagag acaaactttg   6840
tctggcgcta aatattttgc cgagtgtgaa ttcacgggca ctaggcaaag atcttctttg   6900
ccgagtgtta cgctgggcaa agtaagacac taggtaaatc agtcatttgc cgagtgtccg   6960
ccactaggca aagcaaaaca ctggcaaatc aaaagtttac ctagtgccag acactaggca   7020
aaaaaaaaac gctcggcaaa tcggaagttt ccctagtgcc agacactaga caagaaaaa    7080
cacttgataa actagcgtcg tcagctaaca ccatccacca acgttaacg ttgccgagta    7140
tctgacttcg acactcggca aagaaggtct ctttgcctag tgtcggtctg gaacactagg   7200
caaagaggca ctttacctag tgtcgtattt tgacactcag taaaataatt ttttttcttt   7260
ctgcttccaa acttttatg atgtgttcct atagcaccta gaactacatg tcaagttttg    7320
gtaaaatttt tgaagttttt gctatattta cttaatttat tttatttaat tgaatttctt   7380
ttgataattc aaatttgaac tcggcaaggt aagaagcgag ggtagcctgg aaacacactt   7440
tgcctagtgt tacactcggt acaggagcct cccctgccta gtgctgcact cgacaaaaga   7500
ttcgcctttg cctagcgctg cactcggcac aggagtcgcc tttgcctagt gctgcactag   7560
gcaaagcctc cgttaccgtg ccttccatcg tcggaccctt cgaagggatc tttaaacata   7620
cgaacagatc acttaaagtt cttctgaagc aacttaaagt tatcaggcat gcatggatct   7680
tggaggaatc agatgtgcag tcagggacca tagcacagga caggcgtctt ctactggtgc   7740
taccagcaaa tgctggaagc cgggaacact gggtacgttg gaaaccacgt gatgtggagt   7800
aagataaact gtaggagaaa agcatttcgt agtgggccat gaagcctttc aggacatgta   7860
ttgcagtatg ggccggccca ttacgcaatt ggacgacaac aaagactagt attagtacca   7920
cctcggctat ccacatagat caaagctggt ttaaaagagt tgtgcagatg atccgtggca   7980
gctggagctg agcttccggg gttttagagc tagaaatagc aagttaaaat aaggctagtc   8040
cgttatcaac ttgaaaaagt ggcaccgagt cggtgctttt tttttcggac cgcgcctgca   8100
gtgcagcgtg accggtcgt gccctctct agagataatg agcattgcat gtctaagtta    8160
taaaaaatta ccacatattt tttttgtcac acttgtttga agtgcagttt atctatcttt   8220
atacatatat ttaaacttta ctctacgaat aatataatct atagtactac aataatatca   8280
gtgttttaga gaatcatata aatgaacagt tagacatggt ctaaaggaca attgagtatt   8340
ttgacaacag gactctacag ttttatcttt ttagtgtgca tgtgttctcc ttttttttg    8400
caaatagctt cacctatata atacttcatc cattttatta gtacatccat ttagggttta   8460
gggttaatgg tttttataga ctaatttttt tagtacatct attttattct attttagcct   8520
ctaaattaag aaaactaaaa ctctatttta gttttttat ttaataattt agatataaaa    8580
tagaataaaa taaagtgact aaaaattaaa caaatacccct ttaagaaatt aaaaaaacta   8640
aggaaacatt tttcttgttt cgagtagata atgccagcct gttaaacgcc gtcgacgagt   8700
ctaacggaca ccaaccagcg aaccagcagc gtcgcgtcgg gccaagcgaa gcagacggca   8760
cggcatctct gtcgctgcct ctggacccct ctcgagagtt ccgctccacc gttggacttg   8820
ctccgctgtc ggcatccaga aattgcgtgg cggagcggca gacgtgagcc ggcacggcag   8880
gcggcctcct cctcctctca cggcaccggc agctacgggg gattcctttc ccaccgctcc   8940
ttcgctttcc cttcctcgcc cgccgtaata aatagacacc cctcacacac cctctttccc   9000
caacctcgtg ttgttcggag cgcacacaca caaccagga tctcccccaa atccacccgt    9060
cggcacctcc gcttcaaggt acgccgtctc tcctccccc cccccctctc taccttctct    9120
agatcggcgt tccggtccat ggttagggcc cggtagttct acttctgttc atgtttgtgt   9180
tagatccgtg tttgtgttag atccgtgctc ctagcgttcg tacacggatg cgacctgtac   9240
gtcagacacg ttctgattgc taacttgcca gtgtttctct tgggggaatc ctgggatggc   9300
tctagccgtt ccgcagacgg gatcgatttc atgatttttt ttgtttcgtt gcatagggtt   9360
tggtttgccc ttttccttta tttcaatata tgccgtcagt tgttttgtcg ggtcatcttt   9420
tcatgctttt ttttgtcttg gttgtgatga tgtggtctgg ttgggcgtc gttctagatc    9480
ggagtagaat tctgtttcaa actacctggt ggatttatta attttggatc tgtatgtgtg   9540
tgccatacat attcatagtt acgaattgaa gatgatggat ggaaatatcg atctaggata   9600
ggtatacatg ttgatgcggg ttttactgat gcatatacag agatgctttt tgttcgcttg   9660
gttgtgatga tgtggtgtgg ttgggcggtc gttcattcgt tctagatcgg agtagaactac 9720
tgtttcaaac tacctggtgt atttattaat tttggaactg tatgtgtgtg tcatacatct   9780
tcatagttac gagtttaaga tggatggaaa tatcgatcta ggataggtat acatgttgat   9840
gtgggtttta ctgatgcata tacatgatgg catatgcagc atctattcat atgctctaac   9900
cttgagtacc tatctattat aataaacaag tatgtttttat aattattttg atcttgatat   9960
acttggatga tggcatatgc agcagctata tgtgatttt tttagccctg ccttcatacg    10020
ctatttattt gcttggtact gtttcttttg tcgatgctca ccctgttgtt tggtgttact   10080
tctgcaggga tccggcagca gccatgcaga agctgatcaa cagcgttcag aactacgcct   10140
ggggcagcaa gaccgccctg accgagctgt acggcatgga gaaccccagc agccagccca   10200
tggccgagct gtggatgggc gcccacccca agagcagcag ccgcgtgcag aacgccgccg   10260
gcgacatcgt gagcctgcgc gacgtgatcg agagcgacaa gagcacccctg ctgggcgagg   10320
```

```
ccgtggccaa gcgcttcggc gagctgccct tcctgttcaa ggtgctgtgc gccgcccagc   10380
ccctgagcat ccaggtgcac cccaacaagc acaacagcga gatcggcttc gccaaggaga   10440
acgccgccgg catccccatg gacgccgccg agcgcaacta caaggacccc aaccacaagc   10500
ccgagctggt gttcgccctg acccccttcc tggccatgaa cgccttccgc gagttcagcg   10560
agatcgtgag cctgctgcag cccgtggccg gcgcccaccc cgccatcgcc cacttcctgc   10620
agcagcccga cgccgagcgc ctgagcgagc tgttcgccag cctgctgaac atgcagggcg   10680
aggagaagag ccgcgccctg gccatcctga gagcgccct ggacagccag cagggcgagc   10740
cctggcagac catccgcctg atcagcgagt tctaccccga ggacagcggc ctgttcagcc   10800
ccctgctgct gaacgtggtg aagctgaacc ccggcgaggc catgttcctg ttcgccgaga   10860
cccccacgc ctacctgcag ggcgtggccc tggaggtgat ggccaacagc gacaacgtgc   10920
tgcgcgccgg cctgaccccc aagtacatcg acatccccga gctggtggcc aacgtgaagt   10980
tcgaggccaa gcccgccaac cagctgctga cccagcccgt gaagcagggc gccgagctgg   11040
acttcccccat ccccgtggac gacttcgcct tcagcctgca cgacctgagc gacaaggaga   11100
ccaccatcag ccagcagagc gccgccatcc tgttctgcgt ggagggcgac gccaccctgt   11160
ggaagggcag ccagcagctg cagctgaagc ccggcgagag cgccttcatc gccgccaacg   11220
agagcccccgt gaccgtgaag ggccacggcc gcctggcccg cgtgtacaac aagctgtgat   11280
aggagctcga tccgtcgacc tgcagatcgt tcaaacattt ggcaataaag tttcttaaga   11340
ttgaatcctg ttgccggtct tgcgatgatt atcatataat ttctgttgaa ttacgttaag   11400
catgtaataa ttaacatgta atgcatgacg ttatttatga gatgggtttt tatgattaga   11460
gtcccgcaat tatacattta atacgcgata gaaaacaaaa tatagcgcgc aaactaggat   11520
aaattatcgc gcgcggtgtc atctatgtta ctagatcggc gcgccgcaat tgaagtttgg   11580
gcggccagca tggccgtatc cgcaatgtgt tattaagttg tctaagcgtc aatttgttta   11640
caccacaata tatcctgcca ccagccagcc aacagctccc cgaccggcag ctcggcacaa   11700
aatcaccact cgatacaggc agcccatcag aattaattct catgtttgac agcttatcat   11760
cgactgcacg gtgcaccaat gcttctggcg tcaggcagcc atcggaagct gtggtatggc   11820
tgtgcaggtc gtaaatcact gcataattcg tgtcgctcaa gcgcactcc cgttctggat   11880
aatgttttt gcgccgacat cataacggtt ctggcaaata ttctgaaatg agctgttgac   11940
aattaatcat ccggctcgta taatgtgtgg aattgtgagc ggataacaat ttcacacagg   12000
aaacagacca tgagggaagc gttgatcgcc gaagtatcga ctcaactatc agaggtagtt   12060
ggcgtcatcg agcgccatct cgaaccgacg ttgctgccgc tacatttgta cggctccga   12120
gtggatggcg gcctgaagcc acacagtgat attgatttgc tggttacggt gaccgtaagg   12180
cttgatgaaa caacgcggcg agctttgatc aacgaccttt tggaaacttc ggcttcccct   12240
ggagagagcg agattctccg cgctgtgaa gtcaccattg ttgtgcacga cgacatcatt   12300
ccgtggcgtt atccagctaa gcgcgaactg caatttggag aatggcagcg caatgacatt   12360
cttgcaggta tcttcgagcc agccacgatc gacattgatc tggctatctt gctgacaaaa   12420
gcaagagaac atagcgttgc cttggtaggt ccagcggcgg aggaactctt tgatccggtt   12480
cctgaacagg atctatttga ggcgctaaat gaaaccttaa cgctatggaa ctcgccgccc   12540
gactgggctg gcgatgagcg aaatgtagtg cttacgttgt cccgcatttg gtacagcgca   12600
gtaaccggca aaatcgcgcc gaaggatgtc gctgccgact gggcaatgga gcgcctgccg   12660
gcccagtatc agcccgtcat acttgaagct aggcaggctt atcttggaca agaagatcgc   12720
ttggcctcgc gcgcagatca gttggaagaa tttgttcact acgtgaaagg cgagatcacc   12780
aaagtagtcg gcaaataaag ctctagtgga tctccgtacc cggggatctg gctcgcggcg   12840
gacgcacgac gccggggcga gaccataggc gatctcctaa atcaatagta gctgtaacct   12900
cgaagcgttt cacttgtaac aacgattgag aattttttgtc ataaaattga aatacttggt   12960
tcgcatttt gtcatccgcg gtcagccgca attctgacga actgcccatt tagctggaga   13020
tgattgtaca tccttcacgt gaaaatttct caagcgctgt gaacaagggt tcagatttta   13080
gattgaaagg tgagccgttg aaacacgttc ttcttgtcga tgacgtctat gctatgcggc   13140
atcttattat tgaataccctt acgatccacg ccttcaaagt gaccgcgta gccgacagca   13200
cccagttcac aagagtactc tcttccgcga cggtcgatgt cgtggttgtt gatctagatt   13260
taggtcgtga agatgggctc gagctaggag caagtgattt tatcgctaag ccgttcagta   13320
tcagagagtt tctagcacgc attcgggttg ccttgcgat gcgccccaac gttgtccgct   13380
ccaaagaccg acggtctttt tgttttactg actggacact taatctcagg caacgtcgct   13440
tgatgtccga agctggcggt gaggtgaaac ttacggcagg tgagttcaat cttctcctcg   13500
cgttttaga gaaaccccgc gacgttctat cgcgcgagca acttctcatt gccagtcgag   13560
tacgcgacga ggaggtttat gacaggagta tagatgttct catttgagg ctgcgccgca   13620
aacttgaggc agatccgtca agccctcaac tgataaaaac agcaagaggt gccggttatt   13680
tctttgacgc ggacgtgcag gtttcgcacg ggggacgat ggcagcctga gccaattccc   13740
agatccccga ggaatcggcg tgagcggtcg caaaccatcc ggcccggtac aaatcggcgc   13800
ggcgctgggt gatgacctgg tggagaagtt gaaggccgcg caggccgccc agcggcaacg   13860
catcgaggca gaagcacgcc ccggtgaatc gtggcaagcg gccgctgatc gaatccgcaa   13920
agaatcccgg caaccgccgg cagccggtgc gccgtcgatt aggaagccgc ccaagggcga   13980
cgagcaacca gattttttcg ttccgatgct ctatgacgtg ggcacccgcg atagtcgcag   14040
catcatggac gtggccgttt tccgtctgtc gaagcgtgac cgacgagctg gcgaggtgat   14100
ccgctacgag cttccagacg ggcacgtaga ggtttccgca gcgccggcgtc gcatgcccag   14160
tgtgtgggat tacgacctgg tactgatggc ggtttcccat ctaaccgaat ccatgaaccg   14220
ataccgggaa gggaagggag acaagcccgg ccgtgttcc cgtccacacg ttgcggacgt   14280
actcaagttc tgccgcgag ccgatggcgg aaagcagaaa gacgacctgg tagaaacctg   14340
cattcggtta aacaccagcg acgttgccat gcagcgtacg aagaaggcca agaacggccg   14400
cctggtgacg gtatccgtga gtgaagccttt gattagccgc tacaagatcg taaagagcga   14460
aaccgggcgg ccggagtaca tcgagatcga gctagccgat tggatgtacc gcagagatcac   14520
agaaggcaag aacccggacg tgctgacggt tcacccgat tacttttga tcgatcccgg   14580
catcggccgt tttctctacc gcctggcacg ccgcgccgca ggcaaggcag aagccagatg   14640
gttgttcaag acgatctacg aacgcagtgg cagcgccgga gagttcaaga agttctgttt   14700
ccccgtcgc aagctgatcg ggtcaaatga cctgccggag tacgatttga aggaggaagcc   14760
ggggcaggct ggcccgatcc tagtcatgcg ctaccgcaac ctgatcgagg cgaagcatc   14820
cgccggttcc taatgtacgg agcagatgct agggcaaatt gccctagcag gggaaaaagg   14880
tcgaaaaggt ctctttcctg tggatagcac gtacattggg aacccaaagc cgtacattgg   14940
gaaccggaac ccgtacattg ggaacccaaa gccgtacatt gggaaccggt cacacatgta   15000
agtgactgat ataaaagaga aaaaaggcga ttttccgcc taaaactctt taaaacttat   15060
```

-continued

```
taaaactctt aaaacccgcc tggcctgtgc ataactgtct ggccagcgca cagccgaaga 15120
gctgcaaaaa gcgcctaccc ttcggtcgct gcgctcccta cgccccgccg cttcgcgtcg 15180
gcctatcgcg gccgctggcc gctcaaaaat ggctggccta cggccaggca atctaccagg 15240
gcgcggacaa gccgcgccgt cgccactcga ccgccggcgc tgaggtctgc ctcgtgaaga 15300
aggtgttgct gactcatacc aggcctgaat cgccccatca tccagccaga aagtgaggga 15360
gccacggttg atgagagctt tgttgtaggt ggaccagttg gtgatttga acttttgctt 15420
tgccacggaa cggtctgcgt tgtcgggaag atgcgtgatc tgatccttca actcagcaaa 15480
agttcgattt attcaacaaa gccgccgtcc cgtcaagtca gcgtaatgct ctgccagtgt 15540
tacaaccaat taaccaattc tgattagaaa aactcatcga gcatcaaatg aaactgcaat 15600
ttattcatat caggattatc aataccatat ttttgaaaaa gccgtttctg taatgaagga 15660
gaaaactcac cgaggcagtt ccataggatg gcaagatcct ggtatcggtc tgcgattccg 15720
actcgtccaa catcaataca acctattaat ttcccctcgt caaaaataag gttatcaagt 15780
gagaaatcac catgagtgac gactgaatcc ggtgagaatg gcaaaagctc tgcattaatg 15840
aatcggccaa cgcgcgggga gaggcggttt gcgtattggg cgctcttccg cttcctcgct 15900
cactgactcg ctgcgctcgg tcgttcggct gcggcgagcg gtatcagctc actcaaaggc 15960
ggtaatacgg ttatccacag aatcagggga taacgcagga agaacatgt gagcaaaagg 16020
ccagcaaaag gccaggaacc gtaaaaaggc cgcgttgctg gcgtttttcc ataggctccg 16080
cccccctgac gagcatcaca aaaatcgacg ctcaagtcag aggtggcgaa acccgacagg 16140
actataaaga taccaggcgt ttccccctgg aagctccctc gtgcgctctc ctgttccgac 16200
cctgccgctt accggatacc tgtccgcctt tctcccttcg ggaagcgtgg cgctttctca 16260
tagctcacgc tgtaggtatc tcagttcggt gtaggtcgtt cgctccaagc tgggctgtgt 16320
gcacgaaccc cccgttcagc ccgaccgctg cgccttatcc ggtaactatc gtcttgagtc 16380
caacccggta agacacgact tatcgccact ggcagcagcc actggtaaca ggattagcag 16440
agcgaggtat gtaggcggtg ctacagagtt cttgaagtgg tggcctaact acggctacac 16500
tagaagaaca gtatttggta tctgcgctct gctgaagcca gttaccttcg gaaaaagagt 16560
tggtagctct tgatccggca aacaaaccac cgctggtagc ggtggttttt tgtttgcaa 16620
gcagcagatt acgcgcagaa aaaaaggatc tcaagaagat cctttgatct ttttctacgg 16680
gtctgacgct cagtggaacg aaaactcacg ttaagggatt ttggtcatga gattatcaaa 16740
aaggatcttc acctagatcc ttttgatccg gaatta            16776
```

| | | |
|---|---|---|
| SEQ ID NO: 38 | moltype = DNA length = 17475 | |
| FEATURE | Location/Qualifiers | |
| misc_feature | 1..17475 | |
| | note = vector 24094 | |
| misc_feature | 4..259 | |
| | note = bNRB-05 | |
| regulatory | 330..2417 | |
| | note = promoter - prZmGRMZM2G471240-01 | |
| | regulatory_class = promoter | |
| gene | 2420..7288 | |
| | note = cAmCyanCas9-01 | |
| regulatory | 7295..8290 | |
| | note = terminator - tZmGRMZM2G471240-01 | |
| | regulatory_class = terminator | |
| regulatory | 8304..8678 | |
| | note = promoter - prOsU3-01 | |
| | regulatory_class = promoter | |
| misc_feature | 8679..8784 | |
| | note = rsgRNAZmVLHP-02 | |
| misc_feature | 8680..8699 | |
| | note = ZmVLHP2 target | |
| misc_feature | 8700..8711 | |
| | note = rCrRNA-01 | |
| misc_feature | 8716..8784 | |
| | note = rTracrRNA-01 | |
| regulatory | 8795..10786 | |
| | note = promoter - prUbi1-04 | |
| | regulatory_class = promoter | |
| gene | 10803..11981 | |
| | note = cPMI-09 | |
| regulatory | 12004..12256 | |
| | note = terminator - tNOS-05-01 | |
| | regulatory_class = terminator | |
| misc_feature | 12300..12429 | |
| | note = bNLB-03 | |
| gene | 12709..13497 | |
| | note = cSpec-03 | |
| regulatory | 13592..13722 | |
| | note = promoter - prVirG-01 | |
| | regulatory_class = promoter | |
| gene | 13797..14429 | |
| | note = cVirG-09 | |
| gene | 14459..15532 | |
| | note = cRepA-01 | |
| misc_feature | 15575..15979 | |
| | note = oVS1-02 | |
| misc_feature | 16657..17463 | |
| | note = oCOLE-06 | |
| source | 1..17475 | | mol_type = other DNA
organism = synthetic construct

SEQUENCE: 38

```
attcctgtgg ttggcatgca catacaaatg gacgaacgga taaacctttt cacgcccttt   60
taaatatccg attattctaa taaacgctct tttctcttag gtttacccgc caatatatcc  120
tgtcaaacac tgatagttta aactgaaggc gggaaacgac aatctgatca tgagcggaga  180
attaagggag tcacgttatg accccgccg atgacgcggg acaagccgtt ttacgtttgg   240
aactgacaga accgcaacgc tgcaggaatt ggccgcagcg gccatttaaa caaagcttgg  300
tacctcgcga atgcatctag atgggaccct atttgtactc attccatgtc tcataaactt  360
tgggcaccat ccatccaaca catccaatct aaacacacca aacgatgggg aatggaaaga  420
gcagtattcg attcaacaat ggcaaacaaa tatcactgaa ttagaccaag aataaaccta  480
attagacaac gacctcccaa ccatcattcg tcaggctgta aagaagataa agctgccttg  540
gggcatggat caagcagaac accagagatg aatccaaaca cacagaaaat cacgcgcgct  600
gtctacaatg acaacaagcc ccacatttca ttgcagtaca ctgggctaca aaggcacgta  660
caacaaagag ctagggaaac attgcggagg cacgagaga gcagctaact tgacaatata  720
gcagactgag cttgcactgt tagcaggcga ggaagggaat catggggacg agaatgggg   780
tccatgcccg cgaaggagaa ggcggacgcc gccacggtgg caccggcgca cgcgcacaca  840
gggaacccgc acaggcagcc aaggatgctg cctcgccatt gcgccggtcg tctctgccac  900
gctcctctct ctctcccgct gcatcgccgt ggatggggca agcagagagc agggactgcg  960
acgatctggg cggaggactc gccttggaga gcgcggacgc agacgggatt ctagggagag 1020
agcgaagacg gggcgcgcgc ggcgctcgcg cggcgtggtg gcggcgagat tagcgggggt 1080
ggggggaggg cggagcccgtg tgagggtgt ggacgccctc cttaccctct taagtagtag 1140
tagagatata atccgttcca aaatatccat ccgttcaatt tatatttcgt ttgatctttt 1200
taccctaaat ttgattgact catcttatta aaaaagttca taactattat taatctttat 1260
tgagatatca tttagcatat aatatacttt aagtgtggtt ttagattttt tttaaaaaaa 1320
aaaattcgca aaaattaaat gaaacgaccc aatcaaactt gaaaagtaaa actaattata 1380
aatttgaacg gaaggagtaa gaggatgttt gaatgtacta gagctaatag ttggttgctt 1440
taaaatttgc tagtagaatt agctagctaa taaatatcta gataactatt agctaatttg 1500
ctaaaacagc taatagttga actattagct agattgtttg gatgtattcg gctaattta  1560
atggctaact attagctata gtacaatatt caaacacctc ctaattaaaa tggacaaata 1620
tctcttcttt tggtcccttg cgttagattt ttcatatctc cttatttagt ataaagaat  1680
catcaaaaag tggacaaccc ctagtggaac accatttag tagtggttgc atgaaacctt  1740
tcgcgcacca gtttctatgt gtcactctaa aaatgggaca gcatgtacgt agtgcctata 1800
tatatacaag tcatctatcg ttgcctcctc agttcatcac taatcacact tattgtgccc 1860
tcgacgagta tctatagcta gctcattaat cgattcgggg gtgtgttgtc gaaggcggca 1920
ttggcgagct actcgtcgcg gcgtccaagc aatacctgta gcacgaaggc gatcgccggg 1980
agcgtggtcg gcgagcccgt cgtgctgggg cagagggtga cggtgctgac ggtggacggc 2040
ggcggcgtcc ggggtctcat cccgggaacc atcctcgcct tcctggaggc caggctgcag 2100
gagctggacg caccggaggc gaggctggcg gactacttcg actacatcgc cggaaccagc 2160
accggcggtc tcatcaccgc cttgctgacc gcgcccggca aggacaagcg gcctctctag 2220
gctgccaagg acatcaacca cttttacatc cataactgcc cgcgcatctt tcctcagaag 2280
tgagtccgat gctgccgcca ttgttcttgc atccatccag catcgtacgt acgtcctcta 2340
tacatctgcg gatcatcatg tgcgcatgtt tgtggcatgc atgcatgcat gtgagcagga 2400
gcaggcttgc gaaaaccca tggccctgtc caacaagttc atcggcgacg acatgaagat  2460
gacctaccac atggacggct gcgtgaacgg ccactactttc accgtgaagg gcgagggcag 2520
cggcaagccc tacgagggca cccagacctc caccttcaag gtgaccatgg ccaacggcgg 2580
ccccctggcc ttctccttcg acatcctgtc caccgtgttc atgtacggca accgctgctt 2640
caccgcctac cccaccagca tgcccgacta cttcaagcag gccttcccg acggcatgtc  2700
ctacgagaga acccttcacct acgaggacgg cggcgtggcc accgccagct gggagatcag 2760
cctgaagggc aactgcttcg agcacaagtc caccttccac ggcgtgaact tccccgccga 2820
cggccccgtg atggccaaga gaccaccgg ctgggacccc tccttcgaga agatgaccgt 2880
gtgcgacggc atcttgaagg gcgacgtgac cgccttcctg atgctgcagg gcggcggcaa 2940
ctacagatgc cagttccaca cctcctacaa gaccaagaag cccgtgacca tgccccccaa 3000
ccacgtggtg gagcaccgca tcgccagaac cgacctggac aagggcggca acagcgtgca 3060
gctgaccgag cacgccgtgg cccacatcac ctccgtggtg cccttcggcg gcggcggatc 3120
cgacaagaag tacagcatcg gcctggacat cggcaccaac agcgtgggct gggccgtgat 3180
caccgacgag tacaaggtgc cgagcaagaa gttcaaggtg ctgggcaaca ccgacaggca 3240
cagcatcaag aagaacctga tcggcgccct gctgttcgac agcggcgaga ccgccgaggc 3300
caccaggctg aagaggaccg ccaggaggag gtacaccagg aggaagaaca ggatctgcta 3360
cctgcaggag atcttcagca acgagatggc caaggtggac gacagcttct tccacaggct 3420
ggaggagagc ttcctggtgg aggaggacaa gaagcacgag aggcacccga tcttcggcaa 3480
catcgtggac gaggtggcct accacgagaa gtacccgacc atctaccacc tgaggaagaa 3540
gctggtggac agcaccgaca aggccgacct gaggctgatc tacctggccc tggcccacat 3600
gatcaagttc aggggccact tcctgatcga gggcgacctg aacccggaca acagcgacgt 3660
ggacaagctg ttcatccagc tggtgcagac ctacaaccag ctgttcgagg agaacccgat 3720
caacgccagc ggcgtggacg ccaaggccat cctgagcgcc aggctgagca gagcaggag  3780
gctggagaac ctgatcgccc agctgccggg cgagaagaag aacggcctgt tcggcaacct 3840
gatcgccctg agcctgggcc tgacccccaa cttcaagagc aacttcgacc tggccgagga 3900
cgccaagctg cagctgagca aggacaccta cgacgacgac ctggacaacc tgctggccca 3960
gatcggcgac cagtacgccg acctgttcct ggccgccaag aacctgagcg acgccatcct 4020
gctgagcgac atcctgaggg tgaacaccga gatcaccaag gccccgctga gcgccagcat 4080
gatcaagagg tacgacgagc accaccagga cctgaccctg ctgaaggccc tggtgaggca 4140
gcagctgccg gagaagtaca aggagatctt cttcgaccag agcaagaacg gctacgccgg 4200
ctacatcgac ggcggcgcca gccaggagga gttctacaag ttcatcaagc cgatcctgga 4260
gaagatggac ggcaccgagg agctgctggt gaagctgaac agggaggacc tgctgaggaa 4320
gcagaggacc ttcgacaacg gcagcatccc gcaccagatc cacctgggcg agctgcacgc 4380
catcctgagg aggcaggagg acttctaccc gttcctgaag gacaacaggg agaagatcga 4440
gaagatcctg accttccgca tcccgtacta cgtgggcccg ctggccaggg gcaacagcag 4500
gttcgcctgg atgaccagga agagcgagga gaccatcacc ccgtgaact tcgaggaggt  4560
```

```
ggtggacaag ggcgccagcg cccagagctt catcgagagg atgaccaact tcgacaagaa    4620
cctgccgaac gagaaggtgc tgccgaagca cagcctgctg tacgagtact tcaccgtgta    4680
caacgagctg accaaggtga agtacgtgac cgagggcatg aggaagccgg ccttcctgag    4740
cggcgagcag aagaaggcca tcgtggacct gctgttcaag accaacagga aggtgaccgt    4800
gaagcaggtg aaggaggact acttcaagaa gatcgagtgc ttcgacagcg tggagatcag    4860
cggcgtggag gacaggttca acgccagcct gggcacctac cacgacctgc tgaagatcat    4920
caaggacaag gacttcctgg acaacgagga gaacgaggac atcctggagg acatcgtgct    4980
gaccctgacc ctgttcgagg acagggagat gatcgaggag aggctgaaga cctacgccca    5040
cctgttcgac gacaaggtga tgaagcagct gaagaggagg aggtacaccg gctggggcag    5100
gctgagcagg aagctgatca acggcatcag ggacaagcag agcggcaaga ccatcctgga    5160
cttcctgaag agcgacggct tcgccaacag gaacttcatg cagctgatcc acgacgacag    5220
cctgaccttc aaggaggaca tccagaaggc ccaggtgagc ggccagggcg acagcctgca    5280
cgagcacatc gccaacctgg ccggcagccc ggccatcaag aagggcatcc tgcagaccgt    5340
gaaggtggtg gacgagctgg tgaaggtgat gggcaggcac aagccggaga acatcgtgat    5400
cgagatggcc agggagaacc agaccaccca gaagggccag aagaacagca gggagaggat    5460
gaagaggatc gaggagggca tcaaggagct gggcagccag atcctgaagg agcacccggt    5520
ggagaacacc cagctgcaga acgagaagct gtacctgtac tacctgcaga acggcaggga    5580
catgtacgtg gaccaggagc tggacatcaa caggctgagc gactacgacg tggaccacat    5640
cgtgccgcag agcttcctga aggacgacag catcgacaac aaggtgctga ccaggagcga    5700
caagaacagg ggcaagagcg acaacgtgcc gagcgaggag gtggtgaaga gatgaaaaaa    5760
ctactggagg cagctgctga cgccaagctg atcacccag aggaagttcg acaacctgac    5820
caaggccgag aggggcggcc tgagcgagct ggacaaggcc ggcttcatta aaaggcagct    5880
ggtggagacc aggcagatca ccaagcacgt ggcccagatc ctggacagca ggatgaacac    5940
caagtacgac gagaacgaca agctgatcag ggaggtgaag gtgatcaccc tgaagagcaa    6000
gctggtgagc gacttcagga aggacttcca gttctacaag gtgagggaga tcaataatta    6060
ccaccacgcc cacgacgcct acctgaacgc cgtggtgggc accgccctga ttaaaaagta    6120
cccgaagctg gagagcgagt tcgtgtacgg cgactacaag gtgtacgacg tgaggaagat    6180
gatcgccaag agcgagcagg agatcggcaa ggccaccgcc aagtacttct tctacagcaa    6240
catcatgaac ttcttcaaga ccgagatcac cctggccaac ggcgagatca ggaagaggcc    6300
gctgatcgag accaacggcg agaccggcga gatcgtgtgg gacaagggca gggacttcgc    6360
caccgtgagg aaggtgctgt ccatgccgca ggtgaacatc gtgaagaaga ccgaggtgca    6420
gaccggcggc ttcagcaagg agagcatcct gccgaagagg aacagcgaca gctgatcgc    6480
caggaagaag gactgggacc cgaagaagta cggcggcttc gacagcccga ccgtggccta    6540
cagcgtgctg gtggtggcca aggtggagaa gggcaagagc aagaagctga agagcgtgaa    6600
ggagctggtg ggcatcacca tcatggagag gagcagcttc gagaagaacc cagtggactt    6660
cctggaggcc aagggctaca aggaggtgaa gaaggacctg atcattaaac tgccgaagta    6720
cagcctgttc gagctggaga acggcaggaa gaggatgctg gccagcgccg gcgagctgca    6780
gaagggcaac gagctggccc tgccgagcaa gtacgtgaac ttcctgtacc tggccagcca    6840
ctacgagaag ctgaagggca gccccgagga caacgagcag aagcagctgt tcgtggagca    6900
gcacaagcac tacctggacg agatcatcga gcagatcagc gagttcagca agagggtgat    6960
cctggccgac gccaacctgg acaaggtgct gagcgcctac aacaagcaca gggacaagcc    7020
gatcagggag caggccgaga acatcatcca cctgttcacc ctgaccaacc tgggcgcccc    7080
ggccgccttc aagtacttcg acaccaccat cgacaggaag aggtacacca gcaccaagga    7140
ggtgctggac gccaccctga tccaccagag catcaccggc ctgtacgaga ccaggatcga    7200
cctgagccag ctgggcggcg acagcagccc ggccaagaag aaggaggaag tgagctggaa    7260
ggacgccagc ggctggagca ggatgtgacc atgggacaag tggctttact gtcagtcaca    7320
tgcttgtaaa taagtagact ttattttaat aaaacataaa aatatatata tgttcttgaa    7380
tataaaattg ataaccaaat taaaattcga accatcactt atacataatt ttacttttatt    7440
ttttataaaa cgtgaacggg aaggactacc gtgaatgact atagaaccaa tcatactagt    7500
ataaaatata tgatgacact acgggagaga caaactttgt ctggcgctaa atattttgcc    7560
gagtgtgaat tcacgggcac taggcaaaga tcttctttgc cgagtgttac gctgggcaaa    7620
gtaagacact aggtaaatca gtcatttgcc gagtgtccgc cactaggcaa agcaaaacac    7680
tggcaaatca aaagtttacc tagtgccaga cactaggcaa aaaaaaaacg ctcggcaaat    7740
cggaagtttc cctagtgcca gacactagac aaagaaaaac acttgataaa ctagcgtcgt    7800
cagctaacac catccaccaa ccgttaacgt tgccgagtat ctgacttcga cactcggcaa    7860
agaaggtctc tttgcctagt gtcggtctgg aacactaggc aaagaggcac tttacctagt    7920
gtcgtatttt gacactcagt aaaataattt ttttctttc tgcttccaaa ctttttatga    7980
tgtgttccta tagcacctag aactacatgt caagttttgg taaaattttt gaagtttttg    8040
ctatatttac ttaatttatt ttatttaatt gaatttcttt tgataattca aatttgaact    8100
cggcaaggta agaagcgagg gtagcctgga aacacacttt gcctagtgtt acactcggta    8160
caggagcctc ccctgcctag tgctgcactc gacaaaagat tcgcctttgc ctagcgctgc    8220
actcggcaca ggagtcgcct ttgcctagtc ctgcactagg caaagcctcc gttaccgtgc    8280
cttccatcgt cggacccttc gaaggggatct ttaaacatac gaacagatca cttaaagttc    8340
ttctgaagca acttaaagtt atcaggcatg catggatctt gaggaatca gatgtcgcagt    8400
cagggaccat agcacaggac aggcgtcttc tactggtgct accagcaaat gctggaagcc    8460
gggaacactg gtacgttgg aaaccacgtg atgtggagta agataaactg taggagaaaa    8520
gcatttcgta gtgggccatg aagcctttca ggacatgtat tgcagtatgg gccggcccat    8580
tacgcaattg gacgacaaca aagactagta ttagtaccac ctcggctatc cacatagatc    8640
aaagctggtt taaagagagtt gtgcagatga tccgtgactga cctggagctga gcttccgggg    8700
ttttagagct agaaatagca agttaaaata aggctagtcc gttatcaact tgaaaaagtg    8760
gcaccgagtc ggtgcttttt tttcggacc gcgcctgcag tgcagcgtga cccggtcgtg    8820
cccctctcta gagataatga gcattgcatg tctaagttat aaaaaattac cacatatttt    8880
ttttgtcaca cttgttgaa gtgcagttta tctatctttta tacatatatt taaactttac    8940
tctacgaata atataatcta tagtacacta atatatcag tgttttagag aatcatataa    9000
atgaacagtt agacatggtc taaaggacaa ttgagtattt tgacaacagg actctacagt    9060
tttatctttt tagtgtgcat gtgttctcct tttttttgc aaatagcttc acctatataa    9120
tacttcatcc attttattag tacatccatt taggtttag ggttaatggt ttttatagac    9180
taatttttt agtacatcta ttttattcta ttttagcctc taaattaaga aaactaaaac    9240
tctatttag tttttttatt taataattta gatataaaat agaataaaat aaagtgacta    9300
```

```
aaaattaaac aaatacccct taagaaatta aaaaaactaa ggaaacatttt ttcttgtttc    9360
gagtagataa tgccagcctg ttaaacgccg tcgacgagtc taacggacac caaccagcga    9420
accagcagcg tcgcgtcggg ccaagcgaag cagacggcac ggcatctctg tcgctgcctc    9480
tggacccctc tcgagagttc cgctccaccg tttggacttgc tccgctgtcg gcatccagaa   9540
attgcgtggc ggagcggcag acgtgagccg gcacggcagg cggcctcctc ctcctctcac    9600
ggcaccggca gctacggggg attccttttcc caccgctcct tcgctttccc ttcctcgccc   9660
gccgtaataa atagacaccc cctccacacc ctctttcccc aacctcgtgt tgttcggagc    9720
gcacacacac acaaccagat ctcccccaaa tccacccgtc ggcacctccg cttcaaggta    9780
cgccgctcgt cctcccccc ccccctctct accttctcta gatcggcgtt ccggtccatg     9840
gttagggccc ggtagttcta cttctgttca tgtttgtgtt agatccgtgt ttgtgttaga    9900
tccgtgctgc tagcgttcgt acacggatgc gacctgtacg tcagacacgt tctgattgct    9960
aacttgccag tgtttctctt tggggaatcc tgggatggct ctagccgttc cgcagacggg    10020
atcgatttca tgattttttt tgtttcgttg catagggttt ggtttgccct tttcctttat    10080
ttcaatatat gccgtgcact tgttttgtcgg gtcatctttt catgctttttt tttgtcttgg   10140
ttgtgatgat gtggtctggt tgggcggtcg ttctagatcg gagtagaatt ctgtttcaaa    10200
ctacctggtg gatttattaa ttttggatct gtatgtgtgt gccatacata ttcatagtta    10260
cgaattgaag atgatggatg gaaatatcga tctaggatag gtatacatgt tgatgcgggt    10320
tttactgatg catatacaga gatgcttttt gttcgcttgt ttgtgatgat gtggtgtggt    10380
tgggcggtcg ttcattcgtt ctagatcgga gtagaatact gtttcaaact acctggtgta    10440
tttattaatt ttggaactgt atgtgtgtgt catacatctt catagttacg agtttaagat    10500
ggatggaaat atcgatctag gataggtata catgttgatg tgggttttac tgatgcatat    10560
acatgatggc atatgcagca tctattcata tgctctaacc ttgagtacct atctattata    10620
ataaacaagt atgtttttata attattttga tcttgatata cttggatgat ggcatatgca    10680
gcagctatat gtggattttt ttagcccctgc cttcatacgc tatttatttg cttggtactg    10740
tttcttttgt cgatgctcac cctgttgttt ggtgttactt ctgcagggat ccggcagcag    10800
ccatgcagaa gctgatcaac agcgtgcaga actacgcctg gggcagcaag ccggcagcga    10860
ccgagctgta cggcatggag aaccccagca gccagcccat ggccgagctg tggatgggca    10920
cccaccccaa gagcagcagc cgcgtgcaga acgccgccgg cgacatcgtg agcctgcgcg    10980
acgtgatcga gagcgacaag agcaccctgc tgggcgaggc cgtggccaag cgcttcggcg    11040
agctgccctt cctgttcaag gtgctgtgcg ccgcccaacc cctgagcatc caggtgcacc    11100
ccaacaagca caacagcgag atcggcttcg caaggagaa cgccgccggc atccccatcg    11160
acgccgccga gcgcaactac aaggacccca accacaagcc cgagctggtg ttcgccctga    11220
cccccttcct ggccatgaac gccttccgcg agttcagcga gatcgtgagc ctgctgcagc    11280
ccgtggccgg cgcccacccc gccatcgccc acttcctgca gcagcccgac gccgagcgcc    11340
tgagcgagct gttcgccagc ctgctgaaca tgcagggcga ggagaagagc cgcgccctgg    11400
ccatcctgaa gagcgccctg gacagcagcc agggcgagcc ctggcagacc atccgcctga    11460
tcagcgagtt ctaccccgag gacagcggcc tgttcagccc cctgctgctg aacgtggtga    11520
agctgaaccc cggcgaggcc atgttcctgt tcgccgagac cccccacgcc tacctgcagg    11580
gcgtgccct ggaggtgatg gccaacagcg acaacgtgct gcgcgccggc ctgacccccca    11640
agtacatcga catccccgag ctggtggcca acgtgaagtt cgaggccaag cccgccaacc    11700
agctgctgac ccagccgtg aagcagggcg ccgagctgga cttcccccatc cccgtggacg    11760
acttcgcctt cagcctgcac gacctgagcg acaaggagac caccatcagc cagcagagcg    11820
ccgccatcct gttctgcgtg gagggcgacg ccaccctgga cagcagctgc    11880
agctgaagcc cggcgagagc gccttcatcg ccgccaacga gagcccgtg accgtgaagg    11940
gccacggccg cctggcccgc gtgtacaaca agctgtgata ggagctcgat ccgtcgacct    12000
gcagatcgtt caaacatttg gcaataaagt ttcttaagat tgaatcctgt tgccggtctt    12060
gcgatgatta tcatataatt tctgttgaat tacgttaagc atgtaataat taacatgtaa    12120
tgcatgacgt tatttatgag atgggttttt atgattagag tcccgcaatt atacatttaa    12180
tacgcgatag aaaacaaaat atagcgcgca aactaggata aattatcgcg cgcggtgtca    12240
tctatgttac tagatcggcg cgccgcaatt gaagtttggg cggccagcat ggccgtatcc    12300
gcaatgtgtt attaagttgt ctaagcgtca atttgtttac accacaatat atcctgccac    12360
cagccagcca acagctcccc gaccggcagc tcggcacaaa atcaccactc gatacaggca    12420
gcccatcaga attaattctc atgtttgaca gcttatcatc gactgcacgg tgcaccaatg    12480
cttctgcgt caggcagcca tcggaagctg tggtatggct gtgcaggtcg taaatcactg    12540
cataattcgt gtcgctcaag gcgcactccc gttctggata atgttttttg cgccgacatc    12600
ataacggttc tggcaaatat tctgaaatga gctgttgaca attaatcatc cggctcgtat    12660
aatgtgtgga attgtgagcg gataacaatt tcacacagga aacagaccat gagggaagcg    12720
ttgatcgccg aagtatcgac tcaactatca gaggtagttg gcgtcatcga gcgccatctc    12780
gaaccgacgt tgctggccgt acatttgtac ggctccgacc tggatggcgg cctgaagcca    12840
cacagtgata ttgatttgct ggttacggtg accgtaaggc ttgatgaaac aacgcggcga    12900
gctttgatca acgaccttt ggaaacttcg gcttcccctg gagagagcga gattctccgc    12960
gctgtagaag tcaccattgt tgtgcacgac gacatcattc cgtggcgtta tccagctaag    13020
cgcgaactgc aatttggaga atggcagcgc aatgacattc ttgcaggtat cttcgagcca    13080
gccacgatcg acattgatct ggctatcttg ctgacaaaag caagagaaca tagcgttgcc    13140
ttggtaggtc cagcggcgga ggaactctttt gatccggttc ctgaacagga tctatttgag    13200
gcgctaaatg aaaccttaac gctatggaac tcgccgcccg actgggctgg cgatgagcga    13260
aatgtagtgc ttacgttgtc ccgcatttgg tacagcgcag taaccggcaa aatcgcgccg    13320
aaggatgtcg ctgccgactg ggcaatggag cgcctgccgg cccagtatca gcccgtcata    13380
cttgaagcta ggcaggctta tcttgaacaa gaagatcgct tggcctcgcg cgcagatcag    13440
ttggaagaat ttgttcacta cgtgaaaggc gagatcacca agtgtagtcgg caaataaagc    13500
tctagtggat ctccgtaccc ggggatcggg ctcgcggcgg acgcacgacg ccggggcgag    13560
accataggcg atctcctaaa tcaatagtag ctgtaacctc gaagcgtttc acttgtaaca    13620
acgattgaga atttttgtca taaaattgaa atacttggtt cgcattttg tcatccgcgg     13680
tcagccgcaa ttctgacgaa ctgcccattt agctgggaat gattgtacat ccttcacgtg    13740
aaaatttctc aagcgctgtg aacaagggtt cagattttag attgaaaggt gagccgttga    13800
aacacgttct tcttgtcgat gacgacgtcg ctatgcggca tcttattatt gaataccttta    13860
cgatccacgc cttcaaagtg accgcggtag ccgacagcac ccagttcaca agagtactct    13920
cttccgcgac ggtcgatgtc gtggttgttg atctagattt aggtcgtgaa gatgggctcg    13980
agctaggagc aagtgatttt atcgctaagc cgttcagtat cagagagttt ctagcacgca    14040
```

```
ttcgggttgc cttgcgcgtg cgccccaacg ttgtccgctc caaagaccga cggtcttttt    14100
gttttactga ctggacactt aatctcaggc aacgtcgctt gatgtccgaa gctggcggtg    14160
aggtgaaact tacggcaggt gagttcaatc ttctcctcgc gttttttagag aaaccccgcg    14220
acgttctatc gcgcgagcaa cttctcattg ccagtcgagt acgcgacgag gaggtttatg    14280
acaggagtat agatgttctc attttgaggc tgcgccgcaa acttgaggca gatccgtcaa    14340
gccctcaact gataaaaaca gcaagaggtg ccggttattt ctttgacgcg gacgtgcagg    14400
tttcgcacgg ggggacgatg gcagcctgag ccaattccca gatccccgag gaatcggcgt    14460
gagcggtcgc aaaccatccg gcccggtaca aatcggcgcg gcgctgggtg atgacctggt    14520
ggagaagttg aaggccgcgc aggccgccca gcggcaacgc atcgaggcag aagcacgccc    14580
cggtgaatcg tggcaagcgg ccgctgatcg aatccgcaaa gaatccggc aaccgccggc     14640
agccggtgcg ccgtcgatta ggaagccgcc caagggcgac gagcaaccag atttttcgt     14700
tccgatgctc tatgacgtgg gcacccgcga tagtcgcagc atcatggacg tggccgtttt    14760
ccgtctgtcg aagcgtgacc gacgagctgg cgaggtgatc cgctacgagc ttccagacgg    14820
gcacgtagag gtttccgcag ggccggccgg catggccagt gtgtgggatt acgacctggt    14880
actgatggcg gtttcccatc taaccgaatc catgaaccga taccgggaag ggaagggaga    14940
caagcccggc cgcgtgttcc gtccacacgt tgcggacgta ctcaagttct gccggcgagc    15000
cgatggcgga aagcagaaag acgacctggt agaaacctgc attcggttaa acaccacgca    15060
cgttgccatg cagcgtacga agaaggccaa gaacggccgc ctggtgacgg tatccgaggg    15120
tgaagccttg attagccgct acaagatcgt aaagagcgaa accgggcggc cggagtacat    15180
cgagatcgag ctagctgatt ggatgtaccg cgagatcaca gaaggcaaga acccggacgt    15240
gctgacggtt caccccgatt actttttgat cgatcccggc atcggccgtt ttctctaccg    15300
cctggcacgc cgcgccgcag gcaaggcaga agccagatgg ttgttcaaga cgatctacga    15360
acgcagtggc agcgccggag agttcaagaa gttctgtttc accgtgcgca agctgatcgg    15420
gtcaaatgac ctgccggagt acgatttgaa ggaggaggcg gggcaggctg cccgatcct     15480
agtcatgcgc taccgcaacc tgatcgaggg cgaagcatcc gccggttcct aatgtacgga    15540
gcagatgcta gggcaaattg ccctagcagg ggaaaaaggt cgaaaaggtc tctttcctgt    15600
ggatagcacg tacattggga acccaaagcc gtacattggg aaccggaacc cgtacattgg    15660
gaacccaaag ccgtacattg gaaccggtc acacatgtaa gtgactgata taaaagagaa      15720
aaaaggcgat ttttccgcct aaaactcttt aaaacttatt aaaactctta aacccgcct      15780
ggcctgtgca taactgtctg gccagcgcac agccgaagag ctgcaaaaag cgcctaccct    15840
tcggtcgctg cgctccctac gccccgccgc ttcgcgtcgg cctatcgcgg ccgctgccg     15900
ctcaaaaatg gctggcctac ggccaggcaa tctaccaggg cgcggacaag ccgcgccgtc    15960
gccactcgac cgccggcgct gaggtctgcc tcgtgaagaa ggtgttgctg actcatacca    16020
ggcctgaatc gccccatcat ccagccagaa agtgagggag ccacggttga tgagagcttt    16080
gttgtaggtg gaccagttgg tgattttgaa cttttgcttt gccacggaac ggtctgcgtt    16140
gtcgggaaga tgcgtgatct gatccttcaa ctcagcaaaa gttcgattta ttcaacaaag    16200
ccgccgtccc gtcaagtcag cgtaatgctc tgccagtgtt acaaccaatt aaccaattct    16260
gattagaaaa actcatcgag catcaaatga aactgcaatt tattcatatc aggattatca    16320
ataccatatt tttgaaaaag ccgtttctgt aatgaaggag aaaactcacc gaggcagttc    16380
cataggatgg caagatcctg gtatcggtct gcgattccga ctcgtccaac atcaatacaa    16440
cctattaatt tccctcgtc aaaaataagg ttatcaagtg agaaatcacc atgagtgacg      16500
actgaatccg gtgagaatgg caaaagctct gcattaatga atcggccaac gcgcggggag    16560
aggcggtttg cgtattgggc gctcttccgc ttcctcgctc actgactcgc tgcgctcggt    16620
cgttcggctg cggcgagcgg tatcagctca ctcaaaggcg gtaatacggt tatccacaga    16680
atcaggggat aacgcaggaa agaacatgtg agcaaaaggc cagcaaaagg ccaggaaccg    16740
taaaaaggcc gcgttgctgg cgtttttcca taggctccgc cccctgacg agcatcacaa      16800
aaatcgacgc tcaagtcaga ggtggcgaaa cccgacagga ctataaagat accaggcgtt    16860
tccccctgga agctccctcg tgcgctctcc tgttccgacc ctgccgctta ccggatacct    16920
gtccgccttt ctcccttcgg gaagcgtggc gctttctcat agctcacgct gtaggtatct    16980
cagttcggtg taggtcgttc gctccaagct gggctgtgtg cacgaacccc ccgttcagcc    17040
cgaccgctgc gccttatccg gtaactatcg tcttgagtcc aacccggtaa gacacgactt    17100
atcgccactg gcagcagcca ctggtaacag gattagcaga gcgaggtatg taggcggtgc    17160
tacagagttc ttgaagtggt ggcctaacta cggctacact agaagaacag tatttggtat    17220
ctgcgctctg ctgaagccag ttaccttcgg aaaaagagtt ggtagctctt gatccggcaa    17280
acaaaccacc gctggtagcg gtggtttttt tgtttgcaag cagcagatta cgcgcagaaa    17340
aaaaggatct caagaagatc ctttgatctt ttctacgggg tctgacgctc agtggaacga    17400
aaactcacgt taagggattt tggtcatgag attatcaaaa aggatcttca cctagatcct    17460
tttgatccgg aatta                                                     17475

SEQ ID NO: 39         moltype = DNA   length = 19
FEATURE               Location/Qualifiers
misc_feature          1..19
                      note = primer
source                1..19
                      mol_type = other DNA
                      organism = synthetic construct
SEQUENCE: 39
ttgtgctgct ccacgaaca                                                  19

SEQ ID NO: 40         moltype = DNA   length = 20
FEATURE               Location/Qualifiers
misc_feature          1..20
                      note = primer
source                1..20
                      mol_type = other DNA
                      organism = synthetic construct
SEQUENCE: 40
gccagccact acgagaagct                                                 20
```

```
SEQ ID NO: 41           moltype = DNA   length = 24
FEATURE                 Location/Qualifiers
misc_feature            1..24
                        note = probe
source                  1..24
                        mol_type = other DNA
                        organism = synthetic construct
SEQUENCE: 41
ctgcttctgc tcgttgtcct ccgg                                              24

SEQ ID NO: 42           moltype = DNA   length = 17
FEATURE                 Location/Qualifiers
misc_feature            1..17
                        note = promer
source                  1..17
                        mol_type = other DNA
                        organism = synthetic construct
SEQUENCE: 42
gcggatgctg gcacagc                                                      17

SEQ ID NO: 43           moltype = DNA   length = 19
FEATURE                 Location/Qualifiers
misc_feature            1..19
                        note = primer
source                  1..19
                        mol_type = other DNA
                        organism = synthetic construct
SEQUENCE: 43
ggcattgctt ccttctccg                                                    19

SEQ ID NO: 44           moltype = DNA   length = 15
FEATURE                 Location/Qualifiers
misc_feature            1..15
                        note = probe
source                  1..15
                        mol_type = other DNA
                        organism = synthetic construct
SEQUENCE: 44
cagggagcga ggtac                                                        15

SEQ ID NO: 45           moltype = DNA   length = 20
FEATURE                 Location/Qualifiers
misc_feature            1..20
                        note = primer
source                  1..20
                        mol_type = other DNA
                        organism = synthetic construct
SEQUENCE: 45
ctggtggcca acgtgaagtt                                                   20

SEQ ID NO: 46           moltype = DNA   length = 17
FEATURE                 Location/Qualifiers
misc_feature            1..17
                        note = primer
source                  1..17
                        mol_type = other DNA
                        organism = synthetic construct
SEQUENCE: 46
gcttcacggg ctgggtc                                                      17

SEQ ID NO: 47           moltype = DNA   length = 20
FEATURE                 Location/Qualifiers
misc_feature            1..20
                        note = probe
source                  1..20
                        mol_type = other DNA
                        organism = synthetic construct
SEQUENCE: 47
aggccaagcc cgccaaccag                                                   20

SEQ ID NO: 48           moltype = DNA   length = 17
FEATURE                 Location/Qualifiers
misc_feature            1..17
                        note = primer
source                  1..17
                        mol_type = other DNA
                        organism = synthetic construct
SEQUENCE: 48
gcggatgctg gcacaga                                                      17
```

```
SEQ ID NO: 49            moltype = DNA  length = 18
FEATURE                  Location/Qualifiers
misc_feature             1..18
                         note = primer
source                   1..18
                         mol_type = other DNA
                         organism = synthetic construct
SEQUENCE: 49
gcattgcttc cttcgcca                                                      18

SEQ ID NO: 50            moltype = DNA  length = 16
FEATURE                  Location/Qualifiers
misc_feature             1..16
                         note = probe
source                   1..16
                         mol_type = other DNA
                         organism = synthetic construct
SEQUENCE: 50
cagggaggta cgaacc                                                        16

SEQ ID NO: 51            moltype = DNA  length = 16
FEATURE                  Location/Qualifiers
misc_feature             1..16
                         note = primer
source                   1..16
                         mol_type = other DNA
                         organism = synthetic construct
SEQUENCE: 51
gcggcgaaga agcgaa                                                        16

SEQ ID NO: 52            moltype = DNA  length = 17
FEATURE                  Location/Qualifiers
misc_feature             1..17
                         note = primer
source                   1..17
                         mol_type = other DNA
                         organism = synthetic construct
SEQUENCE: 52
gcggcgtctc cagcttc                                                       17

SEQ ID NO: 53            moltype = DNA  length = 12
FEATURE                  Location/Qualifiers
misc_feature             1..12
                         note = probe
source                   1..12
                         mol_type = other DNA
                         organism = synthetic construct
SEQUENCE: 53
ccaggaactg cg                                                            12

SEQ ID NO: 54            moltype = DNA  length = 18
FEATURE                  Location/Qualifiers
misc_feature             1..18
                         note = primer
source                   1..18
                         mol_type = other DNA
                         organism = synthetic construct
SEQUENCE: 54
aagaaacgcc ggctgagt                                                      18

SEQ ID NO: 55            moltype = DNA  length = 15
FEATURE                  Location/Qualifiers
misc_feature             1..15
                         note = primer
source                   1..15
                         mol_type = other DNA
                         organism = synthetic construct
SEQUENCE: 55
accttgcggg gcgtt                                                         15

SEQ ID NO: 56            moltype = DNA  length = 12
FEATURE                  Location/Qualifiers
misc_feature             1..12
                         note = probe
source                   1..12
                         mol_type = other DNA
                         organism = synthetic construct
SEQUENCE: 56
```

```
ccaggaactg cg                                                              12

SEQ ID NO: 57          moltype = DNA   length = 18
FEATURE                Location/Qualifiers
misc_feature           1..18
                       note = primer
source                 1..18
                       mol_type = other DNA
                       organism = synthetic construct
SEQUENCE: 57
aagaaacgcc ggctgagt                                                        18

SEQ ID NO: 58          moltype = DNA   length = 14
FEATURE                Location/Qualifiers
misc_feature           1..14
                       note = primer
source                 1..14
                       mol_type = other DNA
                       organism = synthetic construct
SEQUENCE: 58
ccttgcgcgg cgtc                                                            14

SEQ ID NO: 59          moltype = DNA   length = 12
FEATURE                Location/Qualifiers
misc_feature           1..12
                       note = probe
source                 1..12
                       mol_type = other DNA
                       organism = synthetic construct
SEQUENCE: 59
ccaggaactg cg                                                              12

SEQ ID NO: 60          moltype = DNA   length = 19
FEATURE                Location/Qualifiers
misc_feature           1..19
                       note = primer
source                 1..19
                       mol_type = other DNA
                       organism = synthetic construct
SEQUENCE: 60
tgatcctcga ggccaagct                                                       19

SEQ ID NO: 61          moltype = DNA   length = 18
FEATURE                Location/Qualifiers
misc_feature           1..18
                       note = primer
source                 1..18
                       mol_type = other DNA
                       organism = synthetic construct
SEQUENCE: 61
aggtcgaggt cccctcca                                                        18

SEQ ID NO: 62          moltype = DNA   length = 14
FEATURE                Location/Qualifiers
misc_feature           1..14
                       note = probe
source                 1..14
                       mol_type = other DNA
                       organism = synthetic construct
SEQUENCE: 62
cctgctaccc gggc                                                            14

SEQ ID NO: 63          moltype = DNA   length = 15
FEATURE                Location/Qualifiers
misc_feature           1..15
                       note = primer
source                 1..15
                       mol_type = other DNA
                       organism = synthetic construct
SEQUENCE: 63
cgcgccctgc taccc                                                           15

SEQ ID NO: 64          moltype = DNA   length = 17
FEATURE                Location/Qualifiers
misc_feature           1..17
                       note = primer
source                 1..17
                       mol_type = other DNA
                       organism = synthetic construct
```

| | | |
|---|---|---|
| SEQUENCE: 64 | | |
| gcgcgtgctt accagga | | 17 |
| SEQ ID NO: 65<br>FEATURE<br>misc_feature<br><br>source | moltype = DNA  length = 13<br>Location/Qualifiers<br>1..13<br>note = probe<br>1..13<br>mol_type = other DNA<br>organism = synthetic construct | |
| SEQUENCE: 65 | | |
| tcgaggagtg ccc | | 13 |
| SEQ ID NO: 66<br>FEATURE<br>misc_feature<br><br>source | moltype = DNA  length = 16<br>Location/Qualifiers<br>1..16<br>note = primer<br>1..16<br>mol_type = other DNA<br>organism = synthetic construct | |
| SEQUENCE: 66 | | |
| caccgatgag caggcg | | 16 |
| SEQ ID NO: 67<br>FEATURE<br>misc_feature<br><br>source | moltype = DNA  length = 18<br>Location/Qualifiers<br>1..18<br>note = primer<br>1..18<br>mol_type = other DNA<br>organism = synthetic construct | |
| SEQUENCE: 67 | | |
| agatacacct tccggccg | | 18 |
| SEQ ID NO: 68<br>FEATURE<br>misc_feature<br><br>source | moltype = DNA  length = 14<br>Location/Qualifiers<br>1..14<br>note = probe<br>1..14<br>mol_type = other DNA<br>organism = synthetic construct | |
| SEQUENCE: 68 | | |
| ttcctcccgg aagc | | 14 |
| SEQ ID NO: 69<br>FEATURE<br>misc_feature<br><br>source | moltype = DNA  length = 16<br>Location/Qualifiers<br>1..16<br>note = primer<br>1..16<br>mol_type = other DNA<br>organism = synthetic construct | |
| SEQUENCE: 69 | | |
| caccgatgag caggcg | | 16 |
| SEQ ID NO: 70<br>FEATURE<br>misc_feature<br><br>source | moltype = DNA  length = 20<br>Location/Qualifiers<br>1..20<br>note = primer<br>1..20<br>mol_type = other DNA<br>organism = synthetic construct | |
| SEQUENCE: 70 | | |
| agatacacct tccggccagt | | 20 |
| SEQ ID NO: 71<br>FEATURE<br>misc_feature<br><br>source | moltype = DNA  length = 14<br>Location/Qualifiers<br>1..14<br>note = probe<br>1..14<br>mol_type = other DNA<br>organism = synthetic construct | |
| SEQUENCE: 71 | | |
| ctcctcccgg aagc | | 14 |
| SEQ ID NO: 72<br>FEATURE<br>misc_feature<br><br>source | moltype = DNA  length = 25<br>Location/Qualifiers<br>1..25<br>note = primer<br>1..25<br>mol_type = other DNA | |

```
                       organism = synthetic construct
SEQUENCE: 72
caagtttctg gacaaggaga ttctc                                            25

SEQ ID NO: 73          moltype = DNA   length = 27
FEATURE                Location/Qualifiers
misc_feature           1..27
                       note = primer
source                 1..27
                       mol_type = other DNA
                       organism = synthetic construct
SEQUENCE: 73
aagaattccc ttcttaatag ctggaga                                          27

SEQ ID NO: 74          moltype = DNA   length = 26
FEATURE                Location/Qualifiers
misc_feature           1..26
                       note = probe
source                 1..26
                       mol_type = other DNA
                       organism = synthetic construct
SEQUENCE: 74
cacgagcaca ttgctaacct tgctgg                                           26

SEQ ID NO: 75          moltype = DNA   length = 17
FEATURE                Location/Qualifiers
misc_feature           1..17
                       note = primer
source                 1..17
                       mol_type = other DNA
                       organism = synthetic construct
SEQUENCE: 75
tcaccgatga gcaggca                                                     17

SEQ ID NO: 76          moltype = DNA   length = 18
FEATURE                Location/Qualifiers
misc_feature           1..18
                       note = primer
source                 1..18
                       mol_type = other DNA
                       organism = synthetic construct
SEQUENCE: 76
atacaccttc cggccagc                                                    18

SEQ ID NO: 77          moltype = DNA   length = 14
FEATURE                Location/Qualifiers
misc_feature           1..14
                       note = probe
source                 1..14
                       mol_type = other DNA
                       organism = synthetic construct
SEQUENCE: 77
ttcctcccgg aagc                                                        14

SEQ ID NO: 78          moltype = DNA   length = 24
FEATURE                Location/Qualifiers
misc_feature           1..24
                       note = primer
source                 1..24
                       mol_type = other DNA
                       organism = synthetic construct
SEQUENCE: 78
gatagggcta aagagatgtg ggaa                                             24

SEQ ID NO: 79          moltype = DNA   length = 26
FEATURE                Location/Qualifiers
misc_feature           1..26
                       note = primer
source                 1..26
                       mol_type = other DNA
                       organism = synthetic construct
SEQUENCE: 79
ctttgttcac attagggctc aaataa                                           26

SEQ ID NO: 80          moltype = DNA   length = 16
FEATURE                Location/Qualifiers
misc_feature           1..16
                       note = probe
source                 1..16
```

```
                        mol_type = other DNA
                        organism = synthetic construct
SEQUENCE: 80
tagactgaga tggatg                                                    16

SEQ ID NO: 81           moltype = DNA   length = 20
FEATURE                 Location/Qualifiers
misc_feature            1..20
                        note = primer
source                  1..20
                        mol_type = other DNA
                        organism = synthetic construct
SEQUENCE: 81
aaaaccaccg gagaagacga                                                20

SEQ ID NO: 82           moltype = DNA   length = 17
FEATURE                 Location/Qualifiers
misc_feature            1..17
                        note = primer
source                  1..17
                        mol_type = other DNA
                        organism = synthetic construct
SEQUENCE: 82
aggtgtggcg gcagtga                                                   17

SEQ ID NO: 83           moltype = DNA   length = 14
FEATURE                 Location/Qualifiers
misc_feature            1..14
                        note = probe
source                  1..14
                        mol_type = other DNA
                        organism = synthetic construct
SEQUENCE: 83
caccgtcatt gttc                                                      14

SEQ ID NO: 84           moltype = DNA   length = 25
FEATURE                 Location/Qualifiers
misc_feature            1..25
                        note = primer
source                  1..25
                        mol_type = other DNA
                        organism = synthetic construct
SEQUENCE: 84
caagtttctg gacaaggaga ttctc                                          25

SEQ ID NO: 85           moltype = DNA   length = 27
FEATURE                 Location/Qualifiers
misc_feature            1..27
                        note = primer
source                  1..27
                        mol_type = other DNA
                        organism = synthetic construct
SEQUENCE: 85
aagaattccc ttcttaatag ctggaga                                        27

SEQ ID NO: 86           moltype = DNA   length = 26
FEATURE                 Location/Qualifiers
misc_feature            1..26
                        note = probe
source                  1..26
                        mol_type = other DNA
                        organism = synthetic construct
SEQUENCE: 86
cacgagcaca ttgctaacct tgctgg                                         26

SEQ ID NO: 87           moltype = DNA   length = 15
FEATURE                 Location/Qualifiers
misc_feature            1..15
                        note = primer
source                  1..15
                        mol_type = other DNA
                        organism = synthetic construct
SEQUENCE: 87
gcgacgccgg aaagg                                                     15

SEQ ID NO: 88           moltype = DNA   length = 21
FEATURE                 Location/Qualifiers
misc_feature            1..21
                        note = primer
```

```
source                     1..21
                           mol_type = other DNA
                           organism = synthetic construct
SEQUENCE: 88
tggcgtggtt tcgtcttctt a                                              21

SEQ ID NO: 89              moltype = DNA   length = 25
FEATURE                    Location/Qualifiers
misc_feature               1..25
                           note = probe
source                     1..25
                           mol_type = other DNA
                           organism = synthetic construct
SEQUENCE: 89
aagagcggcg tctggaggtg actca                                          25

SEQ ID NO: 90              moltype = DNA   length = 20
FEATURE                    Location/Qualifiers
misc_feature               1..20
                           note = primer
source                     1..20
                           mol_type = other DNA
                           organism = synthetic construct
SEQUENCE: 90
aaccgcatcg tcagaaaaac                                                20

SEQ ID NO: 91              moltype = DNA   length = 20
FEATURE                    Location/Qualifiers
misc_feature               1..20
                           note = primer
source                     1..20
                           mol_type = other DNA
                           organism = synthetic construct
SEQUENCE: 91
tcaacttaac cggccaaatc                                                20

SEQ ID NO: 92              moltype = DNA   length = 21
FEATURE                    Location/Qualifiers
misc_feature               1..21
                           note = primer
source                     1..21
                           mol_type = other DNA
                           organism = synthetic construct
SEQUENCE: 92
catcccttct cttccctcct g                                              21

SEQ ID NO: 93              moltype = DNA   length = 23
FEATURE                    Location/Qualifiers
misc_feature               1..23
                           note = primer
source                     1..23
                           mol_type = other DNA
                           organism = synthetic construct
SEQUENCE: 93
gccagtgtga gtgtgtatga gca                                            23

SEQ ID NO: 94              moltype = DNA   length = 21
FEATURE                    Location/Qualifiers
misc_feature               1..21
                           note = primer
source                     1..21
                           mol_type = other DNA
                           organism = synthetic construct
SEQUENCE: 94
catcgttttc tcccctcctc a                                              21

SEQ ID NO: 95              moltype = DNA   length = 19
FEATURE                    Location/Qualifiers
misc_feature               1..19
                           note = primer
source                     1..19
                           mol_type = other DNA
                           organism = synthetic construct
SEQUENCE: 95
actgatatgc acggcgcca                                                 19

SEQ ID NO: 96              moltype = DNA   length = 22
FEATURE                    Location/Qualifiers
misc_feature               1..22
```

-continued

```
                        note = primer
source                  1..22
                        mol_type = other DNA
                        organism = synthetic construct
SEQUENCE: 96
tgcagtagct tcattttcac cg                                                 22

SEQ ID NO: 97           moltype = DNA  length = 22
FEATURE                 Location/Qualifiers
misc_feature            1..22
                        note = primer
source                  1..22
                        mol_type = other DNA
                        organism = synthetic construct
SEQUENCE: 97
aggaattgat atgtacgccc gt                                                 22

SEQ ID NO: 98           moltype = DNA  length = 16279
FEATURE                 Location/Qualifiers
misc_feature            1..16279
                        note = vector 24075
misc_feature            1..517
                        note = bNRB-07
regulatory              538..1697
                        note = promoter - prAtEFaA1-02
                        regulatory_class = promoter
gene                    1716..5885
                        note = cCas9-05
variation               5205..5207
                        note = mutation - L to V mutation
variation               5250..5252
                        note = mutation - I to V mutation
regulatory              5894..6146
                        note = terminator - tNOS-05-01
                        regulatory_class = terminator
regulatory              6173..6620
                        note = promoter - prAtU6-01
                        regulatory_class = promoter
misc_feature            6621..6640
                        note = AtGL1 target1
misc_feature            6621..6725
                        note = rsgRNA AtGL1-01
misc_feature            6641..6652
                        note = rCrRNA-01
misc_feature            6657..6725
                        note = rTracrRNA-01
regulatory              6726..7173
                        note = promoter - prAtU6-01
                        regulatory_class = promoter
misc_feature            7174..7193
                        note = AtGl1 target 2
misc_feature            7174..7278
                        note = rsgRNA AtGL1-02
misc_feature            7194..7205
                        note = rCrRNA-01
misc_feature            7210..7278
                        note = rTracrRNA-01
regulatory              7295..7640
                        note = promoter - prCMP-02
                        regulatory_class = promoter
gene                    7653..8447
                        note = cNpt2-10
regulatory              8476..8728
                        note = terminator - tNOS-05-01
                        regulatory_class = terminator
regulatory              8755..10752
                        note = promoter - prGmUBI-01
                        regulatory_class = promoter
gene                    10765..11454
                        note = cAmCyan-06
regulatory              11477..12119
                        note = terminator - tPsE9-01
                        regulatory_class = terminator
misc_feature            12193..12311
                        note = bNLB-03
gene                    12928..13716
                        note = cSpec-03
gene                    13751..14824
                        note = cRepA-08
```

| | | |
|---|---|---|
| misc_feature | 14867..15271 | |
| | note = oVC1-04 | |
| misc_feature | 15441..16247 | |
| | note = oCOLE-06 | |
| source | 1..16279 | |
| | mol_type = other DNA | |
| | organism = synthetic construct | |

SEQUENCE: 98

```
gccaggacgt cggccgaaag agcgacaagc agatcacgct tttcgacagc gtcggatttg  60
cgatcgagga tttttcggcg ctgcgctacg tccgcgaccg cgttgaggga tcaagccaca 120
gcagcccact cgaccttcta gccgacccag acgagcaagg gatcttttt ggaatgctgc 180
tccgtcgtca ggctttccga cgtttgggtg gttgaacaga agtcattatc gcacggaatg 240
ccaagcactc ccgaggggaa ccctgtggtt ggcatgcaca tacaaatgga cgaacggata 300
aaccttttca cgccctttta aatatccgat tattctaata aacgctcttt tctcttaggt 360
ttacccgcca atatatcctg tcaaacactg atagtttaaa ctgaaggcgg gaaacgacaa 420
tctgatcatg agcggagaat taagggagtc acgttatgac ccccgccgat gacgcgggac 480
aagccgtttt acgtttggaa ctgacagaac cgcaacgttg aaggcgcgcc actcagcaag 540
cttgatatcg gaagtttctc tcttgaggga ggttgctcgt ggaatgggac acatatggtt 600
gttataataa accatttcca ttgtcatgag attttgaggt taatatatac tttacttgtt 660
cattatttta tttggtgttt gaataaatga tataaatggc tcttgataat ctgcattcat 720
tgagatatca aatatttact ctagagaaga gtgtcatata gattgatggt ccacaatcaa 780
tgaaattttt gggagacgaa catgtataac catttgcttg aataacctta attaaaaggt 840
gtgattaaat gatgtttgta acatgtagta ctaaacattc ataaaacaca accacccaa 900
gaggtattga gtattcacgg ctaaacaggg gcataatggt aatttaaaga atgatattat 960
tttatgttaa acccctaacat tggtttcgga ttcaacgcta taaataaaac cactctcgtt 1020
gctgattcca tttatcgttc ttattgaccc tagccgctac acacttttct gcgatatctc 1080
tgaggtaagc gttaacgtac ccttagatcg ttcttttct ttttcgtctg ctgatcgttg 1140
ctcatattat ttcgatgatt gttggattcg atgctctttg ttgattgatc gttctgaaaa 1200
ttctgatctg ttgtttagat tttatcgatt gttaatatca acgttcact gcttctaaac 1260
gataatttat tcatgaaact atttttcccat tctgatcgat cttgttttga gatttaatt 1320
tgttcgattg attgttggtt ggtggatcta tatacgagtg aacttgttga tttgcgtatt 1380
taagatgtat gtcgatttga attgtgattg ggtaattctg gagtagcata acaaatccag 1440
tgttcccttt ttctaagggt aattctcgga ttgtttgctt tatatctctt gaaattgccg 1500
atttgattga atttagctcg cttagctcag atgatagagc accacaattt tgtggtaga 1560
aatcggtttg actccgatag cggcttttta ctatgattgt tttgtgttaa agatgatttt 1620
cataatggtt atatatgtct actgttttta ttgattcaat atttgattgt tcttttttt 1680
gcagatttgt tgaccaggga tccgcggccg ctaaaatgga taagaagtat tctattggac 1740
ttgatattgg aaccaactct gtgggatggg ctgttattac tgacgagtat aaggttccat 1800
ctaagaagtt caaggttctt ggaaacactg atagacactc tattaagaag aaccttattg 1860
gtgctcttct tttcgattct ggagagactg ctgaggctac tagacttaag agaactgcta 1920
gaagaagata tactagaaga aagaacagaa tttgctatct tcaagagatt ttctctaacg 1980
agatggctaa ggttgacgat tctttcttcc acagacttga ggagtctttc cttgttgagg 2040
aggataagaa gcacgagaga cacccaattt tcggaaacat tgttgacgag gttgcttatc 2100
acgagaagta tccaactatt tatcaccttta gaaagaagct cgttgattct actgataagg 2160
ctgatcttag acttatttat cttgctcttg ctcacatgat taagttcaga ggacacttcc 2220
ttattgaggg agatcttaac ccagataact ctgacgttga taagctcttc attcaacttg 2280
ttcaaactta taaccaactt ttcgaggaga acccaattaa cgcttctggg gttgacgcta 2340
aggctattct ttctgctaga cttttctaagt ctagaaaggct tgagaacctt attgctcaac 2400
ttccaggaga gaagaagaac ggactttttcg gaaacccttat tgctctttct cttggactta 2460
ctccaaactt caagtctaac ttcgatcttg ctgaggacgc taagctccaa cttttctaagg 2520
atacttacga cgatgatctt gataaccttc ttgctcaaat tggagatcaa tacgactagt 2580
tttttccttgc tgctaagaac cttctgacg ctattcttct ttctgatatt cttagagtta 2640
acactgagat tactaaggct ccactttctg cttctatgat taagagatac gacgagcacc 2700
accaagatct tactcttctt aaggctcttg ttagacaaca acttccagag aagtataagg 2760
agatttttctt cgatcaatct aagaacggat acgctggata tattgacggg ggagcttctc 2820
aagaggagtt ctataagttc attaagccaa ttcttgagaa gatggacgga actgaggagc 2880
ttcttgttaa gctcaacaga gaggatcttt taagaaagca aagaactttc gataacggat 2940
ctattccaca ccaaattcac cttggagagc ttcacgctat tcttagaagg caagaggatt 3000
tctatccatt ccttaaggat aacagagaga agattgaact gattcttact ttccgtattc 3060
catattacgt tggaccactt gctagaggaa actctagatt cgcttggatg actagaaagt 3120
ctgaggagac tattactcct tggaacttcg aggaggttgt tgataaggga gcttctgctc 3180
aatctttcat tgagagaatg actaacttcg ataagaacct tccaaacgag aaggttcttc 3240
caaagcactc tcttctttac gagtatttca ctgttttataa cgagcttact aaggttaagt 3300
acgttactga gggaatgaga aagccagctt ccctttctgg agagcaaaag aaggctattg 3360
ttgatcttct tttcaagact aacagaaagg ttactgttga gcaacttaag gaggattatt 3420
tcaagaagat tgagtgcttc gattctgttg agatttctgg agttgaggat agattcaacg 3480
cttctcttgg aacttatcac gatcttctta agattattaa ggataaggat ttccttgata 3540
acgaggagaa cgaggatatt cttgaggata ttgttcttac tcttactctt ttcgaggata 3600
gagagatgat tgaggagaga cttaagactt acgctcacct tttcgacgat aaggttatga 3660
agcaacttaa gagaagaaga tatactggat ggggtagact ttctagaaag ctcattaacg 3720
gaattagaga taagcaatct ggaaagacta ttcttgattt ccttaagtct gacggattcg 3780
ctaacagaaa cttcatgcaa cttattcacg acgattctct tctttcaag gaggatattc 3840
aaaaggctca agtttctgga caaggagatt cttccagca gcacattgct aaccttgctg 3900
gatctccagc tattaagaag ggaattcttc aaactgttgc ggcttgtta 3960
aggttatggg tagacacaag ccagagaaca ttgttattga gatggctaga gagaaccaaa 4020
ctactcaaaa gggacaaaag aactctagag agagaatgaa gagaattgag gagggaatta 4080
aggagcttgg atctcaaatt cttaaggagc acccagttga gaacactcaa cttcaaaacg 4140
agaagctcta tctttattat cttcaaaacg gaagagatat gtacgttgat caagagcttg 4200
atattaacag acttttctgat tacgacgttg atcacattgt tccacaatct ttccttaagg 4260
```

```
acgattctat tgataacaag gttcttacta gatctgataa gaacagagga aagtctgata   4320
acgttccatc tgaggaggtt gttaagaaga tgaagaacta ttggagacaa cttcttaacg   4380
ctaagctcat tactcaaaga aagttcgata accttactaa ggctgagaga ggaggacttt   4440
ctgagcttga taaggctgga ttcattaaga gacaacttgt tgagactaga caaattacta   4500
agcacgttgc tcaaattctt gattctagaa tgaacactaa gtacgacgag aacgataagc   4560
tcattagaga ggttaaggtt attactctta agtctaagct cgtttctgat ttcagaaagg   4620
atttccaatt ctataaggtt agagagatta acaactatca ccacgctcac gacgcttatc   4680
ttaacgctgt tgttggaact gctcttatta agaagtatcc aaaacttgag tctgagttcg   4740
tttacggaga ttataaggtt tacgacgtta gaaagatgat tgctaagtct gagcaagaga   4800
ttggaaaggc tactgctaag tatttcttct attctaacat tatgaacttc ttcaagactg   4860
agattactct tgctaacgga gagattagaa gaggccact tattgagact aacgagaga    4920
ctggagagat tgtttgggat aagggaagag atttcgctac tgttagaaag gttctttcta   4980
tgccacaagt taacattgtt aagaaaactg aggttcaaac tggaggattc tctaaggagt   5040
ctattcttcc aaagagaaac tctgataagc tcattgctag aaagaaggat tgggacccaa   5100
agaagtacgg aggattcgat tctccaactg ttgcttattc tgttcttgtt gttgctaagg   5160
ttgagaaggg aaagtctaag aagctcaagt ctgttaagga gcttgttgga attactatta   5220
tggagagatc ttcttttcgag aagaacccag ttgatttcct tgaggctaag ggatataagg   5280
aggttaagaa ggatcttatt attaagctcc caaagtattc tcttttcgag cttgagaacg   5340
gaagaaagag aatgccttgct tctgctggag agcttcaaaa gggaaacgag cttgctcttc   5400
catctaagta cgttaacttc ctttatcttg cttctcacta cgagaagctc aagggatctc   5460
cagaggataa cgagcaaaag caacttttcg ttgagcaaca caagcactat cttgacgaga   5520
ttattgagca aatttctgag ttctctaaga gagttattct tgctgacgct aaccttgata   5580
aggttctttc tgcttataac aagcacagag ataagccaat tagagagcaa gctgagaaca   5640
ttattcacct tttcactctt actaaccttg gtgctccagc tgctttcaag tatttcgata   5700
ctactattga tagaaagaga tatacttcta ctaaggaggt tcttgacgct actcttattc   5760
accaatctat tactggactt tacgagacta gaattgactt ttctcaactt ggaggagatt   5820
cttctccacc aaagaagaag agaaaggttt cttggaagga cgcttctgga tggtctagaa   5880
tgtgacgtcg cgtgatcgtt caaacatttg gcaataaagt ttcttaagat tgaatcctgt   5940
tgccggtctt gcgatgatta tcatataatt tctgttgaat tacgttaagc atgtaataat   6000
taacatgtaa tgcatgacgt tatttatgag atgggttttt atgattagag tcccgcaatt   6060
atacatttaa tacgcgatag aaaacaaaat atagcgcgca aactaggata aattatcgcg   6120
cgcggtgtca tctatgttac tagatctgca gatcggaccc ctaattagct aaaagcttcg   6180
ttgaacaacg gaaactcgac ttgccttccg cacaatacat catttcttct tagctttttt   6240
tcttcttctt cgttcataca gtttttttt gtttatcagc ttacattttc ttgaaccgta   6300
gctttcgttt tcttcttttt aactttccat tcggagtttt tgtatcttgt ttcatagttt   6360
gtcccaggat tagaatgatt aggcatcgaa ccttcaagaa tttgattgaa taaaacatct   6420
tcattcttaa gatatgaaga taatcttcaa aaggcccctg ggaatctgaa agaagagaag   6480
caggcccatt tatatgggaa agaacaatag tatttcttat ataggcccat ttaagttgaa   6540
aacaatcttc aaaagtccca catcgcttag ataagaaaac gaagctgagt ttatatacag   6600
ctagagtcga agtagtgatt ggaaaagttg tagactgaga gttttagagc tagaaatagc   6660
aagttaaaat aaggctagtc cgttatcaac ttgaaaaagt ggcaccgagt cggtgctttt   6720
tttttaagct tcgttgaaca acggaaactc gacttgcctt ccgcacaata catcatttct   6780
tcttagcttt ttttcttctt cttcgttcat acagtttttt tttgtttatc agcttacatt   6840
ttcttgaacc gtagctttcg ttttcttctt tttaactttc cattcggagt ttttgtatct   6900
tgtttcatag tttgtcccag gattagaatg attaggcatc gaaccttcaa gaatttgatt   6960
gaataaaaca tcttcattct taagatatga agataatctt caaaaggccc ctgggaatct   7020
gaaagaagag aagcaggccc attttatatgg gaaagaacaa tagtatttct tatataggcc   7080
catttaagtt gaaaacaatc ttcaaaagtc ccacatcgct tagataagaa aacgaagctg   7140
agtttatata cagctagagt cgaagtagtg attgcagtga tgaacaatga cgggttttag   7200
agctagaaat agcaagttaa aataaggcta gtccgttatc aacttgaaaa agtggcaccg   7260
agtcggtgct tttttttggc gcgcctaaa gcttctggca gacaaagtgg cagacatact   7320
gtcccacaaa tgaagatgga atctgtaaaa gaaaacgcgt gaaataatgc gtctgacaaa   7380
ggttaggtcg gctgccttta atcaataccaa aagtggtccc taccacgatg gaaaaactgt   7440
gcagtcggtt tggcttttc tgacgaacaa ataagattcg tggccgacag gtgggggtcc   7500
accatgtgaa ggcatcttca gactccaata atggagcaat gacgtaaggg cttacgaaat   7560
aagtaagggt agtttgggaa atgtccactc acccgtcagt ctataaatac ttagcccctc   7620
cctcattgtt aagggagcaa ggatcctaaa ccatgattga acaagatgga ttgcacgcag   7680
gttctccggc cgcttgggtg gagaggctat tcggctatga ctgggcacaa cagacaatcg   7740
gctgctctga tgccgccgtg ttccggctgt cagcgcaggg gcgcccggtt ctttttgtca   7800
agaccgacct gtccggtgcc ctgaatgaac tgcaggacga ggcagcgcgg ctatcgtggc   7860
tggccacgac gggcgttcct tgcgcagctg tgctcgacgt tgtcactgaa gcgggaaggg   7920
actggctgct attgggcgaa gtgccggggc aggatctcct gtcatctcac cttgctcctg   7980
ccgagaaagt atccatcatg gctgatgcaa tgcggcggct gcatacgctt gatccggcta   8040
cctgcccatt cgaccaccaa gcgaaacatc gcatcgagcg agcacgtact cggatggaag   8100
ccggtcttgt cgatcaggat gatctggacg aagagcatca gggctcgcg ccagccgaac   8160
tgttcgccag gctcaaggcg cgcatgcccg acggcgagga tctcgtcgtg acccatggcg   8220
atgcctgctt gccgaatatc atggtggaaa atggccgctt ttctggattc atcgactgtg   8280
gccggctggg tgtggcggac cgctatcagg acatagcgtt ggctacccgt gatattgctg   8340
aagagcttgg cggcgaatgg gctgaccgct tcctcgtgct ttacggtatc gccgctcccg   8400
attcgcagcg catcgccttc tatcgccttc ttgacgagtt cttctgatga gagctctaga   8460
tccccgaatt ccccgatcg ttcaaacatt tggcaataaa gtttcttaag attgaatcct   8520
gttgccggtc ttgcgatgat tatcatataa tttctgttga attacgttaa gcatgtaata   8580
attaacatgt aatgcatgac gttatttatg agatgggttt tatgattag agtcccgcaa   8640
ttatacattt aatacgcgat agaaaacaaa atatagcgcg caaactagga taaattatcg   8700
cgcgcggtgt catctatgtt actagatcgg gaattgggta ccctaattag ctaaattcca   8760
aaattttcag ttagtcctta ctaattatta aattatagta ttaatccaat gtgattgcgg   8820
ttacatcatg tacggaaaaa taattctaat ccttgattta aatttgatct tgactattta   8880
tttattcttt atttcatttt gtaaatcatt ttatgtatct cctggcaagc aatttttatcc   8940
accttgcacc aacaccttcg ggttccataa tcaaaccacc ttaacttcac accatgctgt   9000
```

```
aactcacacc gcccagcatc tccaatgtga aagaagctaa aatttaataa acaatcatac   9060
gaagcagtga caaaatacca gatggtatta atgctttgat aaaattaatt ggaaagtata   9120
aaatggtaga aataataaa ttataattaa tttaaataag ataaaaaata attaaaaact   9180
aaaatgttaa aattttaaaa aaattatttt aaataatatt taaaaacatt aaaaatcatt   9240
ttaaaaaatt tatttataga acaattaaat aaatatttca gctaataaaa aacaaaagct   9300
tacctagcct tagaagacaa cttgtccaac aattagatga tacccattgc ccttacgttt   9360
tctttaacat caattattgt ttttgtcaac aagctatctt ttagttttat tttattggta   9420
aaaaatatgt cgccttcaag ttgcatcatt taacacatct cgtcattaga aaaataaaac   9480
tcttccctaa acgattagta gaaaaaatca ttcgataata aataagaaag aaaaattaga   9540
aaaaaataac ttcattttaa aaaaatcatt aaggctatat tttttaaatg actaatttta   9600
tatagactgt aactaaaagt atacaattta ttatgctatg tatcttaaag aattacttat   9660
aaaaatctac ggaagaatat cttacaaagt gaaaaacaaa tgagaaagaa tttagtggga   9720
tgattatgat tttatttgaa aattgaaaaa ataattatta aagactttag tggagtaaga   9780
aagctttcct attagtcttt tcttatccat aaaaaaaaaa aaaaatctag cgtgacagct   9840
tttccataga ttttaataat gtaaaatact ggtagcagcc gaccgttcag gtaatggaca   9900
ctgtggtcct aacttgcaac gggtgcgggc ccaatttaat aacgccgtgg taacggataa   9960
agccaagcgt gaagcggtga aggtacatct ctgactccgt caagattacg aaaccgtcaa  10020
ctacgaagta ctccccgaaa tatcatctgt gtcataaaca ccaagtcaca ccatacatgg  10080
gcacgcgtca caatatgatt ggagaacggt tccaccgcat atgctataaa atgccccac   10140
acccctcgac cctaatcgca cttcaattgc aatcaaatta gttcattctc tttgcgcagt  10200
tccctacctc tccttttcaag gttcgtagat ttcttctgtt tttttttctt cttctttatt  10260
gtttgttcta catcagcatg atgttgattt gattgtgttt tctatcgttt catcgattat  10320
aaattttcat aatcagaaga ttcagctttt attaatgcaa gaacgtcctt aattgatgat  10380
tttataaccg taaattaggt ctaattagag ttttttttcat aaagattttc agatccgttt  10440
acaacaagcc ttaattgttg attctgtagt cgtagattaa ggtttttttc atgaactact  10500
tcagatccgt taaacaacag cctttatttgt tgatacttca gtcgtttttc aagaaattgt  10560
tcagatccgt tgataaaagc cttattcgtt gattctgtat ggtatttcaa gagatattgc  10620
tcaggtcctt tagcaactac cttatttgtt gattctgtgg ccatagatta ggatttttttt  10680
tcacgaaatt gcttcttgaa attacgtgat ggattttgat tctgatttat cttgtgattg  10740
ttgactctac agagatctaa aaaaatggcc tcgtccaaca agttcatcgg cgacgacatg  10800
aagatgacct accacatgga cggctgcgtg aacggccact acttcaccgt gaagggcgag  10860
ggcagcggca agcccaacga gggcacccag acctccacct tcaaggtgac gatggccaac  10920
ggcggccccc tggccttctc cttcgacatc ctgtccaccg tgttcatgta cggcaaccgc  10980
tgcttcaccg cctaccccac cagcatgccc gactacttca agcaggcctt ccccgacggc  11040
atgtcctacg agagaaccett cacctacgag gacggcggcg tggccaccgc cagctgggag  11100
atcagcctga agggcaactg cttcgagcac aagtccacct tccacggcgt gaacttcccc  11160
gccgacggcc ccgtgatggc caagaagacc accggctggg atccctcctt cgagaagatg  11220
accgtgtgcg acggcatctt gaagggcgac gtgaccgcct tcctgatgct gcagggcggc  11280
ggcaactaca gatgccagtt ccacacctcc tacaagacca agaagcccgt gaccatgccc  11340
cccaaccacg tggtggagca ccgcatcgcc agaaccgacc tggacaaggg cggcaacagc  11400
gtgcagctga ccgagcacgc cgtggcccac atcacctccg tggtgccctt ctgatgaact  11460
agtgaattgc agctcaagct ttcgttcgta tcatcggttt cgacaacgtt cgtcaagttc  11520
aatgcatcag tttcattgcg cacacaccag aatcctactg agtttgagta ttatggcatt  11580
gggaaaactg tttttcttgt accatttgtt gtgcttgtaa tttactgtgt tttttattcg  11640
gttttcgcta tcgaactgtg aaatggaaat ggatggagaa gagttaatga atgatatggt  11700
ccttttgttc attctcaaat taatattatt tgttttttct cttatttgtt gtgtgttgaa  11760
tttgaaatta taagagatat gcaaacattt tgttttgagt aaaaatgtgt caaatcgtgg  11820
cctctaatga ccgaagttaa tatgaggagt aaaacacttg tagttgtacc attatgctta  11880
ttcactaggc aacaaatata ttttcagacc tagaaaagct gcaaatgtta ctgaatacaa  11940
gtatgtcctc ttgtgtttta gacatttatg aactttcctt tatgtaattt tccagaatcc  12000
ttgtcagatt ctaatcattg ctttataatt atagttatac tcatggattt gtagttgagt  12060
atgaaaatat tttttaatgc attttatgac ttgccaattg attgacaaca tgcatcaatc  12120
ggaccgttaa ctagctagac ggccaggatc gccgcgtgag cctttagcaa ctagctagat  12180
taattaaacg tccgcaatgt gttattaagt tgtctaagcg tcaatttgtt tacaccacaa  12240
tatatcctgc caccagccag ccaacagctc cccgaccggc agctcggcac aaaatcacca  12300
ctcgatacag gcagcccatc agtccggac ggcgtcagcg ggagacgt tgtaagcgg   12360
cagactttgc tcatgttacc gatgctattc ggaagaacgg caactaagct gccgggtttg  12420
aaacacggat gatctcgcgg agggtagcat gttgattgta acgatgacag agcgttgctg  12480
cctgtgatca aatatccatct ccctcgcaga gatccgaatt atcagccttc ttattcattt  12540
ctcgcttaac cgtgcaggc tgtcgatctt gagaactatg ccgacataat aggaaatcgc  12600
tggataaagc cgctgaggaa gctgagtggc gctatttctt tagaagtgaa cgtcgactca  12660
tgtttgcag cttatcatcg actgcacggt gcaccaatgc ttctggcgtc aggcagccat  12720
cggaagctgg ggtatggctg tgcaggtcgt aaatcactgc ataattcgtg tcgctcaagg  12780
cgcactcccg ttctggataa tgttttttgc gccgacatca taacggttct ggcaaatatt  12840
ctgaaatgag ctgttgacaa ttaatcatcc ggctcgatca atgtgtggaa ttgtgagcgg  12900
ataacaattt cacacaggaa acagaccatg agggaagcgt tgatcgccga agtatcgact  12960
caactatcag aggtagttgg cgtcatcgag cgccatctcg aaccgacgtt gctggccgta  13020
catttgtacg gctccgcagt ggatggcggc ctgaagccac acagtgatat tgatttgctg  13080
gttacggtga ccgtaaggct tgatgaaaca acgcggcgag ctttgatcaa cgacctttg   13140
gaaacttcgg cttcccctgg agagagcgag attctccgcg ctgtagaagt caccattgtt  13200
gtgcacgacg acatcattcc gtggcgttat ccagctaagc gcgaactgca atttggagaa  13260
tggcagcgca atgacattct gcaggtatc ttcgagccag ccacgatcga cattgatctg  13320
gctatccttgc tgacaaaagc aagagaacat agcgttgcct tggtaggtcc agcggcggag  13380
gaactttttg atccggttcc tgaacaggat ctatttgagg cgctaaatga aaccttaacg  13440
ctatggaact cgccgcccga ctgggctggc gatgagcgaa atgtagtgct tacgttgtcc  13500
cgcatttggt acagcgcagt aaccggcaaa atcgcgccga aggatgtcgc tgccgactgg  13560
gcaatggagc gcctgccggc ccagtatcag cccgtcatac ttgaagctag gcaggcttat  13620
cttgacaag aagatcgctt ggcctcgcgc gcagatcagt tggaagaatt tgttcactac  13680
gtgaaaggcg agatcaccaa agtagtcggc aaataaagct ctagtggatc tccgtacccg  13740
```

```
aggaatcggc gtgagcggtc gcaaaccatc cggcccggta caaatcggcg cggcgctggg   13800
tgatgacctg gtggagaagt tgaaggccgc gcaggccgcc cagcggcaac gcatcgaggc   13860
agaagcacgc cccggtgaat cgtggcaagc ggccgctgat cgaatccgca aagaatcccg   13920
gcaaccgccg gcagccggtg cgccgtcgat taggaagccg cccaagggcg acgagcaacc   13980
agattttttc gttccgatgc tctatgacgt gggcacccgc gatagtcgca gcatcatgga   14040
cgtggccgtt ttccgtctgt cgaagcgtga ccgacgagct ggcgaggtga tccgctacga   14100
gcttccagac gggcacgtag aggtttccgc agggccggcc ggcatggcca gtgtgtggga   14160
ttacgacctg gtactgatgg cggtttccca tctaaccgaa tccatgaacc gataccggga   14220
agggaaggga gacaagcccg gccgcgtgtt ccgtccacac gttgcggacg tactcaagtt   14280
ctgccggcga gccgatggcg gaaagcagaa agacgacctg gtagaaacct gcattcggtt   14340
aaacaccacg cacgttgcca tgcagcgtac caagaaggcc aagaacggcc gcctggtgac   14400
ggtatccgag ggtgaagcct tgattagccg ctacaagatc gtaaagagcg aaaccgggcg   14460
gccggagtac atcgagatcg agctggctga ttggatgtac cgcgagatca cagaaggcaa   14520
gaaccggac gtgctgacgg ttcaccccga ttacttttg atcgatcccg gcatcggccg   14580
tttttctctac cgcctggcac gccgcgccgc aggcaaggca gaagccagat ggttgttcaa   14640
gacgatctac gaacgcagtg gcagcgccgg agagttcaag aagttctgtt tcaccgtgcg   14700
caagctgatc gggtcaaatg acctgccgga gtacgatttg aaggaggagg cggggcaggc   14760
tggcccgatc ctagtcatgc gctacccgaa cctgatcgag ggcgaagcat ccgccggttc   14820
ctaatgtacg gagcagatgc tagggcaaat tgccctagca ggggaaaaag gtcgaaaagc   14880
actctttcct gtggatagca cgtacattgg gaacccaaag ccgtacattg ggaaccggaa   14940
cccgtacatt gggaacccaa agccgtacat tgggaaccgg acacacatgt aagtgactga   15000
tataaaagag aaaaaaggcg attttccgc ctaaaactct ttaaaactta ttaaaactct   15060
taaaaccgc ctggcctgtg cataactgtc tggccagcgc acagccgaag agctgcaaaa   15120
agcgcctacc cttcggtcgc tgcgctccct acgcccgcc gcttcgcgtc ggcctatcgc   15180
ggccgctggc cgctcaaaaa tggctggcct acggccaggc aatctaccag ggcgcggaca   15240
agccgcgccg tcgccactcg accgccggcg ctgaggtctg cctcgtgaag aaggtgttgc   15300
tgactcatac caggccatta tgaatcggc caacgcgcgg ggagaggcgg tttgcgtatt   15360
gggcgctctt ccgcttcctc gctcactgac tcgctgcgct cggtcgttcg gctgcggcga   15420
gcggtatcag ctcactcaaa ggcggtaata cggttatcca cagaatcagg gataacgca   15480
ggaaagaaca tgtgagcaaa aggccagcaa aaggccagga accgtaaaaa ggccgcgttg   15540
ctggcgtttt tccataggct ccgcccccct gacgagcatc acaaaaatcg acgctcaagt   15600
cagaggtggc gaaacccgac aggactataa agataccagg cgtttccccc tggaagctcc   15660
ctcgtgcgct ctcctgttcc gaccctgccg cttaccggat acctgtccgc ctttctccct   15720
tcgggaagcg tggcgctttc tcatagctca cgctgtaggt atctcagttc ggtgtaggtc   15780
gttcgctcca agctgggctg tgtgcacgaa ccccccgttc agcccgaccg ctgcgccta   15840
tccggtaact atcgtcttga gtccaacccg gtaagacacg acttatcgcc actggcagca   15900
gccactggta acaggattag cagagcgagg tatgtaggcg gtgctacaga gttcttgaag   15960
tggtggccta actacggcta cactagaaga acagtatttg gtatctgcgc tctgctgaag   16020
ccagttacct tcggaaaaag agttggtagc tcttgatccg gcaaacaaac caccgctggt   16080
agcggtggtt tttttgtttg caagcagcag attacgcgca gaaaaaaagg atctcaagaa   16140
gatcctttga tcttttctac ggggtctgac gctcagtgga acgaaaactc acgttaaggg   16200
attttggtca tgagattatc aaaaaggatc ttcacctaga tccttttgat ccggacaaac   16260
aaacaaatac agtaattta                                                16279

SEQ ID NO: 99            moltype = DNA   length = 100
FEATURE                  Location/Qualifiers
source                   1..100
                         mol_type = genomic DNA
                         organism = Zea mays
SEQUENCE: 99
aagctgcgca agctcatcct cgaggccaag ctcgcgccct gctacccggg cgccgacgac   60
gccgcgcccg gcggagggga cctcgaggag tgccccatct                         100

SEQ ID NO: 100           moltype = DNA   length = 100
FEATURE                  Location/Qualifiers
source                   1..100
                         mol_type = genomic DNA
                         organism = Zea mays
SEQUENCE: 100
agatggggca ctcctcgagg tcccctccgc cgggcgcggc gtcgtcggcg cccgggtagc   60
agggcgcgag cttggcctcg aggatgagct tgcgcagctt                         100

SEQ ID NO: 101           moltype = DNA   length = 420
FEATURE                  Location/Qualifiers
misc_feature             15
                         note = n is a, c, g, or t
source                   1..420
                         mol_type = genomic DNA
                         organism = Triticum aestivum
SEQUENCE: 101
ctcatcgagt gttcnccgca atgcgctgtt gctgattctc aagtgcgtgt gggtgcaggt   60
ggagagcaga agaaggccgg ccggcagcgg cggaggagga gggcgaggca ggcagcggca   120
ggcgaaggcg cggaggggga cgatgcggcg aagaaacgcc ggctgagtga cgagcaggcg   180
cagttcctcg agatgagctt caggaaggaa cgtaaactgg aaacgccccg caaggtgcag   240
ctcgccgcgg agctgggcct ggacaccaag caggtcgcgg tgtggttcca gaaccgccgc   300
gcccgctaca agagcaagct catcgaggag gagttctcca agctccgcgc ggcacacgac   360
gccgtcgtcg tccacaactg ccacctcgag gccgaggtac agtgcaacag tccggctgcc   420

SEQ ID NO: 102           moltype = DNA   length = 23
```

```
FEATURE              Location/Qualifiers
misc_feature         1..23
                     note = gRNA target sequence
source               1..23
                     mol_type = other DNA
                     organism = synthetic construct
SEQUENCE: 102
ggaaaagttg tagactgaga tgg                                            23

SEQ ID NO: 103       moltype = DNA   length = 85
FEATURE              Location/Qualifiers
source               1..85
                     mol_type = genomic DNA
                     organism = Arabidopsis thaliana
SEQUENCE: 103
taaatttgat tcgttgatag ggctaaagag atgtgggaaa agttgtagac tgagatggat    60
gaattatttg agccctaatg tgaac                                          85

SEQ ID NO: 104       moltype = DNA   length = 84
FEATURE              Location/Qualifiers
source               1..84
                     mol_type = genomic DNA
                     organism = Arabidopsis thaliana
SEQUENCE: 104
taaatttgat tcgttgatag ggctaaagag atgtgggaaa agttgtagac tagatggatg    60
aattatttga gccctaatgt gaac                                           84

SEQ ID NO: 105       moltype = DNA   length = 86
FEATURE              Location/Qualifiers
source               1..86
                     mol_type = genomic DNA
                     organism = Arabidopsis thaliana
SEQUENCE: 105
taaatttgat tcgttgatag ggctaaagag atgtgggaaa agttgtagac tgtagatgga    60
tgaattattt gagccctaat gtgaac                                         86

SEQ ID NO: 106       moltype = DNA   length = 85
FEATURE              Location/Qualifiers
source               1..85
                     mol_type = genomic DNA
                     organism = Arabidopsis thaliana
SEQUENCE: 106
taaatttgat tcgttgatag ggctaaagag atgtgggaaa agttgtagac tgagatggat    60
gaattatttg agccctaatg tgaac                                          85

SEQ ID NO: 107       moltype = DNA   length = 86
FEATURE              Location/Qualifiers
source               1..86
                     mol_type = genomic DNA
                     organism = Arabidopsis thaliana
SEQUENCE: 107
taaatttgat tcgttgatag ggctaaagag atgtgggaaa agttgtagac tgaagatgga    60
tgaattattt gagccctaat gtgaac                                         86

SEQ ID NO: 108       moltype = DNA   length = 86
FEATURE              Location/Qualifiers
source               1..86
                     mol_type = genomic DNA
                     organism = Arabidopsis thaliana
SEQUENCE: 108
taaatttgat tcgttgatag ggctaaagag atgtgggaaa agttgtagac tgtagatgga    60
tgaattattt gagccctaat gtgaac                                         86

SEQ ID NO: 109       moltype = DNA   length = 82
FEATURE              Location/Qualifiers
source               1..82
                     mol_type = genomic DNA
                     organism = Arabidopsis thaliana
SEQUENCE: 109
taaatttgat tcgttgatag ggctaaagag atgtgggaaa agttgtagaa gatggatgaa    60
ttatttgagc cctaatgtga ac                                             82

SEQ ID NO: 110       moltype = DNA   length = 86
FEATURE              Location/Qualifiers
source               1..86
                     mol_type = genomic DNA
                     organism = Arabidopsis thaliana
SEQUENCE: 110
taaatttgat tcgttgatag ggctaaagag atgtgggaaa agttgtagac tgaagatgga    60
```

```
tgaattattt gagccctaat gtgaac                                                  86

SEQ ID NO: 111          moltype = DNA   length = 84
FEATURE                 Location/Qualifiers
source                  1..84
                        mol_type = genomic DNA
                        organism = Arabidopsis thaliana
SEQUENCE: 111
taaatttgat tcgttgatag ggctaaagag atgtgggaaa agttgtagac tagatggatg            60
aattatttga gccctaatgt gaac                                                   84

SEQ ID NO: 112          moltype = DNA   length = 83
FEATURE                 Location/Qualifiers
source                  1..83
                        mol_type = genomic DNA
                        organism = Arabidopsis thaliana
SEQUENCE: 112
taaatttgat tcgttgatag ggctaaagag atgtgggaaa agttgtagac tgatggatga            60
attatttgag ccctaatgtg aac                                                    83

SEQ ID NO: 113          moltype = DNA   length = 83
FEATURE                 Location/Qualifiers
source                  1..83
                        mol_type = genomic DNA
                        organism = Arabidopsis thaliana
SEQUENCE: 113
taaatttgat tcgttgatag ggctaaagag atgtgggaaa agttgtagac agatggatga            60
attatttgag ccctaatgtg aac                                                    83

SEQ ID NO: 114          moltype = DNA   length = 86
FEATURE                 Location/Qualifiers
source                  1..86
                        mol_type = genomic DNA
                        organism = Arabidopsis thaliana
SEQUENCE: 114
taaatttgat tcgttgatag ggctaaagag atgtgggaaa agttgtagac tgtagatgga            60
tgaattattt gagccctaat gtgaac                                                 86

SEQ ID NO: 115          moltype = DNA   length = 86
FEATURE                 Location/Qualifiers
source                  1..86
                        mol_type = genomic DNA
                        organism = Arabidopsis thaliana
SEQUENCE: 115
taaatttgat tcgttgatag ggctaaagag atgtgggaaa agttgtagac tgaagatgga            60
tgaattattt gagccctaat gtgaac                                                 86

SEQ ID NO: 116          moltype = DNA   length = 86
FEATURE                 Location/Qualifiers
source                  1..86
                        mol_type = genomic DNA
                        organism = Arabidopsis thaliana
SEQUENCE: 116
taaatttgat tcgttgatag ggctaaagag atgtgggaaa agttgtagac tgtagatgga            60
tgaattattt gagccctaat gtgaac                                                 86

SEQ ID NO: 117          moltype = DNA   length = 78
FEATURE                 Location/Qualifiers
source                  1..78
                        mol_type = genomic DNA
                        organism = Arabidopsis thaliana
SEQUENCE: 117
taaatttgat tcgttgatag ggctaaagag atgtgggcta aacatagatg gatgaattat            60
ttgagcccta atgtgaac                                                          78
```